US011883417B2

(12) United States Patent
Pan et al.

(10) Patent No.: US 11,883,417 B2
(45) **Date of Patent: *Jan. 30, 2024**

(54) METHODS AND COMPOSITIONS RELATED TO GLUCOCORTICOID RECEPTOR ANTAGONISTS AND BREAST CANCER

(71) Applicant: The University of Chicago, Chicago, IL (US)

(72) Inventors: Deng Pan, Chicago, IL (US); Masha Kocherginsky, Chicago, IL (US); Suzanne D. Conzen, Park Ridge, IL (US)

(73) Assignee: The University of Chicago, Chicago, IL (US)

(*) Notice: Subject to any disclaimer, the term of this patent is extended or adjusted under 35 U.S.C. 154(b) by 118 days.

This patent is subject to a terminal disclaimer.

(21) Appl. No.: 17/577,882

(22) Filed: Jan. 18, 2022

(65) Prior Publication Data

US 2022/0133746 A1 May 5, 2022

Related U.S. Application Data

(63) Continuation of application No. 16/596,342, filed on Oct. 8, 2019, now Pat. No. 11,234,990, which is a continuation of application No. 15/448,827, filed on Mar. 3, 2017, now Pat. No. 10,441,596, which is a continuation of application No. 14/296,127, filed on Jun. 4, 2014, now Pat. No. 9,623,032, which is a continuation of application No. 14/172,051, filed on Feb. 4, 2014, now Pat. No. 9,149,485, which is a continuation of application No. 13/071,363, filed on Mar. 24, 2011, now Pat. No. 8,710,035.

(60) Provisional application No. 61/317,182, filed on Mar. 24, 2010.

(51) Int. Cl.

| | |
|---|---|
| ***A61K 31/575*** | (2006.01) |
| ***A61K 45/06*** | (2006.01) |
| ***A61K 33/243*** | (2019.01) |
| ***A61K 31/282*** | (2006.01) |
| ***A61K 31/337*** | (2006.01) |
| ***A61K 31/357*** | (2006.01) |
| ***A61K 31/4745*** | (2006.01) |
| ***A61K 31/7068*** | (2006.01) |
| ***A61K 39/395*** | (2006.01) |
| ***A61N 5/00*** | (2006.01) |
| ***A61J 1/00*** | (2023.01) |
| ***A61K 31/567*** | (2006.01) |
| ***A61K 31/58*** | (2006.01) |

(52) U.S. Cl.

CPC ............... *A61K 31/575* (2013.01); *A61J 1/00* (2013.01); *A61K 31/282* (2013.01); *A61K 31/337* (2013.01); *A61K 31/357* (2013.01); *A61K 31/4745* (2013.01); *A61K 31/567* (2013.01); *A61K 31/58* (2013.01); *A61K 31/7068* (2013.01); *A61K 33/243* (2019.01); *A61K 39/3955* (2013.01); *A61K 45/06* (2013.01); *A61N 5/00* (2013.01)

(58) Field of Classification Search

CPC .... A61K 31/575; A61K 45/06; A61K 33/243; A61K 31/282; A61K 31/337; A61K 31/357; A61K 31/4745; A61K 31/7068; A61K 39/3955; A61K 31/567; A61K 31/58; A61N 5/00; A61J 1/00

See application file for complete search history.

(56) References Cited

U.S. PATENT DOCUMENTS

| | | | |
|---|---|---|---|
| 8,003,689 | B2 | 8/2011 | Veverka |
| 8,658,128 | B2 | 2/2014 | Altschul et al. |
| 8,710,035 | B2 | 4/2014 | Pan et al. |
| 9,114,147 | B2 | 8/2015 | Altschul et al. |
| 9,149,485 | B2 | 10/2015 | Pan et al. |
| 9,623,032 | B2 | 4/2017 | Pan et al. |
| 10,071,130 | B2 | 9/2018 | Conzen |
| 10,441,596 | B2 | 10/2019 | Pan et al. |
| 11,234,990 | B2 | 2/2022 | Pan et al. |
| 2002/0115613 | A1 | 8/2002 | Kumar |
| 2005/0124533 | A1 | 6/2005 | Schatzberg et al. |
| 2006/0063748 | A1 | 3/2006 | Belanoff |
| 2008/0287419 | A1 | 11/2008 | Bruncko et al. |
| 2010/0135956 | A1 | 6/2010 | Gant et al. |

FOREIGN PATENT DOCUMENTS

| | | |
|---|---|---|
| WO | 2009064738 A2 | 5/2009 |

OTHER PUBLICATIONS

"Data Sheet: Glucocorticoid Receptor mouse monoclonal antibody NCL-GCR", Novocastra Laboratories Ltd., Available Online at: http://www.ebiotrade.com/buyf/Novocastra/data/hrerp/gcr.pdf, Accessed from internet at Jun. 7, 2011.

U.S. Appl. No. 14/172,051 , Non-Final Office Action, dated Mar. 10, 2015, 9 pages.

U.S. Appl. No. 14/172,051 , Notice of Allowance, dated Jun. 24, 2015, 11 pages.

(Continued)

*Primary Examiner* — Shirley V Gembeh

(74) *Attorney, Agent, or Firm* — Kilpatrick Townsend & Stockton LLP

(57) ABSTRACT

Embodiments of the invention are directed to methods of determining the prognosis of a breast cancer patient by evaluating the activity of the glucocorticoid receptor in tumor cells. Other embodiment include methods of treating breast cancer cells, particularly, chemo-resistant cells, with a glucocorticoid receptor antagonist and an anticancer agent or compound.

20 Claims, 12 Drawing Sheets

Specification includes a Sequence Listing.

(56) References Cited

OTHER PUBLICATIONS

U.S. Appl. No. 14/172,051 , Notice of Allowance, dated Apr. 30, 2015, 5 pages.
U.S. Appl. No. 14/296,127 , Final Office Action, dated Jul. 5, 2016, 9 pages.
U.S. Appl. No. 14/296,127 , Non-Final Office Action, dated Dec. 17, 2015, 10 pages.
U.S. Appl. No. 14/296,127 , Non-Final Office Action, dated Sep. 14, 2016, 7 pages.
U.S. Appl. No. 14/296,127 , Notice of Allowance, dated Dec. 8, 2016, 9 pages.
U.S. Appl. No. 14/296,127 , "Restriction Requirement", dated Oct. 8, 2015, 11 pages.
U.S. Appl. No. 61/317,182 , filed Mar. 24, 2010, 72 pages.
Belanoff et al., "Selective Glucocorticoid Receptor {Type II) Antagonists Prevent Weight Gain Caused by Olanzapine in Rats", European Journal of Pharmacology, vol. 655, Issue 1-3, Mar. 25, 2011, pp. 117-120.
Belova et al., "Glucocorticoid Receptor Expression in Breast Cancer Associates with Older Patient Age", Breast Cancer Research and Treatment, vol. 116, No. 3, Aug. 2009, pp. 441-447.
Cho et al., "Role of Activation function Domain-1, DNA Binding, and Coactivator GRIP1 in the Expression of Partial Agonist Activity of Glucocorticoid Receptor-Antagonist Complexes", Biochemistry, vol. 44, No. 9, Mar. 8, 2005, pp. 3547-3561.
Clark , "Glucocorticoid Receptor Antagonists", Current Topics in Medicinal Chemistry, vol. 8, No. 9, Jun. 1, 2008, pp. 813-838.
Colleoni et al., "Response to Primary Chemotherapy in Breast Cancer Patients with Tumors Not Expressing Estrogen and Progesterone Receptors", Annals of Oncology, vol. 11, No. 8, Aug. 1, 2000, pp. 1057-1059.
Dennis , "Off by a Whisker", Nature, vol. 442, Aug. 7, 2006, pp. 739-741.
Desmedt et al., "Strong Time Dependence of the 76-Gene Prognostic Signature for Node-Negative Breast Cancer Patients in the TRANSBIG Multicenter Independent Validation Series", Clinical Cancer Research, vol. 13, Issue 11, Jun. 2007, pp. 3207-3214.
Gaddy et al., "Mifepristone Induces Growth Arrest, Caspase Activation, and Apoptosis of Estrogen Receptor-Expressing, Antiestrogen-Resistant Breast Cancer Cells", Clinical Cancer Research, vol. 10, No. 15, Aug. 1, 2004, pp. 5215-5225.
Grover et al., "The Initiation of Breast and Prostate Cancer", Carcinogenesis, vol. 23, No. 7, Jul. 1, 2002, pp. 1095-1102.
Gura , "Systems for Identifying New Drugs are Often Faulty", Science, Cancer Models, vol. 278, No. 5340, Nov. 7, 1997, pp. 1041-1042.
Hein et al., "Click Chemistry, A powerful Tool for Pharmaceutical Sciences", Pharmaceutical Research, vol. 25, No. 10, Oct. 2008, pp. 2216-2230.
Henderson et al., "Estrogens as a Cause of Human Cancer: the Richard and Hinda Rosenthal Foundation Award Lecture", Cancer Research, vol. 48, No. 2, Jan. 15, 1988, pp. 246-253.
Huang et al., "Reversal Effect of Mifepristone on Adriamycin Resistance in Human Breast Cancer Cell Line MCF-7/ADM in Vitro and in Vivo", Journal of Central South University, Medical Sciences, vol. 35, No. 6, Jun. 2010, pp. 576-583.
Keen et al., "The Biology of Breast Carcinoma", Cancer, vol. 97, No. 3, Feb. 1, 2003, pp. 825-833.
Kriaucionis et al., "The Nuclear DNA Base 5-Hydroxymethylcytosine is Present in Brain and Enriched in Purkinje Neurons", Science, vol. 324, No. 5929, May 15, 2009, 5 pages.
Loi et al., "Definition of Clinically Distinct Molecular Subtypes in Estrogen Receptor-Positive Breast Carcinomas Through Genomic Grade", Journal of Clinical Oncology, vol. 25, No. 10, Apr. 1, 2007, pp. 1239-1246.
Loi et al., "Predicting Prognosis Using Molecular Profiling in Estrogen Receptor-Positive Breast Cancer Treated With Tamoxifen", BMC Genomics, vol. 9, No. 239, May 22, 2008, pp. 1-12.
Lucci et al., "Modification of Ceramide Metabolism Increases Cancer Cell Sensitivity to Cytotoxics", International Journal of Oncology, vol. 15, No. 3, Sep. 1999, pp. 541-546.
Ma et al., "IL-21 Activates Both Innate and Adaptive Immunity to Generate Potent Antitumor Responses that Require Perforin but Are Independent of IFN-Gamma", Journal of Immunology, vol. 171, No. 2, Jul. 15, 2003, pp. 608-615.
Melhem et al., "Administration of Glucocorticoids to Ovarian Cancer Patients is Associated with Expression of the Anti-apoptotic Genes SGK1 and MKP1/DUSP1 in Ovarian Tissues", Clinical Cancer Research, vol. 15, No. 9, May 1, 2009, pp. 3196-3204.
Mikosz et al., "Glucocorticoid Receptor-Mediated Protection from Apoptosis is Associated with Induction of the Serine/Threonine Survival Kinase Gene, sgk-1", The Journal of Biological Chemistry, vol. 276, No. 20, Feb. 13, 2001, p. 16649-16654.
Minn et al., "Genes that Mediate Breast Cancer Metastasis to Lung", Nature, vol. 436, No. 7050, Jul. 28, 2005, pp. 518-524.
Moran et al., "The Glucocorticoid Receptor Mediates a Survival Signal in Human Mammary Epithelial Cells", Cancer Research, vol. 60, No. 4, Feb. 15, 2000, pp. 867-872.
Moses et al., "The Growing Applications of Click Chemistry", Chemical Society Reviews, vol. 36, No. 8, May 2007, pp. 1249-1262.
Neckers et al., "Heat-Shock Protein 90 Inhibitors As Novel Cancer Chemotherapeutic Agents", Breast Disease, Available Online at: https://content.iospress.com/articles/breast-disease/bd000102 vol. 15, No. 1, Jun. 1, 2002, pp. 1-2.
Pan et al., "Activation of the Glucocorticoid Receptor is Associated with Poor Prognosis in Estrogen Receptor-Negative Breast Cancer", Cancer Research, vol. 71, No. 20, Oct. 15, 2011, 21 pages.
Pan et al., "Identification of Glucocorticoid Receptor (GR) Signatures in Primary Human Breast Cancer: Association with Relapse-Free Survival Time", Poster Presented by S.D. Conzen as a Short Talk, presented at Nuclear Receptors: Signaling, Gene Regulation and Cancer, Keystone Symposia on Molecular and Cellular Biology, Keystone Resort, Keystone, Colorado, Mar. 25, 2010, 1 page.
Pang et al., "Dexamethasone Decreases Xenograft Response to Paclitaxel Through Inhibition of Tumor Cell Apoptosis", Cancer Biology & Therapy, vol. 5, No. 8, Aug. 2006, pp. 933-940.
Peeters et al., "Differential Effects of the New Glucocorticoid Receptor Antagonist ORG 34517 and RU486 (Mifepristone) on Glucocorticoid Receptor Nuclear Translocation in the AtT20 Cell Line", Annals of the New York Academy of Sciences, vol. 1148, No. 1, Dec. 2008, pp. 536-541.
Pike et al., "Estrogens, Progestogens, Normal Breast Cell Proliferation, and Breast Cancer Risk", Epidemiologic Reviews, vol. 15, No. 1, Jan. 1, 1993, pp. 17-30.
Reagan-Shaw et al., "Dose Translation from Animal to Human Studies Revisited", The Faseb Journal, vol. 22, Mar. 2007, pp. 659-661.
Robinson et al., "Octahydrophenanthrene-2, 7-diol Analogues as Dissociated Glucocorticoid Receptor Agonists: Discovery and Lead Exploration", Journal of Medicinal Chemistry, vol. 52, No. 6, 2009, pp. 1731-1743.
Sims et al., "The Removal of Multiplicative, Systematic Bias Allows Integration of Breast Cancer Gene Expression Datasets—Improving Meta-Analysis and Prediction of Prognosis", BMC Medical Genomics, vol. 1, No. 42, Sep. 21, 2008, pp. 1-14.
Smith et al., "Expression of Glucocorticoid and Progesterone Nuclear Receptor Genes in Archival Breast Cancer Tissue", Breast Cancer Research, vol. 5, No. 1, 2003, pp. R9-R12.
Smith et al., "Progesterone, Glucocorticoid, but Not Estrogen Receptor mRNA is Altered in Breast Cancer Stroma", Cancer Letters, vol. 255, No. 1, Sep. 18, 2007, pp. 77-84.
Sorlie et al., "Gene Expression Patterns of Breast Carcinomas Distinguish Tumor Subclasses with Clinical Implications", Proceedings of the National Academy of Sciences of the United States of America, vol. 98, No. 19, Sep. 11, 2001, pp. 10869-10874.
Sotiriou et al., "Gene Expression Profiling in Breast Cancer: Understanding the Molecular Basis of Histologic Grade to Improve Prognosis", Journal of the National Cancer Institute, vol. 98, No. 4, Feb. 15, 2006, pp. 262-272.

(56) References Cited

OTHER PUBLICATIONS

Srinivas et al., "Proteomics for Cancer Biomarker Discovery", Clinical Chemistry, vol. 48, Issue 8, Aug. 2002, pp. 1160-1169.
Sui et al., "Estrogen Receptor α Mediates Breast Cancer Cell Resistance to Paclitaxel Through Inhibition of Apoptotic Cell Death", Cancer Research, vol. 67, No. 11, Jun. 1, 2007, pp. 5337-5344.
Wang et al., "Gene-Expression Profiles to Predict Distant Metastasis of Lymph-Node-Negative Primary Breast Cancer", The Lancet, vol. 365, No. 9460, Feb. 19-25, 2005, pp. 671-679.
Wu et al., "Glucocorticoid Receptor Activation Signals Through Forkhead Transcription Factor 3a in Breast Cancer Cells", Molecular Endocrinology, vol. 20, No. 10, Oct. 1, 2006, pp. 2304-2314.
Wu et al., "Microarray Analysis Reveals Glucocorticoid-Regulated Survival Genes that are Associated with Inhibition of Apoptosis in Breast Epithelial Cells", Cancer Research, vol. 64, No. 5, Mar. 1, 2004, pp. 1757-1764.
Wu et al., "Prevalent Expression of the Immunostimulatory MHC Class I Chain-Related Molecule Is Counteracted by Shedding in Prostate Cancer", Journal of Clinical Investigation, vol. 114, Issue 4, Aug. 16, 2004, pp. 560-568.
U.S. Appl. No. 14/451,207, "Notice of Withdrawal from Issue Under 37 CRF 1.313 (b)," dated Feb. 4, 2016, 2 pages.

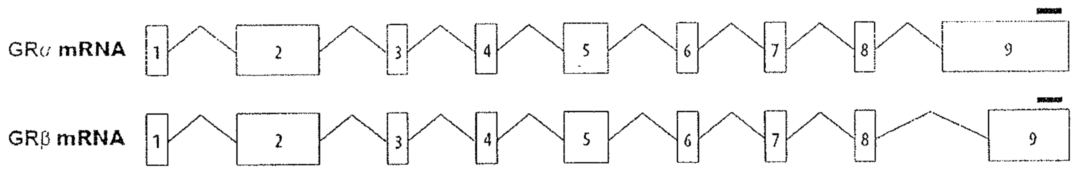

```
Query = GR alpha
Length=6784

18665 = GR beta

ALIGNMENTS

Query  1    GGCGCCGCCTCCACCCGCTCCCCGCTCGGTCCCGCTCGCTCGCCCAGGCCGGGCTGCCCT  60
18665  1    GGCGCCGCCTCCACCCGCTCCCCGCTCGGTCCCGCTCGCTCGCCCAGGCCGGGCTGCCCT  60

Query  61   TTCGCGTGTCCGCGCTCTCTTCCCTCCGCCGCCGCCTCCTCCATTTTGCGAGCTCGTGTC  120
18665  61   TTCGCGTGTCCGCGCTCTCTTCCCTCCGCCGCCGCCTCCTCCATTTTGCGAGCTCGTGTC  120

Query  121  TGTGACGGGAGCCCGAGTCACCGCCTGCCCGTCGGGGACGGATTCTGTGGGTGGAAGGAG  180
18665  121  TGTGACGGGAGCCCGAGTCACCGCCTGCCCGTCGGGGACGGATTCTGTGGGTGGAAGGAG  180

Query  181  ACGCCGCAGCCGGAGCGGCCGAAGCAGCTGGGACCGGGACGGGGCACGCGCGCCCGGAAC  240
18665  181  ACGCCGCAGCCGGAGCGGCCGAAGCAGCTGGGACCGGGACGGGGCACGCGCGCCCGGAAC  240

Query  241  CTCGACCCGCGGAGCCCGGCGCGGGGCGGAGGGCTGGCTTGTCAGCTGGGCAATGGGAGA  300
18665  241  CTCGACCCGCGGAGCCCGGCGCGGGGCGGAGGGCTGGCTTGTCAGCTGGGCAATGGGAGA  300

Query  301  CTTTCTTAAATAGGGGCTCTCCCCCCACCCATGGAGAAAGGGGCGGCTGTTTACTTCCtt  360
18665  301  CTTTCTTAAATAGGGGCTCTCCCCCCACCCATGGAGAAAGGGGCGGCTGTTTACTTCCTT  360

Query  361  tttttAGaaaaaaaaaaTATATTTCCCTCCTGCTCCTTCTGCGTTCACAAGCTAAGTTGT  420
18665  361  TTTTTAGAAAAAAAAAATATATTTCCCTCCTGCTCCTTCTGCGTTCACAAGCTAAGTTGT  420

Query  421  TTATCTCGGCTGCGGCGGGAACTGCGGACGGTGGCGGGCGAGCGGCTCCTCTGCCAGAGT  480
18665  421  TTATCTCGGCTGCGGCGGGAACTGCGGACGGTGGCGGGCGAGCGGCTCCTCTGCCAGAGT  480

Query  481  TGATATTCACTGATGGACTCCAAAGAATCATTAACTCCTGGTAGAGAAGAAAACCCCAGC  540
18665  481  TGATATTCACTGATGGACTCCAAAGAATCATTAACTCCTGGTAGAGAAGAAAACCCCAGC  540

Query  541  AGTGTGCTTGCTCAGGAGAGGGGAGATGTGATGGACTTCTATAAAACCCTAAGAGGAGGA  600
18665  541  AGTGTGCTTGCTCAGGAGAGGGGAGATGTGATGGACTTCTATAAAACCCTAAGAGGAGGA  600

Query  601  GCTACTGTGAAGGTTTCTGCGTCTTCACCCTCACTGGCTGTCGCTTCTCAATCAGACTCC  660
18665  601  GCTACTGTGAAGGTTTCTGCGTCTTCACCCTCACTGGCTGTCGCTTCTCAATCAGACTCC  660

Query  661  AAGCAGCGAAGACTTTTGGTTGATTTTCCAAAAGGCTCAGTAAGCAATGCGCAGCAGCCA  720
18665  661  AAGCAGCGAAGACTTTTGGTTGATTTTCCAAAAGGCTCAGTAAGCAATGCGCAGCAGCCA  720

Query  721  GATCTGTCCAAAGCAGTTTCACTCTCAATGGGACTGTATATGGGAGAGACAGAAACAAAA  780
18665  721  GATCTGTCCAAAGCAGTTTCACTCTCAATGGGACTGTATATGGGAGAGACAGAAACAAAA  780

Query  781  GTGATGGGAAATGACCTGGGATTCCCACAGCAGGGCCAAATCAGCCTTTCCTCGGGGGAA  840
18665  781  GTGATGGGAAATGACCTGGGATTCCCACAGCAGGGCCAAATCAGCCTTTCCTCGGGGGAA  840

Query  841  ACAGACTTAAAGCTTTTGGAAGAAAGCATTGCAAACCTCAATAGGTCGACCAGTGTTCCA  900
18665  841  ACAGACTTAAAGCTTTTGGAAGAAAGCATTGCAAACCTCAATAGGTCGACCAGTGTTCCA  900
```

FIG. 7A

```
Query  901   GAGAACCCCAAGAGTTCAGCATCCACTGCTGTGTCTGCTGCCCCCACAGAGAAGGAGTTT  960
18665  901   GAGAACCCCAAGAGTTCAGCATCCACTGCTGTGTCTGCTGCCCCCACAGAGAAGGAGTTT  960

Query  961   CCAAAAACTCACTCTGATGTATCTTCAGAACAGCAACATTTGAAGGGCCAGACTGGCACC  1020
18665  961   CCAAAAACTCACTCTGATGTATCTTCAGAACAGCAACATTTGAAGGGCCAGACTGGCACC  1020

Query  1021  AACGGTGGCAATGTGAAATTGTATACCACAGACCAAAGCACCTTTGACATTTTGCAGGAT  1080
18665  1021  AACGGTGGCAATGTGAAATTGTATACCACAGACCAAAGCACCTTTGACATTTTGCAGGAT  1080

Query  1081  TTGGAGTTTTCTTCTGGGTCCCCAGGTAAAGAGACGAATGAGAGTCCTTGGAGATCAGAC  1140
18665  1081  TTGGAGTTTTCTTCTGGGTCCCCAGGTAAAGAGACGAATGAGAGTCCTTGGAGATCAGAC  1140

Query  1141  CTGTTGATAGATGAAAACTGTTTGCTTTCTCCTCTGGCGGGAGAAGACGATTCATTCCTT  1200
18665  1141  CTGTTGATAGATGAAAACTGTTTGCTTTCTCCTCTGGCGGGAGAAGACGATTCATTCCTT  1200

Query  1201  TTGGAAGGAAACTCGAATGAGGACTGCAAGCCTCTCATTTTACCGGACACTAAACCCAAA  1260
18665  1201  TTGGAAGGAAACTCGAATGAGGACTGCAAGCCTCTCATTTTACCGGACACTAAACCCAAA  1260

Query  1261  ATTAAGGATAATGGAGATCTGGTTTTGTCAAGCCCCAGTAATGTAACACTGCCCCAAGTG  1320
18665  1261  ATTAAGGATAATGGAGATCTGGTTTTGTCAAGCCCCAGTAATGTAACACTGCCCCAAGTG  1320

Query  1321  AAAACAGAAAAAGAAGATTTCATCGAACTCTGCACCCCTGGGGTAATTAAGCAAGAGAAA  1380
18665  1321  AAAACAGAAAAAGAAGATTTCATCGAACTCTGCACCCCTGGGGTAATTAAGCAAGAGAAA  1380

Query  1381  CTGGGCACAGTTTACTGTCAGGCAAGCTTTCCTGGAGCAAATATAATTGGTAATAAAATG  1440
18665  1381  CTGGGCACAGTTTACTGTCAGGCAAGCTTTCCTGGAGCAAATATAATTGGTAATAAAATG  1440

Query  1441  TCTGCCATTTCTGTTCATGGTGTGAGTACCTCTGGAGGACAGATGTACCACTATGACATG  1500
18665  1441  TCTGCCATTTCTGTTCATGGTGTGAGTACCTCTGGAGGACAGATGTACCACTATGACATG  1500

Query  1501  AATACAGCATCCCTTTCTCAACAGCAGGATCAGAAGCCTATTTTTAATGTCATTCCACCA  1560
18665  1501  AATACAGCATCCCTTTCTCAACAGCAGGATCAGAAGCCTATTTTTAATGTCATTCCACCA  1560

Query  1561  ATTCCCGTTGGTTCCGAAAATTGGAATAGGTGCCAAGGATCTGGAGATGACAACTTGACT  1620
18665  1561  ATTCCCGTTGGTTCCGAAAATTGGAATAGGTGCCAAGGATCTGGAGATGACAACTTGACT  1620

Query  1621  TCTCTGGGGACTCTGAACTTCCCTGGTCGAACAGTTTTTTCTAATGGCTATTCAAGCCCC  1680
18665  1621  TCTCTGGGGACTCTGAACTTCCCTGGTCGAACAGTTTTTTCTAATGGCTATTCAAGCCCC  1680

Query  1681  AGCATGAGACCAGATGTAAGCTCTCCTCCATCCAGCTCCTCAACAGCAACAACAGGACCA  1740
18665  1681  AGCATGAGACCAGATGTAAGCTCTCCTCCATCCAGCTCCTCAACAGCAACAACAGGACCA  1740

Query  1741  CCTCCCAAACTCTGCCTGGTGTGCTCTGATGAAGCTTCAGGATGTCATTATGGAGTCTTA  1800
18665  1741  CCTCCCAAACTCTGCCTGGTGTGCTCTGATGAAGCTTCAGGATGTCATTATGGAGTCTTA  1800

Query  1801  ACTTGTGGAAGCTGTAAAGTTTTCTTCAAAAGAGCAGTGGAAGGACAGCACAATTACCTA  1860
18665  1801  ACTTGTGGAAGCTGTAAAGTTTTCTTCAAAAGAGCAGTGGAAGGACAGCACAATTACCTA  1860

Query  1861  TGTGCTGGAAGGAATGATTGCATCATCGATAAAATTCGAAGAAAAAACTGCCCAGCATGC  1920
18665  1861  TGTGCTGGAAGGAATGATTGCATCATCGATAAAATTCGAAGAAAAAACTGCCCAGCATGC  1920

Query  1921  CGCTATCGAAAATGTCTTCAGGCTGGAATGAACCTGGAAGCTCGaaaaacaaagaaaaaa  1980
18665  1921  CGCTATCGAAAATGTCTTCAGGCTGGAATGAACCTGGAAGCTCGAAAAACAAAGAAAAAA  1980

Query  1981  ataaaaGGAATTCAGCAGGCCACTACAGGAGTCTCACAAGAAACCTCTGAAAATCCTGGT  2040
18665  1981  ATAAAAGGAATTCAGCAGGCCACTACAGGAGTCTCACAAGAAACCTCTGAAAATCCTGGT  2040

Query  2041  AACAAAACAATAGTTCCTGCAACGTTACCACAACTCACCCCTACCCTGGTGTCACTGTTG  2100
18665  2041  AACAAAACAATAGTTCCTGCAACGTTACCACAACTCACCCCTACCCTGGTGTCACTGTTG  2100

Query  2101  GAGGTTATTGAACCTGAAGTGTTATATGCAGGATATGATAGCTCTGTTCCAGACTCAACT  2160
18665  2101  GAGGTTATTGAACCTGAAGTGTTATATGCAGGATATGATAGCTCTGTTCCAGACTCAACT  2160
```

FIG. 7B

```
Query  2161  TGGAGGATCATGACTACGCTCAACATGTTAGGAGGGCGGCAAGTGATTGCAGCAGTGAAA  2220
18665  2161  TGGAGGATCATGACTACGCTCAACATGTTAGGAGGGCGGCAAGTGATTGCAGCAGTGAAA  2220

Query  2221  TGGGCAAAGGCAATACCAGGTTTCAGGAACTTACACCTGGATGACCAAATGACCCTACTG  2280
18665  2221  TGGGCAAAGGCAATACCAGGTTTCAGGAACTTACACCTGGATGACCAAATGACCCTACTG  2280

Query  2281  CAGTACTCCTGGATGTTTCTTATGGCATTTGCTCTGGGGTGGAGATCATATAGACAATCA  2340
18665  2281  CAGTACTCCTGGATGTTTCTTATGGCATTTGCTCTGGGGTGGAGATCATATAGACAATCA  2340

Query  2341  AGTGCAAACCTGCTGTGTTTTGCTCCTGATCTGATTATTAATGAGCAGAGAATGACTCTA  2400
18665  2341  AGTGCAAACCTGCTGTGTTTTGCTCCTGATCTGATTATTAATGAGCAGAGAATGACTCTA  2400

Query  2401  CCCTGCATGTACGACCAATGTAAACACATGCTGTATGTTTCCTCTGAGTTACACAGGCTT  2460
18665  2401  CCCTGCATGTACGACCAATGTAAACACATGCTGTATGTTTCCTCTGAGTTACACAGGCTT  2460

Query  2461  CAGGTATCTTATGAAGAGTATCTCTGTATGAAAACCTTACTGCTTCTCTCTTCAGTTCCT  2520
18665  2461  CAGGTATCTTATGAAGAGTATCTCTGTATGAAAACCTTACTGCTTCTCTCTTCAGTTCCT  2520

Query  2521  AAGGACGGTCTGAAGAGCCAAGAGCTATTTGATGAAATTAGAATGACCTACATCAAAGAG  2580
18665  2521  AAGGACGGTCTGAAGAGCCAAGAGCTATTTGATGAAATTAGAATGACCTACATCAAAGAG  2580

Query  2581  CTAGGAAAAGCCATTGTCAAGAGGGAAGGAAACTCCAGCCAGAACTGGCAGCGGTTTTAT  2640
18665  2581  CTAGGAAAAGCCATTGTCAAGAGGGAAGGAAACTCCAGCCAGAACTGGCAGCGGTTTTAT  2640

Query  2641  CAACTGACAAAACTCTTGGATTCTATGCATGAAGTGGTTGAAAATCTCCTTAACTATTGC  2700
18665  2641  CAACTGACAAAACTCTTGGATTCTATGCATGAA                            2673

Query  2701  TTCCAAACATTTTTGGATAAGACCATGAGTATTGAATTCCCCGAGATGTTAGCTGAAATC  2760

Query  2761  ATCACCAATCAGATACCAAAATATTCAAATGGAAATATCAAAAAACTTCTGTTTCATCAA  2820

Query  2821  AAGTGACTGCCTTAATAAGAATGGTTGCCTTAAAGAAAGTCGAATTAATAGCTTTTATTG  2880

Query  2881  TATAAACTATCAGTTTGTCCTGTAGAGgttttgttgttttatttttttattgttttcatct  2940

Query  2941  gttgttttgttttAAATACGCACTACATGTGGTTTATAGAGGGCCAAGACTTGGCAACAG  3000

Query  3001  AAGCAGTTGAGTCGTCATCACTTTTCAGTGATGGGAGAGTAGATGGTGAAATTTATTAGT  3060

Query  3061  TAATATATCCCAGAAATTAGAAACCTTAATATGTGGACGTAATCTCCACAGTCAAAGAAG  3120

Query  3121  GATGGCACCTAAACCACCAGTGCCCAAAGTCTGTGTGATGAACTTTCTCTTCATACtttt  3180

Query  3181  tttCACAGTTGGCTGGATGAAATTTTCTAGACTTTCTGTTGGTGTATccccccccTGTAT  3240

Query  3241  AGTTAGGATAGCATTTTTGATTTATGCATGGAAACCTGaaaaaaaGTTTACAAGTGTATA  3300

Query  3301  TCAGAAAAGGGAAGTTGTGCCTTTTATAGCTATTACTGTCTGGTTTTAACAATTTCCTTT  3360

Query  3361  ATATTTAGTGAACTACGCTTGCTCATTTTTTTCTTACATAATTTTTTATTCAAGTTATTGT  3420

Query  3421  ACAGCTGTTTAAGATGGGCAGCTAGTTCGTAGCTTTCCCAAATAAACTCTAAACATTAAT  3480

Query  3481  CAATCATCTGTGTGAAAATGGGTTGGTGCTTCTAACCTGATGGCACTTAGCTATCAGAAG  3540

Query  3541  ACCACAAAAATTGACTCAAATCTCCAGTATTCTTGTCaaaaaaaaaaaaaaaaaaGCTCA  3600

Query  3601  TATTTTGTATATATCTGCTTCAGTGGAGAATTATATAGGTTGTGCAAATTAACAGTCCTA  3660

Query  3661  ACTGGTATAGAGCACCTAGTCCAGTGACCTGCTGGGTAAACTGTGGATGATGGTTGCAAA  3720

Query  3721  AGACTAATTTAAAAAATAACTACCAAGAGGCCCTGTCTGTACCTAACGCCCTATTTTTGC  3780
```

FIG. 7C

```
Query  3781  AATGGCTATATGGCAAGAAAGCTGGTAAACTATTTGTCTTTCAGGACCTTTTGAAGTAGT  3840

Query  3841  TTGTATAACTTCTTAAAAGTTGTGATTCCAGATAACCAGCTGTAACACAGCTGAGAGACT  3900

Query  3901  TTTAATCAGACAAAGTAATTCCTCTCACTAAACTTTACCCAAAAACTAAATCTCTAATAT  3960

Query  3961  GGCAAAAATGGCTAGACACCCATTTTCACATTCCCATCTGTCACCAATTGGTTAATCTTT  4020

Query  4021  CCTGATGGTACAGGAAAGCTCAGCTACTGATTTTTGTGATTTAGAACTGTATGTCAGACA  4080

Query  4081  TCCATGTTTGTAAAACTACACATCCCTAATGTGTGCCATAGAGTTTAACACAAGTCCTGT  4140

Query  4141  GAATTTCTTCACTGTTGAAAATTATTTTAAACAAAATAGAAGCTGTAGTAGCCCTTTCTG  4200

Query  4201  TGTGCACCTTACCAACTTTCTGTAAACTCAAAACTTAACATATTTACTAAGCCACAAGAA  4260

Query  4261  ATTTGATTTCTATTCAAGGTGGCCAAATTATTTGTGTAATAGAAAACTGAAAATCTAATA  4320

Query  4321  TTAAAAATATGGAACTTCTAatatatttttatatttagttatagtttcagatatatatca  4380

Query  4381  tatTGGTATTCACTAATCTGGGAAGGGAAGGGCTACTGCAGCTTTACATGCAATTTATTA  4440

Query  4441  AAATGATTGTAAAATAGCTTGTATAGTGTAAAATAAGAATGATTTTTAGATGAGATTGTT  4500

Query  4501  TTATCATGACATGTTATATATTTTTTGTAGGGGTCAAAGAAATGCTGATGGATAACCTAT  4560

Query  4561  ATGATTTATAGTTTGTACATGCATTCATACAGGCAGCGATGGTCTCAGAAACCAAACAGT  4620

Query  4621  TTGCTCTAGGGGAAGAGGGAGATGGAGACTGGTCCTGTGTGCAGTGAAGGTTGCTGAGGC  4680

Query  4681  TCTGACCCAGTGAGATTACAGAGGAAGTTATCCTCTGCCTCCCATTCTGACCACCCTTCT  4740

Query  4741  CATTCCAACAGTGAGTCTGTCAGCGCAGGTTTAGTTTACTCAATCTCCCCTTGCACTAAA  4800

Query  4801  GTATGTAAAGTATGTAAACAGGAGACAGGAAGGTGGTGCTTACATCCTTAAAGGCACCAT  4860

Query  4861  CTAATAGCGGGTTACTTTCACATACAGCCCTCCCCCAGCAGTTGAATGACAACAGAAGCT  4920

Query  4921  TCAGAAGTTTGGCAATAGTTTGCATAGAGGTACCAGCAATATGTAAATAGTGCAGAATCT  4980

Query  4981  CATAGGTTGCCAATAATACACTAATTCCTTTCTATCCTACAACAAGAGTTTATTTCCAAA  5040

Query  5041  TAAAATGAGGACAtgtttttgttttctttgaatgctttttgaatgttatttgttattttc  5100

Query  5101  agtattttggagaaattatttAATaaaaaaaCAATCATTTGCTTTTTGAATGCTCTCTAA  5160

Query  5161  AAGGGAATGTAATATTTTAAGATGGTGTGTAACCCGGCTGGATAAATTTTTGGTGCCTAA  5220

Query  5221  GAAAACTGCTTGAATATTCTTATCAATGACAGTGTTAAGTTTCAAAAAGAGCTTCTAAAA  5280

Query  5281  CGTAGATTATCATTCCTTTATAGAATGTTATGTGGTTAAAACCAGAAAGCACATCTCACA  5340
18665  2674                          AATGTTATGTGGTTAAAACCAGAAAGCACATCTCACA  2710

Query  5341  CATTAATCTGATTTTCATCCCAACAATCTTGGCGCTCAAAAAATAGAACTCAATGAGAAA  5400
18665  2711  CATTAATCTGATTTTCATCCCAACAATCTTGGCGCTCAAAAAATAGAACTCAATGAGAAA  2770

Query  5401  AAGAAGATTATGTGCACTTCGTTGTCAATAATAAGTCAACTGATGCTCATCGACAACTAT  5460
18665  2771  AAGAAGATTATGTGCACTTCGTTGTCAATAATAAGTCAACTGATGCTCATCGACAACTAT  2830

Query  5461  AGGAGGCTTTTCATTAAATGGGAAAAGAAGCTGTGCCCTTTTAGGATACGTGGGGGAAAA  5520
18665  2831  AGGAGGCTTTTCATTAAATGGGAAAAGAAGCTGTGCCCTTTTAGGATACGTGGGGGAAAA  2890

Query  5521  GAAAGTCATCTTAATTATGTTTAATTGTGGATTTAAGTGCTATATGGTGGTGCTGTTTGA  5580
```

FIG. 7D

```
18665  2891  GAAAGTCATCTTAATTATGTTTAATTGTGGATTTAAGTGCTATATGGTGGTGCTGTTTGA  2950

Query  5581  AAGCAGATTTATTTCCTATGTATGTGTTATCTGGCCATCCCAACCCAAACTGTTGAAGTT  5640
18665  2951  AAGCAGATTTATTTCCTATGTATGTGTTATCTGGCCATCCCAACCCAAACTGTTGAAGTT  3010

Query  5641  TGTAGTAACTTCAGTGAGAGTTGGTTACTCACAACAAATCCTGAAAAGTATTTTTAGTGT  5700
18665  3011  TGTAGTAACTTCAGTGAGAGTTGGTTACTCACAACAAATCCTGAAAAGTATTTTTAGTGT  3070

Query  5701  TTGTAGGTATTCTGTGGGATACTATACAAGCAGAACTGAGGCACTTAGGACATAACACTT  5760
18665  3071  TTGTAGGTATTCTGTGGGATACTATACAAGCAGAACTGAGGCACTTAGGACATAACACTT  3130

Query  5761  TTGGGGTATATATATCCAAATGCCTAAAACTATGGGAGGAAACCTTGGCCACCCCAAAAG  5820
18665  3131  TTGGGGTATATATATCCAAATGCCTAAAACTATGGGAGGAAACCTTGGCCACCCCAAAAG  3190

Query  5821  GAAAACTAACATGATTTGTGTCTATGAAGTGCTGGATAATTAGCATGGGATGAGCTCTGG  5880
18665  3191  GAAAACTAACATGATTTGTGTCTATGAAGTGCTGGATAATTAGCATGGGATGAGCTCTGG  3250

Query  5881  GCATGCCATGAAGGAAAGCCACGCTCCCTTCAGAATTCAGAGGCAGGGAGCAATTCCAGT  5940
18665  3251  GCATGCCATGAAGGAAAGCCACGCTCCCTTCAGAATTCAGAGGCAGGGAGCAATTCCAGT  3310

Query  5941  TTCACCTAAGTCTCATAATTTTAGTTCCCTTTTAAAAACCCTGAAAACTACATCACCATG  6000
18665  3311  TTCACCTAAGTCTCATAATTTTAGTTCCCTTTTAAAAACCCTGAAAACTACATCACCATG  3370

Query  6001  GAATGAAAAATATTGTTATACAATACATTGATCTGTCAAACTTCCAGAACCATGGTAGCC  6060
18665  3371  GAATGAAAAATATTGTTATACAATACATTGATCTGTCAAACTTCCAGAACCATGGTAGCC  3430

Query  6061  TTCAGTGAGATTTCCATCTTGGCTGGTCACTCCCTGACTGTAGCTGTAGGTGAAtgtgtt  6120
18665  3431  TTCAGTGAGATTTCCATCTTGGCTGGTCACTCCCTGACTGTAGCTGTAGGTGAATGTGTT  3490

Query  6121  tttgtgtgtgtgtgtCTGGTTTTAGTGTCAGAAGGGAAATAAAAGTGTAAGGAGGACACT  6180
18665  3491  TTTGTGTGTGTGTGTCTGGTTTTAGTGTCAGAAGGGAAATAAAAGTGTAAGGAGGACACT  3550

Query  6181  TTAAACCCTTTGGGTGGAGTTTCGTAATTTCCCAGACTATTTTCAAGCAACCTGGTCCAC  6240
18665  3551  TTAAACCCTTTGGGTGGAGTTTCGTAATTTCCCAGACTATTTTCAAGCAACCTGGTCCAC  3610

Query  6241  CCAGGATTAGTGACCAGGTTTTCAGGAAAGGATTTGCTTCTCTCTAGAAAATGTCTGAAA  6300
18665  3611  CCAGGATTAGTGACCAGGTTTTCAGGAAAGGATTTGCTTCTCTCTAGAAAATGTCTGAAA  3670

Query  6301  GGATTTTATTTTCTGATGAAAGGCTGTATGAAAATACCCTCCTCAAATAACTTGCTTAAC  6360
18665  3671  GGATTTTATTTTCTGATGAAAGGCTGTATGAAAATACCCTCCTCAAATAACTTGCTTAAC  3730

Query  6361  TACATATAGATTCAAGTGTGTCAATATTCTATTTTGTATATTAAATGCTATATAATGGGG  6420
18665  3731  TACATATAGATTCAAGTGTGTCAATATTCTATTTTGTATATTAAATGCTATATAATGGGG  3790

Query  6421  ACAAATCTATATTATACTGTGTATGGCATTATTAAGAAGCTTTTTCATTATTTTTTATCA  6480
18665  3791  ACAAATCTATATTATACTGTGTATGGCATTATTAAGAAGCTTTTTCATTATTTTTTATCA  3850

Query  6481  CAGTAATTTTAAAATGTGTAAAAATTAAAACCAGTGACTCCTGTTTAAAAATAAAAGTTG  6540
18665  3851  CAGTAATTTTAAAATGTGTAAAAATTAAAACCAGTGACTCCTGTTTAAAAATAAAAGTTG  3910

Query  6541  TAGTTTTTTATTCATGCTGAATAATAATCTGTAGTTaaaaaaaaaGTGTCTTTTTACCTA  6600
18665  3911  TAGTTTTTTATTCATGCTGAATAATAATCTGTAGTTAAAAAAAAAGTGTCTTTTTACCTA  3970

Query  6601  CGCAGTGAAATGTCAGACTGTAAAACCTTGTGTGGAAATGTTTAACTTTTATTTTTTCAT  6660
18665  3971  CGCAGTGAAATGTCAGACTGTAAAACCTTGTGTGGAAATGTTTAACTTTTATTTTTTCAT  4030

Query  6661  TTAAATTTGCTGTTCTGGTATTACCAAACCACACATTTGTACCGAATTGGCAGTAAATGT  6720
18665  4031  TTAAATTTGCTGTTCTGGTATTACCAAACCACACATTTGTACCGAATTGGCAGTAAATGT  4090

Query  6721  TAGCCATTTACAGCAATGCCAAATATGGAGAAACATCATAATaaaaaaaTCTGCTTTTTC  6780
18665  4091  TAGCCATTTACAGCAATGCCAAATATGGAGAAACATCATAATAAAAAAATCTGCTTTTTC  4150

Query  6781  ATTA  6784
```

METHODS AND COMPOSITIONS RELATED TO GLUCOCORTICOID RECEPTOR ANTAGONISTS AND BREAST CANCER

CROSS-REFERENCES TO RELATED APPLICATIONS

This application is a Continuation of U.S. application Ser. No. 16/596,342, filed Oct. 8, 2019, which is a Continuation of U.S. application Ser. No. 15/448,827, filed Mar. 3, 2017 (now U.S. Pat. No. 10,441,596, issued Oct. 15, 2019), which is a Continuation of U.S. application Ser. No. 14/296,127, filed Jun. 4, 2014 (now U.S. Pat. No. 9,623,032, issued Apr. 18, 2017), which is a Continuation of U.S. application Ser. No. 14/172,051, filed Feb. 4, 2014 (now U.S. Pat. No. 9,149,485, issued Oct. 6, 2015), which is a Continuation of U.S. application Ser. No. 13/071,363, filed Mar. 24, 2011 (now U.S. Pat. No. 8,710,035, issued Apr. 29, 2014), which claims priority to U.S. Provisional Application No. 61/317,182, filed on Mar. 24, 2010, the disclosures of which are hereby incorporated by reference in their entireties.

This invention was made with government support under CA089208 awarded by the National Institutes of Health. The government has certain rights in the invention.

REFERENCE TO A "SEQUENCE LISTING," A TABLE, OR A COMPUTER PROGRAM LISTING APPENDIX SUBMITTED ON AN ASCII TEXT FILE

The Sequence Listing written in file "SeqListing096487-1293223.TXT", created on Jan. 14, 2022, 225,045 bytes, machine format IBM-PC, MS-Windows operating system, is hereby incorporated by reference in its entirety for all purposes.

BACKGROUND OF THE INVENTION

I. Field of the Invention

Embodiments of this invention are directed generally to biology and medicine. In certain aspects methods involve determining the prognosis for a breast cancer patient. In other embodiments, there are methods and compositions for treating a breast cancer patient with a glucocorticoid antagonist.

II. Background

There are over 1 million cases of breast cancer per year on a global basis, of which around 0.5 million are in the US, 40,000 are in the UK and nearly 2,000 in Ireland. It is the leading cause of cancer deaths among women (Keen and Davidson, 2003). Although the overall incidence of the disease is increasing within the western world, wider screening and improved treatments have led to a gradual decline in the fatality rate of about 1% per year since 1991. Inheritance of susceptibility genes, such as BRCA1 and BRCA2, account for only 5% of breast cancer cases and the factors responsible for the other 95% remain obscure (Grover and Martin, 2002). In the absence of a strategy to reduce causative agents of breast cancer, early detection remains the best approach to reducing the mortality rate of this disease. It is widely held that breast cancer initiates as the pre-malignant stage of atypical ductal hyperplasia (ADH), progresses into the pre-invasive stage of ductal carcinoma in situ (DCIS), and culminates in the potentially lethal stage of invasive ductal carcinoma (IDC). This linear model of breast cancer progression has been the rationale for the use of detection methods such as mammography in the hope of diagnosing and treating breast cancer at earlier clinical stages (Ma et al., 2003).

As more molecular information is being collated, diseases such as breast cancer are being sub-divided according to genetic signatures linked to patient outcome, providing valuable information for the clinician. Emerging novel technologies in molecular medicine have already demonstrated their power in discriminating between disease sub-types that are not recognizable by traditional pathological criteria (Sorlie et al., 2001) and in identifying specific genetic events involved in cancer progression (Srinivas et al., 2002).

Endocrine therapy is a popular mode of treatment for all stages of breast cancer. A majority of breast cancers belong to the type in which growth is stimulated by the female sex hormones, estrogens and progesterone. Therefore some of the therapies are based on depriving the tumor of the hormone-induced growth stimulus. Some of the current modes of endocrine treatments include blockade of the estrogen receptor with an antiestrogen, e.g. tamoxifen; hormonal ablation by surgery (oophorectomy, adrenalectomy or hypophysectomy), radiotherapy or medically by administration of a luteinizing hormone-releasing hormone analogue (LH-RHa), e.g., goserelin; suppression of estrogen synthesis with aromatase inhibitors, e.g., anastrozole; pharmacological doses of estrogens and progestagens, e.g., megestrol acetate.

Despite recent advances, the challenge of cancer treatment, including breast cancer therapy remains. Progress is limited with respect to the development of specific treatment regimens to clinically distinct tumor types, and to personalize tumor treatment in order to maximize outcome and efficiency. Moreover, a number of patients exhibit chemotherapy resistance.

Mere classification of breast cancers into a few subgroups characterized by low to absent gene expression of the estrogen receptor (ER) alone may not reflect the cellular and molecular heterogeneity of breast cancer, and may not allow the design of treatment strategies maximizing patient response. Once a patient is diagnosed with cancer, such as breast or ovarian cancer, or an individual wants predisposition analysis, there is a strong need for methods that allow the physician to predict the expected course of disease, including the likelihood of cancer recurrence, long-term survival of the patient, and the like, and accordingly select an appropriate treatment option that is effective.

SUMMARY OF THE INVENTION

Embodiments concern methods, compositions, and apparatuses related to assessing, prognosing, and/or treating breast cancer patients. It concerns using information related to glucocorticoid receptor (GR) activity and/or expression in conjunction with information related to estrogen receptor (ER) activity or expression to identify patients with the least favorable prognosis based on current standards of care for breast cancer. Patients with relatively low levels of estrogen receptor expression and relatively high levels of glucocorticoid expression fall into a group of breast cancer patients with the least favorable prognosis (i.e., mortality rate).

Accordingly, methods concern evaluating a patient with breast cancer. Embodiments include evaluating a biological sample from a patient; evaluating breast cancer cells from a patient; evaluating a biological sample from a breast cancer patient; assessing a breast cancer patient; testing a breast cancer sample or biopsy; testing a breast tumor; prognosing a breast cancer patient; treating a breast cancer patient, particularly a patient with a particular profile related to ER and GR; determining a treatment for a breast cancer patient; altering a treatment plan for a breast cancer patient; reporting prognosis of a breast cancer patient; determining a prognosis score for a breast cancer patient; generating a prognosis score for a breast cancer patient; assessing the risk of mortality of a breast cancer patient generally or within a certain time frame, such as 150 months from end of cancer treatment; generating an ER and GR expression profile for a breast cancer patient; comparing a patient's ER and GR expression profile to a standardized profile; and/or, determining a breast cancer patient has a poor prognosis based on the patient's ER and GR status.

Embodiments also cover apparatuses, kits, and computer readable medium and systems for assessing the level or activity of ER and/or GR in a patient's breast cancer sample and determining a prognosis; and/or treating the patient accordingly. It is specifically contemplated that a breast cancer patient is a human. Accordingly, in human patients, ER refers to an estrogen receptor in a human and GR refers to a glucocorticoid receptor in a human.

Some embodiments include generating an expression profile for glucocorticoid receptor, which means obtaining the level of expression of GR directly or indirectly by measuring or assaying activity or expression. Methods include directly measuring or assaying the level of expression or activity refers to measuring or assaying a sample to determine the level of GR expression (protein or transcript) in the cell. Indirectly obtaining the level of expression includes measuring or assaying expression or activity of a gene or protein that correlates with GR expression or activity. In some embodiments, the level of GR expression can be indirectly obtained by measuring or assaying expression of a GR-responsive gene, which refers to a gene whose expression is affected in a dose-dependent manner by GR expression or activity. Expression refers to either protein expression or RNA (transcript) expression. Methods may involve either type of expression and a variety of assays are well known to those of skill in the art. For example, quantitative PCR may be performed to obtain RNA expression levels. The Affymetrix chip used in the Examples also provides information regarding RNA expression levels. Alternatively, reagents to detect protein expression levels may be employed in embodiments. Methods may involve probes, primers, and/or antibodies that are specific to GR or ER in order to assess expression levels.

In some embodiments, the activity level of GR is measured by assaying the level of GR expression. In additional embodiments, GR expression is GR transcript expression. In other embodiments, GR expression is GR protein expression. As discussed above, in some embodiments, the activity level of GR is measured by assaying the expression level of one or more GR-responsive genes. A GR-responsive gene may be one or more of the following: MCL1, SAP30, DUSP1, SGK1, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, IDH2, SERPINFL ERBB2, PECAM1, LBH, ST3GAL5, IL1R1, BIN1, WIPF1, TFPI, FN1, FAM134A, NRIP1, RAC2, SPP1, PHF15, BTN3A2, SESN1, MAP3K5, DPYSL2, SEMA4D, STOM, or MAOA.

In some embodiments, there is a step of assaying or measuring the activity level of glucocorticoid receptor (GR) in a biological sample from the patient containing breast cancer cells. As discussed above, the activity level of GR can be obtained directly or indirectly. It is specifically contemplated that levels of glucocorticoid activity or expression refers to activity or expression of GR $\alpha$, GR $\beta$, or both. Unless specifically stated otherwise, the terms "glucocorticoid receptor" or "GR" refer to both forms. Embodiments discussed with respect to glucocorticoid receptor or GR may also be implemented solely with GR$\alpha$ or solely with GR$\beta$.

Methods may also include obtaining a level of estrogen receptor (ER) expression in breast cancer cells from the patient. The level can be obtained by obtaining the results of an assay that measured the level of ER expression. In some embodiments, the level is obtained by measuring or assaying the level of ER expression.

In some embodiments, the level of estrogen receptor expression in breast cancer cells from patient is obtained by measuring the level of estrogen receptor expression from the biological sample from the patient. In other embodiments, the level is obtained by receiving qualitative and/or quantitative data regarding the level.

In some embodiments, methods include identifying the patient as having or not having a risk factor for cancer recurrence based on the levels of ER and GR expression. Methods may involve categorizing the patient as ER+ or ER− based the level of estrogen receptor expression and a predetermined threshold value for ER expression. The term "ER+" refers to a classification of ER expression that indicates the patient expresses estrogen receptor in breast cancer cells at or above a certain level. The term "ER−" refers to a classification of ER expression that indicates the patient expresses estrogen receptor at a relatively low level in breast cancer cells, meaning at or below a certain level. In embodiments of the invention, that certain level or a predetermined threshold value is at, below, or above 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentile, or any range derivable therein.

Methods may involve measuring the activity level of glucocorticoid receptor in a biological sample from the patient containing breast cancer cells and measuring the expression level of estrogen receptor in the biological sample.

In certain embodiments, the predetermined threshold value for ER expression identifies a patient as ER+ if the patient's ER expression level is in the $25^{th}$ percentile or greater compared to a normalized sample. This means the patient may be designated as having a level of ER expression that is at or above 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentile, or any range derivable therein. It is contemplated that in some cases, a patient may be designated as ER+ if the patient's ER expression level is at or above 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. The patient may also be referred to as having a normal or high ER expression level. The higher the percentile, the higher the relative expression level.

In embodiments, methods may also involve categorizing the patient as GR+ or GR− based on a predetermined threshold value for GR activity. In some cases, a predetermined threshold value for GR activity is dependent on whether the patient is categorized as ER+ or ER−. Embodiments may involve a predetermined threshold value for GR activity that identifies a patient as GR+ if the patient is ER− and GR activity level is in the $65^{th}$ percentile or greater compared to a normalized sample. It is contemplated that in some cases, a patient may be designated as GR+ if the patient's GR expression level is at or above 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. The threshold value may or may not be dependent on ER expression levels or status. In some embodiments, the threshold value depends on whether the patient is ER− or not. The higher the percentile, the higher the relative expression level.

Methods may involve the use of a normalized sample or control that is based on one or more breast cancer samples that are not from the patient being tested.

In some embodiments, methods involve calculating a prognosis score for the patient based on the levels of ER and/or GR expression. Methods may alternatively or additionally involve reporting a prognosis score or report the levels of ER and/or GR expression. The score or report may contain or reflect raw data regarding expression levels or it may reflect a categorization of the expression levels obtained. A score could indicate the risk factor for mortality, recurrence, and/or both. The score could be a number within a numeric scale in which one end of the scale is most favorable and the other end is the least favorable with respect to a prognosis for breast cancer.

In certain embodiments, methods may involve identifying the patient as having a poor prognosis if the patient is determined to have a glucocorticoid receptor activity level at or above a certain threshold level and a level of estrogen receptor that is at or below a second threshold level. In each case, the threshold levels are specific for each of GR and ER. In certain embodiments, it is contemplated that a GR level in the 65th percentile or above based on breast cancer patients whose are in the $35^{th}$ percentile or below is indicative of a poor prognosis. In some embodiments, patients with a poor prognosis include a population of breast cancer patients that numbers approximately 10% or less.

Methods also include identifying the patient as having a poor prognosis if the patient is determined to have i) an activity level of glucocorticoid receptor that is higher than the activity level of glucocorticoid receptor in normalized control sample and ii) a expression level of estrogen receptor expression that is lower than the expression level of estrogen receptor in a normalized control sample. Consequently, methods of the invention include prognosing a breast cancer patient. In some cases, a patient is identified as having a relatively good prognosis.

Other embodiments include methods of treating a patient for breast cancer comprising: treating the patient for breast cancer after a biological sample from the patient containing breast cancer cells is analyzed for i) the activity level of glucocorticoid receptor and ii) the expression level of estrogen receptor. A patient may be treated with a different treatment protocol than the patient would have been treated with if the patient's biological sample had not been analyzed. In some embodiments, the patient is categorized as ER− and GR+ based on the activity level of the glucocorticoid receptor and the expression level of estrogen receptor. In some cases, the patient is treated with a more aggressive therapy than the patient would have been treated with if the patient had not been categorized as ER− and GR+. The term "more aggressive" refers to a treatment regimen that may include more drugs or drugs with more severe side effects and/or it may include an increased dosage or increased frequency of drugs. It may also include radiation or a combination of therapies. In some cases, the therapy includes one or more chemotherapeutics and/or biologics. In some embodiments, the patient is treated with a therapy comprising an anti-angiogenic agent. In additional embodiments, the therapy further comprises a chemotherapeutic agent in addition to the anti-angiogenic agent. Embodiments also include administering a glucocorticoid receptor antagonist and/or tyrosine kinase inhibitor.

Embodiments may also include where the patient is treated with more than one type of cancer therapy. This may be after the patient is determined to have a particular prognosis or after the status of the patient's GR and ER expression profile is known. In some embodiments, certain treatments are provided to an ER−/GR+ breast cancer patient who might have otherwise been treated with a less aggressive treatment for breast cancer. In some embodiments, a patient is treated with at least two of the following: radiation, chemotherapy, or a biologic. In particular embodiments, the patient may be treated with a kinase inhibitor and/or anti-angiogenic agent.

Methods may also involve obtaining a biological sample comprising breast cancer cells from the patient and categorizing the patient as i) GR+ or GR− based on the level of glucocorticoid activity assayed in the sample and compared to a predetermined threshold value for GR activity; and ii) ER+ or ER− based on the level of estrogen receptor expression assayed in the sample and compared to a predetermined threshold value for ER expression.

Any method may also include treating the patient for breast cancer, which may include directly administering or providing a cancer therapy. In some embodiments, a practitioner or doctor may prescribe a cancer therapy that the patient administers to herself.

To achieve these methods, a doctor, medical practitioner, or their staff may retrieve a biological sample from a patient for evaluation. The sample may be a biopsy, such as a breast tissue or tumor biopsy. The sample may be analyzed by the practitioner or their staff, or it may be sent to an outside or independent laboratory. The medical practitioner may be cognizant of whether the test is providing information regarding the patient's level of GR and/or ER expression or activity, or the medical practitioner may be aware only that the test indicates directly or indirectly that the test reflects that the patient has a particular prognosis or can be given a particular prognosis score. Furthermore, the practitioner may know the patient's ER or GR status, such as ER+ or ER−, or GR+ or GR−. Alternatively, she may be aware only that the test or assay indicates the patient has a poor prognosis, or the worst prognosis.

Embodiments also concern kits to determine glucocorticoid receptor status in breast cancer cells comprising: (a) one or more reagents for determining expression levels of NR3C1 in a biological sample; and (b) an algorithm and software encoding the algorithm for calculating a risk factor index from the expression of NR3C1 in a sample and the estrogen receptor status of the breast cancer cells to determine a prognosis or a prognosis score. Kits may also include one or more reagents for determining expression levels of ESR1 in the biological sample to provide estrogen receptor status.

Other embodiments include a computer readable medium having software modules for performing a method comprising the acts of: (a) comparing glucocorticoid receptor data obtained from a patient's breast cancer sample with a reference; and (b) providing an assessment of glucocorticoid receptor status to a physician for use in determining an appropriate therapeutic regimen for a patient. In further embodiments, the computer readable medium further comprises a software module for assessing estrogen receptor status of the patient's breast cancer sample.

Computer systems are also included. In some embodiments, they have a processor, memory, external data storage, input/output mechanisms, a display, for assessing glucocorticoid receptor activity, comprising: (a) a database; (b) logic mechanisms in the computer generating for the database a GR-responsive gene expression reference; and (c) a comparing mechanism in the computer for comparing the GR-responsive gene expression reference to expression data from a patient sample using a comparison model to determine a GR gene expression profile of the sample.

Other embodiments include an internet accessible portal for providing biological information constructed and arranged to execute a computer-implemented method for providing: (a) a comparison of gene expression data of one or more GR-responsive genes in a patient sample with a calculated reporter index; and (b) providing an assessment of GR activity or expression to a physician for use in determining an appropriate therapeutic regime for a patient.

In addition to compiling, collecting and or processing data related to GR status, methods, media and systems may also include the same embodiments with respect to data related to ER status. Such aspects may be instead of or in addition to the aspects related to GR status or data.

Embodiments also include methods of killing breast cancer cells comprising administering to a breast cancer patient an effective amount of a combination of anti-cancer compounds, wherein the anticancer compounds comprise a glucocorticoid receptor antagonist and a chemotherapeutic.

In other embodiments, there are methods for treating breast cancer in a patient comprising administering to the patient an effective amount of glucocorticoid receptor antagonist and a chemotherapeutic.

In further embodiments, methods are provided for treating chemotherapy-insensitive breast cancer cells comprising administering to a breast cancer patient an effective amount of a glucocorticoid receptor antagonist followed by chemotherapy.

Other methods include methods for treating breast cancer in a patient comprising: a) administering radiation or at least a first chemotherapeutic to the patient; b) subsequently administering an effective amount of a glucocorticoid receptor antagonist to the patient; and, c) administering radiation again or at least a second chemotherapeutic to the patient after the glucocorticoid receptor antagonist is administered to the patient.

In some embodiments, there are methods for treating breast cancer in a patient comprising: a) administering an effective amount of a glucocorticoid receptor antagonist to the patient, wherein the patient expresses detectable levels of GR prior to administration of the GR antagonist; b) then administering an effective amount of radiation or at least one chemotherapeutic.

It is contemplated that in methods described herein, breast cancer cells may undergo apoptosis following treatment set forth herein. Moreover, in some embodiments, the combination of a glucocorticoid receptor antagonist and an anticancer agent or compound induces more apoptosis than treatment with just the anticancer treatment alone. In other methods, it is specifically contemplated to exclude treatment with a synthetic glucocorticoid, such as dexamethasone.

Glucocorticoid receptor antagonists are known to those of skill in the art. It refers to a compound or substance that that does not provoke a biological response itself upon binding to the glucocorticoid receptor, but blocks or dampens agonist-mediated responses. Examples include, but are not limited to, beclometasone, betamethasone, budesonide, ciclesonide, flunisolide, fluticasone, mifepristone, mometasone, and triamcinolone. In additional embodiments, the glucocorticoid receptor antagonist has undetectable level or a lower level of activity as a progesterone receptor antagonist. In certain embodiments, the glucocorticoid receptor antagonist has greater than 10-fold, 50-fold, 100-fold, 200-fold, 300-fold, 400-fold, 500-fold, 1000-fold lower binding activity (or any range derivable therein) for another hormone receptor compared to its binding activity for glucocorticoid receptor. In specific embodiments the hormone receptor is estrogen receptor or progesterone receptor.

In some embodiments, a patient had been previously treated with an anti-cancer therapy, such as radiation, chemotherapy, or immunotherapy (or a combination or multiple therapies thereof). In certain embodiments, a first anti-cancer therapy prior to therapy with glucocorticoid receptor antagonist was last administered more than two weeks prior to the glucocorticoid receptor antagonist or its combination with a second anti-cancer therapy. In certain embodiments, this first anti-cancer therapy that does not include a glucocorticoid receptor antagonist was last administered to the breast cancer patient at least 7, 8, 9, 10, 11, 12, 13, 14 days, and/or 1, 2, 3, 4, or 5 weeks, and/or 1, 2, 3, 4, 5, 6, 7, 8, 9, 10, 11, or 12 months prior to treatment with a glucocorticoid receptor antagonist. Treatment methods may be applied to breast cancer or breast cancer cells that are chemo-resistant or breast cancer cells that are not chemo-sensitive. Moreover, treatment may be applied to breast cancer or to breast cancer cells that were previously administered a first apoptosis inducing agent, but were resistant to apoptosis.

In some embodiments, the breast cancer cells are determined to be resistant to apoptosis. In additional embodiments, the breast cancer or the breast cancer cells are determined not to be chemo-sensitive or are determined to be chemo-resistant. This determination may be based on the results of a genetic test or based on information obtained from an assessment of a tumor or the breast cancer after treatment with a first anti-cancer therapy. In specific embodiments, the first anti-cancer therapy is a chemotherapeutic, Herceptin®, radiation, a combination of chemotherapeutics, or a combination of one or more chemotherapeutic agents and Herceptin®.

In additional embodiments, the breast cancer cells express a detectable level of glucocorticoid receptor or its transcript. In some embodiments, the patient is determined to have breast cancer cells that express a detectable level of glucocorticoid receptor or its transcript. This may be determined directly or indirectly.

It is contemplated that breast cancer cells may be treated with a glucocorticoid receptor antagonist regardless of estrogen receptor status. Therefore, breast cancer cells may be estrogen receptor-negative (ER−) or estrogen receptor-positive (ER+), accordingly to a standardized and industry accepted test for ER status. In certain embodiments, the breast cancer cells do not express any detectable levels of ER; in other embodiments, ER expression is detectable in the breast cancer cells.

It is contemplated that breast cancer cells may be treated with a glucocorticoid receptor antagonist depending on or regardless of progesterone receptor status. Therefore, breast cancer cells may be progesterone receptor-negative (PR−) or progesterone receptor-positive (PR+), accordingly to a standardized and industry accepted test for ER status. In certain embodiments, the breast cancer cells do not express any detectable levels of PR; in other embodiments, PR expression is detectable in the breast cancer cells.

Methods involve treating breast cancer, particularly a chemo-resistant breast cancer, with a combination of therapies that includes a glucocorticoid receptor antagonist and an anticancer therapy that induces apoptosis (together they may be referred to as a combination of anti-cancer agents or compounds), such as a chemotherapeutic. In some embodiments, the chemotherapeutic is capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), thiotepa, vincristine, or vinorelbin, or a combination of these agents. In other embodiments, therapy with a glucocorticoid receptor antagonist is combined Herceptin®, radiation, chemotherapeutic(s) and radiation, a combination of chemotherapeutics, or a combination of one or more chemotherapeutic agents and Herceptin®.

It is contemplated that in some embodiments of the combination therapy the glucocorticoid receptor antagonist is administered within 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof within administration of at least one or the combination of the anti-cancer agents or compounds. In specific embodiments, the glucocorticoid receptor antagonist is administered within 2 hours, 12 hours or 24 hours of administration of a anticancer agent or compound (or a combination of such agents or compounds).

It is specifically contemplated that treatment may continue or be repeated. In some embodiments, once treated with the combination of a glucocorticoid receptor antagonist and at least one anticancer agent or compound, all or part of the treatment may be repeated alone or in combination with a different anticancer agent or compound.

In certain embodiments, the glucocorticoid receptor antagonist is administered prior to as the other agent or therapy included in the combination therapy. In certain embodiments, the glucocorticoid receptor antagonist is administered 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof prior to administration of at least one or the combination of the anti-cancer agents or compounds. It is specifically contemplated that in some embodiments, the glucocorticoid receptor antagonist is given prior to administration of the anticancer agent or compound but that the glucocorticoid receptor antagonist is also given concurrently with or after administration of the initial or a subsequent dose of the anticancer agent or compound. As discussed throughout, the anticancer agent or compound may be in a combination of such agents or compounds. In certain embodiments, the glucocorticoid receptor antagonist is administered up to three days prior to administering the anticancer agent or compound.

Additionally or alternatively, the glucocorticoid receptor antagonist is administered after administration of the other agent or therapy included in the combination therapy. In certain embodiments, the glucocorticoid receptor antagonist is administered 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof after administration of at least one or the combination of the anti-cancer agents or compounds. It is specifically contemplated that in some embodiments, the glucocorticoid receptor antagonist is given after to administration of the anticancer agent or compound; such administration may be repeated. As discussed throughout, the anticancer agent or compound may be in a combination of such agents or compounds. In certain embodiments, the glucocorticoid receptor antagonist is administered up to three days after administering the anticancer agent or compound.

In certain embodiments, the breast cancer is an unresectable breast cancer. In further embodiments, the breast cancer is inflammatory breast cancer.

It is specifically contemplated that in some methods, dexamethasone has not been administered to the patient within 24 hours of administration of the glucocorticoid receptor antagonist.

Compositions are contemplated to include a glucocorticoid receptor antagonist and any other anticancer compound discussed herein, such a Herceptin or one or more chemotherapeutic compounds. In some embodiments, the composition is in a pharmaceutically acceptable formulation.

Use of the one or more compositions may be employed based on methods described herein. Other embodiments are discussed throughout this application. Any embodiment discussed with respect to one aspect of the invention applies to other aspects of the invention as well and vice versa. The embodiments in the Example section are understood to be embodiments o that are applicable to all aspects of the technology described herein.

"Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, and/or duration of response in a patient or a group of patients susceptible to or diagnosed with a cancer.

In certain aspects, prognosis is an estimation of the likelihood of metastasis free survival of said patient over a predetermined period of time, e.g., over a period of 5 years.

In further aspects, prognosis is an estimation of the likelihood of death of disease of said patient over a predetermined period of time, e.g., over a period of 5 years.

The term "recurrence" refers to the detection of breast cancer in form of metastatic spread of tumor cells, local recurrence, contralateral recurrence or recurrence of breast cancer at any site of the body of the patient after breast cancer had been substantially undetectable or responsive to treatments.

As used herein, "prognostic for cancer" means providing a forecast or prediction of the probable course or outcome of the cancer. In some embodiments, "prognostic for cancer" comprises providing the forecast or prediction of (prognostic for) any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, and/or duration of response in a patient or a group of patients susceptible to or diagnosed with a cancer.

By "gene" is meant any polynucleotide sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The polynucleotide sequence may contain a genetic abnormality within exons, introns, initiation or termination regions, promoter sequences, other regulatory sequences or unique adjacent regions to the gene.

As used herein, "treatment" or "therapy" is an approach for obtaining beneficial or desired clinical results. This includes: reduce the number of cancer cells; reduce the tumor size; inhibit (i.e., slow to some extent and/or stop) cancer cell infiltration into peripheral organs; inhibit (i.e., slow to some extent and/or stop) tumor metastasis; inhibit, to some extent, tumor growth; and/or relieve to some extent one or more of the symptoms associated with the disorder, shrinking the size of the tumor, decreasing symptoms resulting from the disease, increasing the quality of life of those suffering from the disease, decreasing the dose of other medications required to treat the disease, delaying the progression of the disease, and/or prolonging survival of patients.

The term "therapeutically effective amount" refers to an amount of the drug that may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The terms "overexpress", "overexpression", "overexpressed", "up-regulate", or "up-regulated" interchangeably refer to a biomarker that is transcribed or translated at a detectably greater level, usually in a cancer cell, in comparison to a non-cancer cell or cancer cell that is not associated with the worst or poorest prognosis. The term includes overexpression due to transcription, post transcriptional processing, translation, post-translational processing, cellular localization, and/or RNA and protein stability, as compared to a non-cancer cell or cancer cell that is not associated with the worst or poorest prognosis. Overexpression can be detected using conventional techniques for detecting mRNA (i.e., RT-PCR, PCR, hybridization) or proteins (i.e., ELISA, immunohistochemical techniques, mass spectroscopy). Overexpression can be 10%, 20%, 30%, 40%, 50%, 60%, 70%, 80%, 90% or more in comparison to a normal cell or cancer cell that is not associated with the worst or poorest prognosis. In certain instances, overexpression is 1-fold, 2-fold, 3-fold, 4-fold 5, 6, 7, 8, 9, 10, or 15-fold or more higher levels of transcription or translation in comparison to a non-cancer cell or cancer cell that is not associated with the worst or poorest prognosis.

"Biological sample" includes sections of tissues such as biopsy and autopsy samples, and frozen sections taken for histologic purposes. Such samples include breast cancer tissues, cultured cells, e.g., primary cultures, explants, and transformed cells. A biological sample is typically obtained from a mammal, such as a primate, e.g., human.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., breast), the size and type of the tumor, among other factors. Representative biopsy techniques include, but are not limited to, excisional biopsy, incisional biopsy, needle biopsy, and surgical biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy", or a "fine-needle aspiration biopsy" which generally obtains a suspension of cells from within a target tissue. Biopsy techniques are discussed, for example, in Harrison's Principles of Internal Medicine, 2005. Obtaining a biopsy includes both direct and indirect methods, including obtaining the biopsy from the patient or obtaining the biopsy sample after it is removed from the patient.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7A-7F. Schematic of glucocorticoid receptor (GR) isoforms.

DETAILED DESCRIPTION OF THE INVENTION

Figure 1:
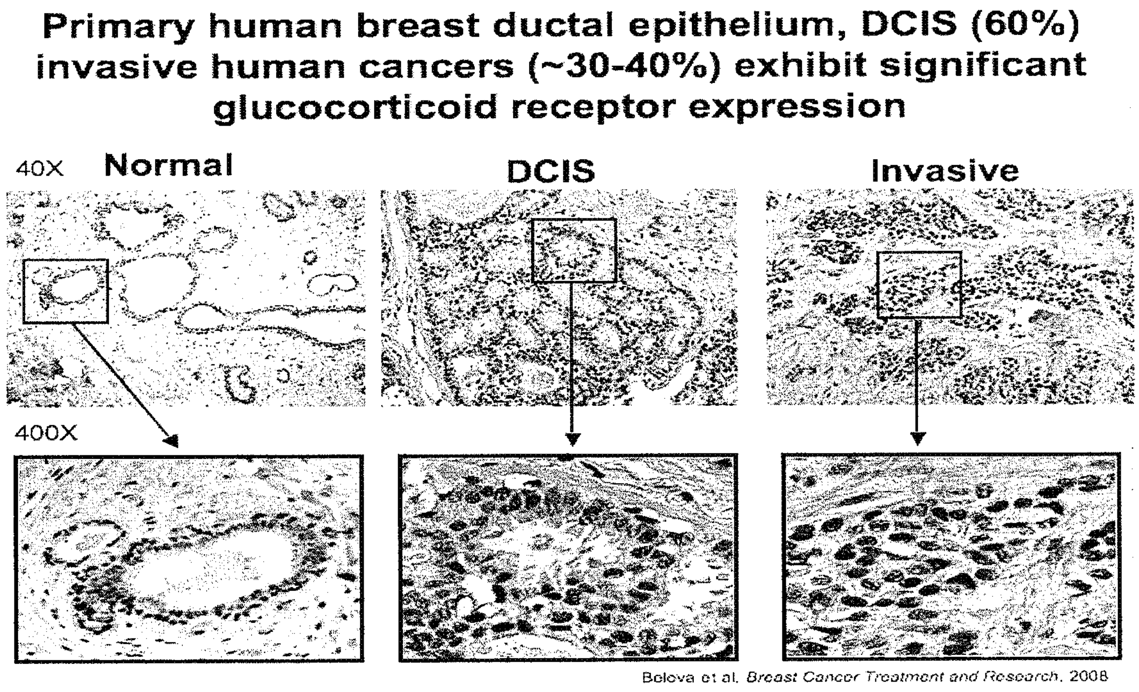
FIG. 1. Primary human breast ductal epithelium, DCIS (60%) in vasive human cancers ('30-40%) exhibit significant glucocorticoid receptor expression.
Figure 2:
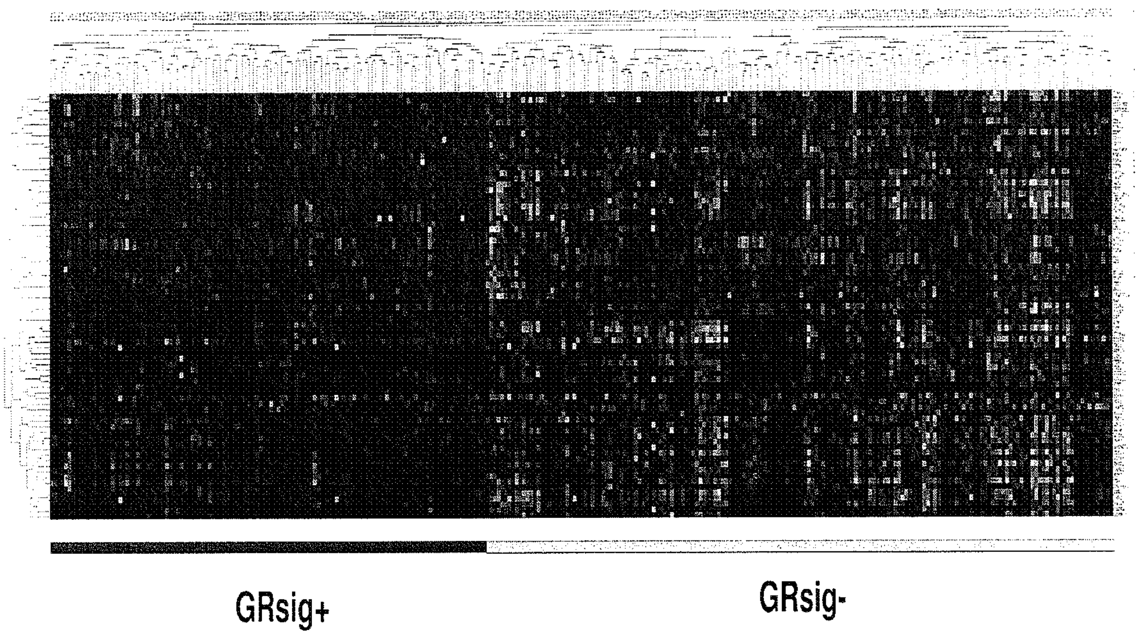
FIG. 2. Unsupervised cluster analysis identifies GR target gene signature (Sig+) vs Sig− tumors (n=68 genes) A GR-regulated gene expression set from MCF10A-Myc (ER−/GR+) cells treated +/−Dex from 30 m-24 h was used to perform a two dimensional unsupervised clustering analysis on the NKI-295 early breast cancer gene expression data set (n=2034 starting genes). GR-regulated genes (n=68) that separate these tumors into two groups (GRsig+=Red and GRsig−=Green) are shown in rows while each column represents a patient. Several EMT genes (e.g. Snail) and known anti-apoptotic genes are included.
Figure 3:
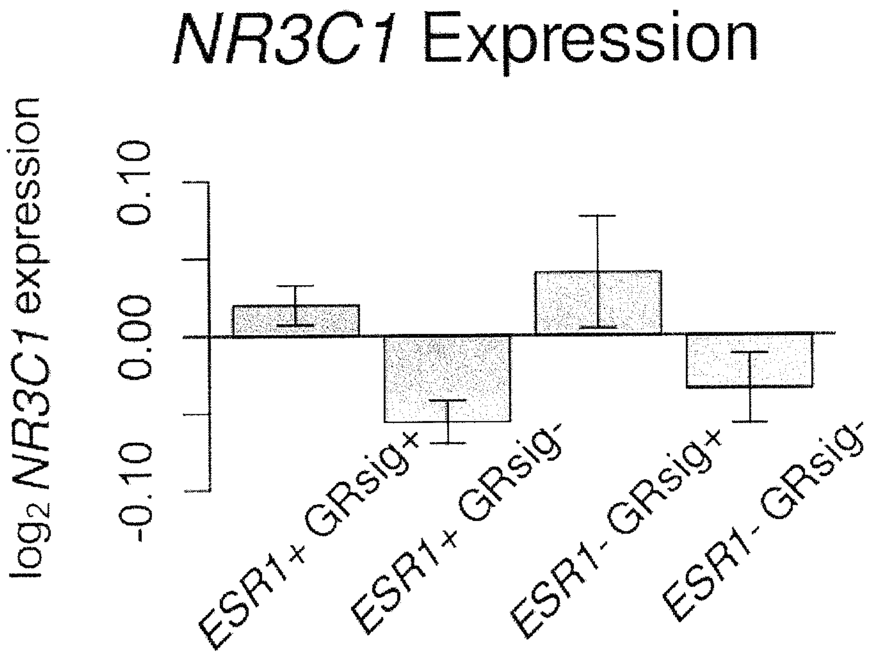
FIG. 3. NR3C1 expression correlates with GR signature gene expression. The GRsig+ vs. GRsig− tumor designations correlate with higher NR3C1 vs. lower expression, respectively. For ESR1+ tumors (orange) the P<0.00001 and for ESR1− tumors (green) p=0.7 (t test). Error bars are +/−SD.
Figure 4:
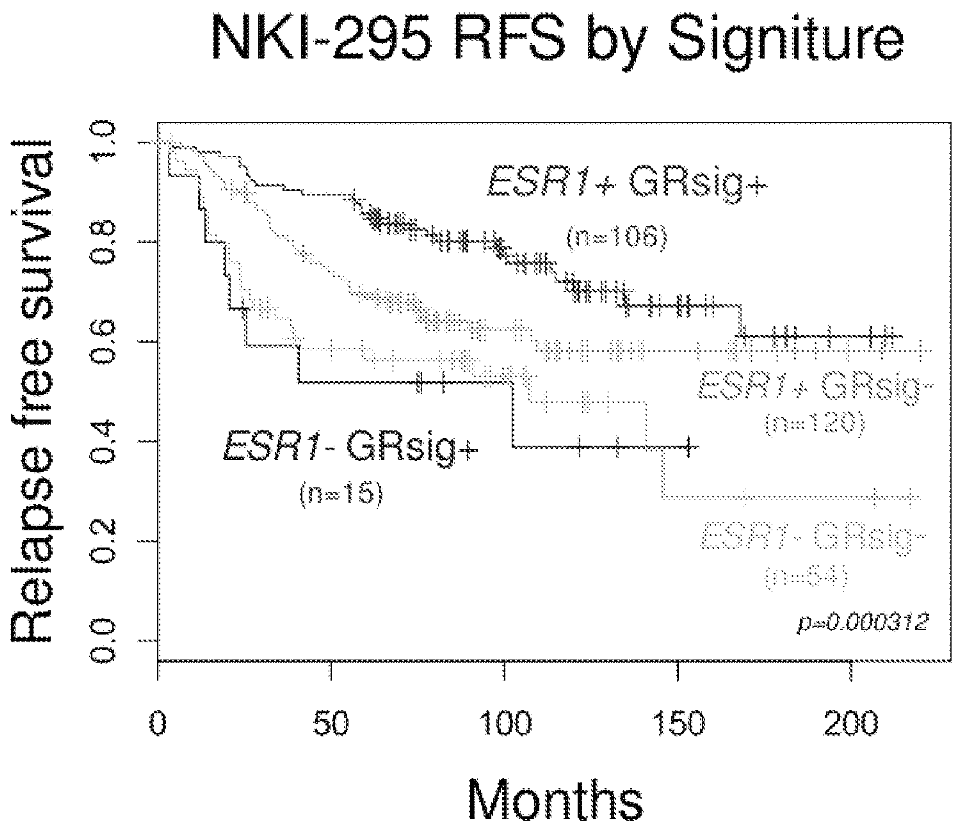
FIG. 4. RFS of GR gene expression signature. The GR signature predicts a differential prognosis for ESR1+ patients and ESR1− pts with respect to GR-signature expression. ESR1−/GR+ signature patients have the worst prognosis.
Figure 5:
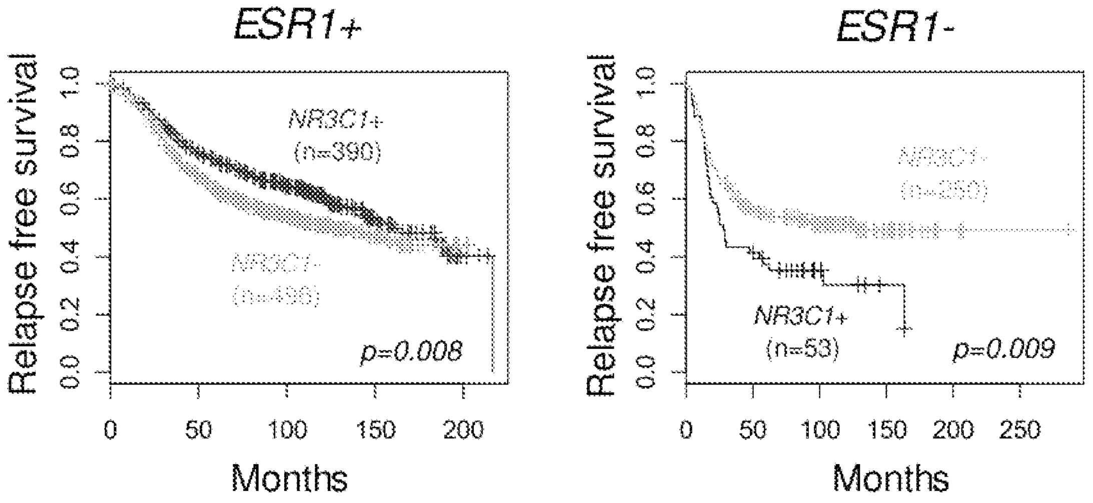
FIG. 5. Meta-analysis of NR3C1 expression and RFS.
Figure 6:
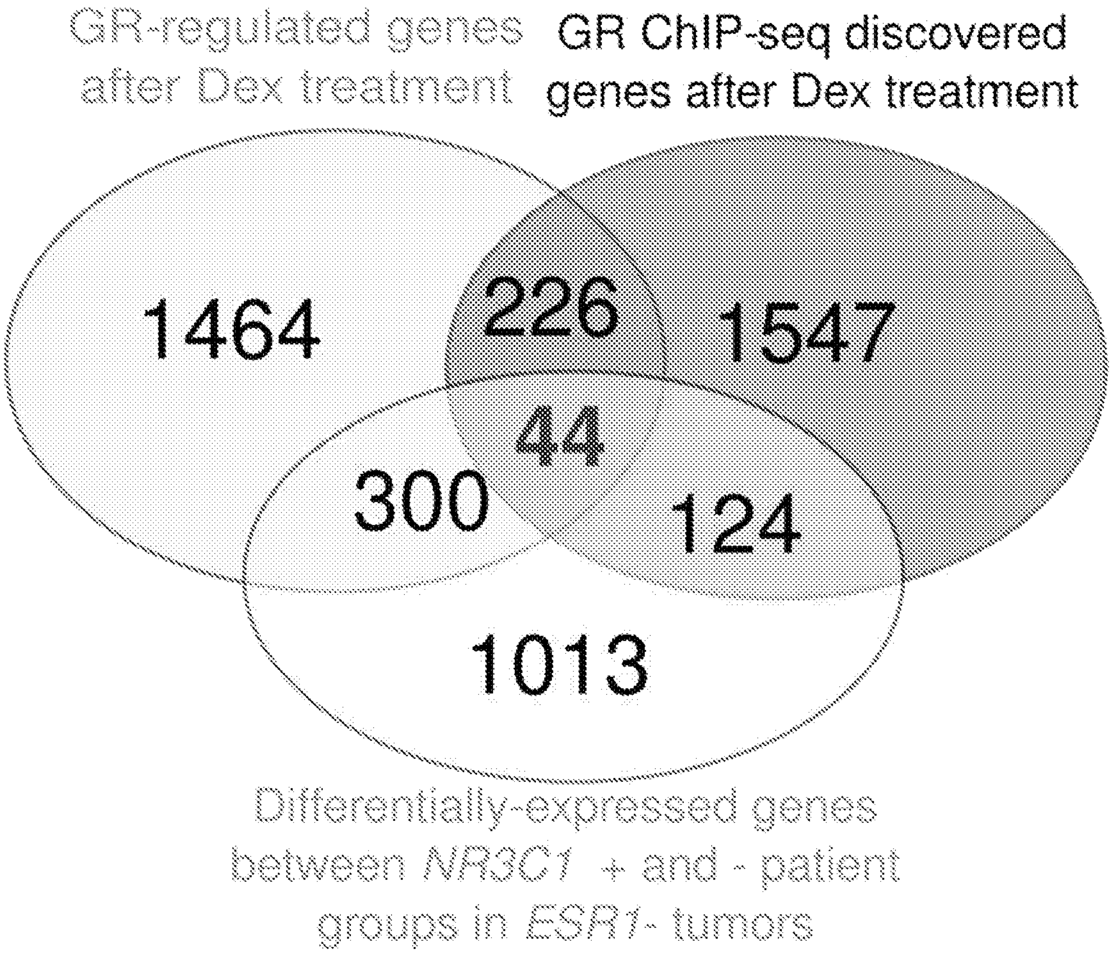
FIG. 6. Common genes differentially expressed in ESR1− and NR3C1+/− tumors, ChIP-seq and gene expression in Dex-treated MCF10A-Myc cells.

Glucocorticoid receptor (GR) activation initiates a potent cell survival signal in ER− breast cancer models. However, GR activity has not been previously examined in primary human breast cancers. Because anti-apoptotic signaling is believed to be an important determinant of breast cancer viability and relapse, the inventors contemplate that early stage primary human breast cancer demonstrates a correlation between high GR (NR3C1) and GR− mediated gene expression and cancer recurrence.

The Dutch NKI 295 data set was examined and the inventors determined that a gene expression signature of 68 GR-regulated genes (based on in vitro data) could cluster patients into different groups with differential outcome. In addition, it was found that GR-mediated gene expression correlated with NR3C1 expression levels. The inventors examined NR3C1 tumor expression in a much larger meta-dataset and again found that ER−/GR (NR3C1)+ patients did the worst. Moreover, key cell survival genes identified as GR gene targets from ChIP-seq experiments were differentially expressed.

I. Hormone Receptor Status of Breast Cancer

Intracellular receptors (IRs) form a class of structurally-related genetic regulators scientists have named "ligand dependent transcription factors" (R. M. Evans, Science, 240:889, 1988). Steroid receptors are a recognized subset of the IRs, including androgen receptor (AR), progesterone receptor (PR), estrogen receptor (ER), glucocorticoid receptor (GR), and mineralocorticoid receptor (MR). Regulation of a gene by such factors requires both the IR itself and a corresponding ligand, which has the ability to selectively bind to the IR in a way that affects gene transcription.

Naturally occurring as well as synthetic steroidal glucocorticoids (e.g., cortisol, cortisone, prednisolone, dexamethasone) have been widely used for over fifty years for the treatment of acute and chronic inflammatory and immune disorders. In particular, glucocorticoids have been prescribed for the treatment of rheumatoid arthritis, osteoarthritis, rheumatic fever, asthma, allergic rhinitis, systemic lupus erythematosus, chronic obstructive pulmonary disease, Crohn's disease, inflammatory bowel disease, and ulcerative colitis. However, the use of glucocorticoids is often associated with severe and sometimes irreversible side effects such as bone loss/osteoporosis, hyperglycemia, diabetes mellitus, hypertension, glaucoma, muscle atrophy, Cushing's syndrome, and psychosis.

Glucocorticoids exert their pharmacological effects by regulating gene transcription after the formation of a complex with the glucocorticoid receptor (GR). GR-glucocorticoid complex affects gene transcription by translocating to the nucleus after binding of the glucocorticoid where it acts as a dimer in binding to DNA glucocorticoid hormone response elements (GREs) in the promoter regions of particular genes. The GR-glucocorticoid/GRE complex then, in turn, activates (transactivation) or inhibits transcription of proximally located genes. Conversely, the GR-glucocorticoid complex may negatively regulate gene transcription by a process that does not involve binding to DNA. In this process, termed transrepression, following binding of the glucocorticoid, the complexed GR enters the nucleus where it acts as a monomer to directly interact (via protein-protein interaction) with other transcription factors, repressing their ability to induce gene transcription and thus protein expression.

Estrogen, mediated through the estrogen receptor (ER), plays a major role in regulating the growth and differentiation of normal breast epithelium (Pike et al. Epidemiologic Reviews (1993) 15(1):17-35; Henderson et al. Cancer Res. (1988) 48:246-253). It stimulates cell proliferation and regulates the expression of other genes, including the progesterone receptor (PgR). PgR then mediates the mitogenic effect of progesterone, further stimulating proliferation (Pike et al., 1993; Henderson et al., 1988). The molecular differences between estrogen receptor ("ER") negative and ER positive tumors are significant in light of clinical observations which indicate that the nature and biological behavior of ER positive and ER negative tumors are distinct even in the absence of hormonal therapy. For example, ER negative cancers tend to recur sooner and show a different rate of recurrence in distant organ sites compared to ER positive tumors. Clinical observations and molecular profiling data suggest that tumors not expressing both ER and PgR represent a different clinical entity in terms of chemotherapy responsiveness. (Colleoni et al., Annals of Oncology 11(8): 1057 (2000)). Thus, ER negative and ER positive breast cancers are two distinct disease entities rather than phenotypic variations of the same disease.

Relatively increased expression of these genes in primary ER-negative human breast tumors is associated with high GR expression and with an earlier relapse in ER-negative breast cancer patients (described herein). Activation of the glucocorticoid receptor (GR) in epithelial cells has been shown to initiate an anti-apoptotic (i.e., cell survival) signaling pathway that prevents breast (Wu et al, 2004) and ovarian cancer (Melhem et al, 2009) cell death in vitro and in vivo (Pang et al, 2006). Blocking or antagonizing GR activation with a GR antagonist such as mifepristone reverses cell survival signaling pathways initiated by the GR (Moran et al., 2000). Other GR antagonists (e.g., dexamethasone oxetanone) also reverse GR-mediated cell survival and potentiate apoptosis in response to cell stressors such as growth factor withdrawal (Mikosz et al, 2001). The mechanism(s) whereby GR activation protects from cell death includes the transcriptional upregulation of genes encoding anti-apoptotic proteins such as SGK1, MKP1, MCL1, and BIRC3. However, experiments with a glucocorticoid receptor antagonist, RU486, in conjunction with dexamethasone did not increase the number of apoptotic cells induced by paclitaxel, compared to paclitaxel alone (Wu et al., 2004).

II. Biomarkers and Evaluating Levels of Biomarkers

Biomarkers for prognosing human breast cancer patients have been identified. They include estrogen receptor (ER) in combination with the activity of the glucocorticoid receptor (GR) activity. It is contemplated that these biomarkers may be evaluated based on their gene products. In some embodiments, the gene product is the RNA transcript. In other embodiments, the gene product is the protein expressed by the RNA transcript. In still another embodiment is the evaluation of surrogate genes or gene targets of ER, GR, or ER and GR.

In certain aspects a meta-analysis of expression or activity can be performed. In statistics, a meta-analysis combines the results of several studies that address a set of related research hypotheses. This is normally done by identification of a common measure of effect size, which is modeled using a form of meta-regression. Generally, three types of models can be distinguished in the literature on meta-analysis: simple regression, fixed effects meta-regression and random effects meta-regression. Resulting overall averages when controlling for study characteristics can be considered meta-effect sizes, which are more powerful estimates of the true effect size than those derived in a single study under a given single set of assumptions and conditions. A meta-gene expression value, in this context, is to be understood as being the median of the normalized expression of a marker gene or activity. Normalization of the expression of a marker gene is preferably achieved by dividing the expression level of the individual marker gene to be normalized by the respective individual median expression of this marker genes, wherein said median expression is preferably calculated from multiple measurements of the respective gene in a sufficiently large cohort of test individuals. The test cohort preferably comprises at least 3, 10, 100, 200, 1000 individuals or more including all values and ranges thereof. Dataset-specific bias can be removed or minimized allowing multiple datasets to be combined for meta-analyses (See Sims et al. BMC Medical Genomics (1:42), 1-14, 2008, which is incorporated herein by reference in its entirety).

The calculation of a meta-gene expression value is performed by: (i) determining the gene expression value of at least two, preferably more genes (ii) "normalizing" the gene expression value of each individual gene by dividing the expression value with a coefficient which is approximately the median expression value of the respective gene in a representative breast cancer cohort (iii) calculating the median of the group of normalized gene expression values.

A gene shall be understood to be specifically expressed in a certain cell type if the expression level of said gene in said cell type is at least 2-fold, 5-fold, 10-fold, 100-fold, 1000-fold, or 10000-fold higher than in a reference cell type, or in a mixture of reference cell types. Reference cell types include non-cancerous breast tissue cells or a heterogenous population of breast cancers.

In certain algorithms a suitable threshold level is first determined for a marker gene. The suitable threshold level can be determined from measurements of the marker gene expression in multiple individuals from a test cohort. The median expression of the marker gene in said multiple expression measurements is taken as the suitable threshold value.

Comparison of multiple marker genes with a threshold level can be performed as follows:

1. The individual marker genes are compared to their respective threshold levels.
2. The number of marker genes, the expression level of which is above their respective threshold level, is determined.
3. If a marker genes is expressed above its respective threshold level, then the expression level of the marker gene is taken to be "above the threshold level".

"A sufficiently large number", in this context, means preferably 30%, 50%, 80%, 90%, or 95% of the marker genes used.

In certain aspects, the determination of expression levels is on a gene chip, such as an Affymetrix™ gene chip.

In another aspect, the determination of expression levels is done by kinetic real time PCR.

In certain aspects, the methods can relate to a system for performing such methods, the system comprising (a) apparatus or device for storing data on the ER or nodal status of the patient; (b) apparatus or device for determining the expression level of at least one marker gene or activity; (c) apparatus or device for comparing the expression level of the first marker gene or activity with a predetermined first threshold value; (d) apparatus or device for determining the expression level of at least one second marker gene or activity; and (e) computing apparatus or device programmed to provide a unfavorable or poor prognosis if the data indicates a negative ER status and an increased or decreased expression level of said first marker gene or activity (e.g., GR expression or activity) with the predetermined first threshold value and, alternatively, the expression level of said second marker gene is above or below a predetermined second threshold level.

The person skilled in the art readily appreciates that an unfavorable or poor prognosis can be given if the expression level of the first marker gene with the predetermined first threshold value indicates a tumor that is likely to recur or not respond well to standard therapies.

The expression patterns can also be compared by using one or more ratios between the expression levels of different breast cancer biomarkers. Other suitable measures or indicators can also be employed for assessing the relationship or difference between different expression patterns.

The GR nucleic acid and protein sequences are provided in GenBank accession number AY436590. The ER nucleic acid and protein sequences are provided in GenBank accession number NG_008493. The content of all of these GenBank Accession numbers is specifically incorporated herein by reference as of the filing date of this application.

The following biomarkers are provided for implementation with embodiments discussed herein. All of them designate nucleic acid sequences for the particular gene identifier. Nucleic acid sequences related to these gene designation can be found in the Genbank sequence databases. Additional biomarkers include the MCL1, SAP30, DUSP1, SGK1, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, IDH2, SERPINF1, ERBB2, PECAM1, LBH, ST3GAL5, IL1R1, BIN1, WIPF1, TFPI, FN1, FAM134A, NRIP1, RAC2, SPP1, PHF15, BTN3A2, SESN1, MAP3K5, DPYSL2, SEMA4D, STOM, and MAOA genes.

One or more of the biomarkers can be used to prognose a human patient with breast cancer. The expression pattern of these biomarkers in breast cancer cells may be used to evaluate a patient to determine whether they are likely to respond to standard chemotherapy, likely not to respond to standard chemotherapy, or likely to relapse after standard chemotherapy.

The expression levels of breast cancer biomarkers can be compared to reference expression levels using various methods. These reference levels can be determined using expression levels of a reference based on all breast cancer patients or all breast cancer patients determined to be ER+ and/or ER−. Alternatively, it can be based on an internal reference such as a gene that is expressed in all cells. In some embodiments, the reference is a gene expressed in breast cancer cells at a higher level than any biomarker. Any comparison can be performed using the fold change or the absolute difference between the expression levels to be compared. One or more breast cancer biomarkers can be used in the comparison. It is contemplated that 1, 2, 3, 4, 5, 6, 7, 8, and/or 9 biomarkers may be compared to each other and/or to a reference that is internal or external. A person of ordinary skill in the art would know how to do such comparisons.

Comparisons or results from comparisons may reveal or be expressed as x-fold increase or decrease in expression relative to a standard or relative to another biomarker or relative to the same biomarker but in a different class of prognosis. In some embodiments, patients with a poor prognosis have a relatively high level of expression (overexpression) or relatively low level of expression (underexpression) when compared to patients with a better or favorable prognosis, or vice versa.

Fold increases or decreases may be, be at least, or be at most 1-, 2-, 3-, 4-, 5-, 6-, 7-, 8-, 9-, 10-, 11-, 12-, 13-, 14-, 15-, 16-, 17-, 18-, 19-, 20-, 25-, 30-, 35-, 40-, 45-, 50-, 55-, 60-, 65-, 70-, 75-, 80-, 85-, 90-, 95-, 100- or more, or any range derivable therein. Alternatively, differences in expression may be expressed as a percent decrease or increase, such as at least or at most 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 1000% difference, or any range derivable therein.

Other ways to express relative expression levels are by normalized or relative numbers such as 0.001, 0.002, 0.003, 0.004, 0.005, 0.006, 0.007, 0.008, 0.009, 0.01, 0.02, 0.03. 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, or any range derivable therein.

Algorithms, such as the weighted voting programs, can be used to facilitate the evaluation of biomarker levels. In addition, other clinical evidence can be combined with the biomarker-based test to reduce the risk of false evaluations. Other cytogenetic evaluations may be considered in some embodiments of the invention.

Any biological sample from the patient that contains breast cancer cells may be used to evaluate the expression pattern of any biomarker discussed herein. In some embodiments, a biological sample from a breast tumor is used. Evaluation of the sample may involve, though it need not involve, panning (enriching) for cancer cells or isolating the cancer cells.

A. Nucleic Acids

Screening methods based on differentially expressed gene products are well known in the art. In accordance with one aspect of the present invention, the differential expression patterns of breast cancer biomarkers can be determined by measuring the levels of RNA transcripts of these genes, or genes whose expression is modulated by the these genes, in the patient's breast cancer cells. Suitable methods for this purpose include, but are not limited to, RT-PCR, Northern Blot, in situ hybridization, Southern Blot, slot-blotting, nuclease protection assay and oligonucleotide arrays.

In certain aspects, RNA isolated from breast cancer cells can be amplified to cDNA or cRNA before detection and/or quantitation. The isolated RNA can be either total RNA or mRNA. The RNA amplification can be specific or non-specific. Suitable amplification methods include, but are not limited to, reverse transcriptase PCR, isothermal amplification, ligase chain reaction, and Qbeta replicase. The amplified nucleic acid products can be detected and/or quantitated through hybridization to labeled probes. In some embodiments, detection may involve fluorescence resonance energy transfer (FRET) or some other kind of quantum dots.

Amplification primers or hybridization probes for a breast cancer biomarker can be prepared from the gene sequence or obtained through commercial sources, such as Affymatrix. In certain embodiments the gene sequence is identical or complementary to at least 8 contiguous nucleotides of the coding sequence.

Sequences suitable for making probes/primers for the detection of their corresponding breast cancer biomarkers include those that are identical or complementary to all or part of genes or SEQ ID NOs described herein. These sequences are all nucleic acid sequences of breast cancer biomarkers.

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

In one embodiment, each probe/primer comprises at least 15 nucleotides. For instance, each probe can comprise at least or at most 20, 25, 50, 75, 100, 125, 150, 175, 200, 225, 250, 275, 300, 325, 350, 400 or more nucleotides (or any range derivable therein). They may have these lengths and have a sequence that is identical or complementary to a gene or SEQ ID NO described herein. Preferably, each probe/primer has relatively high sequence complexity and does not have any ambiguous residue (undetermined "n" residues). The probes/primers preferably can hybridize to the target gene, including its RNA transcripts, under stringent or highly stringent conditions. In some embodiments, because each of the biomarkers has more than one human sequence, it is contemplated that probes and primers may be designed for use with each on of these sequences. For example, inosine is a nucleotide frequently used in probes or primers to hybridize to more than one sequence. It is contemplated that probes or primers may have inosine or other design implementations that accommodate recognition of more than one human sequence for a particular biomarker.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

In another embodiment, the probes/primers for a gene are selected from regions which significantly diverge from the sequences of other genes. Such regions can be determined by checking the probe/primer sequences against a human genome sequence database, such as the Entrez database at the NCBI. One algorithm suitable for this purpose is the BLAST algorithm. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence to increase the cumulative alignment score. Cumulative scores are calculated using, for nucleotide sequences, the parameters M (reward score for a pair of matching residues; always >0) and N (penalty score for mismatching residues; always <0). The BLAST algorithm parameters W, T, and X determine the sensitivity and speed of the alignment. These parameters can be adjusted for different purposes, as appreciated by one of ordinary skill in the art.

In one embodiment, quantitative RT-PCR (such as TaqMan, ABI) is used for detecting and comparing the levels of RNA transcripts in breast cancer samples. Quantitative RT-PCR involves reverse transcription (RT) of RNA to cDNA followed by relative quantitative PCR (RT-PCR). The concentration of the target DNA in the linear portion of the PCR process is proportional to the starting concentration of the target before the PCR was begun. By determining the concentration of the PCR products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived may be determined for the respective tissues or cells. This direct proportionality between the concentration of the PCR products and the relative mRNA abundances is true in the linear range portion of the PCR reaction. The final concentration of the target DNA in the plateau portion of the curve is determined by the availability of reagents in the reaction mix and is independent of the original concentration of target DNA. Therefore, the sampling and quantifying of the amplified PCR products preferably are carried out when the PCR reactions are in the linear portion of their curves. In addition, relative concentrations of the amplifiable cDNAs preferably are normalized to some independent standard, which may be based on either internally existing RNA species or externally introduced RNA species. The abundance of a particular mRNA species may also be determined relative to the average abundance of all mRNA species in the sample.

In one embodiment, the PCR amplification utilizes one or more internal PCR standards. The internal standard may be an abundant housekeeping gene in the cell or it can specifically be GAPDH, GUSB and β-2 microglobulin. These standards may be used to normalize expression levels so that the expression levels of different gene products can be compared directly. A person of ordinary skill in the art would know how to use an internal standard to normalize expression levels.

A problem inherent in clinical samples is that they are of variable quantity and/or quality. This problem can be overcome if the RT-PCR is performed as a relative quantitative RT-PCR with an internal standard in which the internal standard is an amplifiable cDNA fragment that is similar or larger than the target cDNA fragment and in which the abundance of the mRNA encoding the internal standard is roughly 5-100 fold higher than the mRNA encoding the target. This assay measures relative abundance, not absolute abundance of the respective mRNA species.

In another embodiment, the relative quantitative RT-PCR uses an external standard protocol. Under this protocol, the PCR products are sampled in the linear portion of their amplification curves. The number of PCR cycles that are optimal for sampling can be empirically determined for each target cDNA fragment. In addition, the reverse transcriptase products of each RNA population isolated from the various samples can be normalized for equal concentrations of amplifiable cDNAs.

Nucleic acid arrays can also be used to detect and compare the differential expression patterns of breast cancer biomarkers in breast cancer cells. The probes suitable for detecting the corresponding breast cancer biomarkers can be stably attached to known discrete regions on a solid substrate. As used herein, a probe is "stably attached" to a discrete region if the probe maintains its position relative to the discrete region during the hybridization and the subsequent washes. Construction of nucleic acid arrays is well known in the art. Suitable substrates for making polynucleotide arrays include, but are not limited to, membranes, films, plastics and quartz wafers.

A nucleic acid array of the present invention can comprise at least 1, 2, 3, 4, 5, 6, 7, 8, 9, 10, 15, 20, 25, 30, 35, 40, 45, 50, 60, 70, 80, 90, 100, 150, 200, 250 or more different polynucleotide probes, which may hybridize to different and/or the same biomarkers. Multiple probes for the same gene can be used on a single nucleic acid array. Probes for other disease genes can also be included in the nucleic acid array. The probe density on the array can be in any range. In some embodiments, the density may be 50, 100, 200, 300, 400, 500 or more probes/$cm^2$.

Specifically contemplated by the present inventors are chip-based nucleic acid technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al, 1991). It is contemplated that this technology may be used in conjunction with evaluating the expression level of one or more breast cancer biomarkers with respect to diagnostic, prognostic, and treatment methods of the invention.

The present invention may involve the use of arrays or data generated from an array. Data may be readily available. Moreover, an array may be prepared in order to generate data that may then be used in correlation studies.

An array generally refers to ordered macroarrays or microarrays of nucleic acid molecules (probes) that are fully or nearly complementary or identical to a plurality of mRNA molecules or cDNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon. Such arrays may vary in a number of different ways, including average probe length, sequence or types of probes, nature of bond between the probe and the array surface, e.g. covalent or non-covalent, and the like. The labeling and screening methods of the present invention and the arrays are not limited in its utility with respect to any parameter except that the probes detect expression levels; consequently, methods and compositions may be used with a variety of different types of genes.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference.

It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or 15 to 40 nucleotides in length in some embodiments. In certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols include information found in WO 9743450; WO 03023058; WO 03022421; WO 03029485; WO 03067217; WO 03066906; WO 03076928; WO 03093810; WO 03100448A1, all of which are specifically incorporated by reference.

In one embodiment, nuclease protection assays are used to quantify RNAs derived from the breast cancer samples. There are many different versions of nuclease protection assays known to those practiced in the art. The common characteristic that these nuclease protection assays have is that they involve hybridization of an antisense nucleic acid with the RNA to be quantified. The resulting hybrid double-stranded molecule is then digested with a nuclease that digests single-stranded nucleic acids more efficiently than double-stranded molecules. The amount of antisense nucleic acid that survives digestion is a measure of the amount of the target RNA species to be quantified. An example of a nuclease protection assay that is commercially available is the RNase protection assay manufactured by Ambion, Inc. (Austin, Tex.).

B. Proteins and Polypeptides

In other embodiments, the differential expression patterns of breast cancer biomarkers can be determined by measuring the levels of polypeptides encoded by these genes in breast cancer cells. Methods suitable for this purpose include, but are not limited to, immunoassays such as ELISA, RIA, FACS, dot blot, Western Blot, immunohistochemistry, and antibody-based radioimaging. Protocols for carrying out these immunoassays are well known in the art. Other methods such as 2-dimensional SDS-polyacrylamide gel electrophoresis can also be used. These procedures may be used to recognize any of the polypeptides encoded by the breast cancer biomarker genes described herein.

One example of a method suitable for detecting the levels of target proteins in peripheral blood samples is ELISA. In an exemplifying ELISA, antibodies capable of binding to the target proteins encoded by one or more breast cancer biomarker genes are immobilized onto a selected surface exhibiting protein affinity, such as wells in a polystyrene or polyvinylchloride microtiter plate. Then, breast cancer cell samples to be tested are added to the wells. After binding and washing to remove non-specifically bound immunocomplexes, the bound antigen(s) can be detected. Detection can be achieved by the addition of a second antibody which is specific for the target proteins and is linked to a detectable label. Detection may also be achieved by the addition of a second antibody, followed by the addition of a third antibody that has binding affinity for the second antibody, with the third antibody being linked to a detectable label. Before being added to the microtiter plate, cells in the peripheral blood samples can be lysed using various methods known in the art. Proper extraction procedures can be used to separate the target proteins from potentially interfering substances.

In another ELISA embodiment, the breast cancer cell samples containing the target proteins are immobilized onto the well surface and then contacted with the antibodies of the invention. After binding and washing to remove non-specifically bound immunocomplexes, the bound antigen is detected. Where the initial antibodies are linked to a detectable label, the immunocomplexes can be detected directly. The immunocomplexes can also be detected using a second antibody that has binding affinity for the first antibody, with the second antibody being linked to a detectable label.

Another typical ELISA involves the use of antibody competition in the detection. In this ELISA, the target proteins are immobilized on the well surface. The labeled antibodies are added to the well, allowed to bind to the target proteins, and detected by means of their labels. The amount of the target proteins in an unknown sample is then determined by mixing the sample with the labeled antibodies before or during incubation with coated wells. The presence of the target proteins in the unknown sample acts to reduce the amount of antibody available for binding to the well and thus reduces the ultimate signal.

Different ELISA formats can have certain features in common, such as coating, incubating or binding, washing to remove non-specifically bound species, and detecting the bound immunocomplexes. For instance, in coating a plate with either antigen or antibody, the wells of the plate can be incubated with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test samples. Examples of these nonspecific proteins include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means can also be used. After binding of a protein or antibody to the well, coating with a non-reactive material to reduce background, and washing to remove unbound material, the immobilizing surface is contacted with the control and/or clinical or biological sample to be tested under conditions effective to allow immunocomplex (antigen/antibody) formation. These conditions may include, for example, diluting the antigens and antibodies with solutions such as BSA, bovine gamma globulin (BGG) and phosphate buffered saline (PBS)/Tween and incubating the antibodies and antigens at room temperature for about 1 to 4 hours or at 49° C. overnight. Detection of the immunocomplex then requires a labeled secondary binding ligand or antibody, or a secondary binding ligand or antibody in conjunction with a labeled tertiary antibody or third binding ligand.

After all of the incubation steps in an ELISA, the contacted surface can be washed so as to remove non-complexed material. For instance, the surface may be washed with a solution such as PBS/Tween, or borate buffer. Following the formation of specific immunocomplexes between the test sample and the originally bound material, and subsequent washing, the occurrence of the amount of immunocomplexes can be determined.

To provide a detecting means, the second or third antibody can have an associated label to allow detection. In one embodiment, the label is an enzyme that generates color development upon incubating with an appropriate chromogenic substrate. Thus, for example, one may contact and incubate the first or second immunocomplex with a urease, glucose oxidase, alkaline phosphatase or hydrogen peroxidase-conjugated antibody for a period of time and under conditions that favor the development of further immunocomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl)-benzhiazoline-6-sulfonic acid (ABTS) and hydrogen peroxide, in the case of peroxidase as the enzyme label. Quantitation can be achieved by measuring the degree of color generation, e.g., using a spectrophotometer.

Another suitable method is MA (radioimmunoassay). An example of MA is based on the competition between radiolabeled-polypeptides and unlabeled polypeptides for binding to a limited quantity of antibodies. Suitable radiolabels include, but are not limited to, $I^{125}$. In one embodiment, a fixed concentration of $I^{125}$-labeled polypeptide is incubated with a series of dilution of an antibody specific to the polypeptide. When the unlabeled polypeptide is added to the system, the amount of the $I^{125}$-polypeptide that binds to the antibody is decreased. A standard curve can therefore be constructed to represent the amount of antibody-bound $I^{125}$-polypeptide as a function of the concentration of the unlabeled polypeptide. From this standard curve, the concentration of the polypeptide in unknown samples can be determined. Various protocols for conducting RIA to measure the levels of polypeptides in breast cancer cell samples are well known in the art.

Suitable antibodies for this invention include, but are not limited to, polyclonal antibodies, monoclonal antibodies, chimeric antibodies, humanized antibodies, single chain antibodies, Fab fragments, and fragments produced by a Fab expression library.

Antibodies can be labeled with one or more detectable moieties to allow for detection of antibody-antigen complexes. The detectable moieties can include compositions detectable by spectroscopic, enzymatic, photochemical, biochemical, bioelectronic, immunochemical, electrical, optical or chemical means. The detectable moieties include, but are not limited to, radioisotopes, chemiluminescent compounds, labeled binding proteins, heavy metal atoms, spectroscopic markers such as fluorescent markers and dyes, magnetic labels, linked enzymes, mass spectrometry tags, spin labels, electron transfer donors and acceptors, and the like.

Protein array technology is discussed in detail in Pandey and Mann (2000) and MacBeath and Schreiber (2000), each of which is herein specifically incorporated by reference. These arrays typically contain thousands of different proteins or antibodies spotted onto glass slides or immobilized in tiny wells and allow one to examine the biochemical activities and binding profiles of a large number of proteins at once. To examine protein interactions with such an array, a labeled protein is incubated with each of the target proteins immobilized on the slide, and then one determines which of the many proteins the labeled molecule binds. In certain embodiments such technology can be used to quantitate a number of proteins in a sample, such as a breast cancer biomarker proteins.

The basic construction of protein chips has some similarities to DNA chips, such as the use of a glass or plastic surface dotted with an array of molecules. These molecules can be DNA or antibodies that are designed to capture proteins. Defined quantities of proteins are immobilized on each spot, while retaining some activity of the protein. With fluorescent markers or other methods of detection revealing the spots that have captured these proteins, protein microarrays are being used as powerful tools in high-throughput proteomics and drug discovery.

The earliest and best-known protein chip is the ProteinChip by Ciphergen Biosystems Inc. (Fremont, Calif.). The ProteinChip is based on the surface-enhanced laser desorption and ionization (SELDI) process. Known proteins are analyzed using functional assays that are on the chip. For example, chip surfaces can contain enzymes, receptor proteins, or antibodies that enable researchers to conduct protein-protein interaction studies, ligand binding studies, or immunoassays. With state-of-the-art ion optic and laser optic technologies, the ProteinChip system detects proteins ranging from small peptides of less than 1000 Da up to proteins of 300 kDa and calculates the mass based on time-of-flight (TOF).

The ProteinChip biomarker system is the first protein biochip-based system that enables biomarker pattern recognition analysis to be done. This system allows researchers to address important clinical questions by investigating the proteome from a range of crude clinical samples (i.e., laser capture microdissected cells, biopsies, tissue, urine, and serum). The system also utilizes biomarker pattern software that automates pattern recognition-based statistical analysis methods to correlate protein expression patterns from clinical samples with disease phenotypes.

In other aspects, the levels of polypeptides in samples can be determined by detecting the biological activities associated with the polypeptides. If a biological function/activity of a polypeptide is known, suitable in vitro bioassays can be designed to evaluate the biological function/activity, thereby determining the amount of the polypeptide in the sample.

III. Breast Cancer Therapy

Certain embodiments are directed to methods of treating breast cancer based on GR status of the breast cancer tissue. In some embodiments, the hormone receptor status is determined based on the expression of a hormone receptor such as the estrogen receptor (ER) in combination with the glucocorticoid receptor (GR).

In certain aspects, the hormone receptor status is high for GR and may also be low for one or more other hormone receptors such as the estrogen receptor. An individual having an elevated GR and low ER is likely to have a poor prognosis. In the event of a poor prognosis the physician may pursue a more aggressive therapy for those patients. In some embodiments, the method comprises identifying a breast cancer patient based on a hormone receptor status of patients having tumor tissue with elevated levels of GR expression.

In certain aspects, there may be provided methods for treating a subject determined to have cancer and with a predetermined expression profile of one or more biomarkers disclosed herein.

In a further aspect, biomarkers and related systems that can establish a prognosis of cancer patients in this invention can be used to identify patients who may get benefit of conventional single or combined modality therapy. In the same way, the invention can identify those patients who do not get much benefit from such conventional single or combined modality therapy and can offer them alternative treatment(s).

In certain aspects of the present invention, conventional cancer therapy may be applied to a subject wherein the subject is identified or reported as having a good prognosis based on the assessment of the biomarkers as disclosed. On the other hand, at least an alternative cancer therapy may be prescribed, as used alone or in combination with conventional cancer therapy, if a poor prognosis is determined by the disclosed methods, systems, or kits.

Embodiments concern a glucocorticoid receptor antagonist. In some embodiments, the glucocorticoid receptor antagonist is a selective glucocorticoid receptor antagonist, as set forth in Clark, 2008, which is hereby incorporated by reference. In other embodiments, the glucocorticoid receptor antagonist is a non-selective glucocorticoid receptor antagonist, such as mifepristone. In certain embodiments, the glucocorticoid receptor antagonist is steroidal. In other embodiments, the glucocorticoid receptor antagonist is non-steroidal. A glucocorticoid receptor antagonist includes those in the following classes of chemical compounds: octahydrophenanthrenes, spirocyclic dihydropyridines, triphenylmethanes and diaryl ethers, chromenes, dibenzyl anilines, dihydroisoquinolines, pyrimidinediones, azadecalins, and aryl pyrazolo azadecalins, and which are described in more detail in Clark, 2008, which is hereby incorporated by reference. Some embodiments of steroidal antagonists from Clark, 2008 are: RU-486, RU-43044, 11-monoaryl and 11,21 bisaryl steroids (including 11β-substituted steroids), 10β-substituted steroids, 11β-aryl conjugates of mifepristone, and phosphorous-containing mifepristone analogs. Further embodiments of nonsteroidal antagonists from Clark, 2008 are: octahydrophenanthrenes, spirocyclic dihydropyridines, triphenylmethanes and diaryl ethers, chromenes, dibenzyl anilines, dihyrdroquinolines, pyrimidinediones, azadecalins, aryl pyrazolo azadecalins (including 8a-benzyl isoquinolones, N-substituted derivatives, bridgehead alcohol and ethers, bridgehead amines). Additional specific examples include, but are not limited to the following specific antagonists: beclometasone, betamethasone, budesonide, ciclesonide, flunisolide, fluticasone, mifepristone, mometasone, and triamcinolone. Other examples include those described and/or depicted in U.S. Patent Application Publication 2010/0135956, which is hereby incorporated by reference. Even further examples include ORG-34517 (Merck), RU-43044, dexamethasone mesylate (Dex-Mes), dexamethasone oxetanone (Dex-Ox), deoxycorticosterone (DOC) (Peeters et al., 2008, which is hereby incorporated by reference in its entirety and Cho et al. 2005, which is hereby incorporated by reference in its entirety). In additional embodiments the glucocorticoid receptor antagonist may be CORT 0113083 or CORT 00112716, which are described in Belanoff et al. (2011), which is hereby incorporated by reference. It is specifically contemplated that one or more of the antagonists discussed herein or in the incorporated references may be excluded in embodiments of the invention. It is also contemplated that in some embodiments, more than one glucocorticoid receptor antagonist is employed, while in other embodiments, only one is employed as part of the therapeutic method (though it may be administered multiple times). It is contemplated that the second one may be administered concurrently with the first one or they may be administered at different times.

Conventional cancer therapies include one or more selected from the group of chemical or radiation based treatments and surgery. Chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristin, vinblastin and methotrexate, or any analog or derivative variant of the foregoing.

Suitable therapeutic agents include, for example, *vinca* alkaloids, agents that disrupt microtubule formation (such as colchicines and its derivatives), anti-angiogenic agents, therapeutic antibodies, EGFR targeting agents, tyrosine kinase targeting agent (such as tyrosine kinase inhibitors), serine kinase targeting agents, transitional metal complexes, proteasome inhibitors, antimetabolites (such as nucleoside analogs), alkylating agents, platinum-based agents, anthracycline antibiotics, topoisomerase inhibitors, macrolides, therapeutic antibodies, retinoids (such as all-trans retinoic acids or a derivatives thereof); geldanamycin or a derivative thereof (such as 17-AAG), and other standard chemotherapeutic agents well recognized in the art.

Certain chemotherapeutics are well known for use against breast cancer. These breast cancer chemotherapeutics are capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), thiotepa, vincristine, vinorelbine.

In some embodiments, the chemotherapeutic agent is any of (and in some embodiments selected from the group consisting of) adriamycin, colchicine, cyclophosphamide, actinomycin, bleomycin, daunorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, taxotere and derivatives thereof, and the like), topetecan, vinblastine, vincristine, tamoxifen, piposulfan, nab-5404, nab-5800, nab-5801, Irinotecan, HKP, Ortataxel, gemcitabine, Herceptin®, vinorelbine, capecitabine, Gleevec®, Alimta®, Avastin®, Velcade®, Tarceva®, Neulasta®, Lapatinib, STI-571, ZD1839, Iressa® (gefitinib), SH268, genistein, CEP2563, SU6668, SU11248, EMD121974, and Sorafenib.

In some embodiments, the chemotherapeutic agent is a composition comprising nanoparticles comprising a thiocolchicine derivative and a carrier protein (such as albumin).

In further embodiments a combination of chemotherapeutic agents is administered to breast cancer cells. The chemotherapeutic agents may be administered serially (within minutes, hours, or days of each other) or in parallel; they also may be administered to the patient in a pre-mixed single composition. The composition may or may not contain a glucocorticoid receptor antagonist. Combinations of breast cancer therapeutics include, but are not limited to the following: AT (Adriamycin and Taxotere), AC±T: (Adriamycin and Cytoxan, with or without Taxol or Taxotere), CMF (Cytoxan, methotrexate, and fluorouracil), CEF (Cytoxan, Ellence, and fluorouracil), FAC (fluorouracil, Adriamycin, and Cytoxan), CAF (Cytoxan, Adriamycin, and fluorouracil) (the FAC and CAF regimens use the same medicines but use different doses and frequencies), TAC (Taxotere, Adriamycin, and Cytoxan), and GET (Gemzar, Ellence, and Taxol). In some embodiments trastuzumab (Herceptin®) is administered to a breast cancer patient with a glucocorticoid receptor antagonist, which may be with or without a chemotherapeutic or a combination of chemotherapeutics.

Various combinations with a glucocorticoid receptor antagonist and an anticancer agent or compound (or a combination of such agents and/or compounds) may be employed, for example glucocorticoid receptor antagonist is “A” and the anticancer agent or compound (or a combination of such agents and/or compounds) given as part of an anticancer therapy regime, is

| | | | | | | | | |
|---|---|---|---|---|---|---|---|---|
| A/B/A | B/A/B | B/B/A | A/A/B | A/B/B | B/A/A | A/B/B/B | B/A/B/B | |
| B/B/B/A | B/B/A/B | A/A/B/B | A/B/A/B | A/B/B/A | B/B/A/A | | | |
| B/A/B/A | B/A/A/B | A/A/A/B | B/A/A/A | A/B/A/A | A/A/B/A | | | |

Administration of the therapeutic compounds or agents to a patient will follow general protocols for the administration of such compounds, taking into account the toxicity, if any, of the therapy. It is expected that the treatment cycles would be repeated as necessary. It also is contemplated that various standard therapies, as well as surgical intervention, may be applied in combination with the described therapy.

The term “a serine/threonine kinase inhibitor”, as used herein, relates to a compound which inhibits serine/threonine kinases. An example of a target of a serine/threonine kinase inhibitor includes, but is not limited to, dsRNA-dependent protein kinase (PKR). Examples of indirect targets of a serine/threonine kinase inhibitor include, but are not limited to, MCP-1, NF-kappaB, eIF2alpha, COX2, RANTES, IL8, CYP2A5, IGF-1, CYP2B1, CYP2B2, CYP2H1, ALAS-1, HIF-1, erythropoietin and/or CYP1A1. An example of a serine/theronin kinase inhibitor includes, but is not limited to, Sorafenib and 2-aminopurine, also known as 1H-purin-2-amine(9CI). Sorafenib is marketed as NEXAVAR.

The term “an angiogenesis inhibitor”, as used herein, relates to a compound which targets, decreases or inhibits the production of new blood vessels. Targets of an angiogenesis inhibitor include, but are not limited to, methionine aminopeptidase-2 (MetAP-2), macrophage inflammatory protein-1 (MIP-1a), CCL5, TGF-.beta., lipoxygenase, cyclooxygenase, and topoisomerase. Indirect targets of an angiogenesis inhibitor include, but are not limited to, p21, p53, CDK2 and collagen synthesis. Examples of an angiogenesis inhibitor include, but are not limited to, Fumagillin, which is known as 2,4,6,8-decatetraenedioic acid, mono[3R, 4S,5S,6R)-5-methoxy-4-[(2R,3R)-2-methyl-3-(3-methyl-2-butenyl)oxi-ranyl]-1-oxaspiro[2.5]oct-6-yl] ester, (2E,4E, 6E,8E)-(9CI); Shikonin, which is also known as 1,4-naphthalenedione, 5,8-dihydroxy-2-[(1R)-1-hydroxy-4-methyl-3-pentenyl]-(9CI); Tranilast, which is also known as benzoic acid, 2-[[3-(3,4-dimethoxyphenyl)-1-oxo-2-propenyl]amino]-(9CI); ursolic acid; suramin; thalidomide and lenalidomide, and marketed as REVLIMID.

Radiation therapy that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Laser therapy is the use of high-intensity light to destroy tumor cells. Laser therapy affects the cells only in the treated area. Laser therapy may be used to destroy cancerous tissue and relieve a blockage in the esophagus when the cancer cannot be removed by surgery. The relief of a blockage can help to reduce symptoms, especially swallowing problems.

Photodynamic therapy (PDT), a type of laser therapy, involves the use of drugs that are absorbed by cancer cells; when exposed to a special light, the drugs become active and destroy the cancer cells. PDT may be used to relieve symptoms of esophageal cancer such as difficulty swallowing.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well. A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg (or any range derivable therein). A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg/kg/day (or any range derivable therein).

Alternative cancer therapy include any cancer therapy other than surgery, chemotherapy and radiation therapy in the present invention, such as immunotherapy, gene therapy, hormonal therapy or a combination thereof. Subjects identified with poor prognosis using the present methods may not have favorable response to conventional treatment(s) alone and may be prescribed or administered one or more alternative cancer therapy per se or in combination with one or more conventional treatments.

For example, the alternative cancer therapy may be a targeted therapy. The targeted therapy may be an anti-EGFR treatment. In one embodiment of the method of the invention, the anti-EGFR agent used is a tyrosine kinase inhibitor. Examples of suitable tyrosine kinase inhibitors are the quinazoline derivatives described in WO 96/33980, in particular gefitinib (Iressa). Other examples include quinazoline derivatives described in WO 96/30347, in particular erlotinib (Tarceva), dual EGFR/HER2 tyrosine kinase inhibitors, such as lapatinib, or pan-Erb inhibitors. In a preferred embodiment of the method or use of the invention, the anti-EGFR agent is an antibody capable of binding to EGFR, i.e. an anti-EGFR antibody.

In a further embodiment, the anti-EGFR antibody is an intact antibody, i.e. a full-length antibody rather than a fragment. An anti-EGFR antibody used in the method of the present invention may have any suitable affinity and/or avidity for one or more epitopes contained at least partially in EGFR. Preferably, the antibody used binds to human EGFR with an equilibrium dissociation constant ($K_D$) of $10^{-8}$M or less, more preferably $10^{-10}$ M or less.

Particularly antibodies for use in the present invention include zalutumumab (2F8,), cetuximab (Erbitux), nimotuzumab (h-R3), panitumumab (ABX-EGF), and matuzumab (EMD72000), or a variant antibody of any of these, or an antibody which is able to compete with any of these, such as an antibody recognizing the same epitope as any of these. Competition may be determined by any suitable technique. In one embodiment, competition is determined by an ELISA assay. Often competition is marked by a significantly greater relative inhibition than 5% as determined by ELISA analysis.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Gene therapy is the insertion of polynucleotides, including DNA or RNA, into an individual's cells and tissues to treat a disease. Antisense therapy is also a form of gene therapy in the present invention. A therapeutic polynucleotide may be administered before, after, or at the same time of a first cancer therapy. Delivery of a vector encoding a variety of proteins is encompassed within the invention. For example, cellular expression of the exogenous tumor suppressor oncogenes would exert their function to inhibit excessive cellular proliferation, such as p53, p16 and C-CAM.

Additional agents to be used to improve the therapeutic efficacy of treatment include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

II. Kits

Certain aspects of the present invention also encompass kits for performing the diagnostic and prognostic methods of the invention. Such kits can be prepared from readily available materials and reagents. For example, such kits can comprise any one or more of the following materials: enzymes, reaction tubes, buffers, detergent, primers, probes, antibodies. In a preferred embodiment, these kits allow a practitioner to obtain samples of neoplastic cells in blood, tears, semen, saliva, urine, tissue, serum, stool, sputum, cerebrospinal fluid and supernatant from cell lysate. In another preferred embodiment these kits include the needed apparatus for performing RNA extraction, RT-PCR, and gel electrophoresis. Instructions for performing the assays can also be included in the kits.

In a particular aspect, these kits may comprise a plurality of agents for assessing the differential expression of a plurality of biomarkers, for example, GR and/or ER, wherein the kit is housed in a container. The kits may further comprise instructions for using the kit for assessing expression, means for converting the expression data into expression values and/or means for analyzing the expression values to generate prognosis. The agents in the kit for measuring biomarker expression may comprise a plurality of PCR probes and/or primers for qRT-PCR and/or a plurality of antibody or fragments thereof for assessing expression of the biomarkers. In another embodiment, the agents in the kit for measuring biomarker expression may comprise an array of polynucleotides complementary to the mRNAs of the biomarkers of the invention. Possible means for converting the expression data into expression values and for analyzing the expression values to generate scores that predict survival or prognosis may be also included.

Kits may comprise a container with a label. Suitable containers include, for example, bottles, vials, and test tubes. The containers may be formed from a variety of materials such as glass or plastic. The container may hold a composition which includes a probe that is useful for prognostic or non-prognostic applications, such as described above. The label on the container may indicate that the composition is used for a specific prognostic or non-prognostic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Tumor Biomarker Status

A. Results

The glucocorticoid receptor (GR) is highly expressed in the myoepithelium of the normal human breast and in a subset of both ERalpha-positive and negative human breast cancers. In vitro and in vivo experiments suggest that activation of the GR in ER− pre-malignant breast epithelial and cancer cells triggers cell survival pathways under stress conditions (e.g. chemotherapy) that usually induce apoptosis. The inventors examined the association between NR3C1 gene expression and GR target gene expression in human ER− breast cancers and found that ER− breast cancers with high NR3C1 expression also express GR target genes associated with EMT and anti-apoptotic signaling, and that those ER− patients with high NR3C1 gene expression have a significantly worse outcome than NR3C1-low patients. Interestingly, the high NR3C1 gene expression in the ER+ (ESR1-high) subset of patients suggests a slight better outcome, implying a crosstalk between the ER and the GR that is absent in ER− tumors.

Using a global approach of gene expression studies merged with data from GR ChIP-sequencing in ER− pre-malignant breast cells (MCF10A-Myc), the inventors have identified direct GR target genes are significantly associated with cell survival signaling pathways. Interestingly, a meta-analysis of the high NR3C1-expressing ER− tumors reveals that many genes identified by ChIP-sequencing/gene expression analysis are indeed differentially expressed in high versus low NR3C1-primary breast cancers. These results suggest that GR expression may be a functional biomarker in ER− breast cancer.

TABLE 1

Clinical studies used for meta-analysis

| GEO ID | # of pts | Reference |
|---|---|---|
| GSE9195 | 77 | Loi S, et al |
| GSE7390 | 189 | Desmedt C, et al |
| GSE6532 | 212 | Loi S, et al |
| GSE2603 | 73 | Minn AJ, et al |
| GSE2990 | 183 | Sotiriou C, et al |
| GSE2034 | 280 | Wang YX, et al |
| TOTAL | 1206 | |

TABLE 2

Differentially expressed genes with concordant expression by all three methods (33/44 genes)

| Gene expression after Dex-treatment in MCF10A-Myc | Gene expression in NR3C1 + vs. − tumors | GR-binding within distance to TSS after Dex-treatment in MCF10A-Myc | Genes |
|---|---|---|---|
| Up | Up | 10 kb | DUSP1, SGK1, SMARCA2, PTGDS, MCL1 |
| | | 10-100 kb | DPYSL2, STOM, LAPTM5, NNMT, SERPINF1, NRIP1, WIPF1, BIN1, IL1R1, ST3GAL5, SEMA4D, MAP3K5, SMARCA2, DPT, BIRC3, PTGDS, PHF15, MAOA, TFPI, SLC46A3, PIAS1, ACSL5, SESN1, C14orf139, LBH |
| Down | Down | 10 kb | NONE |
| | | 10-100 kb | SFN, SPP1, ERBB2 |
| Overlapping genes with NKI-295 gene signature | | | DUSP1, DPT, NNMT SERPINF1, IL1R1, FN1, DPYSL2 |

B. Materials and Methods

Cell Culture and Glucocorticoid Treatment:

MCF10A-Myc cells were cultured in a 1:1 mixture of DMEM and Hams/F12 medium supplemented with 10% fetal bovine serum, hydrocortisone (0.5 μg/ml), EGF (10 ng/ml), insulin (5 ng/ml) and 100 U/ml penicillin/streptomycin were also added. The cells were then starved for three days of all growth factors and treated with dexamethasone (10-6M) and ethanol of the same volume as a control.

Microarray Gene Expression: MCF10A-Myc Cells:

Time course (0.5 h, 2 h, 4 h and 24 h) microarray data were obtained using Affymetrix gene arrays (HG-U133A) (Wu et al., 2006). Genes that were induced or repressed >1.5 fold-change were considered to be regulated.

GR ChIP-Seq Experiment and Analysis for MCF10A-Myc Cells:

Cells were collected for the ChIP assay following 1 hour of Dex (10-6M) or EtOH treatment. The ChIP assay was done basically following Millipore's ChIP Assay Kit instructions. The DNA input (1%) was also sequenced using Illumina's Solexa Sequencer. Short-tag reads (36 bp) were mapped to the Human Genome (UCSC, hg18) by using Maq aligner. GR-binding peaks were called by using MACS software. Known SGK1 and GILZ promoter GR binding-regions (GBRs) were used as positive controls to determine the FDR threshold for retrieving significant GBRs.

Human Primary Breast Cancer Analysis:

1) Data Collection: All the clinical data and raw CEL files (all Affymetrix HU-133A and HU-133+2) were obtained from GEO (see Table 1). Low quality arrays were removed by AffyPLM. Arrays were normalized by using RMA and then centered by mean within each study and pooled together. 2) Determination of ESR1 and NR3C1 positivity: Expression data of tumors with known ER IHC status were analyzed using ROC analysis. The Youden Index of the best ESR1 probe's ROC curve was used as the cut-off point to separate ESR1+ and ESR1− tumors. Due to the lack of tumors with both GR IHC and NR3C1 gene expression information, we were unable to use ROC analysis to determine the NR3C1 cutoff. Therefore, based on published and our unpublished GR IHC data, we used the percentiles of NR3C1 gene expression levels that correspond to the observed proportion of GR+ patients. 3) Clustering: Unsupervised clustering was performed by Cluster using Pearson correlation distance and complete-linkage method. Heat-maps were plotted by Treeview. 4) Statistical analysis: Relapse-free survival (RFS) Kaplan-Meier plot and log-rank test were done by using R's "survival" package. Microarray SAM analysis was performed by using R's "siggenes" package.

Tumor Assessment.

pAUC areas were calculated for all the probes on the chip by setting p=0.2 (meaning can separate at least 80% patients) for tumors with known ER status (n=1000). A probe was then selected that has biggest pAUC area, which is the ESR1 probe 205225_at. So, this probe is the best one that can separate ER IHC + versus −. Using the 205225_at probe, the Youden Index of its ROC curve was calculated, that is the max (sensitivity+specificity−1) as the cut-off value for ESR1+ and −. The range of ESR1 expression after normalization was [−5.223868−3.944120]. The Youden Index, i.e. the cut-off is −1.257434. In the n=1000, training set, n=773>−1.257434 (ESR1+), and n=227<=−1.257434. (ESR1−) or i.e. 77.3% quantile This cut-off was applied to the entire dataset, n=898 (ESR+), n=308 (ESR−). In addition to the method, the ACTUAL Log 2 value cutoff is needed for ESR1 positivity in normalized meta-dataset, as well as the range of ESR1 values encountered following batched mean normalization. If in one study, samples are obtained from different hospitals, they were normalized separately. So, to be precisely accurate, the normalization is done within the samples from the same source.

The ESR1 probe ID from Affymetrix is 205225_at.

The NR3C1 probe ID from Affymetrix is 216321_s_at

The range for NR3C1 probe (216321_s_at) is [−3.145456 to 2.158716] for the entire data set. For ESR1+, the range is [−3.009359 2.158716] and for ESR1−, the range is [−3.145456 1.917823] Thus, the cut-off for ESR1+, is 0.172189, 55.98% quantile (or about 44% NR3C1+ percentage) and the cut-off for ESR1−, is 0.47332, 82.51% quantile (or about 17.5% NR3C1+ percentage). All the cut-off are log 2 values.

The cutoffs used are the best cut-off that can separate patients with a $p<0.01$. If the p-value is loosened to 0.05, the range can be widened.

For ESR1+ patients, NR3C1+ patients can be from about 35% to 60% (about 44% is the best). For ESR1− patients, NR3C1+ patients can be from about 30% to 15% (about 17.5% is the best)

Example 2

Figure 8:
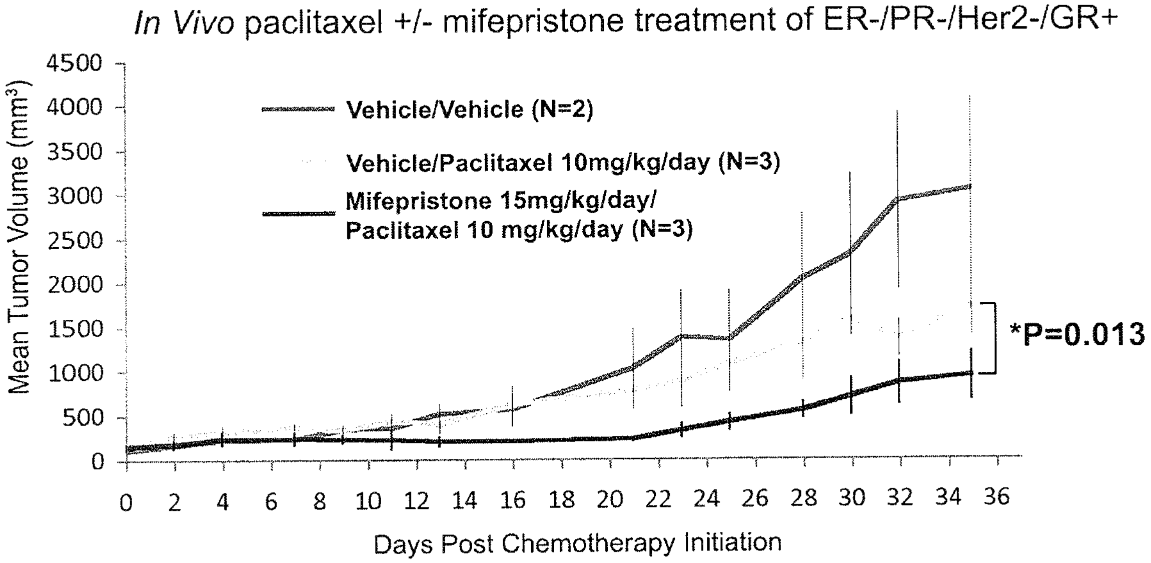
FIG. 8. Administration of mifepristone increases MDA-MB-231 tumor susceptibility to paclitaxel treatment in vivo.

Mifepristone Pretreatment Enhances Paclitaxel Anti-Tumor Effectiveness in Models of Human Breast Cancer Xenografted ER−/PR−/HER2− (GR+) MDA-MB-231 human breast cancer cells ($1\times10^7$ cells in 50 μl of PBS) were injected into the mammary fat pad of female Severe Combined Immunodeficient Mice (SCID) mice and allowed to grow until reaching approximately 100 $mm^3$. Mice were then injected intraperitoneally with either both vehicles, paclitaxel (10 mg/kg)+the mifepristone vehicle, or the combination of mifepristone (15 mg/kg) administered two hours prior to paclitaxel (10 mg/kg) for five successive days. The longest (L) and shortest (S) diameters of the tumors were measured bi-weekly with electronic calipers and tumor volume was calculated using the formula for an ellipsoid sphere: volume=S2×L×0.52. Mifepristone pretreatment significantly decreased tumor volume over time (P=0.013) compared to treatment with paclitaxel alone (FIG. 8).

Example 3

Figure 9:
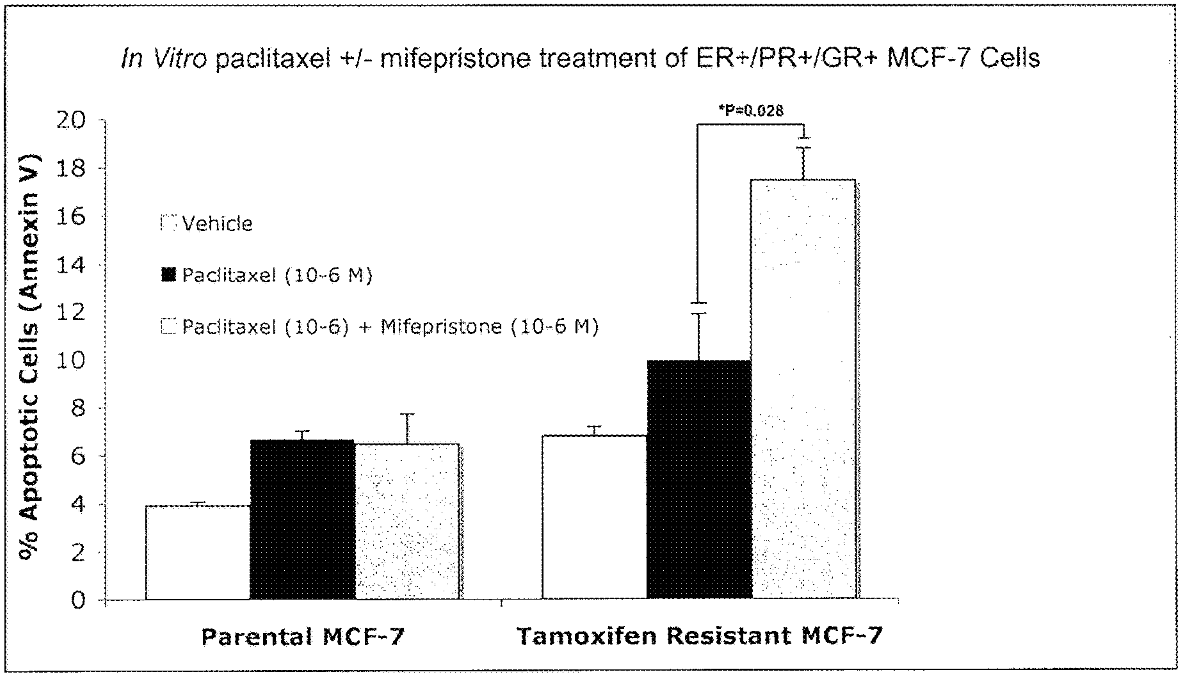
FIG. 9. Mifepristone pretreatment increases tamoxifen-resistant MCF-7 (T-R-MCF-7), but not parental MCF-7 cell susceptibility to paclitaxel in vitro.

Mifepristone Pretreatment Increases Tamoxifen-Resistant MCF-7 (T-R-MCF-7), but not Parental MCF-7 Cell Susceptibility to Paclitaxel In Vitro Parental MCF-7 (ER+/PR+/GR+) and T-R MCF-7 (ER+/PR+/GR+) cells were treated with the appropriate vehicle (ethanol for mifepristone and castor oil/saline for paclitaxel), paclitaxel alone ($10^{-6}$ M), and paclitaxel/mifepristone ($10^{-6}$ M). Apoptosis was measured using FITC conjugated-anti-Annexin V antibody labeling followed FACS analysis to determine the percentage of the total cell population undergoing apoptosis after 20 hours of treatment. Mean+/−SE is shown. Significantly more apoptosis (P=0.028) was observed in the T-R MCF-7 cells when treated with mifepristone/paclitaxel compared to paclitaxel alone (FIG. 9). No difference was seen in the parental MCF-7 cells.

```
Sequence Listing
NR3C1 GenBank AY436590 - 127687 bp, incorporated herein by reference
ESR1 GenBank NG_008493 - 419779 bp, incorporated herein by reference
NR3C1 mRNA
                                                          SEQ ID NO: 1
TTTTTAGAAAAAAAAAATATATTTCCCTCCTGCTCCTTCTGCGTTCACAAGCTAAGTTGTTTATCTCGGC

TGCGGCGGGAACTGCGGACGGTGGCGGGCGAGCGGCTCCTCTGCCAGAGTTGATATTCACTGATGGACTC

CAAAGAATCATTAACTCCTGGTAGAGAAGAAAACCCCAGCAGTGTGCTTGCTCAGGAGAGGGGAGATGTG

ATGGACTTCTATAAAACCCTAAGAGGAGGAGCTACTGTGAAGGTTTCTGCGTCTTCACCCTCACTGGCTG

TCGCTTCTCAATCAGACTCCAAGCAGCGAAGACTTTTGGTTGATTTTCCAAAAGGCTCAGTAAGCAATGC

GCAGCAGCCAGATCTGTCCAAAGCAGTTTCACTCTCAATGGGACTGTATATGGGAGAGACAGAAACAAAA

GTGATGGGAAATGACCTGGGATTCCCACAGCAGGGCCAAATCAGCCTTTCCTCGGGGGAAACAGACTTAA

AGCTTTTGGAAGAAAGCATTGCAAACCTCAATAGGTCGACCAGTGTTCCAGAGAACCCCAAGAGTTCAGC

ATCCACTGCTGTGTCTGCTGCCCCCACAGAGAAGGAGTTTCCAAAAACTCACTCTGATGTATCTTCAGAA

CAGCAACATTTGAAGGGCCAGACTGGCACCAACGGTGGCAATGTGAAATTGTATACCACAGACCAAAGCA

CCTTTGACATTTTGCAGGATTTGGAGTTTTCTTCTGGGTCCCCAGGTAAAGAGACGAATGAGAGTCCTTG

GAGATCAGACCTGTTGATAGATGAAAACTGTTTGCTTTCTCCTCTGGCGGGAGAAGACGATTCATTCCTT

TTGGAAGGAAACTCGAATGAGGACTGCAAGCCTCTCATTTTACCGGACACTAAACCCAAAATTAAGGATA

ATGGAGATCTGGTTTTGTCAAGCCCCAGTAATGTAACACTGCCCCAAGTGAAAACAGAAAAAGAAGATTT

CATCGAACTCTGCACCCCTGGGGTAATTAAGCAAGAGAAACTGGGCACAGTTTACTGTCAGGCAAGCTTT

CCTGGAGCAAATATAATTGGTAATAAAATGTCTGCCATTTCTGTTCATGGTGTGAGTACCTCTGGAGGAC

AGATGTACCACTATGACATGAATACAGCATCCCTTTCTCAACAGCAGGATCAGAAGCCTATTTTTAATGT

CATTCCACCAATTCCCGTTGGTTCCGAAAATTGGAATAGGTGCCAAGGATCTGGAGATGACAACTTGACT

TCTCTGGGGACTCTGAACTTCCCTGGTCGAACAGTTTTTTCTAATGGCTATTCAAGCCCCAGCATGAGAC
```

-continued

CAGATGTAAGCTCTCCTCCATCCAGCTCCTCAACAGCAACAACAGGACCACCTCCCAAACTCTGCCTGGT

GTGCTCTGATGAAGCTTCAGGATGTCATTATGGAGTCTTAACTTGTGGAAGCTGTAAAGTTTTCTTCAAA

AGAGCAGTGGAAGGACAGCACAATTACCTATGTGCTGGAAGGAATGATTGCATCATCGATAAAATTCGAA

GAAAAAACTGCCCAGCATGCCGCTATCGAAAATGTCTTCAGGCTGGAATGAACCTGGAAGCTCGAAAAAC

AAAGAAAAAAATAAAAGGAATTCAGCAGGCCACTACAGGAGTCTCACAAGAAACCTCTGAAAATCCTGGT

AACAAAACAATAGTTCCTGCAACGTTACCACAACTCACCCCTACCCTGGTGTCACTGTTGGAGGTTATTG

AACCTGAAGTGTTATATGCAGGATATGATAGCTCTGTTCCAGACTCAACTTGGAGGATCATGACTACGCT

CAACATGTTAGGAGGGCGGCAAGTGATTGCAGCAGTGAAATGGGCAAAGGCAATACCAGGTTTCAGGAAC

TTACACCTGGATGACCAAATGACCCTACTGCAGTACTCCTGGATGTTTCTTATGGCATTTGCTCTGGGGT

GGAGATCATATAGACAATCAAGTGCAAACCTGCTGTGTTTTGCTCCTGATCTGATTATTAATGAGCAGAG

AATGACTCTACCCTGCATGTACGACCAATGTAAACACATGCTGTATGTTTCCTCTGAGTTACACAGGCTT

CAGGTATCTTATGAAGAGTATCTCTGTATGAAAACCTTACTGCTTCTCTCTTCAGTTCCTAAGGACGGTC

TGAAGAGCCAAGAGCTATTTGATGAAATTAGAATGACCTACATCAAAGAGCTAGGAAAAGCCATTGTCAA

GAGGGAAGGAAACTCCAGCCAGAACTGGCAGCGGTTTTATCAACTGACAAAACTCTTGGATTCTATGCAT

GAAGTGGTTGAAAATCTCCTTAACTATTGCTTCCAAACATTTTTGGATAAGACCATGAGTATTGAATTCC

CCGAGATGTTAGCTGAAATCATCACCAATCAGATACCAAAATATTCAAATGGAAATATCAAAAAACTTCT

GTTTCATCAAAAGTGACTGCCTTAATAAGAATGGTTGCCTTAAAGAAAGTCGAATTAATAGCTTTTATTG

TATAAACTATCAGTTTGTCCTGTAGAGGTTTTGTTGTTTTATTTTTTATTGTTTTCATCTGTTGTTTTGT

TTTAAATACGCACTACATGTGGTTTATAGAGGGCCAAGACTTGGCAACAGAAGCAGTTGAGTCGTCATCA

CTTTTCAGTGATGGGAGAGTAGATGGTGAAATTTATTAGTTAATATATCCCAGAAATTAGAAACCTTAAT

ATGTGGACGTAATCTCCACAGTCAAAGAAGGATGGCACCTAAACCACCAGTGCCCAAAGTCTGTGTGATG

AACTTTCTCTTCATACTTTTTTTCACAGTTGGCTGGATGAAATTTTCTAGACTTTCTGTTGGTGTATCCC

CCCCCCTGTATAGTTAGGATAGCATTTTTGATTTATGCATGGAAACCTGAAAAAAAGTTTACAAGTGTAT

ATCAGAAAAGGGAAGTTGTGCCTTTTATAGCTATTACTGTCTGGTTTTAACAATTTCCTTTATATTTAGT

GAACTACGCTTGCTCATTTTTTCTTACATAATTTTTTATTCAAGTTATTGTACAGCTGTTTAAGATGGGC

AGCTAGTTCGTAGCTTTCCCAAATAAACTCTAAACATTAATCAATCATCTGTGTGAAAATGGGTTGGTGC

TTCTAACCTGATGGCACTTAGCTATCAGAAGACCACAAAAATTGACTCAAATCTCCAGTATTCTTGTCAA

AAAAAAAAAAAAAAAAGCTCATATTTTGTATATATCTGCTTCAGTGGAGAATTATATAGGTTGTGCAAAT

TAACAGTCCTAACTGGTATAGAGCACCTAGTCCAGTGACCTGCTGGGTAAACTGTGGATGATGGTTGCAA

AAGACTAATTTAAAAAATAACTACCAAGAGGCCCTGTCTGTACCTAACGCCCTATTTTTGCAATGGCTAT

ATGGCAAGAAAGCTGGTAAACTATTTGTCTTTCAGGACCTTTTGAAGTAGTTTGTATAACTTCTTAAAAG

TTGTGATTCCAGATAACCAGCTGTAACACAGCTGAGAGACTTTTAATCAGACAAAGTAATTCCTCTCACT

AAACTTTACCCAAAAACTAAATCTCTAATATGGCAAAAATGGCTAGACACCCATTTTCACATTCCCATCT

GTCACCAATTGGTTAATCTTTCCTGATGGTACAGGAAAGCTCAGCTACTGATTTTTGTGATTTAGAACTG

TATGTATGTCAGACATCCATGTTTGTAAAACTACACATCCCTAATGTGTGCCATAGAGTTTAACACAAGT

CCTGTGAATTTCTTCACTGTTGAAAATTATTTTAAACAAAATAGAAGCTGTAGTAGCCCTTTCTGTGTGC

ACCTTACCAACTTTCTGTAAACTCAAAACTTAACATATTTACTAAGCCACAAGAAATTTGATTTCTATTC

AAGGTGGCCAAATTATTTGTGTAATAGAAAACTGAAAATCTAATATTAAAAATATGGAACTTCTAATATA

TTTTTATATTTAGTTATAGTTTCAGATATATATCATATTGGTATTCACTAATCTGGGAAGGGAAGGGCTA

CTGCAGCTTTACATGCAATTTATTAAAATGATTGTAAAATAGCTTGTATAGTGTAAAATAAGAATGATTT

TTAGATGAGATTGTTTTATCATGACATGTTATATATTTTTTGTAGGGGTCAAAGAAATGCTGATGGATAA

-continued

CCTATATGATTTATAGTTTGTACATGCATTCATACAGGCAGCGATGGTCTCAGAAACCAAACAGTTTGCT

CTAGGGGAAGAGGGAGATGGAGACTGGTCCTGTGTGCAGTGAAGGTTGCTGAGGCTCTGACCCAGTGAGA

TTACAGAGGAAGTTATCCTCTGCCTCCCATTCTGACCACCCTTCTCATTCCAACAGTGAGTCTGTCAGCG

CAGGTTTAGTTTACTCAATCTCCCCTTGCACTAAAGTATGTAAAGTATGTAAACAGGAGACAGGAAGGTG

GTGCTTACATCCTTAAAGGCACCATCTAATAGCGGGTTACTTTCACATACAGCCCTCCCCCAGCAGTTGA

ATGACAACAGAAGCTTCAGAAGTTTGGCAATAGTTTGCATAGAGGTACCAGCAATATGTAAATAGTGCAG

AATCTCATAGGTTGCCAATAATACACTAATTCCTTTCTATCCTACAACAAGAGTTTATTTCCAAATAAAA

TGAGGACATGTTTTTGTTTTCTTTGAATGCTTTTTGAATGTTATTTGTTATTTTCAGTATTTTGGAGAAA

TTATTTAATAAAAAAAACAATCATTTGCTTTTTG

ESR1 mRNA

SEQ ID NO: 2

AGGAGCTGGC GGAGGGCGTT CGTCCTGGGA CTGCACTTGC TCCCGTCGGG TCGCCCGGCT

TCACCGGACC CGCAGGCTCC CGGGGCAGGG CCGGGGCCAG AGCTCGCGTG TCGGCGGGAC

ATGCGCTGCG TCGCCTCTAA CCTCGGGCTG TGCTCTTTTT CCAGGTGGCC CGCCGGTTTC

TGAGCCTTCT GCCCTGCGGG GACACGGTCT GCACCCTGCC CGCGGCCACG GACCATGACC

ATGACCCTCC ACACCAAAGC ATCTGGGATG GCCCTACTGC ATCAGATCCA AGGGAACGAG

CTGGAGCCCC TGAACCGTCC GCAGCTCAAG ATCCCCCTGG AGCGGCCCCT GGGCGAGGTG

TACCTGGACA GCAGCAAGCC CGCCGTGTAC AACTACCCCG AGGGCGCCGC CTACGAGTTC

AACGCCGCGG CCGCCGCCAA CGCGCAGGTC TACGGTCAGA CCGGCCTCCC CTACGGCCCC

GGGTCTGAGG CTGCGGCGTT CGGCTCCAAC GGCCTGGGGG GTTTCCCCCC ACTCAACAGC

GTGTCTCCGA GCCCGCTGAT GCTACTGCAC CCGCCGCCGC AGCTGTCGCC TTTCCTGCAG

CCCCACGGCC AGCAGGTGCC CTACTACCTG GAGAACGAGC CCAGCGGCTA CACGGTGCGC

GAGGCCGGCC CGCCGGCATT CTACAGGCCA AATTCAGATA ATCGACGCCA GGGTGGCAGA

GAAAGATTGG CCAGTACCAA TGACAAGGGA AGTATGGCTA TGGAATCTGC CAAGGAGACT

CGCTACTGTG CAGTGTGCAA TGACTATGCT TCAGGCTACC ATTATGGAGT CTGGTCCTGT

GAGGGCTGCA AGGCCTTCTT CAAGAGAAGT ATTCAAGGAC ATAACGACTA TATGTGTCCA

GCCACCAACC AGTGCACCAT TGATAAAAAC AGGAGGAAGA GCTGCCAGGC CTGCCGGCTC

CGCAAATGCT ACGAAGTGGG AATGATGAAA GGTGGGATAC GAAAAGACCG AAGAGGAGGG

AGAATGTTGA AACACAAGCG CCAGAGAGAT GATGGGGAGG GCAGGGGTGA AGTGGGGTCT

GCTGGAGACA TGAGAGCTGC CAACCTTTGG CCAAGCCCGC TCATGATCAA ACGCTCTAAG

AAGAACAGCC TGGCCTTGTC CCTGACGGCC GACCAGATGG TCAGTGCCTT GTTGGATGCT

GAGCCCCCCA TACTCTATTC CGAGTATGAT CCTACCAGAC CCTTCAGTGA AGCTTCGATG

ATGGGCTTAC TGACCAACCT GGCAGACAGG GAGCTGGTTC ACATGATCAA CTGGGCGAAG

AGGGTGCCAG GCTTTGTGGA TTTGACCCTC CATGATCAGG TCCACCTTCT AGAATGTGCC

TGGCTAGAGA TCCTGATGAT TGGTCTCGTC TGGCGCTCCA TGGAGCACCC AGGGAAGCTA

CTGTTTGCTC CTAACTTGCT CTTGGACAGG AACCAGGGAA AATGTGTAGA GGGCATGGTG

GAGATCTTCG ACATGCTGCT GGCTACATCA TCTCGGTTCC GCATGATGAA TCTGCAGGGA

GAGGAGTTTG TGTGCCTCAA ATCTATTATT TTGCTTAATT CTGGAGTGTA CACATTTCTG

TCCAGCACCC TGAAGTCTCT GGAAGAGAAG GACCATATCC ACCGAGTCCT GGACAAGATC

ACAGACACTT TGATCCACCT GATGGCCAAG GCAGGCCTGA CCCTGCAGCA GCAGCACCAG

CGGCTGGCCC AGCTCCTCCT CATCCTCTCC CACATCAGGC ACATGAGTAA CAAAGGCATG

-continued

GAGCATCTGT ACAGCATGAA GTGCAAGAAC GTGGTGCCCC TCTATGACCT GCTGCTGGAG

ATGCTGGACG CCCACCGCCT ACATGCGCCC ACTAGCCGTG GAGGGGCATC CGTGGAGGAG

ACGGACCAAA GCCACTTGGC CACTGCGGGC TCTACTTCAT CGCATTCCTT GCAAAAGTAT

TACATCACGG GGGAGGCAGA GGGTTTCCCT GCCACGGTCT GAGAGCTCCC TGGCTCCCAC

ACGGTTCAGA TAATCCCTGC TGCATTTTAC CCTCATCATG CACCACTTTA GCCAAATTCT

GTCTCCTGCA TACACTCCGG CATGCATCCA ACACCAATGG CTTTCTAGAT GAGTGGCCAT

TCATTTGCTT GCTCAGTTCT TAGTGGCACA TCTTCTGTCT TCTGTTGGGA ACAGCCAAAG

GGATTCCAAG GCTAAATCTT TGTAACAGCT CTCTTTCCCC CTTGCTATGT TACTAAGCGT

GAGGATTCCC GTAGCTCTTC ACAGCTGAAC TCAGTCTATG GGTTGGGGCT CAGATAACTC

TGTGCATTTA AGCTACTTGT AGAGACCCAG GCCTGGAGAG TAGACATTTT GCCTCTGATA

AGCACTTTTT AAATGGCTCT AAGAATAAGC CACAGCAAAG AATTTAAAGT GGCTCCTTTA

ATTGGTGACT TGGAGAAAGC TAGGTCAAGG GTTTATTATA GCACCCTCTT GTATTCCTAT

GGCAATGCAT CCTTTTATGA AAGTGGTACA CCTTAAAGCT TTTATATGAC TGTAGCAGAG

TATCTGGTGA TTGTCAATTC ATTCCCCCTA TAGGAATACA AGGGGCACAC AGGGAAGGCA

GATCCCCTAG TTGGCAAGAC TATTTTAACT TGATACACTG CAGATTCAGA TGTGCTGAAA

GCTCTGCCTC TGGCTTTCCG GTCATGGGTT CCAGTTAATT CATGCCTCCC ATGGACCTAT

GGAGAGCAGC AAGTTGATCT TAGTTAAGTC TCCCTATATG AGGGATAAGT TCCTGATTTT

TGTTTTTATT TTTGTGTTAC AAAAGAAAGC CCTCCCTCCC TGAACTTGCA GTAAGGTCAG

CTTCAGGACC TGTTCCAGTG GGCACTGTAC TTGGATCTTC CCGGCGTGTG TGTGCCTTAC

ACAGGGGTGA ACTGTTCACT GTGGTGATGC ATGATGAGGG TAAATGGTAG TTGAAAGGAG

CAGGGGCCCT GGTGTTGCAT TTAGCCCTGG GGCATGGAGC TGAACAGTAC TTGTGCAGGA

TTGTTGTGGC TACTAGAGAA CAAGAGGGAA AGTAGGGCAG AAACTGGATA CAGTTCTGAG

GCACAGCCAG ACTTGCTCAG GGTGGCCCTG CCACAGGCTG CAGCTACCTA GGAACATTCC

TTGCAGACCC CGCATTGCCC TTTGGGGGTG CCCTGGGATC CCTGGGGTAG TCCAGCTCTT

CTTCATTTCC CAGCGTGGCC CTGGTTGGAA GAAGCAGCTG TCACAGCTGC TGTAGACAGC

TGTGTTCCTA CAATTGGCCC AGCACCCTGG GGCACGGGAG AAGGGTGGGG ACCGTTGCTG

TCACTACTCA GGCTGACTGG GGCCTGGTCA GATTACGTAT GCCCTTGGTG GTTTAGAGAT

AATCCAAAAT CAGGGTTTGG TTTGGGGAAG AAAATCCTCC CCCTTCCTCC CCCGCCCCGT

TCCCTACCGC CTCCACTCCT GCCAGCTCAT TTCCTTCAAT TTCCTTTGAC CTATAGGCTA

AAAAAGAAAG GCTCATTCCA GCCACAGGGC AGCCTTCCCT GGGCCTTTGC TTCTCTAGCA

CAATTATGGG TTACTTCCTT TTTCTTAACA AAAAAGAATG TTTGATTTCC TCTGGGTGAC

CTTATTGTCT GTAATTGAAA CCCTATTGAG AGGTGATGTC TGTGTTAGCC AATGACCCAG

GTGAGCTGCT CGGGCTTCTC TTGGTATGTC TTGTTTGGAA AAGTGGATTT CATTCATTTC

TGATTGTCCA GTTAAGTGAT CACCAAAGGA CTGAGAATCT GGGAGGGCAA AAAAAAAAAA

AAAGTTTTTA TGTGCACTTA AATTTGGGGA CAATTTTATG TATCTGTGTT AAGGATATGT

TTAAGAACAT AATTCTTTTG TTGCTGTTTG TTTAAGAAGC ACCTTAGTTT GTTTAAGAAG

CACCTTATAT AGTATAATAT ATATTTTTTT GAAATTACAT TGCTTGTTTA TCAGACAATT

GAATGTAGTA ATTCTGTTCT GGATTTAATT TGACTGGGTT AACATGCAAA AACCAAGGAA

AAATATTTAG TTTTTTTTTT TTTTTTTGTA TACTTTTCAA GCTACCTTGT CATGTATACA

GTCATTTATG CCTAAAGCCT GGTGATTATT CATTTAAATG AAGATCACAT TTCATATCAA

CTTTTGTATC CACAGTAGAC AAAATAGCAC TAATCCAGAT GCCTATTGTT GGATACTGAA

-continued

TGACAGACAA TCTTATGTAG CAAAGATTAT GCCTGAAAAG GAAAATTATT CAGGGCAGCT
AATTTTGCTT TTACCAAAAT ATCAGTAGTA ATATTTTTGG ACAGTAGCTA ATGGGTCAGT
GGGTTCTTTT TAATGTTTAT ACTTAGATTT TCTTTTAAAA AAATTAAAAT AAAACAAAAA
AAAATTTCTA GGACTAGACG ATGTAATACC AGCTAAAGCC AAACAATTAT ACAGTGGAAG
GTTTTACATT ATTCATCCAA TGTGTTTCTA TTCATGTTAA GATACTACTA CATTTGAAGT
GGGCAGAGAA CATCAGATGA TTGAAATGTT CGCCCAGGGG TCTCCAGCAA CTTTGGAAAT
CTCTTTGTAT TTTTACTTGA AGTGCCACTA ATGGACAGCA GATATTTTCT GGCTGATGTT
GGTATTGGGT GTAGGAACAT GATTTAAAAA AAAACTCTTG CCTCTGCTTT CCCCCACTCT
GAGGCAAGTT AAAATGTAAA AGATGTGATT TATCTGGGGG GCTCAGGTAT GGTGGGGAAG
TGGATTCAGG AATCTGGGGA ATGGCAAATA TATTAAGAAG AGTATTGAAA GTATTTGGAG
GAAAATGGTT AATTCTGGGT GTGCACCAGG GTTCAGTAGA GTCCACTTCT GCCCTGGAGA
CCACAAATCA ACTAGCTCCA TTTACAGCCA TTTCTAAAAT GGCAGCTTCA GTTCTAGAGA
AGAAAGAACA ACATCAGCAG TAAAGTCCAT GGAATAGCTA GTGGTCTGTG TTTCTTTTCG
CCATTGCCTA GCTTGCCGTA ATGATTCTAT AATGCCATCA TGCAGCAATT ATGAGAGGCT
AGGTCATCCA AAGAGAAGAC CCTATCAATG TAGGTTGCAA AATCTAACCC CTAAGGAAGT
GCAGTCTTTG ATTTGATTTC CCTAGTAACC TTGCAGATAT GTTTAACCAA GCCATAGCCC
ATGCCTTTTG AGGGCTGAAC AAATAAGGGA CTTACTGATA ATTTACTTTT GATCACATTA
AGGTGTTCTC ACCTTGAAAT CTTATACACT GAAATGGCCA TTGATTTAGG CCACTGGCTT
AGAGTACTCC TTCCCCTGCA TGACACTGAT TACAAATACT TTCCTATTCA TACTTTCCAA
TTATGAGATG GACTGTGGGT ACTGGGAGTG ATCACTAACA CCATAGTAAT GTCTAATATT
CACAGGCAGA TCTGCTTGGG GAAGCTAGTT ATGTGAAAGG CAAATAGAGT CATACAGTAG
CTCAAAAGGC AACCATAATT CTCTTTGGTG CAGGTCTTGG GAGCGTGATC TAGATTACAC
TGCACCATTC CCAAGTTAAT CCCCTGAAAA CTTACTCTCA ACTGGAGCAA ATGAACTTTG
GTCCCAAATA TCCATCTTTT CAGTAGCGTT AATTATGCTC TGTTTCCAAC TGCATTTCCT
TTCCAATTGA ATTAAAGTGT GGCCTCGTTT TTAGTCATTT AAAATTGTTT TCTAAGTAAT
TGCTGCCTCT ATTATGGCAC TTCAATTTTG CACTGTCTTT TGAGATTCAA GAAAAATTTC
TATTCTTTTT TTTGCATCCA ATTGTGCCTG AACTTTTAAA ATATGTAAAT GCTGCCATGT
TCCAAACCCA TCGTCAGTGT GTGTGTTTAG AGCTGTGCAC CCTAGAAACA ACATATTGTC
CCATGAGCAG GTGCCTGAGA CACAGACCCC TTTGCATTCA CAGAGAGGTC ATTGGTTATA
GAGACTTGAA TTAATAAGTG ACATTATGCC AGTTTCTGTT CTCTCACAGG TGATAAACAA
TGCTTTTTGT GCACTACATA CTCTTCAGTG TAGAGCTCTT GTTTTATGGG AAAAGGCTCA
AATGCCAAAT TGTGTTTGAT GGATTAATAT GCCCTTTTGC CGATGCATAC TATTACTGAT
GTGACTCGGT TTTGTCGCAG CTTTGCTTTG TTTAATGAAA CACACTTGTA AACCTCTTTT
GCACTTTGAA AAAGAATCCA GCGGGATGCT CGAGCACCTG TAAACAATTT TCTCAACCTA

SEQ ID NO: 3-46

MCL1, SAP30, DUSP1, SGK1, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, IDH2, SERPINF1, ERBB2, PECAM1, LBH, ST3GAL5, IL1R1, BIN1, WIPF1, TFPI, FN1, FAM134A, NRIP1, RAC2, SPP1, PHF15, BTN3A2, SESN1, MAP3K5, DPYSL2, SEMA4D, STOM, and MAOA gene.

REFERENCES

The following references, to the extent that they provide exemplary procedural or other details supplementary to those set forth herein, are specifically incorporated herein by reference.

U.S. Pat. No. 5,143,854
U.S. Pat. No. 5,202,231
U.S. Pat. No. 5,242,974
U.S. Pat. No. 5,288,644
U.S. Pat. No. 5,324,633
U.S. Pat. No. 5,384,261
U.S. Pat. No. 5,405,783
U.S. Pat. No. 5,412,087
U.S. Pat. No. 5,424,186
U.S. Pat. No. 5,429,807
U.S. Pat. No. 5,432,049
U.S. Pat. No. 5,436,327
U.S. Pat. No. 5,445,934
U.S. Pat. No. 5,468,613
U.S. Pat. No. 5,470,710
U.S. Pat. No. 5,472,672
U.S. Pat. No. 5,492,806
U.S. Pat. No. 5,503,980
U.S. Pat. No. 5,510,270
U.S. Pat. No. 5,525,464
U.S. Pat. No. 5,527,681
U.S. Pat. No. 5,529,756
U.S. Pat. No. 5,532,128
U.S. Pat. No. 5,545,531
U.S. Pat. No. 5,547,839
U.S. Pat. No. 5,554,501
U.S. Pat. No. 5,556,752
U.S. Pat. No. 5,561,071
U.S. Pat. No. 5,571,639
U.S. Pat. No. 5,580,726
U.S. Pat. No. 5,580,732
U.S. Pat. No. 5,593,839
U.S. Pat. No. 5,599,672
U.S. Pat. No. 5,599,695
U.S. Pat. No. 5,610,287
U.S. Pat. No. 5,624,711
U.S. Pat. No. 5,631,134
U.S. Pat. No. 5,639,603
U.S. Pat. No. 5,654,413
U.S. Pat. No. 5,658,734
U.S. Pat. No. 5,661,028
U.S. Pat. No. 5,665,547
U.S. Pat. No. 5,667,972
U.S. Pat. No. 5,695,940
U.S. Pat. No. 5,700,637
U.S. Pat. No. 5,744,305
U.S. Pat. No. 5,800,992
U.S. Pat. No. 5,807,522
U.S. Pat. No. 5,830,645
U.S. Pat. No. 5,837,196
U.S. Pat. No. 5,847,219
U.S. Pat. No. 5,871,928
U.S. Pat. No. 5,876,932
U.S. Pat. No. 5,919,626
U.S. Pat. No. 6,004,755
U.S. Pat. No. 6,087,102
U.S. Pat. No. 6,368,799
U.S. Pat. No. 6,383,749
U.S. Pat. No. 6,617,112
U.S. Pat. No. 6,638,717
U.S. Pat. No. 6,720,138
U.S. Patent Publn. 2010/0135956
Belanoff et al., *Eur. J. Pharmacol.,* 655(1-3):117-20, 2011.
Cho et al. *Biochemistry,* 44(9):3547-61, 2005.
Clark, *Curr. Top. Med. Chem.* 8(9):813-838, 2008.
Colleoni et al., *Annals of Oncology,* 11(8):1057, 2000.
European Appln. EP 373 203
European Appln. EP 785 280
European Appln. EP 799 897
Evans, *Science,* 240:889, 1988.
Fodor et al., *Science,* 251:767-777, 1991.
Grover and Martin, *Carcinogenesis,* 23(7):1095-102, 2002.
Hacia et al., *Nature Genet.,* 14:441-449, 1996.
Harrison's Principles of Internal Medicine, Kasper et al. (Eds.), $16^{th}$ Ed., Chapter 70, 2005.
Henderson et al. *Cancer Res.,* 48:246-253, 1988.
Keen and Davidson, *Cancer,* 97(3 Suppl):825-33, 2003.
Ma et al., *J. Immunol.,* 171(2):608-615, 2003.
MacBeath and Schreiber, *Science,* 289(5485):1760-3, 2000.
Melhem et al, *Clin. Cancer Res.,* 15(9):3196-204, 2009.
Mikosz et al., *J. Biol. Chem.,* 276:16649-54, 2001.
Moran et al., *Cancer Res.,* 60:867-872, 2000.
Pandey and Mann, *Nature,* 405(6788):837-46, 2000.
Pang and Conzen, *Cancer Biol. Ther. Cancer Biol. Ther.,* 5(8):933-40, 2006.
PCT Appln. WO 01/68255
PCT Appln. WO 03/020898
PCT Appln. WO 03/022421
PCT Appln. WO 03/023058
PCT Appln. WO 03/029485
PCT Appln. WO 03/040410
PCT Appln. WO 03/053586
PCT Appln. WO 03/066906
PCT Appln. WO 03/067217
PCT Appln. WO 03/076928
PCT Appln. WO 03/087297
PCT Appln. WO 03/091426
PCT Appln. WO 03/093810
PCT Appln. WO 03/100448A1
PCT Appln. WO 04/020085
PCT Appln. WO 04/027093
PCT Appln. WO 09/923256
PCT Appln. WO 09/936760
PCT Appln. WO 93/17126
PCT Appln. WO 95/11995
PCT Appln. WO 95/21265
PCT Appln. WO 95/21944
PCT Appln. WO 95/35505
PCT Appln. WO 96/30347
PCT Appln. WO 96/31622
PCT Appln. WO 96/33980
PCT Appln. WO 97/10365
PCT Appln. WO 97/27317
PCT Appln. WO 9743450
PCT Appln. WO 99/35505
PCT Appln. WO 01/38580
PCT Appln. WO 03/100012
Pease et al., *Proc. Natl. Acad. Sci. USA,* 91:5022-5026, 1994.
Peeters et al., *Ann. NY Acad. Sci.,* 1148:536-41, 2008.
Pike et al., *Epidemiologic Revi.,* 15(1):17-35, 1993.
Shoemaker et al., *Nature Genetics,* 14:450-456, 1996.
Sims et al. *BMC Medical Genomics,* 1(42):1-14, 2008.
Sorlie et al., *Proc. Natl. Acad. Sci. USA,* 98:10869-10874., 2001.
Srinivas et al., *Clin. Chem.,* 48(8):1160-9, 2002.
UK Appln. 8 803 000
Wu et al., *Cancer Res.,* 64:1757-64, 2004.
Wu et al., *J. Clin. Invest.,* 114:560-568, 2004.
Wu et al., *Mol Endocrinol.,* 2006

What is claimed is:

1. A method for treating breast cancer in a patient having breast cancer cells, the method comprising:
   a) administering an effective amount of a glucocorticoid receptor antagonist to said patient, wherein said glucocorticoid receptor antagonist is selected from beclometasone, betamethasone, budesonide, ciclesonide, flunisolide, fluticasone, mifepristone, mometasone, triamcinolone, ORG-34517 (Merck), RU-43044, dexamethasone mesylate (Dex-Mes), dexamethasone oxetanone (Dex-Ox), deoxycorticosterone (DOC), CORT 0113083, and CORT 00112716, and wherein the patient expresses a detectable level of glucocorticoid receptor (GR) prior to administration of the GR antagonist;
   b) then administering an effective amount of radiation, immunotherapy, or at least one chemotherapeutic agent.

2. The method of claim 1, wherein said breast cancer cells undergo apoptosis.

3. The method of claim 1, wherein said breast cancer patient was previously treated with chemotherapy.

4. The method of claim 1, wherein the breast cancer patient is determined to have breast cancer cells that express a detectable level of glucocorticoid receptor.

5. The method of claim 1, wherein the breast cancer patient is determined to have breast cancer cells that do not express a detectable level of estrogen receptor but do express a detectable level of glucocorticoid receptor.

6. The method of claim 5, wherein the effective amount of radiation, immunotherapy, or at least one chemotherapeutic agent is administered within 1 week of administration of the glucocorticoid receptor antagonist.

7. The method of claim 6, wherein the effective amount of radiation, immunotherapy, or at least one chemotherapeutic agent is administered within 24 hours of the administration of the glucocorticoid receptor antagonist.

8. The method of claim 6, wherein the glucocorticoid receptor antagonist is administered up to three days prior to administering the effective amount of radiation, immunotherapy, or at least one chemotherapeutic agent.

9. The method of claim 5, comprising further administration of the glucocorticoid receptor antagonist after administration of the effective amount of radiation, immunotherapy, or at least one chemotherapeutic agent.

10. The method of claim 5, wherein the breast cancer cells are PR- and HER2-.

11. The method of claim 1, wherein the glucocorticoid receptor antagonist is GR-selective.

12. The method of claim 1, wherein the breast cancer patient was previously administered said effective amount of radiation, immunotherapy, or at least one chemotherapeutic agent more than two weeks prior to the administration of said glucocorticoid receptor antagonist.

13. The method of claim 12, wherein breast cancer cells in the breast cancer patient were resistant to apoptosis.

14. The method of claim 12, wherein breast cancer cells in the breast cancer patient express a detectable level of glucocorticoid receptor.

15. The method of claim 12, wherein the breast cancer cells in the breast cancer patient do not express a detectable level of estrogen receptor.

16. The method of claim 1, wherein the effective amount of radiation, immunotherapy, or at least one chemotherapeutic agent is administered within 1 week of the administration of the glucocorticoid receptor antagonist.

17. The method of claim 16, wherein the effective amount of radiation, immunotherapy, or at least one chemotherapeutic agent is administered within 24 hours of the administration of the glucocorticoid receptor antagonist.

18. The method of claim 16, wherein the glucocorticoid receptor antagonist is administered up to three days prior to administering the effective amount of radiation, immunotherapy, or at least one chemotherapeutic agent.

19. The method of claim 1, comprising further administration of the glucocorticoid receptor antagonist after administration of the effective amount of radiation, immunotherapy, or at least one chemotherapeutic agent.

20. The method of claim 1, wherein the breast cancer cells are PR- and HER2-.

* * * * *

SEQUENCE LISTING

<160> NUMBER OF SEQ ID NOS: 46

<210> SEQ ID NO 1
<211> LENGTH: 4794
<212> TYPE: DNA
<213> ORGANISM: Homo sapiens

<400> SEQUENCE: 1

```
tttttagaaa aaaaaaatat atttccctcc tgctccttct gcgttcacaa gctaagttgt     60
ttatctcggc tgcggcggga actgcggacg gtggcgggcg agcggctcct ctgccagagt    120
tgatattcac tgatggactc caaagaatca ttaactcctg gtagagaaga aaaccccagc    180
agtgtgcttg ctcaggagag gggagatgtg atggacttct ataaaaccct aagaggagga    240
gctactgtga aggtttctgc gtcttcaccc tcactggctg tcgcttctca atcagactcc    300
aagcagcgaa gacttttggt tgattttcca aaaggctcag taagcaatgc gcagcagcca    360
gatctgtcca aagcagtttc actctcaatg ggactgtata tgggagagac agaaacaaaa    420
gtgatgggaa atgacctggg attcccacag cagggccaaa tcagcctttc ctcgggggaa    480
acagacttaa agcttttgga agaaagcatt gcaaacctca ataggtcgac cagtgttcca    540
gagaacccca agagttcagc atccactgct gtgtctgctg cccccacaga gaaggagttt    600
ccaaaaactc actctgatgt atcttcagaa cagcaacatt tgaagggcca gactggcacc    660
aacggtggca atgtgaaatt gtataccaca gaccaaagca cctttgacat tttgcaggat    720
ttggagtttt cttctgggtc cccaggtaaa gagacgaatg agagtccttg gagatcagac    780
ctgttgatag atgaaaactg tttgctttct cctctggcgg gagaagacga ttcattcctt    840
ttggaaggaa actcgaatga ggactgcaag cctctcattt taccggacac taaacccaaa    900
attaaggata atggagatct ggttttgtca agccccagta atgtaacact gccccaagtg    960
aaaacagaaa aagaagattt catcgaactc tgcacccctg gggtaattaa gcaagagaaa   1020
ctgggcacag tttactgtca ggcaagcttt cctggagcaa atataattgg taataaaatg   1080
tctgccattt ctgttcatgg tgtgagtacc tctggaggac agatgtacca ctatgacatg   1140
aatacagcat ccctttctca acagcaggat cagaagccta tttttaatgt cattccacca   1200
attcccgttg gttccgaaaa ttggaatagg tgccaaggat ctggagatga caacttgact   1260
tctctgggga ctctgaactt ccctggtcga acagtttttt ctaatggcta ttcaagcccc   1320
agcatgagac cagatgtaag ctctcctcca tccagctcct caacagcaac aacaggacca   1380
cctcccaaac tctgcctggt gtgctctgat gaagcttcag gatgtcatta tggagtctta   1440
acttgtggaa gctgtaaagt tttcttcaaa agagcagtgg aaggacagca caattaccta   1500
tgtgctggaa ggaatgattg catcatcgat aaaattcgaa gaaaaaactg cccagcatgc   1560
cgctatcgaa aatgtcttca ggctggaatg aacctggaag ctcgaaaaac aaagaaaaaa   1620
ataaaaggaa ttcagcaggc cactacagga gtctcacaag aaacctctga aaatcctggt   1680
aacaaaacaa tagttcctgc aacgttacca caactcaccc ctaccctggt gtcactgttg   1740
gaggttattg aacctgaagt gttatatgca ggatatgata gctctgttcc agactcaact   1800
tggaggatca tgactacgct caacatgtta ggagggcggc aagtgattgc agcagtgaaa   1860
tgggcaaagg caataccagg tttcaggaac ttacacctgg atgaccaaat gaccctactg   1920
cagtactcct ggatgtttct tatggcattt gctctggggt ggagatcata tagacaatca   1980
agtgcaaacc tgctgtgttt tgctcctgat ctgattatta atgagcagag aatgactcta   2040
ccctgcatgt acgaccaatg taaacacatg ctgtatgttt cctctgagtt acacaggctt   2100
```

-continued

```
caggtatctt atgaagagta tctctgtatg aaaaccttac tgcttctctc ttcagttcct   2160
aaggacggtc tgaagagcca agagctattt gatgaaatta gaatgaccta catcaaagag   2220
ctaggaaaag ccattgtcaa gagggaagga aactccagcc agaactggca gcggttttat   2280
caactgacaa aactcttgga ttctatgcat gaagtggttg aaaatctcct taactattgc   2340
ttccaaacat ttttggataa gaccatgagt attgaattcc ccgagatgtt agctgaaatc   2400
atcaccaatc agataccaaa atattcaaat ggaaatatca aaaaacttct gtttcatcaa   2460
aagtgactgc cttaataaga atggttgcct taaagaaagt cgaattaata gcttttattg   2520
tataaactat cagtttgtcc tgtagaggtt ttgttgtttt attttttatt gttttcatct   2580
gttgttttgt tttaaatacg cactacatgt ggtttataga gggccaagac ttggcaacag   2640
aagcagttga gtcgtcatca cttttcagtg atgggagagt agatggtgaa atttattagt   2700
taatatatcc cagaaattag aaaccttaat atgtggacgt aatctccaca gtcaaagaag   2760
gatggcacct aaaccaccag tgcccaaagt ctgtgtgatg aactttctct tcatactttt   2820
tttcacagtt ggctggatga aattttctag actttctgtt ggtgtatccc ccccccctgta   2880
tagttaggat agcatttttg atttatgcat ggaaacctga aaaaaagttt acaagtgtat   2940
atcagaaaag ggaagttgtg ccttttatag ctattactgt ctggttttaa caatttcctt   3000
tatatttagt gaactacgct tgctcatttt ttcttacata atttttattt caagttattg   3060
tacagctgtt taagatgggc agctagttcg tagctttccc aaataaactc taaacattaa   3120
tcaatcatct gtgtgaaaat gggttggtgc ttctaacctg atggcactta gctatcagaa   3180
gaccacaaaa attgactcaa atctccagta ttcttgtcaa aaaaaaaaaa aaaaaagctc   3240
atattttgta tatatctgct tcagtggaga attatatagg ttgtgcaaat taacagtcct   3300
aactggtata gagcacctag tccagtgacc tgctgggtaa actgtggatg atggttgcaa   3360
aagactaatt taaaaaataa ctaccaagag gccctgtctg tacctaacgc cctatttttg   3420
caatggctat atggcaagaa agctggtaaa ctatttgtct ttcaggacct tttgaagtag   3480
tttgtataac ttcttaaaag ttgtgattcc agataaccag ctgtaacaca gctgagagac   3540
ttttaatcag acaaagtaat tcctctcact aaactttacc caaaaactaa atctctaata   3600
tggcaaaaat ggctagacac ccattttcac attcccatct gtcaccaatt ggttaatctt   3660
tcctgatggt acaggaaagc tcagctactg atttttgtga tttagaactg tatgtatgtc   3720
agacatccat gtttgtaaaa ctacacatcc ctaatgtgtg ccatagagtt taacacaagt   3780
cctgtgaatt tcttcactgt tgaaaattat tttaaacaaa atagaagctg tagtagccct   3840
ttctgtgtgc accttaccaa ctttctgtaa actcaaaact taacatattt actaagccac   3900
aagaaatttg atttctattc aaggtggcca aattatttgt gtaatagaaa actgaaaatc   3960
taatattaaa aatatggaac ttctaatata tttttatatt tagttatagt ttcagatata   4020
tatcatattg gtattcacta atctgggaag ggaagggcta ctgcagcttt acatgcaatt   4080
tattaaaatg attgtaaaat agcttgtata gtgtaaaata agaatgattt ttagatgaga   4140
ttgttttatc atgacatgtt atatattttt tgtaggggtc aaagaaatgc tgatggataa   4200
cctatatgat ttatagtttg tacatgcatt catacaggca gcgatggtct cagaaaccaa   4260
acagtttgct ctaggggaag agggagatgg agactggtcc tgtgtgcagt gaaggttgct   4320
gaggctctga cccagtgaga ttacagagga agttatcctc tgcctcccat tctgaccacc   4380
cttctcattc caacagtgag tctgtcagcg caggtttagt ttactcaatc tcccccttgca   4440
```

-continued ctaaagtatg taaagtatgt aaacaggaga caggaaggtg gtgcttacat ccttaaaggc 4500
accatctaat agcgggttac tttcacatac agccctcccc cagcagttga atgacaacag 4560
aagcttcaga agtttggcaa tagtttgcat agaggtacca gcaatatgta aatagtgcag 4620
aatctcatag gttgccaata atacactaat tcctttctat cctacaacaa gagtttattt 4680
ccaaataaaa tgaggacatg tttttgtttt ctttgaatgc tttttgaatg ttatttgtta 4740
ttttcagtat tttggagaaa ttatttaata aaaaaaacaa tcatttgctt tttg 4794

<210> SEQ ID NO 2
<211> LENGTH: 6330
<212> TYPE: DNA
<213> ORGANISM: Homo sapiens

<400> SEQUENCE: 2
aggagctggc ggagggcgtt cgtcctggga ctgcacttgc tcccgtcggg tcgcccggct 60
tcaccggacc cgcaggctcc cggggcaggg ccggggccag agctcgcgtg tcggcgggac 120
atgcgctgcg tcgcctctaa cctcgggctg tgctcttttt ccaggtggcc cgccggtttc 180
tgagccttct gccctgcggg gacacggtct gcaccctgcc cgcggccacg gaccatgacc 240
atgaccctcc acaccaaagc atctgggatg gccctactgc atcagatcca agggaacgag 300
ctggagcccc tgaaccgtcc gcagctcaag atccccctgg agcggcccct gggcgaggtg 360
tacctggaca gcagcaagcc cgccgtgtac aactaccccg agggcgccgc ctacgagttc 420
aacgccgcgg ccgccgccaa cgcgcaggtc tacggtcaga ccggcctccc ctacggcccc 480
gggtctgagg ctgcggcgtt cggctccaac ggcctggggg gtttcccccc actcaacagc 540
gtgtctccga gcccgctgat gctactgcac ccgccgccgc agctgtcgcc tttcctgcag 600
ccccacggcc agcaggtgcc ctactacctg gagaacgagc ccagcggcta cacggtgcgc 660
gaggccggcc cgccggcatt ctacaggcca aattcagata atcgacgcca gggtggcaga 720
gaaagattgg ccagtaccaa tgacaaggga agtatggcta tggaatctgc caaggagact 780
cgctactgtg cagtgtgcaa tgactatgct tcaggctacc attatggagt ctggtcctgt 840
gagggctgca aggccttctt caagagaagt attcaaggac ataacgacta tatgtgtcca 900
gccaccaacc agtgcaccat tgataaaaac aggaggaaga gctgccaggc ctgccggctc 960
cgcaaatgct acgaagtggg aatgatgaaa ggtgggatac gaaaagaccg aagaggaggg 1020
agaatgttga aacacaagcg ccagagagat gatggggagg gcaggggtga agtggggtct 1080
gctggagaca tgagagctgc caacctttgg ccaagcccgc tcatgatcaa acgctctaag 1140
aagaacagcc tggccttgtc cctgacggcc gaccagatgg tcagtgcctt gttggatgct 1200
gagcccccca tactctattc cgagtatgat cctaccagac ccttcagtga agcttcgatg 1260
atgggcttac tgaccaacct ggcagacagg gagctggttc acatgatcaa ctgggcgaag 1320
agggtgccag gctttgtgga tttgaccctc catgatcagg tccaccttct agaatgtgcc 1380
tggctagaga tcctgatgat tggtctcgtc tggcgctcca tggagcaccc agggaagcta 1440
ctgtttgctc ctaacttgct cttggacagg aaccagggaa aatgtgtaga gggcatggtg 1500
gagatcttcg acatgctgct ggctacatca tctcggttcc gcatgatgaa tctgcaggga 1560
gaggagtttg tgtgcctcaa atctattatt ttgcttaatt ctggagtgta cacatttctg 1620
tccagcaccc tgaagtctct ggaagagaag gaccatatcc accgagtcct ggacaagatc 1680
acagacactt tgatccacct gatggccaag gcaggcctga ccctgcagca gcagcaccag 1740
cggctggccc agctcctcct catcctctcc cacatcaggc acatgagtaa caaaggcatg 1800

-continued gagcatctgt acagcatgaa gtgcaagaac gtggtgcccc tctatgacct gctgctggag 1860
atgctggacg cccaccgcct acatgcgccc actagccgtg gaggggcatc cgtggaggag 1920
acggaccaaa gccacttggc cactgcgggc tctacttcat cgcattcctt gcaaaagtat 1980
tacatcacgg gggaggcaga gggtttccct gccacggtct gagagctccc tggctcccac 2040
acggttcaga taatccctgc tgcattttac cctcatcatg caccacttta gccaaattct 2100
gtctcctgca tacactccgg catgcatcca acaccaatgg ctttctagat gagtggccat 2160
tcatttgctt gctcagttct tagtggcaca tcttctgtct tctgttggga acagccaaag 2220
ggattccaag gctaaatctt tgtaacagct ctctttcccc cttgctatgt tactaagcgt 2280
gaggattccc gtagctcttc acagctgaac tcagtctatg ggttggggct cagataactc 2340
tgtgcattta agctacttgt agagacccag gcctggagag tagacatttt gcctctgata 2400
agcacttttt aaatggctct aagaataagc cacagcaaag aatttaaagt ggctccttta 2460
attggtgact tggagaaagc taggtcaagg gtttattata gcaccctctt gtattcctat 2520
ggcaatgcat ccttttatga aagtggtaca ccttaaagct tttatatgac tgtagcagag 2580
tatctggtga ttgtcaattc attcccccta taggaataca aggggcacac agggaaggca 2640
gatcccctag ttggcaagac tattttaact tgatacactg cagattcaga tgtgctgaaa 2700
gctctgcctc tggctttccg gtcatgggtt ccagttaatt catgcctccc atggacctat 2760
ggagagcagc aagttgatct tagttaagtc tccctatatg agggataagt tcctgatttt 2820
tgtttttatt tttgtgttac aaaagaaagc cctccctccc tgaacttgca gtaaggtcag 2880
cttcaggacc tgttccagtg ggcactgtac ttggatcttc ccggcgtgtg tgtgccttac 2940
acaggggtga actgttcact gtggtgatgc atgatgaggg taaatggtag ttgaaaggag 3000
caggggccct ggtgttgcat ttagccctgg ggcatggagc tgaacagtac ttgtgcagga 3060
ttgttgtggc tactagagaa caagagggaa agtagggcag aaactggata cagttctgag 3120
gcacagccag acttgctcag ggtggccctg ccacaggctg cagctaccta ggaacattcc 3180
ttgcagaccc cgcattgccc tttgggggtg ccctgggatc cctggggtag tccagctctt 3240
cttcatttcc cagcgtggcc ctggttggaa gaagcagctg tcacagctgc tgtagacagc 3300
tgtgttccta caattggccc agcaccctgg ggcacgggag aagggtgggg accgttgctg 3360
tcactactca ggctgactgg ggcctggtca gattacgtat gcccttggtg gtttagagat 3420
aatccaaaat cagggtttgg tttggggaag aaaatcctcc cccttcctcc cccgccccgt 3480
tccctaccgc ctccactcct gccagctcat ttccttcaat ttcctttgac ctataggcta 3540
aaaaagaaag gctcattcca gccacagggc agccttccct gggcctttgc ttctctagca 3600
caattatggg ttacttcctt tttcttaaca aaaaagaatg tttgatttcc tctgggtgac 3660
cttattgtct gtaattgaaa ccctattgag aggtgatgtc tgtgttagcc aatgacccag 3720
gtgagctgct cgggcttctc ttggtatgtc ttgtttggaa aagtggattt cattcatttc 3780
tgattgtcca gttaagtgat caccaaagga ctgagaatct gggagggcaa aaaaaaaaaa 3840
aaagttttta tgtgcactta aatttgggga caattttatg tatctgtgtt aaggatatgt 3900
ttaagaacat aattcttttg ttgctgtttg tttaagaagc accttagttt gtttaagaag 3960
caccttatat agtataatat atattttttt gaaattacat tgcttgttta tcagacaatt 4020
gaatgtagta attctgttct ggatttaatt tgactgggtt aacatgcaaa aaccaaggaa 4080
aaatatttag tttttttttt tttttttgta tacttttcaa gctaccttgt catgtataca 4140

```
gtcatttatg cctaaagcct ggtgattatt catttaaatg aagatcacat ttcatatcaa   4200
cttttgtatc cacagtagac aaaatagcac taatccagat gcctattgtt ggatactgaa   4260
tgacagacaa tcttatgtag caaagattat gcctgaaaag gaaaattatt cagggcagct   4320
aattttgctt ttaccaaaat atcagtagta atatttttgg acagtagcta atgggtcagt   4380
gggttctttt taatgtttat acttagattt tcttttaaaa aaattaaaat aaaacaaaaa   4440
aaaatttcta ggactagacg atgtaatacc agctaaagcc aaacaattat acagtggaag   4500
gttttacatt attcatccaa tgtgtttcta ttcatgttaa gatactacta catttgaagt   4560
gggcagagaa catcagatga ttgaaatgtt cgcccagggg tctccagcaa ctttggaaat   4620
ctctttgtat ttttacttga agtgccacta atggacagca gatattttct ggctgatgtt   4680
ggtattgggt gtaggaacat gatttaaaaa aaaactcttg cctctgcttt cccccactct   4740
gaggcaagtt aaaatgtaaa agatgtgatt tatctggggg gctcaggtat ggtggggaag   4800
tggattcagg aatctgggga atggcaaata tattaagaag agtattgaaa gtatttggag   4860
gaaaatggtt aattctgggt gtgcaccagg gttcagtaga gtccacttct gccctggaga   4920
ccacaaatca actagctcca tttacagcca tttctaaaat ggcagcttca gttctagaga   4980
agaaagaaca acatcagcag taaagtccat ggaatagcta gtggtctgtg tttcttttcg   5040
ccattgccta gcttgccgta atgattctat aatgccatca tgcagcaatt atgagaggct   5100
aggtcatcca aagagaagac cctatcaatg taggttgcaa aatctaaccc ctaaggaagt   5160
gcagtctttg atttgatttc cctagtaacc ttgcagatat gtttaaccaa gccatagccc   5220
atgccttttg agggctgaac aaataaggga cttactgata atttactttt gatcacatta   5280
aggtgttctc accttgaaat cttatacact gaaatggcca ttgatttagg ccactggctt   5340
agagtactcc ttcccctgca tgacactgat tacaaatact ttcctattca tactttccaa   5400
ttatgagatg gactgtgggt actgggagtg atcactaaca ccatagtaat gtctaatatt   5460
cacaggcaga tctgcttggg gaagctagtt atgtgaaagg caaatagagt catacagtag   5520
ctcaaaaggc aaccataatt ctctttggtg caggtcttgg gagcgtgatc tagattacac   5580
tgcaccattc ccaagttaat cccctgaaaa cttactctca actggagcaa atgaactttg   5640
gtcccaaata tccatctttt cagtagcgtt aattatgctc tgtttccaac tgcatttcct   5700
ttccaattga attaaagtgt ggcctcgttt ttagtcattt aaaattgttt tctaagtaat   5760
tgctgcctct attatggcac ttcaattttg cactgtcttt tgagattcaa gaaaaatttc   5820
tattcttttt tttgcatcca attgtgcctg aacttttaaa atatgtaaat gctgccatgt   5880
tccaaaccca tcgtcagtgt gtgtgtttag agctgtgcac cctagaaaca acatattgtc   5940
ccatgagcag gtgcctgaga cacagacccc tttgcattca cagagaggtc attggttata   6000
gagacttgaa ttaataagtg acattatgcc agtttctgtt ctctcacagg tgataaacaa   6060
tgctttttgt gcactacata ctcttcagtg tagagctctt gttttatggg aaaaggctca   6120
aatgccaaat tgtgtttgat ggattaatat gcccttttgc cgatgcatac tattactgat   6180
gtgactcggt tttgtcgcag ctttgctttg tttaatgaaa cacacttgta aacctctttt   6240
gcactttgaa aaagaatcca gcgggatgct cgagcacctg taaacaattt tctcaaccta   6300
tttgatgttc aaataaagaa ttaaactaaa                                    6330
```

<210> SEQ ID NO 3
<211> LENGTH: 4107
<212> TYPE: DNA
<213> ORGANISM: Homo sapiens -continued

<400> SEQUENCE: 3

```
gcgcaaccct ccggaagctg ccgccccttt cccctttat gggaatactt tttttaaaaa     60
aaaagagttc gctggcgcca ccccgtagga ctggccgccc taaaaccgtg ataaaggagc    120
tgctcgccac ttctcacttc cgcttccttc cagtaaggag tcggggtctt ccccagtttt    180
ctcagccagg cggcggcggc gactggcaat gtttggcctc aaaagaaacg cggtaatcgg    240
actcaacctc tactgtgggg gggccggctt gggggccggc agcggcggcg ccacccgccc    300
gggagggcga cttttggcta cggagaagga ggcctcggcc cggcgagaga tagggggagg    360
ggaggccggc gcggtgattg gcggaagcgc cggcgcaagc cccccgtcca ccctcacgcc    420
agactcccgg agggtcgcgc ggccgccgcc cattggcgcc gaggtccccg acgtcaccgc    480
gacccccgcg aggctgcttt tcttcgcgcc cacccgccgc gcggcgccgc ttgaggagat    540
ggaagccccg gccgctgacg ccatcatgtc gcccgaagag gagctggacg ggtacgagcc    600
ggagcctctc gggaagcggc cggctgtcct gccgctgctg gagttggtcg ggaatctgg    660
taataacacc agtacggacg ggtcactacc ctcgacgccg ccgccagcag aggaggagga    720
ggacgagttg taccggcagt cgctggagat tatctctcgg taccttcggg agcaggccac    780
cggcgccaag gacacaaagc caatgggcag gtctggggcc accagcagga aggcgctgga    840
gaccttacga cgggttgggg atggcgtgca gcgcaaccac gagacggcct tccaaggcat    900
gcttcggaaa ctggacatca aaaacgaaga cgatgtgaaa tcgttgtctc gagtgatgat    960
ccatgttttc agcgacggcg taacaaactg gggcaggatt gtgactctca tttcttttgg   1020
tgcctttgtg gctaaacact tgaagaccat aaaccaagaa agctgcatcg aaccattagc   1080
agaaagtatc acagacgttc tcgtaaggac aaaacgggac tggctagtta aacaaagagg   1140
ctgggatggg tttgtggagt tcttccatgt agaggaccta gaaggtggca tcaggaatgt   1200
gctgctggct tttgcaggtg ttgctggagt aggagctggt ttggcatatc taataagata   1260
gccttactgt aagtgcaata gttgactttt aaccaaccac caccaccacc aaaaccagtt   1320
tatgcagttg gactccaagc tgtaacttcc tagagttgca ccctagcaac ctagccagaa   1380
aagcaagtgg caagaggatt atggctaaca agaataaata catgggaaga gtgctcccca   1440
ttgattgaag agtcactgtc tgaaagaagc aaagttcagt ttcagcaaca aacaaacttt   1500
gtttgggaag ctatggagga ggacttttag atttagtgaa gatggtaggg tggaaagact   1560
taatttcctt gttgagaaca ggaaagtggc cagtagccag gcaagtcata gaattgatta   1620
cccgccgaat tcattaattt actgtagtgt taagagaagc actaagaatg ccagtgacct   1680
gtgtaaaagt tacaagtaat agaactatga ctgtaagcct cagtactgta caagggaagc   1740
ttttcctctc tctaattagc tttcccagta tacttcttag aaagtccaag tgttcaggac   1800
ttttatacct gttatacttt ggcttggttt ccatgattct tactttatta gcctagttta   1860
tcaccaataa tacttgacgg aaggctcagt aattagttat gaatatggat atcctcaatt   1920
cttaagacag cttgtaaatg tatttgtaaa aattgtatat atttttacag aaagtctatt   1980
tctttgaaac gaaggaagta tcgaatttac attagttttt ttcataccct tttgaacttt   2040
gcaacttccg taattaggaa cctgtttctt acagcttttc tatgctaaac tttgttctgt   2100
tcagttctag agtgtataca gaacgaattg atgtgtaact gtatgcagac tggttgtagt   2160
ggaacaaatc tgataactat gcaggtttaa attttcttat ctgattttgg taagtattcc   2220
ttagataggt ttttctttga aaacctggga ttgagaggtt gatgaatgga aattctttca   2280
```

-continued cttcattata tgcaagtttt caataattag gtctaagtgg agttttaagg ttactgatga 2340
cttacaaata atgggctctg attgggcaat actcatttga gttccttcca tttgacctaa 2400
tttaactggt gaaatttaaa gtgaattcat gggctcatct ttaaagcttt tactaaaaga 2460
ttttcagctg aatggaactc attagctgtg tgcatataaa aagatcacat caggtggatg 2520
gagagacatt tgatcccttg tttgcttaat aaattataaa atgatggctt ggaaaagcag 2580
gctagtctaa ccatggtgct attattaggc ttgcttgtta cacacacagg tctaagccta 2640
gtatgtcaat aaagcaaata cttactgttt tgtttctatt aatgattccc aaaccttgtt 2700
gcaagttttt gcattggcat ctttggattt cagtcttgat gtttgttcta tcagacttaa 2760
ccttttattt cctgtccttc cttgaaattg ctgattgttc tgctccctct acagatattt 2820
atatcaattc ctacagcttt cccctgccat ccctgaactc tttctagccc ttttagattt 2880
tggcactgtg aaacccctgc tggaaacctg agtgaccctc cctccccacc aagagtccac 2940
agacctttca tctttcacga acttgatcct gttagcaggt ggtaatacca tgggtgctgt 3000
gacactaaca gtcattgaga ggtgggagga agtccctttt ccttggactg gtatcttttc 3060
aactattgtt ttatcctgtc tttgggggca atgtgtcaaa agtcccctca ggaattttca 3120
gaggaaagaa cattttatga ggctttctct aaagtttcct ttgtatagga gtatgctcac 3180
ttaaatttac agaaagaggt gagctgtgtt aaacctcaga gtttaaaagc tactgataaa 3240
ctgaagaaag tgtctatatt ggaactaggg tcatttgaaa gcttcagtct cggaacatga 3300
cctttagtct gtggactcca tttaaaaata ggtatgaata agatgactaa gaatgtaatg 3360
gggaagaact gccctgcctg cccatctcag agccataagg tcatctttgc tagagctatt 3420
tttacctatg tatttatcgt tcttgatcat aagccgctta tttatatcat gtatctctaa 3480
ggacctaaaa gcactttatg tagtttttaa ttaatcttaa gatctggtta cggtaactaa 3540
aaaagcctgt ctgccaaatc cagtggaaac aagtgcatag atgtgaattg gtttttaggg 3600
gccccacttc ccaattcatt aggtatgact gtggaaatac agacaaggat cttagttgat 3660
attttgggct tggggcagtg agggcttagg acaccccaag tggtttggga aaggaggagg 3720
ggagtggtgg gtttataggg ggaggaggag gcaggtggtc taagtgctga ctggctacgt 3780
agttcgggca aatcctccaa aagggaaagg gaggatttgc ttagaaggat ggcgctccca 3840
gtgactactt tttgacttct gtttgtctta cgcttctctc agggaaaaac atgcagtcct 3900
ctagtgtttc atgtacattc tgtggggggt gaacaccttg gttctggtta aacagctgta 3960
cttttgatag ctgtgccagg aagggttagg accaactaca aattaatgtt ggttgtcaaa 4020
tgtagtgtgt ttccctaact ttctgttttt cctgagaaaa aaaaataaat cttttattca 4080
aatacaggga aaaaaaaaaa aaaaaaa 4107

<210> SEQ ID NO 4
<211> LENGTH: 1126
<212> TYPE: DNA
<213> ORGANISM: Homo sapiens

<400> SEQUENCE: 4
tccccatgtg acagtgagcg gggtccccgc tccaggagac gctcgagtct gcgtcccggc 60
cctcagcact gtccactgtt tcggtgccag cagagaccag caggcccggg acagttggtg 120
tttggccgtg ccgctgtcta acttggtgtg cagagtgaat tgccgctgcc ggagcggaga 180
gaggcggagc ggccaggaga gaggggattt ctgtcagcgc cggcctcggg agctcggaga 240
catgaacggc ttcacgcctg acgagatgag ccgcggcggg gatgcggccg ccgcagtggc 300

-continued

```
cgcagtggtc gctgccgcgg ccgccgccgc ctcggcgggg aacgggaccg gcgcgggcac    360

cggggctgag gtgccgggcg cgggggcggt ctcagcggct gggcccccgg gggcggccgg    420

gccgggcccc gggcaactgt gctgcctgcg ggaggatggt gagcggtgcg gccgggcggc    480

aggcaacgcc agcttcagca agaggatcca gaagagcatc tcccagaaga aggtgaagat    540

cgagctggat aagagcgcaa ggcatcttta catatgtgat tatcataaaa acttaattca    600

gagtgttcga aacagaagaa agagaaaagg gagtgatgat gatggaggtg attcacctgt    660

tcaagatatt gataccccag aggttgattt ataccaatta caagtaaata cacttaggag    720

atacaaaaga cacttcaagc taccaaccag accaggactt aataaagcac aacttgttga    780

gatagttggt tgccacttta ggtctattcc agtgaatgaa aaagacacct taacatattt    840

catctactca gtgaagaatg acaagaacaa atcagatctc aaggttgata gtggtgttca    900

ctaggagacg tggaattgag actaataact tggatgttaa cactgtttac tgtttttttca    960

catgtagaaa tgttctttgt gtatttttttc tacagaggat tttctctgat tttattttct   1020

ttgtttctga ctctaataat tagttggaaa ctcatataaa atgagctttc ctaaattaaa   1080

tctattttaa ataaaggtta ttactattaa aaaaaaaaaa aaaaaa                   1126
```

<210> SEQ ID NO 5
<211> LENGTH: 2040
<212> TYPE: DNA
<213> ORGANISM: Homo sapiens

<400> SEQUENCE: 5

```
tcgctgcgaa ggacatttgg gctgtgtgtg cgacgcgggt cggaggggca gtcgggggaa     60

ccgcgaagaa gccgaggagc ccggagcccc gcgtgacgct cctctctcag tccaaaagcg    120

gcttttggtt cggcgcagag agacccgggg gtctagcttt tcctcgaaaa gcgccgccct    180

gcccttggcc ccgagaacag acaaagagca ccgcagggcc gatcacgctg gggcgctga    240

ggccggccat ggtcatggaa gtgggcaccc tggacgctgg aggcctgcgg gcgctgctgg    300

gggagcgagc ggcgcaatgc ctgctgctgg actgccgctc cttcttcgct ttcaacgccg    360

gccacatcgc cggctctgtc aacgtgcgct tcagcaccat cgtgcggcgc cgggccaagg    420

gcgccatggg cctggagcac atcgtgccca acgccgagct ccgcggccgc ctgctggccg    480

gcgcctacca cgccgtggtg ttgctggacg agcgcagcgc cgccctggac ggcgccaagc    540

gcgacggcac cctggccctg gcggccggcg cgctctgccg cgaggcgcgc gccgcgcaag    600

tcttcttcct caaaggagga tacgaagcgt tttcggcttc ctgcccggag ctgtgcagca    660

aacagtcgac cccccatgggg ctcagccttc ccctgagtac tagcgtccct gacagcgcgg    720

aatctgggtg cagttcctgc agtaccccac tctacgatca gggtggcccg gtggaaatcc    780

tgccctttct gtacctgggc agtgcgtatc acgcttcccg caaggacatg ctggatgcct    840

tgggcatcac tgccttgatc aacgtctcag ccaattgtcc caaccatttt gagggtcact    900

accagtacaa gagcatccct gtggaggaca accacaaggc agacatcagc tcctggttca    960

acgaggccat tgacttcata gactccatca agaatgctgg aggaagggtg tttgtccact   1020

gccaggcagg catttcccgg tcagccacca tctgccttgc ttaccttatg aggactaatc   1080

gagtcaagct ggacgaggcc tttgagtttg tgaagcagag gcgaagcatc atctctccca   1140

acttcagctt catgggccag ctgctgcagt ttgagtccca ggtgctggct ccgcactgtt   1200

cggcagaggc tgggagcccc gccatggctg tgctcgaccg aggcacctcc accaccaccg   1260
```

-continued

```
tgttcaactt ccccgtctcc atccctgtcc actccacgaa cagtgcgctg agctaccttc   1320

agagccccat tacgacctct cccagctgct gaaaggccac gggaggtgag gctcttcaca   1380

tcccattggg actccatgct ccttgagagg agaaatgcaa taactctggg aggggctcga   1440

gagggctggt ccttatttat ttaacttcac ccgagttcct ctgggtttct aagcagttat   1500

ggtgatgact tagcgtcaag acatttgctg aactcagcac attcgggacc aatatatagt   1560

gggtacatca agtccatctg acaaaatggg gcagaagaga aaggactcag tgtgtgatcc   1620

ggtttctttt tgctcgcccc tgttttttgt agaatctctt catgcttgac atacctacca   1680

gtattattcc cgacgacaca tatacatatg agaatatacc ttatttattt ttgtgtaggt   1740

gtctgccttc acaaatgtca ttgtctactc ctagaagaac caaatacctc aatttttgtt   1800

tttgagtact gtactatcct gtaaatatat cttaagcagg tttgttttca gcactgatgg   1860

aaaataccag tgttgggttt ttttttagtt gccaacagtt gtatgtttgc tgattattta   1920

tgacctgaaa taatatattt cttcttctaa gaagacattt tgttacataa ggatgacttt   1980

tttatacaat ggaataaatt atggcatttc tattgaaatt tcaaaaaaaa aaaaaaaaaa   2040


<210> SEQ ID NO 6
<211> LENGTH: 3208
<212> TYPE: DNA
<213> ORGANISM: Homo sapiens

<400> SEQUENCE: 6

agatattcat gaaccgttgc ttcttccagc ctcgccttct cgctccctct gcctttctgg     60

cgctgttctc cctccctccc tctggcttct gctctttctt actccttctc tcagctgctt    120

aactacagct cccactggaa cttgcacaat caaaaacaac tctcctctct caagccgcct    180

ccaggagcgc atcacctgga gaagagcgac tcgctccccg cgccggccgc ggaagagcag    240

ccaggtagct gggggcgggg aggcgtaccc ttctcccgct cggtaagagc cacagcatct    300

ccccggagat tggccgtatc ccaccgtccg gcccccaggg tcctgcagcg gtgatgcata    360

tgtttcggag caatgatgga aggagaaaag ccgctgtcgg tggcaactga aagtggggag    420

aggttgctgc agtagctggt gctgcagaat gcgcgagtga agaactgagc cccgctagat    480

tctccatccc gctcagtctt cattaactgt ctgcaggagg taaaccgggg aaacagatat    540

gcactaacca ggcgggtgcc aacctggatc tataactgtg aattccccac ggtggaaaat    600

ggtaaacaaa gacatgaatg gattcccagt caagaaatgc tcagccttcc aatttttttaa   660

gaagcgggta cgaaggtgga tcaagagccc aatggtcagt gtggacaagc atcagagtcc    720

cagcctgaag tacaccggct cctccatggt gcacatccct ccaggggagc cagacttcga    780

gtcttccttg tgtcaaacat gcctgggtga acatgctttc caaagagggg ttctccctca    840

ggagaacgag tcatgttcat gggaaactca atctgggtgt gaagtgagag agccatgtaa    900

tcatgccaac atcctgacca agcccgatcc aagaaccttc tggactaatg atgatccagc    960

tttcatgaag cagaggagga tgggtctgaa cgactttatt cagaagattg ccaataactc   1020

ctatgcatgc aaacaccctg aagttcagtc catcttgaag atctcccaac ctcaggagcc   1080

tgagcttatg aatgccaacc cttctcctcc accaagtcct tctcagcaaa tcaaccttgg   1140

cccgtcgtcc aatcctcatg ctaaaccatc tgactttcac ttcttgaaag tgatcggaaa   1200

gggcagtttt ggaaaggttc ttctagcaag acacaaggca gaagaagtgt tctatgcagt   1260

caaagtttta cagaagaaag caatcctgaa aaagaaagag gagaagcata ttatgtcgga   1320

gcggaatgtt ctgttgaaga atgtgaagca ccctttcctg gtgggccttc acttctcttt   1380
```

```
ccagactgct gacaaattgt actttgtcct agactacatt aatggtggag agttgttcta   1440
ccatctccag agggaacgct gcttcctgga accacgggct cgtttctatg ctgctgaaat   1500
agccagtgcc ttgggctacc tgcattcact gaacatcgtt tatagagact taaaaccaga   1560
gaatattttg ctagattcac agggacacat tgtccttact gacttcggac tctgcaagga   1620
gaacattgaa cacaacagca caacatccac cttctgtggc acgccggagt atctcgcacc   1680
tgaggtgctt cataagcagc cttatgacag gactgtggac tggtggtgcc tgggagctgt   1740
cttgtatgag atgctgtatg gcctgccgcc tttttatagc cgaaacacag ctgaaatgta   1800
cgacaacatt ctgaacaagc ctctccagct gaaaccaaat attacaaatt ccgcaagaca   1860
cctcctggag ggcctcctgc agaaggacag gacaaagcgg ctcggggcca aggatgactt   1920
catggagatt aagagtcatg tcttcttctc cttaattaac tgggatgatc tcattaataa   1980
gaagattact cccccttta acccaaatgt gagtgggccc aacgacctac ggcactttga    2040
ccccgagttt accgaagagc ctgtccccaa ctccattggc aagtcccctg acagcgtcct   2100
cgtcacagcc agcgtcaagg aagctgccga ggctttccta ggcttttcct atgcgcctcc   2160
cacggactct ttcctctgaa ccctgttagg gcttggtttt aaaggatttt atgtgtgttt   2220
ccgaatgttt tagttagcct tttggtggag ccgccagctg acaggacatc ttacaagaga   2280
atttgcacat ctctggaagc ttagcaatct tattgcacac tgttcgctgg aagctttttg   2340
aagagcacat tctcctcagt gagctcatga ggttttcatt tttattcttc cttccaacgt   2400
ggtgctatct ctgaaacgag cgttagagtg ccgccttaga cggaggcagg agtttcgtta   2460
gaaagcggac gctgttctaa aaaaggtctc ctgcagatct gtctgggctg tgatgacgaa   2520
tattatgaaa tgtgcctttt ctgaagagat tgtgttagct ccaaagcttt tcctatcgca   2580
gtgtttcagt tctttatttt cccttgtgga tatgctgtgt gaaccgtcgt gtgagtgtgg   2640
tatgcctgat cacagatgga ttttgttata agcatcaatg tgacacttgc aggacactac   2700
aacgtgggac attgtttgtt tcttccatat ttggaagata aatttatgtg tagacttttt   2760
tgtaagatac ggttaataac taaaatttat tgaaatggtc ttgcaatgac tcgtattcag   2820
atgcttaaag aaagcattgc tgctacaaat atttctattt ttagaaaggg tttttatgga   2880
ccaatgcccc agttgtcagt cagagccgtt ggtgtttttc attgtttaaa atgtcacctg   2940
taaaatgggc attatttatg tttttttttt tgcattcctg ataattgtat gtattgtata   3000
aagaacgtct gtacattggg ttataacact agtatattta aacttacagg cttatttgta   3060
atgtaaacca ccattttaat gtactgtaat taacatggtt ataatacgta caatccttcc   3120
ctcatcccat cacacaactt tttttgtgtg tgataaactg attttggttt gcaataaaac   3180
cttgaaaaat atttacatat aaaaaaaa                                     3208

<210> SEQ ID NO 7
<211> LENGTH: 5758
<212> TYPE: DNA
<213> ORGANISM: Homo sapiens

<400> SEQUENCE: 7

tttctgtact ctgggtgact cagagaggga agagattcag ccagcacact cctcgcgagc     60
aagcattact ctactgactg gcagagacag gagaggtaga tgtccacgcc cacagaccct    120
ggtgcgatgc cccacccagg gccttcgccg gggcctgggc cttcccctgg gccaattctt    180
gggcctagtc caggaccagg accatcccca ggttccgtcc acagcatgat ggggccaagt    240
```

-continued

```
cctggacctc caagtgtctc ccatcctatg ccgacgatgg ggtccacaga cttcccacag    300
gaaggcatgc atcaaatgca taagcccatc gatggtatac atgacaaggg gattgtagaa    360
gacatccatt gtggatccat gaagggcact ggtatgcgac cacctcaccc aggcatgggc    420
cctccccaga gtccaatgga tcaacacagc caaggttata tgtcaccaca cccatctcca    480
ttaggagccc cagagcacgt ctccagccct atgtctggag gaggcccaac tccacctcag    540
atgccaccaa gccagccggg ggccctcatc ccaggtgatc cgcaggccat gagccagccc    600
aacagaggtc cctcaccttt cagtcctgtc cagctgcatc agcttcgagc tcagatttta    660
gcttataaaa tgctggcccg aggccagccc ctccccgaaa cgctgcagct tgcagtccag    720
gggaaaagga cgttgcctgg cttgcagcaa caacagcagc agcaacagca gcagcagcag    780
cagcagcagc agcagcagca gcagcaacag cagccgcagc agcagccgcc gcaaccacag    840
acgcagcaac aacagcagcc ggcccttgtt aactacaaca gaccatctgg cccggggccg    900
gagctgagcg gcccgagcac ccgcagaag ctgccggtgc ccgcgcccgg cggccggccc    960
tcgcccgcgc cccccgcagc cgcgcagccg cccgcggccg cagtgcccgg gccctcagtg   1020
ccgcagccgg ccccggggca gccctcgccc gtcctccagc tgcagcagaa gcagagccgc   1080
atcagcccca tccagaaacc gcaaggcctg gaccccgtgg aaattctgca agagcgggaa   1140
tacagacttc aggcccgcat agctcatagg atacaagaac tggaaaatct gcctggctct   1200
ttgccaccag atttaagaac caaagcaacc gtggaactaa aagcacttcg gttactcaat   1260
ttccagcgtc agctgagaca ggaggtggtg gcctgcatgc gcagggacac gaccctggag   1320
acggctctca actccaaagc atacaaacgg agcaagcgcc agactctgag agaagctcgc   1380
atgaccgaga agctggagaa gcagcagaag attgagcagg agaggaaacg ccgtcagaaa   1440
caccaggaat acctgaacag tattttgcaa catgcaaaag attttaagga atatcatcgg   1500
tctgtggccg gaaagatcca gaagctctcc aaagcagtgg caacttggca tgccaacact   1560
gaaagagagc agaagaagga gacagagcgg attgaaaagg agagaatgcg gcgactgatg   1620
gctgaagatg aggagggtta tagaaaactg attgatcaaa agaaagacag gcgtttagct   1680
taccttttgc agcagaccga tgagtatgta gccaatctga ccaatctggt ttgggagcac   1740
aagcaagccc aggcagccaa agagaagaag aagaggagga ggaggaagaa gaaggctgag   1800
gagaatgcag agggtgggga gtctgccctg ggaccggatg gagagcccat agatgagagc   1860
agccagatga gtgacctccc tgtcaaagtg actcacacag aaaccggcaa ggttctgttc   1920
ggaccagaag cacccaaagc aagtcagctg gacgcctggc tggaaatgaa tcctggttat   1980
gaagttgccc ctagatctga cagtgaagag agtgattctg attatgagga agaggatgag   2040
gaagaagagt ccagtaggca ggaaaccgaa gagaaaatac tcctggatcc aaatagcgaa   2100
gaagtttctg agaaggatgc taagcagatc attgagacag ctaagcaaga cgtggatgat   2160
gaatacagca tgcagtacag tgccaggggc tcccagtcct actacaccgt ggctcatgcc   2220
atctcggaga gggtggagaa acagtctgcc ctcctaatta atgggaccct aaagcattac   2280
cagctccagg gcctggaatg gatggtttcc ctgtataata acaacttgaa cggaatctta   2340
gccgatgaaa tggggcttgg aaagaccata cagaccattg cactcatcac ttatctgatg   2400
gagcacaaaa gactcaatgg cccctatctc atcattgttc ccctttcgac tctatctaac   2460
tggacatatg aatttgacaa atgggctcct tctgtggtga agatttctta caagggtact   2520
cctgccatgc gtcgctccct tgtcccccag ctacggagtg gcaaattcaa tgtcctcttg   2580
actacttatg agtatattat aaaagacaag cacattcttg caaagattcg gtggaaatac   2640
```

-continued

```
atgatagtgg acgaaggcca ccgaatgaag aatcaccact gcaagctgac tcaggtcttg   2700
aacactcact atgtggcccc cagaaggatc ctcttgactg ggaccccgct gcagaataag   2760
ctccctgaac tctgggccct cctcaacttc ctcctcccaa caatttttaa gagctgcagc   2820
acatttgaac aatggttcaa tgctccattt gccatgactg gtgaaagggt ggacttaaat   2880
gaagaagaaa ctatattgat catcaggcgt ctacataagg tgttaagacc atttttacta   2940
aggagactga agaaagaagt tgaatcccag cttcccgaaa aagtggaata tgtgatcaag   3000
tgtgacatgt cagctctgca gaagattctg tatcgccata tgcaagccaa ggggatcctt   3060
ctcacagatg gttctgagaa agataagaag gggaaaggag gtgctaagac acttatgaac   3120
actattatgc agttgagaaa aatctgcaac cacccatata tgtttcagca cattgaggaa   3180
tcctttgctg aacacctagg ctattcaaat ggggtcatca atggggctga actgtatcgg   3240
gcctcaggga agtttgagct gcttgatcgt attctgccaa aattgagagc gactaatcac   3300
cgagtgctgc ttttctgcca gatgacatct ctcatgacca tcatggagga ttattttgct   3360
tttcggaact tcctttacct acgccttgat ggcaccacca agtctgaaga tcgtgctgct   3420
ttgctgaaga aattcaatga acctggatcc cagtatttca ttttcttgct gagcacaaga   3480
gctggtggcc tgggcttaaa tcttcaggca gctgatacag tggtcatctt tgacagcgac   3540
tggaatcctc atcaggatct gcaggcccaa gaccgagctc accgcatcgg gcagcagaac   3600
gaggtccggg tactgaggct ctgtaccgtg aacagcgtgg aggaaaagat cctcgcggcc   3660
gcaaaataca agctgaacgt ggatcagaaa gtgatccagg cgggcatgtt tgaccaaaag   3720
tcttcaagcc acgagcggag ggcattcctg caggccatct tggagcatga ggaggaaaat   3780
gaggaagaag atgaagtacc ggacgatgag actctgaacc aaatgattgc tcgacgagaa   3840
gaagaatttg accttttat gcggatggac atggaccggc ggagggaaga tgcccggaac   3900
ccgaaacgga agccccgttt aatggaggag gatgagctgc cctcctggat cattaaggat   3960
gacgctgaag tagaaaggct cacctgtgaa gaagaggagg agaaaatatt tgggaggggg   4020
tcccgccagc gccgtgacgt ggactacagt gacgccctca cggagaagca gtggctaagg   4080
gccatcgaag acggcaattt ggaggaaatg gaagaggaag tacggcttaa gaagcgaaaa   4140
agacgaagaa atgtggataa agatcctgca aaagaagatg tggaaaaagc taagaagaga   4200
agaggccgcc ctcccgctga gaaactgtca ccaaatcccc ccaaactgac aaagcagatg   4260
aacgctatca tcgatactgt gataaactac aaagataggt gtaacgtgga gaaggtgccc   4320
agtaattctc agttggaaat agaaggaaac agttcagggc gacagctcag tgaagtcttc   4380
attcagttac cttcaaggaa agaattacca gaatactatg aattaattag gaagccagtg   4440
gatttcaaaa aaataaagga aaggattcgt aatcataagt accggagcct aggcgacctg   4500
gagaaggatg tcatgcttct ctgtcacaac gctcagacgt tcaacctgga gggatcccag   4560
atctatgaag actccatcgt cttacagtca gtgtttaaga gtgcccggca gaaaattgcc   4620
aaagaggaag agagtgagga tgaaagcaat gaagaggagg aagaggaaga tgaagaagag   4680
tcagagtccg aggcaaaatc agtcaaggtg aaaattaagc tcaataaaaa agatgacaaa   4740
ggccgggaca aagggaaagg caagaaaagg ccaaatcgag gaaaagccaa acctgtagtg   4800
agcgattttg acagcgatga ggagcaggat gaacgtgaac agtcagaagg aagtgggacg   4860
gatgatgagt gatcagtatg gacctttttc cttggtagaa ctgaattcct tcctcccctg   4920
tctcatttct acccagtgag ttcatttgtc atataggcac tgggttgttt ctatatcatc   4980
```

-continued

```
atcgtctata aactagcttt aggatagtgc cagacaaaca tatgatatca tggtgtaaaa   5040

aacacacaca tacacaaata tttgtaacat attgtgacca aatgggcctc aaagattcag   5100

attgaaacaa acaaaaagct tttgatggaa aatatgtggg tggatagtat atttctatgg   5160

gtgggtctaa tttggtaacg gtttgattgt gcctggtttt atcacctgtt cagatgagaa   5220

gatttttgtc ttttgtagca ctgataacca ggagaagcca ttaaaagcca ctggttattt   5280

tatttttcat caggcaattt tcgaggtttt tatttgttcg gtattgtttt tttacactgt   5340

ggtacatata agcaacttta ataggtgata aatgtacagt agttagattt cacctgcata   5400

tacatttttc cattttatgc tctatgatct gaacaaaagc tttttgaatt gtataagatt   5460

tatgtctact gtaaacattg cttaattttt ttgctcttga tttaaaaaaa agttttgttg   5520

aaagcgctat tgaatattgc aatctatata gtgtattgga tggcttcttt tgtcaccctg   5580

atctcctatg ttaccaatgt gtatcgtctc cttctcccta aagtgtactt aatctttgct   5640

ttctttgcac aatgtctttg gttgcaagtc ataagcctga ggcaaataaa attccagtaa   5700

tttcgaagaa tgtggtgttg gtgctttcct aataaagaaa taatttagct tgacaaaa     5758
```

<210> SEQ ID NO 8
<211> LENGTH: 837
<212> TYPE: DNA
<213> ORGANISM: Homo sapiens

<400> SEQUENCE: 8

```
gctcctcctg cacacctccc tcgctctccc acaccactgg caccaggccc cggacacccg     60

ctctgctgca ggagaatggc tactcatcac acgctgtgga tgggactggc cctgctgggg    120

gtgctgggcg acctgcaggc agcaccggag gcccaggtct ccgtgcagcc caacttccag    180

caggacaagt tcctggggcg ctggttcagc gcgggcctcg cctccaactc gagctggctc    240

cgggagaaga aggcggcgtt gtccatgtgc aagtctgtgg tggcccctgc cacggatggt    300

ggcctcaacc tgacctccac cttcctcagg aaaaaccagt gtgagacccg aaccatgctg    360

ctgcagcccg cggggtccct cggctcctac agctaccgga gtccccactg ggcagcacc    420

tactccgtgt cagtggtgga gaccgactac gaccagtacg cgctgctgta cagccagggc    480

agcaagggcc ctggcgagga cttccgcatg gccaccctct acagccgaac ccagaccccc    540

agggctgagt taaaggagaa attcaccgcc ttctgcaagg cccagggctt cacagaggat    600

accattgtct tcctgcccca aaccgataag tgcatgacgg aacaatagga ctccccaggg    660

ctgaagctgg gatcccggcc agccaggtga cccccacgct ctggatgtct ctgctctgtt    720

ccttccccga gcccctgccc cggctccccg ccaaagcaac cctgcccact caggcttcat    780

cctgcacaat aaactccgga agcaagtcag taaaaaaaaa aaaaaaaaaa aaaaaaa       837
```

<210> SEQ ID NO 9
<211> LENGTH: 6001
<212> TYPE: DNA
<213> ORGANISM: Homo sapiens

<400> SEQUENCE: 9

```
caaggaggga tcccacagat gtcacagggc tgtcacagag ctgtggtggg aatttcccat     60

gagaccccgc ccctggctga gtcaccgcac tcctgtgttt gacctgaagt cctctcgagc    120

tgcagaagcc tgaagaccaa ggagtggaaa gttctccggc agccctgaga tctcaagagt    180

gacatttgtg agaccagcta atttgattaa aattctcttg gaatcagctt tgctagtatc    240

atacctgtgc cagatttcat catgggaaac agctgttaca acatagtagc cactctgttg    300
```

-continued

```
ctggtcctca actttgagag gacaagatca ttgcaggatc cttgtagtaa ctgcccagct    360
ggtacattct gtgataataa caggaatcag atttgcagtc cctgtcctcc aaatagtttc    420
tccagcgcag gtggacaaag gacctgtgac atatgcaggc agtgtaaagg tgttttcagg    480
accaggaagg agtgttcctc caccagcaat gcagagtgtg actgcactcc agggtttcac    540
tgcctggggg caggatgcag catgtgtgaa caggattgta aacaaggtca agaactgaca    600
aaaaaaggtt gtaaagactg ttgctttggg acatttaacg atcagaaacg tggcatctgt    660
cgaccctgga caaactgttc tttggatgga aagtctgtgc ttgtgaatgg gacgaaggag    720
agggacgtgg tctgtggacc atctccagcc gacctctctc cgggagcatc ctctgtgacc    780
ccgcctgccc ctgcgagaga gccaggacac tctccgcaga tcatctcctt ctttcttgcg    840
ctgacgtcga ctgcgttgct cttcctgctg ttcttcctca cgctccgttt ctctgttgtt    900
aaacggggca gaaagaaact cctgtatata ttcaaacaac catttatgag accagtacaa    960
actactcaag aggaagatgg ctgtagctgc cgatttccag aagaagaaga aggaggatgt   1020
gaactgtgaa atggaagtca atagggctgt tgggactttc ttgaaaagaa gcaaggaaat   1080
atgagtcatc cgctatcaca gctttcaaaa gcaagaacac catcctacat aatacccagg   1140
attcccccaa cacacgttct tttctaaatg ccaatgagtt ggcctttaaa aatgcaccac   1200
tttttttttt tttttgacag ggtctcactc tgtcacccag gctggagtgc agtggcacca   1260
ccatggctct ctgcagcctt gacctctggg agctcaagtg atcctcctgc ctcagtctcc   1320
tgagtagctg gaactacaag gaagggccac cacacctgac taactttttt gtttttttgtt   1380
tggtaaagat ggcatttcac catgttgtac aggctggtct caaactccta ggttcacttt   1440
ggcctcccaa agtgctggga ttacagacat gaactgccag gcccggccaa aataatgcac   1500
cacttttaac agaacagaca gatgaggaca gagctggtga taaaaaaaaa aaaaaaaaag   1560
cattttctag ataccactta acaggtttga gctagttttt ttgaaatcca aagaaaatta   1620
tagtttaaat tcaattacat agtccagtgg tccaactata attataatca aaatcaatgc   1680
aggtttgttt tttggtgcta atatgacata tgacaataag ccacgaggtg cagtaagtac   1740
ccgactaaag tttccgtggg ttctgtcatg taacacgaca tgctccaccg tcagggggga   1800
gtatgagcag agtgcctgag tttagggtca aggacaaaaa acctcaggcc tggaggaagt   1860
tttggaaaga gttcaagtgt ctgtatatcc tatggtcttc tccatcctca caccttctgc   1920
ctttgtcctg ctccctttta agccaggtta cattctaaaa attcttaact tttaacataa   1980
tattttatac caaagccaat aaatgaactg catatgatag gtatgaagta cagtgagaaa   2040
attaacacct gtgagctcat tgtcctacca cagcactaga gtgggggccg ccaaactccc   2100
atggccaaac ctggtgcacc atttgccttt gtttgtctgt tggtttgctt gagacagtct   2160
tgctctgttg cccaggctgg aatggagtgg ctattcacag gcacaatcat agcacacttt   2220
agccttaaac tcctgggctc aagtgatcca cccgcctcag tctcccaagt agctgggatt   2280
acaggtgcaa acctggcatg cctgccattg tttggcttat gatctaagga tagcttttta   2340
aattttattc attttatttt tttttgagac agtgtctcac tctgtctccc aggctggagt   2400
acagtggtac aatcttggat caccgcctcc cagtttcaag tgatctccct gcctcagcct   2460
cctaagtagc tgggactaca ggtatgtgcc accacgcctg gctaattttt atatttttag   2520
tagagacggg gtttcaccat gttgtccagg ctggtctcaa actcctgacc tcaggtgatc   2580
tgcccacctc tgcctcccaa agtgctggga ttacaggcat gagccaccat gcctggccat   2640
```

-continued

```
ttcttacact tttgtatgac atgcctattg caagcttgcg tgcctctgtc ccatgttatt   2700
ttactctggg atttaggtgg agggagcagc ttctatttgg aacattggcc atcgcatggc   2760
aaatgggtat ctgtcacttc tgctcctatt tagttggttc tactataacc tttagagcaa   2820
atcctgcagc caagccaggc atcaataggg cagaaaagta tattctgtaa ataggggtga   2880
ggagaagata tttctgaaca atagtctact gcagtaccaa attgcttttc aaagtggctg   2940
ttctaatgta ctcccgtcag tcatataagt gtcatgtaag tatcccattg atccacatcc   3000
ttgctaccct ctggtactat caggtgccct taattttgcc aagccagtgg gtatagaatg   3060
agatctcact gtggtcttag tttgcatttg cttggttact gatgagcacc ttgtcaaata   3120
tttatatacc atttgtgttt attttttaa ataaaatgct tgctcatgct tttttgccca   3180
tttgcaaaaa aacttggggc cgggtgcagt ggctcatgcc tgtagtccca gctctttggg   3240
aggccaaggt gggcagatcg cttgagccca ggagttcgag accagccttg gcaacatggc   3300
gaaaccctgt ctttacaaaa aatacaaaaa ttagccgggt gtggtggtgt gcacctgaag   3360
tcccagctac tcagtaggtt cgctttgagc ctgggaggca gaggttgcag tgagctggga   3420
ccgcatcact acacttcagc ctgggcaaca gagaaaaacc ttttctcaga aacaaacaaa   3480
cccaaatgtg gttgtttgtc ctgattccta aaaggtcttt atgtattcta gataataatc   3540
tttggtcagt tatatgtgtt aaaaaatatc ttctttgtgg ccaggcacgg tagctcacac   3600
ctgtaatccc agcactttgc ggggctgagg tgggtggatc atctgaggtc aagagttcaa   3660
gatcagcctg gccaacacag tgaaacccca tctctactaa acatgtacaa aacttagctg   3720
ggtatggtgg cgggtgcctg taaccccagc tgctccagag gctgtggcag aagaatcgct   3780
tgaacccagg aggcagaggt tgcagcgagc caagattgtg ccattgcact ccagactggg   3840
tgacaagagt gaaattctgc ctatctatct atctatctat ctatatctat atatatatat   3900
atatatatcc tttgtaattt atttttccct ttttaaaatt ttttataaaa ttcttttttta   3960
tttttatttt tagcagaggt gaggtttctg aggtttcatt atgttgccca ggctggtctt   4020
gaactcctga gctcaagtga tcctcccacc tcagccttcc aaagtgctgg aattgcagac   4080
atgagccacc gcgcccctcc tgtttttctc taattaatgg tgtctttctt tgtctttctg   4140
gtaataagca aaaagttctt catttgattt ggttaaattt ataactgttt tctcatatgg   4200
ttaacatttt ttcttgcctg gctaaagaaa tccttttctg cccaatacta taaagaggtt   4260
tgcccacatt ttattccaaa agttttaagt tttgtctttc atcttgaagt ctaatgtatc   4320
aggaactggc ttttgtgcct gttgggaggt agtgatccaa ttccatgtct tgcatgtagg   4380
taaccactgg tccctgcgcc atgtattcaa tacgtcgtct ttctcctgcg ggtctgcaat   4440
ctcacctacc atccatcaag tttccatagg gccatgggtc tgcttctggg ctccctgttc   4500
tgttccattg tcaatttgtc tatcctgtgc cagtatcaca ctgtgtttat tacaatagct   4560
ttgtaacagc tctcgatatc cggtaggaca tctccctcca ccttcttttt ctacttcaga   4620
agtgtcttag ctaggtcagg cacggtggct cacgcctgta atcccagcac tttgggaggc   4680
cgacgcggat ggatcacctg aggtcaggag ttttgagaca gcctggccaa catggtgaaa   4740
ccccatctct actaaaaaat acaaaaatta gtcaggcatg gtggcatgtg cctgtaatcc   4800
cagctatttg ggaggctgag gccggagaat tgcttgaacc cggggggcgg aggttgcagt   4860
gagccgagat cgtaccattg cactccagcc tgggtgacag agcgaaactc tgtctcagga   4920
aaaaaaagaa aagagatgtc ttggttattc ttggttcttt attattcaat ataaatttta   4980
gaagctgaat ttgaaaagat ttggattgga atttcattaa atctacaggt caatttaggg   5040
```

agagttgata attttacaga attgagtcat ctggtgttcc aataagaata agagaacaat 5100
tattggctgt acaattcttg ccaaatagta ggcaaagcaa agcttaggaa gtatactggt 5160
gccatttcag gaacaaagct aggtgcgaat atttttgtct ttctgaatca tgatgctgta 5220
agttctaaag tgatttctcc tcttggcttt ggacacatgg tgtttaatta cctactgctg 5280
actatccaca aacagaaaga gactggtcat gccccacagg gttggggtat ccaagataat 5340
ggagcgaggc tctcatgtgt cctaggttac acaccgaaaa tccacagttt attctgtgaa 5400
gaaaggaggc tatgtttatg atacagactg tgatattttt atcatagcct attctggtat 5460
catgtgcaaa agctataaat gaaaaacaca ggaacttggc atgtgagtca ttgctccccc 5520
taaatgacaa ttaataagga aggaacattg agacagaata aaatgatccc cttctgggtt 5580
taatttagaa agttccataa ttaggtttaa tagaaataaa tgtaaatttc tatgattaaa 5640
aataaattag cacatttagg gatacacaaa ttataaatca ttttctaaat gctaaaaaca 5700
agctcaggtt tttttcagaa gaaagtttta attttttttc tttagtggaa gatatcactc 5760
tgacggaaag ttttgatgtg aggggcggat gactataaag tgggcatctt cccccacagg 5820
aagatgtttc catctgtggg tgagaggtgc ccaccgcagc tagggcaggt tacatgtgcc 5880
ctgtgtgtgg taggacttgg agagtgatct ttatcaacgt ttttatttaa aagactatct 5940
aataaaacac aaaactatga tgttcacagg aaaaaaagaa taagaaaaaa agaaaaaaaa 6000
a 6001

<210> SEQ ID NO 10
<211> LENGTH: 1336
<212> TYPE: DNA
<213> ORGANISM: Homo sapiens

<400> SEQUENCE: 10
gagagacaca gagtccggca ttggtcccag gcagcagtta gcccgccgcc cgcctgtgtg 60
tccccagagc catggagaga gccagtctga tccagaaggc caagctggca gagcaggccg 120
aacgctatga ggacatggca gccttcatga aaggcgccgt ggagaagggc gaggagctct 180
cctgcgaaga gcgaaacctg ctctcagtag cctataagaa cgtggtgggc ggccagaggg 240
ctgcctggag ggtgctgtcc agtattgagc agaaaagcaa cgaggagggc tcggaggaga 300
aggggcccga ggtgcgtgag taccgggaga aggtggagac tgagctccag ggcgtgtgcg 360
acaccgtgct gggcctgctg gacagccacc tcatcaagga ggccggggac gccgagagcc 420
gggtcttcta cctgaagatg aagggtgact actaccgcta cctggccgag gtggccaccg 480
gtgacgacaa gaagcgcatc attgactcag cccggtcagc ctaccaggag gccatggaca 540
tcagcaagaa ggagatgccg cccaccaacc ccatccgcct gggcctggcc ctgaactttt 600
ccgtcttcca ctacgagatc gccaacagcc ccgaggaggc catctctctg gccaagacca 660
ctttcgacga ggccatggct gatctgcaca ccctcagcga ggactcctac aaagacagca 720
ccctcatcat gcagctgctg cgagacaacc tgacactgtg gacggccgac aacgccgggg 780
aagagggggg cgaggctccc caggagcccc agagctgagt gttgcccgcc accgccccgc 840
cctgccccct ccagtccccc accctgccga gaggactagt atggggtggg aggccccacc 900
cttctcccct aggcgctgtt cttgctccaa agggctccgt ggagagggac tggcagagct 960
gaggccacct ggggctgggg atcccactct tcttgcagct gttgagcgca cctaaccact 1020
ggtcatgccc ccacccctgc tctccgcacc cgcttcctcc cgaccccagg accaggctac 1080

```
ttctcccctc ctcttgcctc cctcctgccc ctgctgcctc tgatcgtagg aattgaggag   1140

tgtcccgcct tgtggctgag aactggacag tggcaggggc tggagatggg tgtgtgtgtg   1200

tgtgtgtgtg tgtgtgtgtg tgtgcgcgcg cgccagtgca agaccgagat tgagggaaag   1260

catgtctgct gggtgtgacc atgtttcctc tcaataaagt tcccctgtga cactcaaaaa   1320

aaaaaaaaaa aaaaaa                                                   1336
```

<210> SEQ ID NO 11
<211> LENGTH: 2240
<212> TYPE: DNA
<213> ORGANISM: Homo sapiens

<400> SEQUENCE: 11

```
ggagggcagc cagcagcttc cccttctctg ccctgctcca ggcaccaggc tctttcccct     60

tcagtgtctc agaggagggg acggcagcac catggacccc cgcttgtcca ctgtccgcca    120

gacctgctgc tgcttcaatg tccgcatcgc aaccaccgcc ctggccatct accatgtgat    180

catgagcgtc ttgttgttca tcgagcactc agtagaggtg gcccatggca aggcgtcctg    240

caagctctcc cagatgggct acctcaggat cgctgacctg atctccagct tcctgctcat    300

caccatgctc ttcatcatca gcctgagcct actgatcggc gtagtcaaga accgggagaa    360

gtacctgctg cccttcctgt ccctgcaaat catggactat ctcctgtgcc tgctcaccct    420

gctgggctcc tacattgagc tgcccgccta cctcaagttg gcctcccgga gccgtgctag    480

ctcctccaag ttcccccctga tgacgctgca gctgctggac ttctgcctga gcatcctgac    540

cctctgcagc tcctacatgg aagtgcccac ctatctcaac ttcaagtcca tgaaccacat    600

gaattacctc cccagccagg aggatatgcc tcataaccag ttcatcaaga tgatgatcat    660

cttttccatc gccttcatca ctgtccttat cttcaaggtc tacatgttca agtgcgtgtg    720

gcggtgctac agattgatca agtgcatgaa ctcggtggag gagaagagaa actccaagat    780

gctccagaag gtggtcctgc cgtcctacga ggaagccctg tctttgccat cgaagacccc    840

agagggggc ccagcaccac ccccatactc agaggtgtga ccctcgccag gccccagccc    900

cagtgctggg aggggtggag ctgcctcata atctgctttt ttgctttggt ggcccctgtg    960

gcctgggtgg gccctcccgc ccctccctgg caggacaatc tgcttgtgtc tccctcgctg   1020

gcctgctcct cctgcagggc ctgtgagctg ctcacaactg ggtcaacgct ttaggctgag   1080

tcactcctcg ggtctctcca taattcagcc caacaatgct tggtttattt caatcagctc   1140

tgacacttgt ttagacgatt ggccattcta aagttggtga gtttgtcaag caactatcga   1200

cttgatcagt tcagccaagc aactgacaaa tcaaaaaccc acttgtcagt tcagtaaaat   1260

aatttggtca aacaacagtc tattgcattg atttataaat agttgtcagt tcacatagca   1320

atttaatcaa gtaatcatta attagttacc ccctatatat aaatatatgt aatcaatttc   1380

ttcaaatagc ttgcttacat gataatcaat tagccaacca tgagtcattt agaatagtga   1440

taaatagaat acacagaata gtgatgaaat tcaatttaaa aaatcacgtt agcctccaaa   1500

ccatttaatt caaatgaacc catcaactgg atgccaactc tggcgaatgt aggacctctg   1560

agtggctgta taattgttaa ttcaaatgaa attcatttaa acagttgaca aactgtcatt   1620

caacaattag ctccaggaaa taacagttat ttcatcataa aacagtccct tcaaacacac   1680

aattgttctg ctgaagagtt gtcatcaaca atccaatgct cacctattca gttgctctgt   1740

ggtcagtgtg gctgcataac agtggattcc atgaaaggag tcattttagt gatgagctgc   1800

cagtccattc ccaggccagg ctgtcgctgg ccatccattc agtcgattca gtcataggcg   1860
```

aatctgttct gcccgaggct tgtggtcaag caaaaattca gccctgaaat caggcacatc 1920
tgttcgttgg actaaaccca caggttagtt cagtcaaagc aggcaacccc cttgtgggca 1980
ctgaccctgc cactggggtc atggcggttg tggcagctgg ggaggtttgg ccccaacagc 2040
cctcctgtgc ctgcttccct gtgtgtcggg gtcctccagg gagctgaccc agaggtggag 2100
gccacggagg cagggtctct ggggactgtc ggggggtaca gagggagaag gctctgcaag 2160
agctccctgg caatacccc ttgtgtaatt gctttgtgtg cgacagggag gaagtttcaa 2220
taaagcagca acaagcttct 2240

<210> SEQ ID NO 12
<211> LENGTH: 3039
<212> TYPE: DNA
<213> ORGANISM: Homo sapiens

<400> SEQUENCE: 12
aggcgcagag gagggcggtg ttgagaccgg cggagcggcg ggaccccctag gtggcggagg 60 gacgctccgg gaaagcgagg ggcgctacga gctctggccc acgtgacctg ccgggggcgg 120
gagcaggggg cgcgccggcc tcctgcggtg cccctgcctt ggggaggggc cgtgaccacc 180
cgtctgtcgc ccgaggcggc cgccgctgca ccttcaccgc gtacccggga cccgcccgcc 240
cgcgggagaa atgttgctga agtgctgctg aaagggccag agatgcaagg atttgggata 300
cattttgaac ctttaagctg tctgacattg acctcctttc attattaata aagaagaatc 360
aggagcttag gatgtattaa caccaactca ttaatatact aaccggacaa tgttctacaa 420
acaattctac attgtaaagg actggattgg cacaaaataa aataatttta ttttattcag 480
cttataatat gactcgatgg aggaaaattt gataagcatg agagaagacc attcttttca 540
tgttcgttac agaatggaag cttcttgcct agagctggcc ttggaagggg aacgtctatg 600
taaatcagga gactgccgcg ctggcgtgtc attctttgaa gctgcagttc aagttggaac 660
tgaagaccta aaaacactta gcgctattta cagccagttg ggcaatgctt atttctattt 720
gcatgattat gccaaagcat tagaatatca ccatcatgat ttaaccttg caaggactat 780 tggagaccag ctgggggaag cgaaagctag tggtaatctg ggaaacacct taaaagttct 840
tgggaatttt gacgaagcca tagtttgttg tcagcgacac ctagatattt ccagagagct 900
taatgacaag gtgggagaag caagagcact ttacaatctt gggaatgtgt atcatgccaa 960
agggaaaagt tttggttgcc ctggtcccca ggatgtagga gaatttccag aagaagtgag 1020
agatgctctg caggcagccg tggattttta tgaggaaaac ctatcattag tgactgcttt 1080
gggtgaccga gcggcacaag gacgtgcctt tggaaatctt ggaaacacac attacctcct 1140
tggcaacttc agggatgcag ttatagctca tgagcagcgt ctccttattg caaaagaatt 1200
tggagataaa gcagctgaaa gaagagcata tagcaacctt ggaaatgcat atatatttct 1260
tggtgaattt gaaactgcct cggaatacta caagaagaca ctactgttgg cccgacagct 1320
taaagaccga gctgtagaag cacagtcttg ttacagtctt ggaaatacat atactttact 1380
tcaagactat gaaaaggcca ttgattatca tctgaagcac ttagcaattg ctcaagagct 1440
gaatgataga attggtgaag gaagagcatg ttggagctta ggaaatgcat acacagcact 1500
aggaaatcat gatcaagcaa tgcattttgc tgaaaagcac ttggaaattt caagagaggt 1560
tggggataaa agtggtgaac taacagcacg acttaatctc tcagaccttc aaatggttct 1620
tggtctgagc tacagcacaa ataactccat aatgtctgaa aatactgaaa ttgatagcag 1680

-continued tttgaatggt gtacgcccca agttgggacg ccggcatagt atggaaaata tggaacttat 1740
gaagttaaca ccagaaaagg tacagaactg gaacagtgaa attcttgcta agcaaaaacc 1800
tcttattgcc aaaccttctg caaagctact ctttgtcaac agactgaagg ggaaaaaata 1860
caaaacgaat tcctccacta aagttctcca agatgccagt aattctattg accaccgaat 1920
tccaaattct cagaggaaaa tcagtgcaga tactattgga gatgaagggt tctttgactt 1980
attaagccga tttcaaagca ataggatgga tgatcagaga tgttgcttac aagaaaagaa 2040
ctgccataca gcttcaacaa caacttcttc cactcccccct aaaatgatgc taaaaacatc 2100
atctgttcct gtggtatccc ccaacacgga tgagttttta gatcttcttg ccagctcaca 2160
gagtcgccgt ctggatgacc agagggctag tttcagtaat ttgccagggc ttcgtctaac 2220
acaaaacagc cagtcggtac ttagccacct gatgactaat gacaacaaag aggctgatga 2280
agatttcttt gacatccttg taaaatgtca aggatccaga ttagatgatc aaagatgtgc 2340
tccaccacct gctaccacaa agggtccgac agtaccagat gaagactttt tcagccttat 2400
tttacggtcc cagggaaaga gaatggatga acagagagtt cttttacaaa gagatcaaaa 2460
cagagacact gactttgggc taaaggactt tttgcaaaat aatgctttgt tggagtttaa 2520
aaattcaggg aaaaaatcgg cagaccatta gttactatgg atttattttt tttcctttca 2580
aacacggtaa ggaaacaatc tattactttt ttccttaaaa ggagaattta tagcactgta 2640
atacagctta aaatattttt agaatgatgt aaatagttaa ccttcagtag tctattaagg 2700
cattaatact tctctggaca tgcgcgtttg agggtggagg ggtcctgtaa ggtgcttcat 2760
cgtctgtgat tactgcttgg gatgtgttct ttggcagctt gtgagattac tttacctagt 2820
gtttataaag taggaagtta agtgaatcat agattagaat ttaatactct tatggaaata 2880
attttttaac atcttaattg acaatggcgt ttttttatac ataaccatgg atgtagtggg 2940
aaacaatgtt gtttggtaaa aataatgtac ttgatcaatg taaaaaagta tataaaatag 3000
tcttactaaa aatctaggtt ttttttcct ccaaaaaaa 3039

<210> SEQ ID NO 13
<211> LENGTH: 7018
<212> TYPE: DNA
<213> ORGANISM: Homo sapiens

<400> SEQUENCE: 13
ggcgggcgcg ccgggcggca ggtgtcggcg tcggcggcat tcggcggcga tggagcggcc 60
ctggggagct gcggacggcc tctcgcgctg gccccatggc ctcggcctcc tcctcctcct 120
gcagctgctg ccgccgtcga ccctcagcca ggaccggctg gacgcgccgc cgccgcccgc 180
tgcgccgctg ccgcgctggt ctggccccat cggggtgagc tgggggctgc gggcggccgc 240
agccgggggc gcgtttcccc gcggcggccg ttggcgtcgc agcgcgccgg gcgaggacga 300
ggagtgcggc cgggtccggg acttcgtcgc caagctggcc aacaacacgc accagcatgt 360
gtttgatgat ctcagaggct cagtatcctt gtcctgggtt ggagatagca ctggggtcat 420
tctagtcttg actaccttcc atgtaccact ggtaattatg acttttggac agtccaagct 480
atatcgaagt gaggattatg ggaagaactt taaggatatt acagatctca tcaataacac 540
ctttattcgg actgaatttg gcatggctat tggtcctgag aactctggaa aggtggtgtt 600
aacagcagag gtgtctggag gaagtcgtgg aggaagaatc ttcagatcat cagattttgc 660
gaagaatttt gtgcaaacag atctcccttt tcatcctctc actcagatga tgtatagccc 720
tcagaattct gattatcttt tagctctcag cactgaaaat ggcctgtggg tgtccaagaa 780

-continued

```
ttttggggga aaatgggaag aaatccacaa agcagtatgt ttggccaaat ggggatcaga    840
caacaccatc ttctttacaa cctatgcaaa tggctcctgc aaagctgacc ttggggctct    900
ggaattatgg agaacttcag acttgggaaa aagcttcaaa actattggtg tgaaaatcta    960
ctcatttggt cttgggggac gtttcctttt tgcctctgtg atggctgata aggataccac   1020
aagaaggatc cacgtttcaa cagatcaagg ggacacatgg agcatggccc agctcccctc   1080
cgtgggacag gaacagttct attctattct ggcagcaaat gatgacatgg tattcatgca   1140
tgtagatgaa cctggagaca ctgggtttgg cacaatcttt acctcagatg atcgaggcat   1200
tgtctattcc aagtctttgg accgacatct ctacactacc acaggcggag agacggactt   1260
taccaacgtg acctccctcc gcggcgtcta cataacaagc gtgctctccg aagataattc   1320
tatccagacc atgatcactt ttgaccaagg aggaaggtgg acgcacctga ggaagcctga   1380
aaacagtgaa tgtgatgcta cagcaaaaaa caagaatgag tgcagccttc atattcatgc   1440
ttcctacagc atctcccaga aactgaatgt tccaatggcc ccactctcag agccgaatgc   1500
cgtaggcatt gtcattgctc atggtagcgt gggggatgcc atctcagtga tggttccaga   1560
tgtgtacatc tcagatgatg gggggttactc ctggacaaag atgctggaag gaccccacta   1620
ttacaccatc ctggattctg gaggcatcat tgtggccatt gagcacagca gccgtcctat   1680
caatgtgatt aagttctcca cagacgaagg tcaatgctgg caaacctaca cgttcaccag   1740
ggaccccatc tatttcactg gcctagcttc agaacctgga gctaggtcca tgaatatcag   1800
catttggggc ttcacagaat ctttcctgac cagccagtgg gtctcctaca ccattgattt   1860
taaagatatc cttgaaagga actgtgaaga gaaggactat accatatggc tggcacactc   1920
cacagaccct gaagattatg aagatggctg cattttgggc tacaaagaac agtttctgcg   1980
gctacgcaag tcatccgtgt gtcagaatgg tcgagactat gttgtgacca agcagccctc   2040
catctgcctc tgttccctgg aggactttct ctgtgatttt ggctactacc gtccagaaaa   2100
tgactccaag tgtgtggaac agccagaact gaagggccac gacctggagt tttgtctgta   2160
cggaagagaa gaacacctaa caacaaatgg gtaccggaaa attccagggg acaaatgcca   2220
gggtggggta aatccagttc gagaagtaaa agacttgaaa aagaaatgca caagcaactt   2280
tttgagtccg gaaaaacaga attccaagtc aaattctgtt ccaattatcc tggccatcgt   2340
gggattgatg ctggtcacag tcgtagcagg agtgctcatt gtgaagaaat atgtctgtgg   2400
gggaaggttc ctggtgcatc gatactctgt gctgcagcag catgcagagg ccaatggtgt   2460
ggatggtgtg gatgctttgg acacagcctc ccacactaat aaaagtggtt atcatgatga   2520
ctcagatgag gacctcttgg aatagctctt cagaggagct ggacccagca tggatggtgg   2580
aaccacagta cctcttacac tccctgtggc tccaacttca ggaaataaat ttcccattgc   2640
gagggaccca gctctgtttc tgctgcttcc atcaaagcca aaaggaccta cactaaagaa   2700
atgcagggtg ggggtgggga accctgagca ctttttttaca attggctctg agaaaaaggg   2760
agacatttta aattctttaa cttcttattt ctcgtcctgt ctctttgcaa agtatgggct   2820
tttttgtttt tgttttttaa gggaaacgaa atggaattcg aagggacctt ttcactaacc   2880
ccacttctgt gtgttctgca tggcgcctgc cccagggcat ctgccaactc cagtatcagc   2940
tctcacagtg tacttggtac catccctggg ctctgctggc gagacgaaac agctgtagag   3000
atgaaaacag gctgcagagg ctggcacagc ctggccggct tttctccatc tggggacagt   3060
cctactccaa gaacactgca caccagctcc tcacacagat cccacttact cttttttttt   3120
```

-continued

```
ttttcagaga ccacagacca cagtgatttt tcttttccct tgtttaatta ggcaataccc   3180
ttgttaattg ccctttggca actaacttaa ccatgtgctt cccacacagt acatcaggaa   3240
aacttacagg gcaatatttt taacttgggg caggaagaag ggagcagcag agaattgact   3300
agatatagca cctattaaaa gagaactctt gcttcttctg agatttttca agctgtgctt   3360
tgtgtgtgtg ccagtagact tacgcaagga cagggtacaa acttagctgg aagtctgccc   3420
aggctgaatg atctcttccc tagagttgat tgtcgggtac acagtgtgaa cccccgaaga   3480
cggaacctca cagtcttcca tgttcccttc ttaactgtcg tgtggctcgt tgctaaatca   3540
tgacaatggc tgcctatctg ctgcttctta ggttgctgtt gtacatggaa ccaggactag   3600
agatttttc agatttatag acttaaaaaa ttagaatttt attaccaggc tttccttctc   3660
acccctttt tctgactttg ccaagtaatt tgttgacacg aaaattttgg aggaaccaat   3720
tgaaaacaca cttccagtct agatgatgct ttgtgtgata cattaagttc ttattttgga   3780
ttaaaagaag ttttccattt gatacttctc taaattaaat aaattataga atgtagttgg   3840
gtggattttg gggtggccat atagtaatgg aaagctgcaa taattagttt taatacagct   3900
tgaatatttg ctatatagaa atatagtatg gaaagttttt ggtcttaatg tagctactgt   3960
gcgggtcaca gtttctccca atgattatga ctgggacatt ctttggtaga taccatttgc   4020
tactagttta ttttgtggct agaaagtcag ttttgtgtgt ttttttttt ttttatttga   4080
agtgccaaat taactttagt cagaatgtga gcagatggct aagttctctc ctccccagaa   4140
tggattaaca gctgcgtgga aagtggggga gagagtggat ggagactttt agagatgtta   4200
aaactgcagt agaatgaaat gagtcaggga gcttcagtta gaaaataaag ttgaggcagt   4260
ttttgtgaag ataatatggt tagggctgga gtgcactagt ctttttgctt attcattttg   4320
catggtttta aaattaaaaa taattccgaa gatacaccag ctcacaaatg aaaacgtcag   4380
cctctgcccc accctccctc ctgcccaaag tgaatttggt actcagaaaa gaactgttta   4440
taccactcac ctttctccca gcatgtactc actgtgggca gatgcaccaa tacatggtaa   4500
tcctcttact cattttaaga cgtaggaaac tcaatattct tctctaacca tatacgatag   4560
ggctcttcgc ttttaatgat atctgggatt tctgtggaac ttggcaaatt ttcagagcac   4620
cttcactcac ataatgtcat ttgaacctca caatgttctt gggatggagt cagttgttca   4680
gggtccccgt gtgtgtgata agcagtgctg gctggctgtc ttcagaactc ttggaaatct   4740
ttacacatgc gagtgctaac cactttgagc aaggctgcct tcttgtagat gacttgctgt   4800
tctttatgac agggatcagt ggcatttgtt tcctagcagt atttagcacc tttttgccac   4860
cttggtgaac agaaaattgt attttcctgt ctttcatggc tgaaaacaaa agtaatggga   4920
attttaaata cgtttgcaga aactgcccct cccctcattg agggtcactg ctcaagagtg   4980
caggagtgga ctctccactg atgggtctcc ctccccatcc tggtttccac cccgggctgg   5040
ctagctctgt tggtttgaag actgacagcc agcctggctc attctcatta ttggctagtt   5100
agctttcttt atcaacctgc tcactcacaa atgtgtgccc tcagccagag agtaagaaag   5160
cccaaatctg ttacagcttc taaaaaaata gatttctaat ttgtcctact catgttagga   5220
gcattatctt tgaaggtaaa acatagtgta tcattgtgta aactcccagg cttgatgtag   5280
cagaagagat catttctgga ggcttcagca atggaattta gcattataag agagattgga   5340
caaaccagtc caaagtggtc cgagttctta aatccaggta gggaactcac tcttctttct   5400
tctctggacc taattgggca ttgggcttta gtgagaccac agaccaggcc cgtctctcct   5460
gtaggctttt aattcaatgg caactctatt tcaaagaata aaagcctttg gagagttgcg   5520
```

-continued gcagttctgg gggcgggctc aggagagtcc atagatcagc cgtaactgga acgtagaatc 5580
tacgtctgcc tctgaatgga cttcccacct cctctctctt gctctgatgc ttgcctctgg 5640
gcctctccat gcccaaggtg gtctttcatc cttgacaggc tggtaatgtg ctggccacct 5700
ccagctcctg catcgagtct gtaaaccaga gctggttctc atggccttcg tcacgatacc 5760
aggatacgga ggggagccca gggccatcca tacccacccc agggtaacgg ggctggcctg 5820
gcattagtca ttatttagtt tccaggccaa ccatccagat agagattccc tctttccttt 5880
gagcagtgct ctcaagagct ccgtgcctgt ccacaatgac ctagagtgca tcctgctcat 5940
tgtcagtgta gcccctcgcc cctatattca tccaggatac ttggaagtgc taaaatagga 6000
agggattcgg ctttcaactt tgctaccatc ttccctgaag caggaaaatg aacatggact 6060
taaatgttct ttgaaaaaac caaagtttta agatttgctg tgtgatgaag tgacagggag 6120
ggccggagtc agcaggtgcc agactttctg ttctgtctgc catgggtttg tccagctcag 6180
gtagctctag gagcaccatc ctgccctagc agagcccagg ccttgccctc atgaagcatc 6240
attgaaatag caggagcatg ttgatttctt ggttaggttg cattataata acaagagtca 6300
gaacattaat tcgaaacaac ttgcagtatg catttcttca caccagtaca ttcttaagtg 6360
tacttgttta taaggaataa cataaactaa tctgtacctt tatatatatg tgtgtgtaca 6420
tatatacata tataaactgt atagtgtaca tggtaatgat ttattgctat gccccagatc 6480
cttaatgtag ttctcatcct ccgcatgccc tcagccacaa gcgggtgact gactgttccc 6540
tgatgatttg gcccacctcc tgtgtttgga cctctaggga ggagggtttt ggtcatactc 6600
tccttatcct cgtgcacaga aatgctcagg gtccccatgt gcctgttgtt cagccctctc 6660
tcttgttccc tttctgagca tgtggtcctt ccccaggctg tgggacagct gccttcccac 6720
gaaagtgtaa agcagtatta agatcattac tgcatgtgcc ctaaaaaccc aagttttcta 6780
ttcccttagg acagaaaatt gcatgtgagg tgggataatc gagtttcagt gacccacgtc 6840
agttacacat taaagccaga ccccatgata aaattccaca aaatggaaat aaaactcaaa 6900
tttctttagc attgtgtaaa taaatctgaa tgtgtttaac tttgtactgg taattttctg 6960
tatatttgga atatttgggt taaaaataaa acagactgga ctttgttacc tgacctac 7018

<210> SEQ ID NO 14
<211> LENGTH: 1749
<212> TYPE: DNA
<213> ORGANISM: Homo sapiens

<400> SEQUENCE: 14
gtgacattgt ttgccaaaat cccaggcagc atggacctca gtcttctctg ggtacttctg 60
cccctagtca ccatggcctg gggccagtat ggcgattatg gatacccata ccagcagtat 120
catgactaca gcgatgatgg gtgggtgaat ttgaaccggc aaggcttcag ctaccagtgt 180
ccccaggggc aggtgatagt ggccgtgagg agcatcttca gcaagaagga aggttctgac 240
agacaatgga actacgcctg catgcccacg ccacagagcc tcggggaacc cacggagtgc 300
tggtgggagg agatcaacag ggctggcatg gaatggtacc agacgtgctc caacaatggg 360
ctggtggcag gattccagag ccgctacttc gagtcagtgc tggatcggga gtggcagttt 420
tactgttgtc gctacagcaa gaggtgccca tattcctgct ggctaacaac agaatatcca 480
ggtcactatg gtgaggaaat ggacatgatt tcctacaatt atgattacta tatccgagga 540
gcaacaacca ctttctctgc agtggaaagg gatcgccagt ggaagttcat aatgtgccgg 600

-continued

```
atgactgaat acgactgtga atttgcaaat gtttagattt gccacatacc aaatctgggt    660

gaaaggaaag gggccgggga caggagggtg tccacatatg ttaacatcag ttggatctcc    720

tatagaagtt tctgctgctc tctttccttc tccctgagct ggtaactgca atgccaactt    780

cctgggcctt tctgactagt atcacacttc taataaaatc cacaattaaa ccatgtttct    840

cacttttcac atgtttcata gcaactgctt tatatgactg atgatggctt ccttgcacac    900

cacatataca gtgcgcatgc ttacagccgg gcttctggag caccagctgc agcctggcta    960

ctgcttttta ctgcagaatg aactgcaagt tcagcatagt ggaggggaga ggcagaactg   1020

gaggagaggt gcagtgaagg ttctctacag ctaagcctgt ttgaatgata cgtaggttcc   1080

ccaccaaaag caggctttct gccctgaggg acatcttccc actcccctgc tccacatgag   1140

ccatgcatgc ttagcaatcc aagtgcagag ctctttgctc caggagtgag gagactggga   1200

ggtgaaatgg ggaaatggaa gggtttggag gcagagctga aaacagggtt ggaaggattt   1260

cctgaattag aagacaaacg ttagcatacc cagtaaggaa aatgagtgca ggggccaggg   1320

gaacccgtga ggatcactct caaatgagat taaaaacaag gaagcagaga atggtcagag   1380

aatgggattc agattgggaa cttgtgggga tgagagtgac caggttgaac tgggaagtgg   1440

aaaaaggagt ttgagtcact ggcacctaga agcctgccca cgattcctag gaaggctggc   1500

agacaccctg gaaccctggg gagctactgg caaactctcc tggattgggc ctgatttttt   1560

tggtgggaaa ggctgccctg gggatcaact ttccttctgt gtgtggctca ggagttcttc   1620

tgcagagatg gcgctatctt tcctcctcct gtgatgtcct gctcccaacc atttgtactc   1680

ttcattacaa aagaaataaa aatattaacg ttcactatgc tgaaaataaa aaaaaaaaaa   1740

aaaaaaaaa                                                           1749
```

```
<210> SEQ ID NO 15
<211> LENGTH: 2478
<212> TYPE: DNA
<213> ORGANISM: Homo sapiens

<400> SEQUENCE: 15
```

```
gcagttggtg aaactcctct gtctcccgct catcttttca ttgctcgttc ccctccttcc     60

cgcagacacc cggacctccc ctgggcgcca gctccgcggc tccaacgggt ccagaaacaa    120

gccggatttt tttttttttct tcctggaaat tggctttggt gtgtgttgcc ctacctccct    180

cctccccctc ccacccacag cccccccccg gccttttttt tttttttttt tttttttgag    240

acatggcccg ggcagtggct cctggaagag gaacaagtgt gggaaaaggg agaggaagcc    300

ggagctaaat gacaggatgc aggcgacttg agacacaaaa agagaagcgt tcctctcgga    360

tccaggcatt gcctcgctgc tttcttttct ccaagacggg ctgaggattg tacagctcta    420

ggcggagttg gggctcttcg gatcgcttag attctcctct ttgctgcatt tccccccacg    480

tcctcgttct cccgcgtctg cctgcggacc cggagaaggg agaatggaga gggggctgcc    540

gctcctctgc gccgtgctcg ccctcgtcct cgccccggcc ggcgcttttc gcaacgataa    600

atgtggcgat actataaaaa ttgaaagccc cgggtacctt acatctcctg gttatcctca    660

ttcttatcac ccaagtgaaa aatgcgaatg gctgattcag gctccggacc cataccagag    720

aattatgatc aacttcaacc ctcacttcga tttggaggac agagactgca agtatgacta    780

cgtggaagtc ttcgatggag aaaatgaaaa tggacatttt aggggaaagt tctgtggaaa    840

gatagcccct cctcctgttg tgtcttcagg gccatttctt tttatcaaat ttgtctctga    900

ctacgaaaca catggtgcag gattttccat acgttatgaa attttcaaga gaggtcctga    960
```

-continued

```
atgttcccag aactacacaa cacctagtgg agtgataaag tcccccggat tccctgaaaa   1020
atatcccaac agccttgaat gcacttatat tgtctttgcg ccaaagatgt cagagattat   1080
cctggaattt gaaagctttg acctggagcc tgactcaaat cctccagggg ggatgttctg   1140
tcgctacgac cggctagaaa tctgggatgg attccctgat gttggccctc acattgggcg   1200
ttactgtgga cagaaaacac caggtcgaat ccgatcctca tcgggcattc tctccatggt   1260
tttttacacc gacagcgcga tagcaaaaga aggtttctca gcaaactaca gtgtcttgca   1320
gagcagtgtc tcagaagatt tcaaatgtat ggaagctctg ggcatggaat caggagaaat   1380
tcattctgac cagatcacag cttcttccca gtatagcacc aactggtctg cagagcgctc   1440
ccgcctgaac taccctgaga atgggtggac tcccggagag gattcctacc gagagtggat   1500
acaggtagac ttgggccttc tgcgctttgt cacggctgtc gggacacagg gcgccatttc   1560
aaaagaaacc aagaagaaat attatgtcaa gacttacaag atcgacgtta gctccaacgg   1620
ggaagactgg atcaccataa aagaaggaaa caaacctgtt ctctttcagg gaaacaccaa   1680
ccccacagat gttgtggttg cagtattccc caaaccactg ataactcgat ttgtccgaat   1740
caagcctgca acttgggaaa ctggcatatc tatgagattt gaagtatacg gttgcaagat   1800
aacagattat ccttgctctg gaatgttggg tatggtgtct ggacttattt ctgactccca   1860
gatcacatca tccaaccaag ggacagaaa ctggatgcct gaaaacatcc gcctggtaac   1920
cagtcgctct ggctgggcac ttccacccgc acctcattcc tacatcaatg agtggctcca   1980
aatagacctg gggaggaga agatcgtgag ggcatcatc attcagggtg ggaagcaccg   2040
agagaacaag gtgttcatga ggaagttcaa gatcgggtac agcaacaacg gctcggactg   2100
gaagatgatc atggatgaca gcaaacgcaa ggcgaagtct tttgagggca acaacaacta   2160
tgatacacct gagctgcgga cttttccagc tctctccacg cgattcatca ggatctaccc   2220
cgagagagcc actcatggcg gactggggct cagaatggag ctgctgggct gtgaagtgga   2280
agcccctaca gctggaccga ccactcccaa cgggaacttg gtggatgaat gtgatgacga   2340
ccaggccaac tgccacagtg gaacaggtga tgacttccag ctcacaggtg gcaccactgt   2400
gctggccaca gaaaagccca cggtcataga cagcaccata caatcaggta tcaaataaaa   2460
tacgaaatgt gacagatt                                                  2478
```

<210> SEQ ID NO 16
<211> LENGTH: 3372
<212> TYPE: DNA
<213> ORGANISM: Homo sapiens

<400> SEQUENCE: 16

```
taaaaccagg aagtgaagtc cccgagcacg ttagaaagcc tgacatggcc tgactcggga     60
cagctcagag cagggcagaa ctggggacac tctgggccgg ccttctgcct gcatggacgc    120
tctgaagcca ccctgtctct ggaggaacca cgagcgaggg aagaaggaca gggactcgtg    180
tggcaggaag aactcagagc cgggaagccc ccattcacta gaagcactga gagatgcggc    240
cccctcgcag ggtctgaatt tcctgctgct gttcacaaag atgcttttta tctttaactt    300
tttgttttcc ccacttccga ccccggcgtt gatctgcatc ctgacatttg gagctgccat    360
cttcttgtgg ctgatcacca gacctcaacc cgtcttacct cttcttgacc tgaacaatca    420
gtctgtggga attgagggag gagcacggaa gggggtttcc cagaagaaca atgacctaac    480
aagttgctgc ttctcagatg ccaagactat gtatgaggtt ttccaaagag gactcgctgt    540
```

-continued

```
gtctgacaat gggccctgct tgggatatag aaaaccaaac cagccctaca gatggctatc    600
ttacaaacag gtgtctgata gagcagagta cctgggttcc tgtctcttgc ataaaggtta    660
taaatcatca ccagaccagt ttgtcggcat ctttgctcag aataggccag agtggatcat    720
ctccgaattg gcttgttaca cgtactctat ggtagctgta cctctgtatg acaccttggg    780
accagaagcc atcgtacata ttgtcaacaa ggctgatatc gccatggtga tctgtgacac    840
accccaaaag gcattggtgc tgatagggaa tgtagagaaa ggcttcaccc cgagcctgaa    900
ggtgatcatc cttatggacc cctttgatga tgacctgaag caaagagggg agaagagtgg    960
aattgagatc ttatccctat atgatgctga gaacctaggc aaagagcact tcagaaaacc   1020
tgtgcctcct agcccagaag acctgagcgt catctgcttc accagtggga ccacaggtga   1080
ccccaaagga gccatgataa cccatcaaaa tattgtttca aatgctgctg cctttctcaa   1140
atgtgtggag catgcttatg agcccactcc tgatgatgtg gccatatcct acctccctct   1200
ggctcatatg tttgagagga ttgtacaggc tgttgtgtac agctgtggag ccagagttgg   1260
attcttccaa ggggatattc ggttgctggc tgacgacatg aagactttga agcccacatt   1320
gtttcccgcg gtgcctcgac tccttaacag gatctacgat aaggtacaaa atgaggccaa   1380
gacacccttg aagaagttct tgttgaagct ggctgtttcc agtaaattca aagagcttca   1440
aaagggtatc atcaggcatg atagtttctg ggacaagctc atctttgcaa agatccagga   1500
cagcctgggc ggaagggttc gtgtaattgt cactggagct gcccccatgt ccacttcagt   1560
catgacattc ttccgggcag caatgggatg tcaggtgtat gaagcttatg gtcaaacaga   1620
atgcacaggt ggctgtacat ttacattacc tggggactgg acatcaggtc acgttggggt   1680
gcccctggct tgcaattacg tgaagctgga agatgtggct gacatgaact actttacagt   1740
gaataatgaa ggagaggtct gcatcaaggg tacaaacgtg ttcaaaggat acctgaagga   1800
ccctgagaag acacaggaag ccctggacag tgatggctgg cttcacacag gagacattgg   1860
tcgctggctc ccgaatggaa ctctgaagat catcgaccgt aaaaagaaca ttttcaagct   1920
ggcccaagga gaatacattg caccagagaa gatagaaaat atctacaaca ggagtcaacc   1980
agtgttacaa atttttgtac acggggagag cttacggtca tccttagtag gagtggtggt   2040
tcctgacaca gatgtacttc cctcatttgc agccaagctt ggggtgaagg gctcctttga   2100
ggaactgtgc caaaaccaag ttgtaaggga agccatttta gaagacttgc agaaaattgg   2160
gaaagaaagt ggccttaaaa cttttgaaca ggtcaaagcc atttttcttc atccagagcc   2220
attttccatt gaaaatgggc tcttgacacc aacattgaaa gcaaagcgag gagagctttc   2280
caaatacttt cggacccaaa ttgacagcct gtatgagcac atccaggatt aggataaggt   2340
acttaagtac ctgccggccc actgtgcact gcttgtgaga aaatggatta aaaactattc   2400
ttacatttgt tttgcctttc ctcctatttt tttttaacct gttaaactct aaagccatag   2460
cttttgtttt atattgagac atataatgtg taaacttagt tcccaaataa atcaatcctg   2520
tctttcccat cttcgatgtt gctaatatta aggcttcagg gctactttta tcaacatgcc   2580
tgtcttcaag atcccagttt atgttctgtg tccttcctca tgatttccaa ccttaatact   2640
attagtaacc acaagttcaa gggtcaaagg gaccctctgt gccttcttct ttgttttgtg   2700
ataaacataa cttgccaaca gtctctatgc ttatttacat cttctactgt tcaaactaag   2760
agatttttaa attctgaaaa actgcttaca attcatgttt tctagccact ccacaaacca   2820
ctaaaatttt agttttagcc tatcactcat gtcaatcata tctatgagac aaatgtctcc   2880
gatgctcttc tgcgtaaatt aaattgtgta ctgaagggaa aagtttgatc ataccaaaca   2940
```

```
tttcctaaac tctctagtta gatatctgac ttgggagtat taaaaattgg gtctatgaca   3000

tattgtccaa aaggaatgct gttcttaaag cattatttac agtaggaact ggggagtaaa   3060

tctgttccct acagtttgct gctgagctgg aagctgtggg ggaaggagtt gacaggtggg   3120

cccagtgaac ttttccagta aatgaagcaa gcactgaata aaaacctcct gaactgggaa   3180

caaagatcta caggcaagca agatgcccac acaacaggct tattttctgt gaaggaacca   3240

actgatctcc cccacccttg gattagagtt cctgctctac cttacccaca gataacacat   3300

gttgtttcta cttgtaaatg taaagtcttt aaaataaact attacagata cttaaaaaaa   3360

aaaaaaaaaa aa                                                        3372

<210> SEQ ID NO 17
<211> LENGTH: 5243
<212> TYPE: DNA
<213> ORGANISM: Homo sapiens

<400> SEQUENCE: 17

agcgtgagac tcgcgccctc cggcacggaa aaggccaggc gacaggtgtc gcttgaaaag     60

actgggcttg tccttgctgg tgcatgcgtc gtcggcctct gggcagcagg tttacaaagg    120

aggaaaacga cttcttctag attttttttt cagtttcttc tataaatcaa aacatctcaa    180

aatggagacc taaaatcctt aaagggactt agtctaatct cgggaggtag ttttgtgcat    240

gggtaaacaa attaagtatt aactggtgtt ttactatcca aagaatgcta attttataaa    300

catgatcgag ttatataagg tataccataa tgagtttgat tttgaatttg atttgtggaa    360

ataaaggaaa agtgattcta gctggggcat attgttaaag cattttttttc agagttggcc    420

aggcagtctc ctactggcac attctcccat tatgtagaat agaaatagta cctgtgtttg    480

ggaaagattt taaaatgagt gacagttatt tggaacaaag agctaataat caatccactg    540

caaattaaag aaacatgcag atgaaagttt tgacacatta aaatacttct acagtgacaa    600

agaaaaatca agaacaaagc tttttgatat gtgcaacaaa tttagaggaa gtaaaaagat    660

aaatgtgatg attggtcaag aaattatcca gttatttaca aggccactga tattttaaac    720

gtccaaaagt ttgtttaaat gggctgttac cgctgagaat gatgaggatg agaatgatgg    780

ttgaaggtta cattttagga aatgaagaaa cttagaaaat taatataaag acagtgatga    840

atacaaagaa gatttttata acaatgtgta aaatttttgg ccagggaaag gaatattgaa    900

gttagataca attacttacc tttgagggaa ataattgttg gtaatgagat gtgatgtttc    960

tcctgccacc tggaaacaaa gcattgaagt ctgcagttga aaagcccaac gtctgtgaga   1020

tccaggaaac catgcttgca aaccactggt aaaaaaaaaa aaaaaaaaaa aaaaaagcca   1080

cagtgacttg cttattggtc attgctagta ttatcgactc agaacctctt tactaatggc   1140

tagtaaatca taattgagaa attctgaatt ttgacaaggt ctctgctgtt gaaatggtaa   1200

atttattatt ttttttgtca tgataaattc tggttcaagg tatgctatcc atgaaataat   1260

ttctgaccaa aactaaattg atgcaatttg attatccatc ttagcctaca gatggcatct   1320

ggtaactttt gactgtttta aaaaataaat ccactatcag agtagatttg atgttggctt   1380

cagaaacatt tagaaaaaca aaagttcaaa aatgttttca ggaggtgata agttgaataa   1440

ctctacaatg ttagttcttt gagggggaca aaaaatttaa aatctttgaa aggtcttatt   1500

ttacagccat atctaaatta tcttaagaaa atttttaaca aagggaatga aatatatatc   1560

atgattctgt ttttccaaaa gtaacctgaa tatagcaatg aagttcagtt ttgttattgg   1620
```

-continued

```
tagtttgggc agagtctctt tttgcagcac ctgttgtcta ccataattac agaggacatt   1680
tccatgttct agccaagtat actattagaa taaaaaaact taacattgag ttgcttcaac   1740
agcatgaaac tgagtccaaa agaccaaatg aacaaacaca ttaatctctg attatttatt   1800
ttaaatagaa tatttaattg tgtaagatct aatagtatca ttatacttaa gcaatcatat   1860
tcctgatgat ctatgggaaa taactattat ttaattaata ttgaaaccag gttttaagat   1920
gtgttagcca gtcctgttac tagtaaatct ctttatttgg agagaaattt tagattgttt   1980
tgttctcctt attagaagga ttgtagaaag aaaaaaatga ctaattggag aaaaattggg   2040
gatatatcat atttcactga attcaaaatg tcttcagttg taaatcttac cattatttta   2100
cgtacctcta agaaataaaa gtgcttctaa ttaaaatatg atgtcattaa ttatgaaata   2160
cttcttgata acagaagttt taaaatagcc atcttagaat cagtgaaata tggtaatgta   2220
ttattttcct cctttgagtt aggtcttgtg cttttttttc ctggccacta aatttcacaa   2280
tttccaaaaa gcaaaataaa catattctga atatttttgc tgtgaaacac ttgacagcag   2340
agctttccac catgaaaaga agcttcatga gtcacacatt acatctttgg gttgattgaa   2400
tgccactgaa acattctagt agcctggaga agttgaccta cctgtggaga tgcctgccat   2460
taaatggcat cctgatggct taatacacat cactcttctg tgaagggttt taattttcaa   2520
cacagcttac tctgtagcat catgtttaca ttgtatgtat aaagattata caaaggtgca   2580
attgtgtatt tcttccttaa aatgtatcag tataggattt agaatctcca tgttgaaact   2640
ctaaatgcat agaaataaaa ataataaaaa atttttcatt ttggcttttc agcctagtat   2700
taaaactgat aaaagcaaag ccatgcacaa aactacctcc ctagagaaag gctagtccct   2760
tttcttcccc attcatttca ttatgaacat agtagaaaac agcatattct tatcaaattt   2820
gatgaaaagc gccaacacgt ttgaactgaa atacgacttg tcatgtgaac tgtaccgaat   2880
gtctacgtat tccacttttc ctgctggggt tcctgtctca gaaaggagtc ttgctcgtgc   2940
tggtttctat tacactggtg tgaatgacaa ggtcaaatgc ttctgttgtg gcctgatgct   3000
ggataactgg aaaagaggag acagtcctac tgaaaagcat aaaaagttgt atcctagctg   3060
cagattcgtt cagagtctaa attccgttaa caacttggaa gctacctctc agcctacttt   3120
tccttcttca gtaacaaatt ccacacactc attacttccg ggtacagaaa acagtggata   3180
tttccgtggc tcttattcaa actctccatc aaatcctgta aactccagag caaatcaaga   3240
tttttctgcc ttgatgagaa gttcctacca ctgtgcaatg aataacgaaa atgccagatt   3300
acttactttt cagacatggc cattgacttt tctgtcgcca acagatctgg caaaagcagg   3360
cttttactac ataggacctg gagacagagt ggcttgcttt gcctgtggtg gaaaattgag   3420
caattgggaa ccgaaggata atgctatgtc agaacacctg agacattttc ccaaatgccc   3480
atttatagaa aatcagcttc aagacacttc aagatacaca gtttctaatc tgagcatgca   3540
gacacatgca gcccgcttta aaacattctt taactggccc tctagtgttc tagttaatcc   3600
tgagcagctt gcaagtgcgg gtttttatta tgtgggtaac agtgatgatg tcaaatgctt   3660
ttgctgtgat ggtggactca ggtgttggga atctggagat gatccatggg ttcaacatgc   3720
caagtggttt ccaaggtgtg agtacttgat aagaattaaa ggacaggagt tcatccgtca   3780
agttcaagcc agttaccctc atctacttga acagctgcta tccacatcag acagcccagg   3840
agatgaaaat gcagagtcat caattatcca ttttgaacct ggagaagacc attcagaaga   3900
tgcaatcatg atgaatactc ctgtgattaa tgctgccgtg gaaatgggct ttagtagaag   3960
cctggtaaaa cagacagttc agagaaaaat cctagcaact ggagagaatt atagactagt   4020
```

caatgatctt gtgttagact tactcaatgc agaagatgaa ataagggaag aggagagaga 4080
aagagcaact gaggaaaaag aatcaaatga tttattatta atccggaaga atagaatggc 4140
actttttcaa catttgactt gtgtaattcc aatcctggat agtctactaa ctgccggaat 4200
tattaatgaa caagaacatg atgttattaa acagaagaca cagacgtctt tacaagcaag 4260
agaactgatt gatacgattt tagtaaaagg aaatattgca gccactgtat tcagaaactc 4320
tctgcaagaa gctgaagctg tgttatatga gcatttattt gtgcaacagg acataaaata 4380
tattcccaca gaagatgttt cagatctacc agtggaagaa caattgcgga gactacaaga 4440
agaaagaaca tgtaaagtgt gtatggacaa agaagtgtcc atagtgttta ttccttgtgg 4500
tcatctagta gtatgcaaag attgtgctcc ttctttaaga aagtgtccta tttgtaggag 4560
tacaatcaag ggtacagttc gtacatttct ttcatgaaga agaaccaaaa catcgtctaa 4620
actttagaat taatttatta aatgtattat aactttaact tttatcctaa tttggtttcc 4680
ttaaaatttt tatttattta caactcaaaa aacattgttt tgtgtaacat atttatatat 4740
gtatctaaac catatgaaca tatatttttt agaaactaag agaatgatag gcttttgttc 4800
ttatgaacga aaaagaggta gcactacaaa cacaatattc aatcaaaatt tcagcattat 4860
tgaaattgta agtgaagtaa aacttaagat atttgagtta acctttaaga attttaaata 4920
ttttggcatt gtactaatac cgggaacatg aagccaggtg tggtggtatg tgcctgtagt 4980
cccaggctga ggcaagagaa ttacttgagc ccaggagttt gaatccatcc tgggcagcat 5040
actgagaccc tgcctttaaa aacaaacaga acaaaaacaa aacaccaggg acacatttct 5100
ctgtcttttt tgatcagtgt cctatacatc gaaggtgtgc atatatgttg aatgacattt 5160
tagggacatg gtgtttttat aaagaattct gtgagaaaaa atttaataaa gcaacaaaaa 5220
ttactcttaa aaaaaaaaaa aaa 5243

<210> SEQ ID NO 18
<211> LENGTH: 1579
<212> TYPE: DNA
<213> ORGANISM: Homo sapiens

<400> SEQUENCE: 18
gaggaggtgc ttgccagaca ctgggtcatg gcagtggtcg gtgaagctgc agttgcctag 60
ggcagggatg gagagagagt ctgggcatga ggagagggtc tcgggatgtt tggctggact 120
agattttaca gaaagcctta tccaggcttt taaaattact ctttccagac ttcatctgag 180
actccttctt cagccaacat tccttagccc tgaatacatt tcctatcctc atctttccct 240
tctttttttt cctttctttt acatgtttaa atttaaacca ttcttcgtga ccccttttct 300
tgggagattc atggcaagaa cgagaagaat gatggtgctt gttaggggat gtcctgtctc 360
tctgaacttt ggggtcctat gcattaaata attttcctga cgagctcaag tgctccctct 420
ggtctacaat ccctggcggc tggccttcat cccttgggca agcattgcat acagctcatg 480
gccctccctc taccataccc tccacccccg ttcgcctaag ctcccttctc cgggaatttc 540
atcatttcct agaacagcca gaacatttgt ggtctatttc tctgttagtg tttaaccaac 600
catctgttct aaaagaaggg ctgaactgat ggaaggaatg ctgttagcct gagactcagg 660
aagacaactt ctgcagggtc actccctggc ttctggagga aagagaagga gggcagtgct 720
ccagtggtac agaagtgaga cataatggaa tcaggcttca cctccaagga cacctatcta 780
agccatttta accctcggga ttacctagaa aaatattaca agtttggttc taggcactct 840

-continued

```
gcagaaagcc agattcttaa gcaccttctg aaaaatcttt tcaagatatt ctgcctagac    900

ggtgtgaagg gagacctgct gattgacatc ggctctggcc ccactatcta tcagctcctc    960

tctgcttgtg aatcctttaa ggagatcgtc gtcactgact actcagacca gaacctgcag   1020

gagctggaga agtggctgaa gaaagagcca gaggcctttg actggtcccc agtggtgacc   1080

tatgtgtgtg atcttgaagg gaacagagtc aagggtccag agaaggagga gaagttgaga   1140

caggcggtca agcaggtgct gaagtgtgat gtgactcaga gccagccact gggggccgtc   1200

cccttacccc cggctgactg cgtgctcagc acactgtgtc tggatgccgc ctgcccagac   1260

ctccccacct actgcagggc gctcaggaac ctcggcagcc tactgaagcc agggggcttc   1320

ctggtgatca tggatgcgct caagagcagc tactacatga ttggtgagca gaagttctcc   1380

agcctccccc tgggccggga ggcagtagag gctgctgtga aagaggctgg ctacacaatc   1440

gaatggtttg aggtgatctc gcaaagttat tcttccacca tggccaacaa cgaaggactt   1500

ttctccctgg tggcgaggaa gctgagcaga cccctgtgat gcctgtgacc tcaattaaag   1560

caattccttt gacctgtca                                                1579
```

```
<210> SEQ ID NO 19
<211> LENGTH: 980
<212> TYPE: DNA
<213> ORGANISM: Homo sapiens

<400> SEQUENCE: 19

gcggcggcgg gcagcagctg cgctgcgact gctctggaag gagaggacgg ggcacaaacc     60

ctgaccatga ccccccacag gctgctgcca ccgctgctgc tgctgctagc tctgctgctc    120

gctgccagcc caggaggcgc cttggcgcgg tgcccaggct gcgggcaagg ggtgcaggcg    180

ggttgtccag gggctgcgt ggaggaggag gatgggggt cgccagccga gggctgcgcg    240

gaagctgagg gctgtctcag gagggagggg caggagtgcg ggtctacac ccctaactgc    300

gccccaggac tgcagtgcca tccgcccaag gacgacgagg cgcctttgcg ggcgctgctg    360

ctcggccgag gccgctgcct tccggcccgc gcgcctgctg ttgcagagga gaatcctaag    420

gagagtaaac cccaagcagg cactgcccgc ccacaggatg tgaaccgcag agaccaacag    480

aggaatccag gcacctctac cacgccctcc cagcccaatt ctgcgggtgt ccaagacact    540

gagatgggcc catgccgtag acatctggac tcagtgctgc agcaactcca gactgaggtc    600

taccgagggg ctcaaacact ctacgtgccc aattgtgacc atcgaggctt ctaccggaag    660

cggcagtgcc gctcctccca ggggcagcgc cgaggtccct gctggtgtgt ggatcggatg    720

ggcaagtccc tgccagggtc tccagatggc aatggaagct cctcctgccc cactgggagt    780

agcggctaaa gctgggggat agaggggctg cagggccact ggaaggaaca tggagctgtc    840

atcactcaac aaaaaaccga ggccctcaat ccaccttcag gccccgcccc atgggcccct    900

caccgctggt tggaaagagt gttggtgttg gctggggtgt caataaagct gtgcttgggg    960

tcgctgaaaa aaaaaaaaaa                                                980
```

```
<210> SEQ ID NO 20
<211> LENGTH: 7346
<212> TYPE: DNA
<213> ORGANISM: Homo sapiens

<400> SEQUENCE: 20

gcgaggagga aacggtgccg gagcgcgcag ggcttgctgc cgccaccgcc gctgcacagg     60

ctgccggagc gagcctgccg cgcgccgccc tccccgctct ccttcctggg cgagctgcgg    120
```

-continued

```
ggatggggcg gccgcgggag cccgagcgcg cgcaggaacc gccgccgccg ccgcccgcgt    180
ctccgttgcc gcgcgcctga gccgccgtcg ccgccgcgcg ccctgcccgg gggcggcccc    240
cccagcccca tggaggtctc ccggaggaag gcgccgccgc gccccccgcg ccccgcagcg    300
ccactgcccc tgctcgccta tctgctggca ctggcggctc ccggccgggg cgcggacgag    360
cccgtgtggc ggtcggagca agccatcgga gccatcgcgg cgagccagga ggacggcgtg    420
tttgtggcga gcggcagctg cctggaccag ctggactaca gcctggagca cagcctctcg    480
cgcctgtacc gggaccaagc gggcaactgc acagagccgg tctcgctggc gccccccgcg    540
cggccccggc ccgggagcag cttcagcaag ctgctgctgc cctaccgcga gggggcggcc    600
ggcctcgggg ggctgctgct caccggctgg accttcgacc ggggcgcctg cgaggtgcgg    660
cccctgggca acctgagccg caactccctg cgcaacggca ccgaggtggt gtcgtgccac    720
ccgcagggct cgacggccgg cgtggtgtac cgcgcgggcc ggaacaaccg ctggtacctg    780
gcggtggccg ccacctacgt gctgcctgag ccggagacgg cgagccgctg caaccccgcg    840
gcatccgacc acgacacggc catcgcgctc aaggacacgg aggggcgcag cctggccacg    900
caggagctgg ggcgcctcaa gctgtgcgag ggcgcgggca gcctgcactt cgtggacgcc    960
tttctctgga acggcagcat ctacttcccc tactacccct acaactacac gagcggcgct   1020
gccaccggct ggcccagcat ggcgcgcatc gcgcagagca ccgaggtgct gttccagggc   1080
caggcatccc tcgactgcgg ccacggccac cccgacggcc gccgcctgct cctctcctcc   1140
agcctagtgg aggccctgga cgtctgggcg ggagtgttca gcgcggccgc tggagagggc   1200
caggagcggc gctcccccac caccacggcg ctctgcctct tcagaatgag tgagatccag   1260
gcgcgcgcca agagggtcag ctgggacttc aagacggccg agagccactg caaagaaggg   1320
gatcaacctg aaagagtcca accaatcgca tcatctacct tgatccattc cgacctgaca   1380
tccgtttatg gcaccgtggt aatgaacagg actgttttat tcttggggac tggagatggc   1440
cagttactta aggttattct tggtgagaat ttgacttcaa attgtccaga ggttatctat   1500
gaaattaaag aagagacacc tgttttctac aaactcgttc ctgatcctgt gaagaatatc   1560
tacatttatc taacagctgg gaaagaggtg aggagaattc gtgttgcaaa ctgcaataaa   1620
cataaatcct gttcggagtg tttaacagcc acagaccctc actgcggttg gtgccattcg   1680
ctacaaaggt gcacttttca aggagattgt gtacattcag agaacttaga aaactggctg   1740
gatatttcgt ctggagcaaa aaagtgccct aaaattcaga taattcgaag cagtaaagaa   1800
aagactacag tgactatggt gggaagcttc tctccaagac actcaaagtg catggtgaag   1860
aatgtggact ctagcaggga gctctgccag aataaaagtc agcccaaccg gacctgcacc   1920
tgtagcatcc caaccagagc aacctacaaa gatgtttcag ttgtcaacgt gatgttctcc   1980
ttcggttctt ggaatttatc agacagattc aactttacca actgctcatc attaaaagaa   2040
tgcccagcat gcgtagaaac tggctgcgcg tggtgtaaaa gtgcaagaag gtgtatccac   2100
cccttcacag cttgcgaccc ttctgattat gagagaaacc aggaacagtg tccagtggct   2160
gtcgagaaga catcaggagg aggaagaccc aaggagaaca aggggaacag aaccaaccag   2220
gctttacagg tcttctacat taagtccatt gagccacaga aagtatcgac attagggaaa   2280
agcaacgtga tagtaacggg agcaaacttt acccgggcat cgaacatcac aatgatcctg   2340
aaaggaacca gtacctgtga taaggatgtg atacaggtta gccatgtgct aaatgacacc   2400
cacatgaaat tctctcttcc atcaagccgg aaagaaatga aggatgtgtg tatccagttt   2460
```

-continued

```
gatggtggga actgctcttc tgtgggatcc ttatcctaca ttgctctgcc acattgttcc   2520
cttatatttc ctgctaccac ctggatcagt ggtggtcaaa atataaccat gatgggcaga   2580
aattttgatg taattgacaa cttaatcatt tcacatgaat taaaaggaaa cataaatgtc   2640
tctgaatatt gtgtggcgac ttactgcggg tttttagccc ccagtttaaa gagttcaaaa   2700
gtgcgcacga atgtcactgt gaagctgaga gtacaagaca cctacttgga ttgtggaacc   2760
ctgcagtatc gggaggaccc cagattcacg gggtatcggg tggaatccga ggtggacaca   2820
gaactggaag tgaaaattca aaaagaaaat gacaacttca acatttccaa aaaagacatt   2880
gaaattactc tcttccatgg ggaaaatggg caattaaatt gcagttttga aaatattact   2940
agaaatcaag atcttaccac catcctttgc aaaattaaag gcatcaagac tgcaagcacc   3000
attgccaact cttctaagaa agttcgggtc aagctgggaa acctggagct ctacgtcgag   3060
caggagtcag ttccttccac atggtatttt ctgattgtgc tccctgtctt gctagtgatt   3120
gtcatttttg cggccgtggg ggtgaccagg cacaaatcga aggagctgag tcgcaaacag   3180
agtcaacaac tagaattgct ggaaagcgag ctccggaaag agatacgtga cggctttgct   3240
gagctgcaga tggataaatt ggatgtggtt gatagttttg gaactgttcc cttccttgac   3300
tacaaacatt ttgctctgag aactttcttc cctgagtcag gtggcttcac ccacatcttc   3360
actgaagata tgcataacag agacgccaac gacaagaatg aaagtctcac agctttggat   3420
gccctaatct gtaataaaag ctttcttgtt actgtcatcc acacccttga aaagcagaag   3480
aacttttctg tgaaggacag gtgtctgttt gcctccttcc taaccattgc actgcaaacc   3540
aagctggtct acctgaccag catcctagag gtgctgacca gggacttgat ggaacagtgt   3600
agtaacatgc agccgaaact catgctgaga cgcacggagt ccgtcgtcga aaaactcctc   3660
acaaactgga tgtccgtctg cctttctgga tttctccggg agactgtcgg agagcccttc   3720
tatttgctgg tgacgactct gaaccagaaa attaacaagg gtcccgtgga tgtaatcact   3780
tgcaaagccc tgtacacact taatgaagac tggctgttgt ggcaggttcc ggaattcagt   3840
actgtggcat taaacgtcgt ctttgaaaaa atcccggaaa acgagagtgc agatgtctgt   3900
cggaatattt cagtcaatgt tctcgactgt gacaccattg gccaagccaa agaaaagatt   3960
ttccaagcat tcttaagcaa aaatggctct ccttatggac ttcagcttaa tgaaattggt   4020
cttgagcttc aaatgggcac acgacagaaa gaacttctgg acatcgacag ttcctccgtg   4080
attcttgaag atggaatcac caagctaaac accattggcc actatgagat atcaaatgga   4140
tccactataa aagtctttaa gaagatagca aattttactt cagatgtgga gtactcggat   4200
gaccactgcc atttgatttt accagattcg gaagcattcc aagatgtgca aggaaagaga   4260
catcgaggga agcacaagtt caaagtaaaa gaaatgtatc tgacaaagct gctgtcgacc   4320
aaggtggcaa ttcattctgt gcttgaaaaa ctttttagaa gcatttggag tttacccaac   4380
agcagagctc catttgctat aaaatacttt tttgactttt tggacgccca ggctgaaaac   4440
aaaaaaatca cagatcctga cgtcgtacat atttggaaaa caaacagcct tcctcttcgc   4500
ttctgggtaa acatcctgaa gaaccctcag tttgtctttg acattaagaa gacaccacat   4560
atagacggct gtttgtcagt gattgcccag gcattcatgg atgcattttc tctcacagag   4620
cagcaactag ggaaggaagc accaactaat aagcttctct atgccaagga tatcccaacc   4680
tacaaagaag aagtaaaatc ttattacaaa gcaatcaggg atttgcctcc attgtcatcc   4740
tcagaaatgg aagaattttt aactcaggaa tctaagaaac atgaaaatga atttaatgaa   4800
gaagtggcct tgacagaaat ttacaaatac atcgtaaaat attttgatga gattctaaat   4860
```

```
aaactagaaa gagaacgagg gctggaagaa gctcagaaac aactcttgca tgtaaaagtc   4920
ttatttgatg aaaagaagaa atgcaagtgg atgtaagcac tctggggcct ggcttaatct   4980
ggcaaagttc ttcagacgac ttgggagcaa aatggctgct tgagctactc tgtgtcgtta   5040
atttgttgtt tgcacatagg ttccactttg ggcactgtct ttttaagaga ccaaggcaca   5100
tgcacagctt ttagaaagca taccaaccct tgtgcctgtg tgtataccgt gggaacccctt  5160
ctgtaaatag agttgaagtg gttgttgcaa acagcctcct tgtttacaga gaatacaagg   5220
ccagtaagcg aatgtcagta ttgtaactac agtctccact taagcacaat gatataagtg   5280
gttttgtttg aaaactacag ctatgtagca cttgtgctac actgcacctc tgcattgtaa   5340
agggatactg ccagtgctca aaacaaaatg tgaaatgagt catttggaaa caaggtgggg   5400
gtgttagggc aacctcgagg atttgcagca ttgaaacttt ccccagtagt tcttggaaaa   5460
gctgaccgca gaatttggta gtgtacactt agcatttgtg agtgtgtgtg tgtgtttaaa   5520
ccaaaaacta acagtgttgc aacattgttg aaagggctcg tgtttttcag tggtcatcaa   5580
ctgcactcca tcaaactcac ctccatttca ccaaggagct ctaaagtaag gagagtgggc   5640
tttatttaaa tgaacagcat tttaaccaga tactttgtcc taatgtatgt tccttttctt   5700
catctgtttt ttcatactaa atgtatttga tagtggacat gttggatatt atacaaaaaa   5760
atcattaatt catttctgtt ccaaaacctt tgatcagaac gatctgtgga agagtaactc   5820
catttctata tgagtgagtg tctccttgct ttagatttct ggtgaaccct gtggttatga   5880
atacttgtgt gtgatttaaa aaaaaaaaga tacattttac atttcatcga attgctgttc   5940
acactggagt attatatata aatatatata tttgaggccc aaggcctgaa aaatattagt   6000
atacaacttg gtatcttagt cttactatgt actttttgaa agtattcctc gcaggagaaa   6060
gaatttaaaa tacccatttt attcatgcct ttctttttaa agaattctct atccagttat   6120
actgtagtct ttttagtgct gatttttttaa ttcctgaatt tttgctgctc atgaccagtt  6180
ttaataccac tgtgttttcc ttctattaaa ccagaagaag taaacagcat aattggcaac   6240
tcttgagctt ttcttgtggc aggcaccttt tacccttggt gctccaaatc cccatctag    6300
gaaagaaaat tttttcaagt caaataacat tgatcacata ttccttgaaa tcatttacca   6360
acactgtatg gagcattagg atttaaatat gaatttgtct taaaggcaat tcctttttgc   6420
ttctgtatta tctggaaaag catgagagag gtgacacctc aacaaactga tcagagaaaa   6480
taagcagtta ctaccctgat aggcaccttc ccaatcctgt tgcttttgac cattgtctgt   6540
ccaacggaca cacctcaaac aaacaaaact accaaataga tgacagatca gaataaaggt   6600
gagaggtctg gtccccattg aaggctgcta cagtcttcaa agaggtgaag gagttcataa   6660
gagaacaaca gtaggaaagt tgagagccaa gggtaggaga gttgcccaaa agacttcccc   6720
tactacttta gggtactgaa aactcaaagg atcagctaca gctttatcta agtatttact   6780
aaatgctaca tgagggtgtc cctgtccagc tttctggcac atgagtcctg tgtggagagt   6840
tacctcctct tccagggact gtgctgttgg gaactttggg caagtcactt acctctttgt   6900
gcctcaattt ctgtataata tttctaagct acctcactga ggtggtatga agattcacta   6960
atgtatgtag cgtgtttgtc aatcctccag tgaaaagcac tatctagatc acattttgga   7020
tcacattagc caaatgcagt aaatggccaa attagatgtg tgctgaagac aatcagtcac   7080
tgggtctata ttaaacagca accagagcaa caaatggcaa acaatttcta ttttcaagtt   7140
tctttgcata tttttttggt gcaaaaccat ttataaactt ttttttctaa cactagtgtc   7200
```

-continued tacagcagca ttcaaaaaaa ttctgttacc ttttctgtat taggatttaa agtctatttc 7260
ttattgtata cctgattgaa gctgttcttg gagatgaatg ttttaaatgt ctatatccaa 7320
aaaataaaca ttttgatgta actgtg 7346

<210> SEQ ID NO 21
<211> LENGTH: 2828
<212> TYPE: DNA
<213> ORGANISM: Homo sapiens

<400> SEQUENCE: 21
agaacagtga cagcgccgcg gcagccgacc ccgcctcctc ggcggacagc gatgctcagc 60
tggctgcggc cgagtcatcg cctagcgctg gcagggccgc tgaccgaccg acggaggcgc 120
cgattggccg attgtccact gcgcagaagg agcagctgct ccgcgccccg ccgcgccgcg 180
ctgaggccga ggtccgcagg gccgcgggga agccgagggc tgccggagaa ccctgcaggt 240
gtcactcggg acgcggaagt gcgcttgccg aggtttgctt tacaatacgc ttgagactcc 300
ccgacaagcg taatttggtc gagttcgacg ggaaagtact ctccccaccc cagcgccggc 360
cgcgtagtcc gaggttactg tccccggcgc gtcctctgtt gccccagtcc agaggctgcc 420
cttgaacccg ggcgcgcacg agcgcagggc atccgaggcg acagcccctg gcacggcccg 480
acctgtaccc agcctggcag gaagactgta atcgtgggaa tacagctacc tacccaggca 540
atatgaagat tttatttgta gaacctgcca ttttccttag tgcatttgct atgactttga 600
ccggtccact gacaacgcaa tatgtttatc ggagaatatg ggaagaaact ggcaactaca 660
ctttttcatc tgatagcaat atttctgagt gtgaaaaaaa caaaagcagc ccaatttttg 720
cattccagga ggaagttcag aaaaaagtgt cacgttttaa tctgcagatg gacataagtg 780
gattaattcc tggtctagtg tctacattca tacttttgtc tattagtgat cactacggac 840
gaaaattccc tatgattttg tcttccgttg gtgctcttgc aaccagcgtt tggctctgtt 900
tgctttgcta ttttgccttt ccattccagc ttttgattgc atctaccttc attggtgcat 960
tttgtggcaa ttataccaca ttttggggag cttgctttgc ctatatagtt gatcagtgta 1020
aagaacacaa acaaaaaaca attcgaatag ctatcattga ctttctactt ggacttgtta 1080
ctggactaac aggactgtca tctggctatt ttattagaga gctaggtttt gagtggtcgt 1140
ttctaattat tgctgtgtct cttgctgtta atttgatcta tattttattt tttctcggag 1200
atccagtgaa agagtgttca tctcagaatg ttactatgtc atgtagtgaa ggcttcaaaa 1260
acctatttta ccgaacttac atgcttttta agaatgcttc tggtaagaga cgatttttgc 1320
tctgtttgtt actttttaca gtaatcactt atttttttgt ggtaattggc attgccccaa 1380
tttttatcct ttatgaattg gattcaccac tctgctggaa tgaagttttt ataggttatg 1440
gatcagcttt gggtagtgcc tcttttttga ctagtttcct aggaatatgg ctttttttctt 1500 attgtatgga agatattcat atggccttca ttgggatttt taccacgatg acaggaatgg 1560
ctatgaccgc gtttgccagt acaacactga tgatgttttt agccagggtg ccgttccttt 1620
tcactattgt gccattctct gttctacggt ccatgttgtc aaaagtggtt cgttcgactg 1680
aacaaggtac cctgtttgct tgtattgctt tcttagaaac acttggagga gtcactgcag 1740
tttctacttt taatggaatt tactcagcca ctgttgcttg gtaccctggc ttcactttcc 1800
tgctgtctgc tggtctgtta ctacttccag ccatcagtct atgtgttgtc aagtgtacca 1860
gctggaatga gggaagctat gaacttctta tacaagaaga atccagtgaa gatgcttcag 1920
acagagcctg ttaagctgct attgatagtc ggagcttata tactgtgact tctgaagact 1980
atacatgaat tccacaatca gtgctttgtt gatacaaaat ccttaaaagg gaggcacttt 2040
aaagaatatg tatttttcac ttttcttaat atgtttcatc ggtgacaggc atgataatat 2100
ttctatatgt aatgggtaat tgggaaaaaa tagatgataa ataaaattgc tctaaagaag 2160
ttaaaaaact gaatgaacag ctaatactgg tataaagtaa ctaatgtttg gagccaacat 2220
ttgttccttg tgtcagcaaa aggatattca cattccatga tccctggctg agaattctgc 2280
ctctagtctt tcttacccag ctgttgtcta tccttgttca attataaata ctgctaaggg 2340
catttttaaa atacgatctt gtactcctta aatttgaatc cgtcagcacg gtcactcata 2400
ggaaaatgat caaacaagca agccagtcat gatttgactc cttcccatct catttcttac 2460
tgccttacgc tcatcctgag gtccaccttg gtctctaaaa acaccatgtg ttctcatgcc 2520
tccatgtctt ttcacacact gttccatttg ctcttcctcc cacattacat tgaaactttc 2580
aagcctcagt cgaaacattg cttcttctgg atagcagcct tcttgacatc cctcctcact 2640
ccccagtccc tacagggctt ccatagctct ttgtgtgcac ttcgatccca gcattttcca 2700
tcgacttgta attgtttctg ctacctgaca atcatcgcct tgagtactgg gacaaccttt 2760
gattactcat tatatcctca ataaatattt gttgaactaa aaaaaaaaaa aaaaaaaaaa 2820
aaaaaaaa 2828

<210> SEQ ID NO 22
<211> LENGTH: 2840
<212> TYPE: DNA
<213> ORGANISM: Homo sapiens

<400> SEQUENCE: 22
gtttttgtgc aggaacagcc cctcccgtct ttgtcctggc ggtgagcacc cagggctaag 60
cttttgaaca ctttctttgt gtttggattc agcccaggca atgcatattt gctttcattt 120
cttcttgagc ttgaggagct cctgggtgca aatcttggaa aatgaggatc tctgagcctt 180
tccaggccag ctctttgttt tgtagcagac aattgaggct ttgaaaagga aagtgggtgg 240
gggcacccca caggtggccc tcatcaccca attgccagtg cctgcaggct gcttcagcag 300
aggcccagag tcaaagagga cttaaaacca gctgtcgttt ctcccttagc ttctgtgtat 360
gagagaaacg acttctgttt ttcaaagtaa gaacaaggag gaatttgttt ctaaaagaac 420
attaaaacac aggctcgtgg tctaaaagca aatggttcag caggatgttc agggccttaa 480
agcacagtca gcaggactca gcatctccca gcacctgctc tccggttgtc atggtaacat 540
catccccaac ccaaccacct tgtccagccg agagacagca atcataagga gggacctcgg 600
tttcccccga ggatcctggg cttcctttct gaaacgcttg cttctgagct cagcaaccag 660
gaacaccagg ccagcccatc cccagcacct ctgtggagat gagggacaaa gtcctacagt 720
ccctcttcct gttctgatga gaaagggagg gaagaaaaca taccccgagc gcctgcaata 780
tggtcatgac actttcaaaa agcctgtgct atggagtcat gatcagaaac cagagtgtgg 840
agagggtcag cagcctgcct cagagcagcc agctaggcgg ggagtggtaa atttgggact 900
tgtacccagg catgactggc tccgagccca gtgctccact ctatggaatg ttccctgggc 960
ctcagttgct ttcctttcct ttgcaggccg cgggctgctg ccactctggc agctggtgag 1020
ttagctggag ggcaacattc caaagcaggg gcagcatgct gctttcctcc tgtgcccact 1080
cctgcgggga agtccgttga ctcccaccgc tgaagggagc tggcaacacc aggatgaggt 1140
cccaggggac gggagcaggt acccactgtc tgtctacctt cccactggaa aagcacggac 1200

-continued

```
aggccagccc ttgcgggggc aggcagagga cagagttggc tttgcgcggt ctctgcctgc   1260

tgagcagttc caattcctct catgggagaa acaaggaggc agtcgcttgt gcatgttcca   1320

gaagttttac tggggaggag gaagcggaca gaggaagctg tgtgtgcatg tgaaggggtg   1380

ggcagggtgg gagggatgca cgcgtatgtg agcatagcat gtgtgagtac tacacacatc   1440

tccatgcaga agcacaactg ggcagccctg gcttccagct ctgggcttca gcacaacaga   1500

caccagcctg tggtctctca gaagccaggg agaccacatc gggctcagga cgttttaccc   1560

aaagtccaga gtttttatgc ctctccctgg cattctccat aaagaaggga aggtcagatg   1620

accccttaga tctgtgtcat ctgggaattt ccttgggctg gtttagacac gatgccctct   1680

ttttctcagg atagcagata acctgctttg aaagagggct taattctgtg ggtcctaaat   1740

tttctccttt ctctctctct ttctgtgtgt gtgtgttggg aaaatggcaa gtttccaata   1800

ccagctttgg aggaacgatt acgttttccc tccaatttca agtccgaaag accagagccc   1860

tcattccaaa gccccccacc cagatggatt ttttcgtttc atttgtcatc cgtcccatgg   1920

gagggcccca tgtctcctca gaacccatcc tggaggcagc aggtcgggta gagtgagttt   1980

ggcctgctca tgacctccac ccctgagatt gtgaacaagg atgtctgggg cgatgctgag   2040

aatgtttttg aagctgctcc cagatgacgc tgatgatcac accagattga gtgctgcgat   2100

cgccttgagt ccaacctctg cataaacgag gttctcataa acaagttcac tctaccctaa   2160

gctaagtcta tgtgagcaaa cccacttcat cctttgtacc tggagacctg gttacactaa   2220

cctgatactg acctgttcat gtagctggaa tggtgtgttt catgcagtgt ggaccaagca   2280

atggcatggg gtgtgtgtgt gtgtgtgtgt gtgtctgtgt gtgtgtgttt gtgtatgcgt   2340

tcacacttgt gtgtgtatat gtgcatgtag atgctgcata aatgattttt gatgtcaaag   2400

acaaacacat tccattgttt taaatattct attatgtaaa caatacgcag agggaccata   2460

tctactcttg tcatattatt tgtgatggta aaacatgcat ttgcaataaa ttaagctttc   2520

tgggaaggca agcagtattg gagccaaacg actgtctcgg aacatgtgtg tgttatctcg   2580

gttcatatca agtccaaagc taatggagcc ttccccgcca tccagggagg aacaccagga   2640

ccccggagtt tcttcttagt gctatatttt aaagttgcat tgacgttttc ctccccttcc   2700

ttttgtgcaa gttggaagta gcagtgttct aaaagatggt ttgacgtttt tgctgttgtt   2760

ttatgttttt aaaaatgtat ctgctttgtg tttggaaata aaaatctcta ttttggtcta   2820

tgaaaaaaaa aaaaaaaaaa                                                2840
```

<210> SEQ ID NO 23
<211> LENGTH: 2309
<212> TYPE: DNA
<213> ORGANISM: Homo sapiens

<400> SEQUENCE: 23

```
gcgggggcgg gccggggcgg ggccaggccg gctagagggg cgggtctagc ggcggccccc     60

ggcgaagttc actgcgcttg cgctgacaga cgcaagatgg cggacagtgc ggaactaaag    120

caaatggtta tgagccttag agtttctgaa ctccaagtac tgttgggcta cgccgggaga    180

aacaagcacg gacgcaaaca cgaacttctc acaaaagccc tgcatttgct aaaggctggc    240

tgtagtcctg ctgtgcaaat gaaaattaag gaactctata ggcggcggtt cccacagaaa    300

atcatgacgc ctgcagactt gtccatcccc aacgtacatt caagtcctat gccagcaact    360

ttgtctccat ctaccattcc acaactcact tacgatggtc accctgcatc atcgccatta    420

ctccctgttt ctcttctggg acctaaacat gaactggaac tcccacatct tacatcagct    480
```

-continued

```
cttcacccag tccatccgga tataaaactt caaaaattac cattttatga tttactggat    540

gaactgataa aacccaccag tctagcatca gacaacagtc agcgctttcg agaaacctgt    600

tttgcatttg ccttgacacc acaacaagtg cagcaaatca gtagttccat ggatatttct    660

gggaccaaat gtgacttcac agtacaggtc cagttaaggt tttgtttatc agaaaccagt    720

tgtccacaag aagatcactt cccacccaat ctttgtgtga aagtgaatac aaaaccttgc    780

agccttccag gttaccttcc acctacaaaa aatggcgtgg aaccaaagcg acccagccga    840

ccaattaata tcacctcact tgtccgactg tccacaacag taccaaacac gattgttgtt    900

tcttggactg cagaaattgg aagaaactat tccatggcag tatatcttgt aaaacagttg    960

tcctcaacag ttcttcttca gaggttacga gcaaagggaa taaggaatcc ggatcattct   1020

agagctttaa ttaaagagaa gttgactgcg gatccagaca gtgaaatagc tacaaccagc   1080

ctaagggttt ctctactatg tccacttggt aaaatgcggc tgacaattcc gtgtcgggcc   1140

cttacatgtt ctcatctaca atgttttgac gcaactcttt acattcagat gaatgagaaa   1200

aaaccaacct gggtttgtcc tgtctgtgat aagaaggctc catatgaaca ccttattatt   1260

gatggcttgt ttatggaaat cctaaagtac tgtacagact gtgatgaaat acaatttaag   1320

gaggatggca cttgggcacc gatgagatca aaaaaggaag tacaggaagt ttctgcctct   1380

tacaatggag tcgatggatg cttgagctcc acattggagc atcaggtagc gtctcaccac   1440

cagtcctcaa ataaaaacaa gaaagtagaa gtgattgacc taaccataga cagttcatct   1500

gatgaagagg aagaagagcc atctgccaag aggacctgtc cttccctatc tcccacatca   1560

ccactaaata ataaaggcat tttaagtctt ccacatcaag catctccagt atcccgcacc   1620

ccaagccttc ctgctgtaga cacaagctac attaatacct ccctcatcca agactatagg   1680

catcctttcc acatgacacc catgccttac gacttacaag gattagattt ctttcctttc   1740

ttatcaggag acaatcagca ttacaacacc tccttgcttg ccgctgcagc agcagcagtt   1800

tcagatgatc aagacctcct acactcgtct cggtttttcc cgtatacctc ctcacagatg   1860

tttcttgatc agttaagtgc aggaggcagt acttctctgc caaccaccaa tggaagcagt   1920

agtggcagta acagcagcct ggtttcttcc aacagcctaa gggaaagcca tagccacacc   1980

gtcacaaaca ggagcagcac ggacacggca tccatctttg gcatcatacc agacattatt   2040

tcattggact gattcccagg ccctgctgct cccatcccca ccccagatcg aatgaacttg   2100

gcagaaagaa gagaactttg tgctctgttt taccttactc tgtttagaaa agtatacaag   2160

cgtgtttttt ttcctttttt tagggaaaaa attaaaagaa atgtacagag aacaaaacta   2220

tattttcagt tttacttttg tatataaatc taagactgcc tgtgtgataa aacacttgtt   2280

taaaaaaaaa aaaaaaaaaa aaaaaaaaa                                     2309
```

<210> SEQ ID NO 24
<211> LENGTH: 1740
<212> TYPE: DNA
<213> ORGANISM: Homo sapiens

<400> SEQUENCE: 24

```
ccagcgttag cccgcggcca ggcagccggg aggagcggcg cgcgctcgga cctctcccgc     60

cctgctcgtt cgctctccag cttgggatgg ccggctacct gcgggtcgtg cgctcgctct    120

gcagagcctc aggctcgcgg ccggcctggg cgccggcggc cctgacagcc cccacctcgc    180

aagagcagcc gcggcgccac tatgccgaca aaaggatcaa ggtggcgaag cccgtggtgg    240
```

-continued

```
agatggatgg tgatgagatg acccgtatta tctggcagtt catcaaggag aagctcatcc    300

tgccccacgt ggacatccag ctaaagtatt ttgacctcgg gctcccaaac cgtgaccaga    360

ctgatgacca ggtcaccatt gactctgcac tggccaccca gaagtacagt gtggctgtca    420

agtgtgccac catcacccct gatgaggccc gtgtggaaga gttcaagctg aagaagatgt    480

ggaaaagtcc caatggaact atccggaaca tcctgggggg gactgtcttc cgggagccca    540

tcatctgcaa aaacatccca cgcctagtcc ctggctggac caagcccatc accattggca    600

ggcacgccca tggcgaccag tacaaggcca cagactttgt ggcagaccgg gccggcactt    660

tcaaaatggt cttcacccca aaagatggca gtggtgtcaa ggagtgggaa gtgtacaact    720

tccccgcagg cggcgtgggc atgggcatgt acaacaccga cgagtccatc tcaggttttg    780

cgcacagctg cttccagtat gccatccaga agaaatggcc gctgtacatg agcaccaaga    840

acaccatact gaaagcctac gatgggcgtt tcaaggacat cttccaggag atctttgaca    900

agcactataa gaccgacttc gacaagaata agatctggta tgagcaccgg ctcattgatg    960

acatggtggc tcaggtcctc aagtcttcgg gtggctttgt gtgggcctgc aagaactatg   1020

acggagatgt gcagtcagac atcctggccc agggctttgg ctcccttggc ctgatgacgt   1080

ccgtcctggt ctgccctgat gggaagacga ttgaggctga ggccgctcat gggaccgtca   1140

cccgccacta tcgggagcac cagaagggcc ggcccaccag caccaacccc atcgccagca   1200

tctttgcctg gacacgtggc ctggagcacc gggggaagct ggatgggaac caagacctca   1260

tcaggtttgc ccagatgctg gagaaggtgt gcgtggagac ggtggagagt ggagccatga   1320

ccaaggacct ggcgggctgc attcacggcc tcagcaatgt gaagctgaac gagcacttcc   1380

tgaacaccac ggacttcctc gacaccatca agagcaacct ggacagagcc ctgggcaggc   1440

agtaggggga ggcgccaccc atggctgcag tggaggggcc agggctgagc cggcgggtcc   1500

tcctgagcgc ggcagagggt gagcctcaca gcccctctct ggaggccttt ctaggggatg   1560

tttttttata agccagatgt ttttaaaagc atatgtgtgt ttcccctcat ggtgacgtga   1620

ggcaggagca gtgcgtttta cctcagccag tcagtatgtt ttgcatactg taatttatat   1680

tgcccttgga acacatggtg ccatatttag ctactaaaaa gctcttcaca aaaaaaaaaa   1740


<210> SEQ ID NO 25
<211> LENGTH: 1552
<212> TYPE: DNA
<213> ORGANISM: Homo sapiens

<400> SEQUENCE: 25

ggtcgcttta agaaaggagt agctgtaatc tgaagcctgc tggacgctgg attagaaggc     60

agcaaaaaaa gctctgtgct ggctggagcc ccctcagtgt gcaggcttag agggactagg    120

ctgggtgtgg agctgcagcg tatccacagg ccccaggatg caggccctgg tgctactcct    180

ctgcattgga gccctcctcg ggcacagcag ctgccagaac cctgccagcc ccccggagga    240

gggctcccca gaccccgaca gcacaggggc gctggtggag gaggaggatc ctttcttcaa    300

agtccccgtg aacaagctgg cagcggctgt ctccaacttc ggctatgacc tgtaccgggt    360

gcgatccagc acgagcccca cgaccaacgt gctcctgtct cctctcagtg tggccacggc    420

cctctcggcc ctctcgctgg gagcggagca gcgaacagaa tccatcattc accgggctct    480

ctactatgac ttgatcagca gcccagacat ccatggtacc tataaggagc tccttgacac    540

ggtcactgcc ccccagaaga acctcaagag tgcctcccgg atcgtctttg agaagaagct    600

gcgcataaaa tccagctttg tggcacctct ggaaaagtca tatgggacca ggcccagagt    660
```

```
cctgacgggc aaccctcgct tggacctgca agagatcaac aactgggtgc aggcgcagat    720

gaaagggaag ctcgccaggt ccacaaagga aattcccgat gagatcagca ttctccttct    780

cggtgtggcg cacttcaagg ggcagtgggt aacaaagttt gactccagaa agacttccct    840

cgaggatttc tacttggatg aagagaggac cgtgagggtc cccatgatgt cggaccctaa    900

ggctgtttta cgctatggct tggattcaga tctcagctgc aagattgccc agctgccctt    960

gaccggaagc atgagtatca tcttcttcct gcccctgaaa gtgacccaga atttgacctt   1020

gatagaggag agcctcacct ccgagttcat tcatgacata gaccgagaac tgaagaccgt   1080

gcaggcggtc ctcactgtcc ccaagctgaa gctgagttat gaaggcgaag tcaccaagtc   1140

cctgcaggag atgaagctgc aatccttgtt tgattcacca gactttagca agatcacagg   1200

caaacccatc aagctgactc aggtggaaca ccgggctggc tttgagtgga acgaggatgg   1260

ggcgggaacc acccccagcc cagggctgca gcctgcccac ctcaccttcc cgctggacta   1320

tcaccttaac cagcctttca tcttcgtact gagggacaca gacacagggg cccttctctt   1380

cattggcaag attctggacc ccaggggccc ctaatatccc agtttaatat tccaataccc   1440

tagaagaaaa cccgagggac agcagattcc acaggacacg aaggctgccc ctgtaaggtt   1500

tcaatgcata caataaaaga gctttatccc taaaaaaaaa aaaaaaaaaa aa           1552
```

<210> SEQ ID NO 26
<211> LENGTH: 4816
<212> TYPE: DNA
<213> ORGANISM: Homo sapiens

<400> SEQUENCE: 26

```
gttcccggat ttttgtgggc gcctgccccg cccctcgtcc ccctgctgtg tccatatatc     60

gaggcgatag ggttaaggga aggcggacgc ctgatgggtt aatgagcaaa ctgaagtgtt    120

ttccatgatc tttttgagt cgcaattgaa gtaccacctc ccgagggtga ttgcttcccc    180

atgcggggta gaacctttgc tgtcctgttc accactctac ctccagcaca gaatttggct    240

tatgcctact caatgtgaag atgatgagga tgaaaacctt tgtgatgatc cacttccact    300

taatgaatgg tggcaaagca aagctatatt caagaccaca tgcaaagcta ctccctgagc    360

aaagagtcac agataaaacg ggggcaccag tagaatggcc aggacaaacg cagtgcagca    420

cagagactca gaccctggca gccatgcctg cgcaggcagt gatgagagtg acatgtactg    480

ttgtggacat gcacaaaagt gagtgtgcac cggcacagac atgaagctgc ggctccctgc    540

cagtcccgag acccacctgg acatgctccg ccacctctac cagggctgcc aggtggtgca    600

gggaaacctg gaactcacct acctgcccac caatgccagc ctgtccttcc tgcaggatat    660

ccaggaggtg cagggctacg tgctcatcgc tcacaaccaa gtgaggcagg tcccactgca    720

gaggctgcgg attgtgcgag gcacccagct ctttgaggac aactatgccc tggccgtgct    780

agacaatgga gacccgctga acaataccac ccctgtcaca ggggcctccc caggaggcct    840

gcgggagctg cagcttcgaa gcctcacaga gatcttgaaa ggagggggtct tgatccagcg    900

gaacccccag ctctgctacc aggacacgat tttgtggaag gacatcttcc acaagaacaa    960

ccagctggct ctcacactga tagacaccaa ccgctctcgg gcctgccacc cctgttctcc   1020

gatgtgtaag ggctcccgct gctggggaga gagttctgag gattgtcaga gcctgacgcg   1080

cactgtctgt gccggtggct gtgcccgctg caaggggcca ctgcccactg actgctgcca   1140

tgagcagtgt gctgccggct gcacgggccc caagcactct gactgcctgg cctgcctcca   1200
```

-continued

```
cttcaaccac agtggcatct gtgagctgca ctgcccagcc ctggtcacct acaacacaga   1260

cacgtttgag tccatgccca atcccgaggg ccggtataca ttcggcgcca gctgtgtgac   1320

tgcctgtccc tacaactacc tttctacgga cgtgggatcc tgcaccctcg tctgccccct   1380

gcacaaccaa gaggtgacag cagaggatgg aacacagcgg tgtgagaagt gcagcaagcc   1440

ctgtgcccga gtgtgctatg gtctgggcat ggagcacttg cgagaggtga gggcagttac   1500

cagtgccaat atccaggagt ttgctggctg caagaagatc tttgggagcc tggcatttct   1560

gccggagagc tttgatgggg acccagcctc caacactgcc ccgctccagc cagagcagct   1620

ccaagtgttt gagactctgg aagagatcac aggttaccta tacatctcag catggccgga   1680

cagcctgcct gacctcagcg tcttccagaa cctgcaagta atccggggac gaattctgca   1740

caatggcgcc tactcgctga ccctgcaagg gctgggcatc agctggctgg ggctgcgctc   1800

actgagggaa ctgggcagtg gactggccct catccaccat aacacccacc tctgcttcgt   1860

gcacacggtg ccctgggacc agctctttcg gaacccgcac caagctctgc tccacactgc   1920

caaccggcca gaggacgagt gtgtgggcga gggcctggcc tgccaccagc tgtgcgcccg   1980

agggcactgc tggggtccag ggcccaccca gtgtgtcaac tgcagccagt tccttcgggg   2040

ccaggagtgc gtggaggaat gccgagtact gcaggggctc cccagggagt atgtgaatgc   2100

caggcactgt ttgccgtgcc accctgagtg tcagccccag aatggctcag tgacctgttt   2160

tggaccggag gctgaccagt gtgtggcctg tgcccactat aaggaccctc ccttctgcgt   2220

ggcccgctgc cccagcggtg tgaaacctga cctctcctac atgcccatct ggaagtttcc   2280

agatgaggag ggcgcatgcc agccttgccc catcaactgc acccactcct gtgtggacct   2340

ggatgacaag ggctgccccg ccgagcagag agccagccct ctgacgtcca tcatctctgc   2400

ggtggttggc attctgctgg tcgtggtctt gggggtggtc tttgggatcc tcatcaagcg   2460

acggcagcag aagatccgga agtacacgat gcggagactg ctgcaggaaa cggagctggt   2520

ggagccgctg acacctagcg gagcgatgcc caaccaggcg cagatgcgga tcctgaaaga   2580

gacggagctg aggaaggtga aggtgcttgg atctggcgct tttggcacag tctacaaggg   2640

catctggatc cctgatgggg agaatgtgaa aattccagtg gccatcaaag tgttgaggga   2700

aaacacatcc cccaaagcca acaaagaaat cttagacgaa gcatacgtga tggctggtgt   2760

gggctcccca tatgtctccc gccttctggg catctgcctg acatccacgg tgcagctggt   2820

gacacagctt atgccctatg gctgcctctt agaccatgtc cgggaaaacc gcggacgcct   2880

gggctcccag gacctgctga actggtgtat gcagattgcc aaggggatga gctacctgga   2940

ggatgtgcgg ctcgtacaca gggacttggc cgctcggaac gtgctggtca agagtcccaa   3000

ccatgtcaaa attacagact tcgggctggc tcggctgctg gacattgacg agacagagta   3060

ccatgcagat gggggcaagg tgcccatcaa gtggatggcg ctggagtcca ttctccgccg   3120

gcggttcacc caccagagtg atgtgtggag ttatggtgtg actgtgtggg agctgatgac   3180

ttttggggcc aaaccttacg atgggatccc agcccgggag atccctgacc tgctggaaaa   3240

gggggagcgg ctgccccagc cccccatctg caccattgat gtctacatga tcatggtcaa   3300

atgttggatg attgactctg aatgtcggcc aagattccgg gagttggtgt ctgaattctc   3360

ccgcatggcc agggaccccc agcgctttgt ggtcatccag aatgaggact tgggcccagc   3420

cagtcccttg gacagcacct tctaccgctc actgctggag gacgatgaca tgggggacct   3480

ggtggatgct gaggagtatc tggtacccca gcagggcttc ttctgtccag accctgcccc   3540

gggcgctggg ggcatggtcc accacaggca ccgcagctca tctaccagga gtggcggtgg   3600
```

ggacctgaca ctagggctgg agccctctga agaggaggcc cccaggtctc cactggcacc 3660
ctccgaaggg gctggctccg atgtatttga tggtgacctg ggaatggggg cagccaaggg 3720
gctgcaaagc ctccccacac atgaccccag ccctctacag cggtacagtg aggaccccac 3780
agtacccctg ccctctgaga ctgatggcta cgttgccccc ctgacctgca gcccccagcc 3840
tgaatatgtg aaccagccag atgttcggcc ccagcccccct tcgccccgag agggccctct 3900
gcctgctgcc cgacctgctg gtgccactct ggaaaggccc aagactctct ccccagggaa 3960
gaatggggtc gtcaaagacg tttttgcctt tgggggtgcc gtggagaacc ccgagtactt 4020
gacaccccag ggaggagctg cccctcagcc ccaccctcct cctgccttca gcccagcctt 4080
cgacaacctc tattactggg accaggaccc accagagcgg ggggctccac ccagcacctt 4140
caaagggaca cctacggcag agaacccaga gtacctgggt ctggacgtgc cagtgtgaac 4200
cagaaggcca agtccgcaga agccctgatg tgtcctcagg gagcagggaa ggcctgactt 4260
ctgctggcat caagaggtgg gagggccctc cgaccacttc caggggaacc tgccatgcca 4320
ggaacctgtc ctaaggaacc ttccttcctg cttgagttcc cagatggctg gaaggggtcc 4380
agcctcgttg gaagaggaac agcactgggg agtctttgtg gattctgagg ccctgcccaa 4440
tgagactcta gggtccagtg gatgccacag cccagcttgg ccctttcctt ccagatcctg 4500
ggtactgaaa gccttaggga agctggcctg agaggggaag cggccctaag ggagtgtcta 4560
agaacaaaag cgacccattc agagactgtc cctgaaacct agtactgccc cccatgagga 4620
aggaacagca atggtgtcag tatccaggct ttgtacagag tgcttttctg tttagttttt 4680
actttttttg ttttgttttt ttaaagatga aataaagacc caggggggaga atgggtgttg 4740 tatggggagg caagtgtggg gggtccttct ccacacccac tttgtccatt tgcaaatata 4800
ttttggaaaa cagcta 4816

<210> SEQ ID NO 27
<211> LENGTH: 6831
<212> TYPE: DNA
<213> ORGANISM: Homo sapiens

<400> SEQUENCE: 27
ccaggcccca ttgttcccgg tttccagcca tggctgccat tacctgacca gcgccacagc 60
cggtctctct gcaggcgccg ggagaagtga ccagagcaat ttctgctttt cacagggcgg 120
gtttctcaac ggtgacttgt gggcagtgcc ttctgctgag cgagtcatgg cccgaaggca 180
gaactaactg tgcctgcagt cttcactctc aggatgcagc cgaggtgggc ccaaggggcc 240
acgatgtggc ttggagtcct gctgaccctt ctgctctgtt caagccttga gggtcaagaa 300
aactctttca caatcaacag tgttgacatg aagagcctgc cggactggac ggtgcaaaat 360
gggaagaacc tgaccctgca gtgcttcgcg gatgtcagca ccacctctca cgtcaagcct 420
cagcaccaga tgctgttcta taaggatgac gtgctgtttt acaacatctc ctccatgaag 480
agcacagaga gttattttat tcctgaagtc cggatctatg actcagggac atataaatgt 540
actgtgattg tgaacaacaa agagaaaacc actgcagagt accaggtgtt ggtggaagga 600
gtgcccagtc ccagggtgac actggacaag aaagaggcca tccaaggtgg gatcgtgagg 660
gtcaactgtt ctgtcccaga ggaaaaggcc ccaatacact tcacaattga aaaacttgaa 720
ctaaatgaaa aaatggtcaa gctgaaaaga gagaagaatt ctcgagacca gaattttgtg 780
atactggaat tccccgttga ggaacaggac cgcgttttat ccttccgatg tcaagctagg 840

-continued

```
atcatttctg ggatccatat gcagacctca gaatctacca agagtgaact ggtcaccgtg    900
acggaatcct tctctacacc caagttccac atcagcccca ccggaatgat catggaagga    960
gctcagctcc acattaagtg caccattcaa gtgactcacc tggcccagga gtttccagaa   1020
atcataattc agaaggacaa ggcgattgtg gcccacaaca gacatggcaa caaggctgtg   1080
tactcagtca tggccatggt ggagcacagt ggcaactaca cgtgcaaagt ggagtccagc   1140
cgcatatcca aggtcagcag catcgtggtc aacataacag aactattttc caagcccgaa   1200
ctggaatctt ccttcacaca tctggaccaa ggtgaaagac tgaacctgtc ctgctccatc   1260
ccaggagcac ctccagccaa cttcaccatc cagaaggaag atacgattgt gtcacagact   1320
caagatttca ccaagatagc ctcaaagtcg gacagtggga cgtatatctg cactgcaggt   1380
attgacaaag tggtcaagaa aagcaacaca gtccagatag tcgtatgtga aatgctctcc   1440
cagcccagga tttcttatga tgcccagttt gaggtcataa aaggacagac catcgaagtc   1500
cgttgcgaat cgatcagtgg aactttgcct atttcttacc aacttttaaa aacaagtaaa   1560
gttttggaga atagtaccaa gaactcaaat gatcctgcgg tattcaaaga caaccccact   1620
gaagacgtcg aataccagtg tgttgcagat aattgccatt cccatgccaa aatgttaagt   1680
gaggttctga gggtgaaggt gatagccccg gtggatgagg tccagatttc tatcctgtca   1740
agtaaggtgg tggagtctgg agaggacatt gtgctgcaat gtgctgtgaa tgaaggatct   1800
ggtcccatca cctataagtt ttacagagaa aaagagggca aacccttcta tcaaatgacc   1860
tcaaatgcca cccaggcatt ttggaccaag cagaaggcta gcaaggaaca ggagggagag   1920
tattactgca cagccttcaa cagagccaac cacgcctcca gtgtccccag aagcaaaata   1980
ctgacagtca gagtcattct tgccccatgg aagaaaggac ttattgcagt ggttatcatc   2040
ggagtgatca ttgctctctt gatcattgcg gccaaatgtt attttctgag gaaagccaag   2100
gccaagcaga tgccagtgga aatgtccagg ccagcagtac cacttctgaa ctccaacaac   2160
gagaaaatgt cagatcccaa tatggaagct aacagtcatt acggtcacaa tgacgatgtc   2220
agaaaccatg caatgaaacc aataaatgat aataaagagc ctctgaactc agacgtgcag   2280
tacacggaag ttcaagtgtc ctcagctgag tctcacaaag atctaggaaa gaaggacaca   2340
gagacagtgt acagtgaagt ccggaaagct gtccctgatg ccgtggaaag cagatactct   2400
agaacggaag gctcccttga tggaacttag acagcaaggc cagatgcaca tccctggaag   2460
gacatccatg ttccgagaag aacagataat ccctgtattt caagacctct gtgcacttat   2520
ttatgaacct gccctgctcc cacagaacac agcaattcct caggctaagc tgccggttct   2580
taaatccatc ctgctaagtt aatgttgggt agaaagagat acagaggggc tgttgaattt   2640
cccacatacc ctccttccac caagttggaa catccttgga aattggaaga gcacaagagg   2700
agatccaggg caaggccatt gggatattct gaaacttgaa tattttgttt tgtgcagaga   2760
taaagacctt ttccatgcac cctcatacac agaaaccaat ttctttttt atactcaatc   2820
atttctagcg catggcctgg ttagaggctg gtttttctc ttttcctttg gtccttcaaa   2880
ggcttgtagt tttggctagt ccttgttctt tggaaataca cagtgctgac cagacagcct   2940
ccccctgtcc cctctatgac ctcgccctcc acaaatggga aaaccagact acttgggagc   3000
accgcctgtg aaataccaac ctgaagacac cgttcattca ggcaacgcac aaaacagaaa   3060
atgaaggtgg aacaagcaca gatgttcttc aactgttttt gtctacactc tttctctttt   3120
cctctaccat gctgaaggct gaaagacagg aagatggtgc catcagcaaa tattattctt   3180
aattgaaaac ttgaaatgtg tatgtttctt actaattttt aaaaatgtat tccttgccag   3240
```

-continued

```
ggcaggcaag gtggctcacg cctgtaatcc cagcacttca ggaggctgag gtgggcggat   3300
cacctgaggt caggagtttg agaccagcct gatgaaaccc tgtctctact aaaaatacaa   3360
gaattagccg ggcgtggtgg cgcatgcctg tagtatcagc tactcaagag gctgaggtga   3420
gattatcgct tgaacccagg aaacggaggt tgtagtgagc ggagatcgcg ccactgcact   3480
ccagcctgag tgacagagtg agaatccatc tcaaaaaaaa caaaaaaacaa aattgcttgc   3540
taaagaagtg gtctcctgag gtcttaagac attcctgaca gtgtcttgag tgggtgggag   3600
agaggctgct gtcattgcgc tgtggaattt cacagatgag aaccacgcct agccaaaatc   3660
acttttcctg tttgcctcag tgacacagct gcagggaccc tcgtggatgt tgtattaaat   3720
aaatttgacc tttgctcttt gcagatctgt gaaatgttgt cttctgaggg gccacatgca   3780
tctatagtgc tgaggactcc ttgggcctct gaagtcacag agagaaccga gcaggtctat   3840
gtttttgttt tgttgttttg agacggagat tcgctcttgt tgcccgggct ggactgcagc   3900
ggcgcaacct ctgctcactg caacctccgc ctcctgggtt caagcagttc tcctgtctca   3960
gcctcccgag tagctgggat tacaggcaca tgtcaccacg cctggctaat ttttgtattt   4020
ttagtagaga tggggtttca ccacgttggc caggctgatc tcgaatgcct gacctttggt   4080
gatctgcccg ccttgtcctc atgtgtgctc cacaggcctt tgggttggga ttgcaggcgt   4140
gagccaccat gcccagccta gactcttttg acaatatgat gaaagctgtt ggttcctttc   4200
cccaacacac acacaccgag ttgtatcacg aaaatgtcat acaatttcca ggtttctga    4260
gtggtgggct cagattgagg tcaaaggatc agacgacctc taacgacctt catgtctctg   4320
ttgatgatct ggggacagcc agatcccctg tgtccaggga gttccttagt cccttgccac   4380
caccagagaa gggcaattgc cacgggagct gcaaagaccc tattcctact cctggtgcct   4440
tacttatgca gcacgactga attttttgtt ttgttttgtt ttgttgagac aggggcttgc   4500
tctgttgccc aggctggagt gcagtggcac aacaatggct caccgcagcc tcgaacccct   4560
gggctcaagc gatcctccca tctcagcttc ctgggtagct gggaccagag gcgtgagccg   4620
ccatagctgg ctaattttta attttttttt tgcagagatg aggtttcacc atggtgccca   4680
ggctggtctc gaacttctgg gctcaagtga tcctccctcc ttggcctcgc aaagtgctgg   4740
gattgcaggc atgagccacc gcccccggcc tgtggagcac acatgagttt aaaattactt   4800
tcccttctgc ctatatttcc gaggaggaaa cttcatgcgc agggatcttt cttagtggat   4860
ttaatggcta aaaggtctgt ctgaatccag gacgctggct ttagccttcc tcggcagctg   4920
ccgtaacccc ggtgtctaaa cctgaagcat cccaggagca cccactccag gagttttctc   4980
ggccgcggaa ctcattagtt agagcgccct cttgtgttct catgtggtaa tcggtcactg   5040
aaggacttaa aatggtcctt agccaacaca cagtaaaact tttccctctt ctgaccccaa   5100
gaggtcagcc acccatttca tgagcatata ctggtcgccc catcagcgtt ctctgattgg   5160
ctaactgaac ccactccccg acctagactc aagacaggcg aagtgacgct taggtcaaca   5220
ttcactcact aaagcaacga ctgtcgggcg attttgtctc ccgctggttt tggaatggtg   5280
tctggagaca tttttggttg tcacagctgg gtgggtgtgc tcccggcatc tggtgggtag   5340
aaaccaagca tgctcctaaa catcctacag gcacagaacc gtctcccacg accaagcatg   5400
atcaagtccc aaatgccaat aatggccagg ttgagaaact ctgcacagaa gcatccagtt   5460
atttgtctgt ttgctcaaca agcttgtgct catcatgctc tgtgttcctg acgctgtgct   5520
gggtgttggc ggtgggaaga ttacaagagt cacatggcag ctgtcctcct ggaaggtaca   5580
```

-continued acccagtaga gatgcagact aacagagagc caattacaaa gcagtgtgac aagcgtcatg 5640
gtggaaaatt aaaagctcaa acaagggcac atgggagggg cttccaacac agactttggg 5700
ggatccagga aggtctaaga ggaaagtggg tctcaccaaa gccttgacca taggcagagg 5760
gtaccagtgg aaaaggtggg gtgaagaaca ttgaggacaa aaggaagaag tgcaggaagg 5820
ccctgaggca agggagtggg gggtgccctg gagggatggc agcagggcag tctgtcagac 5880
ccaagtggcc tccagcccta gaagccaatt agtcctcctc aaaaagctgt cactgtcccc 5940
taagaattgc tgccaggctc ccactggcct gactcagtct ttgagagtct taaggaggag 6000
gtctctgaaa ggtacacacc aagaactctc cccagcacag ctgtttttaa gactctccac 6060
cagcgtcatt ggcgtgttgg gaagaaaccc tctgccacag aggccagctt cagcctttgc 6120
ctaacaccgc aagggcaaat ggaaaggtaa acgggaagga gatgtctccc cagcaggcta 6180
tttgaggaca gtcttccctg cagaagatct caacctgggg tccacagagt ggaaatgtta 6240
gagtagggag ctaggcaaac atgagcagga caggtgaggg cccccacagg aatgtcaggc 6300
taccatcagg tgatggtcag gtggttgtta aactgtctct gtaaaataat aattggttgc 6360
agccagctcc aagcaaggac agtctctcaa tagatacaaa acaccctgat ctggtgatca 6420
gccgcttccc gataagatct caggagctgg gcaagcagcc tggagcatgc gcaccaagag 6480
gcaaaatggc ggaatttaac cagtatatga cctaccttcc tctgggaacg cacgactggt 6540
aaggggaaaa atgcctcaag tgagcatgcg cgcaacttca gtaatcacac tgtgcatgcg 6600 acccccttcca agtgctggca ggtcaccaca tacgcggaca gcctgctgca agggaagaat 6660
caggggagat gagacgtaaa tcccagaact atgccaaata cataaaaccc caagttaagg 6720
gtcaggcagg gcacttagat ctctcaagtt gcctgcctga cccaagtgta gtgtacttcc 6780
ttttgttcct gctctaaaac tttttaataa actctcactc ctgctctaaa a 6831

<210> SEQ ID NO 28
<211> LENGTH: 2956
<212> TYPE: DNA
<213> ORGANISM: Homo sapiens

<400> SEQUENCE: 28
ggggctgagt gctcagtgga gagcggggag ttgtgtccac cttgccgacg tcgctagccg 60
tggggctgtc ctgggaaggc ggacggcgag cgcccggtgt ccgcactcgg ccgcctgccg 120
tgcccgtctg cgcccgtgtc atcctcactc gggacgcagg gaccgttttt aaatcacagg 180
ggcgtgtgtc agcctgccct aggacttcat gtctatatat ttccccattc actgccccga 240
ctatctgaga tcggccaaga tgactgaggt gatgatgaac acccagccca tggaggagat 300
cggcctcagc cccgcaagg atggcctttc ctaccagatc ttcccagacc cgtcagattt 360
tgaccgctgc tgcaaactga aggaccgtct gccctccata gtggtggaac ccacagaagg 420
ggaggtggag agcggggagc tccggtggcc ccctgaggag ttcctggtcc aggaggatga 480
gcaagataac tgcgaagaga cagcgaaaga aaataaagag cagtagagtc cctgtggact 540
cccatgggtc ataccagcca gcatctgttc ctgaactgtg tttttcccat catgacggaa 600
gaagagagtg agccgcaatt gttctgaaaa tgtcaaacga ggcttctgtt ttgcacctgc 660
agatcaccga gttggttttc ttttcttttc ttgccttttt tttttttga aatttgccga 720 gcagtggagc cctctgacaa tttgcaaggc cctctgagaa aggaagctgc ttagagccag 780
ggggttagtg ggtgagggga gcgagtgctg tttttgagat cattatctga actcaggcag 840
cctagtagag gcagtggtgg gattccaatg ggtcttggtg ggtgggaggt ggggcatgtg 900

```
caaagcaagc aaggaacatt tggggtaaga aaacaaacat gaggcaaaag aaaaaataca    960
tgtttttaag aaaacattga gcagagaact gcagccagga tgcgctcagc agacattcac   1020
tctggctgct gggacatcag aaaacaaagt cttcatctct ctctccagtt tcacccaccc   1080
cacccttttgc tttcatttca ggtgtgttgg tctatatgac agggaggaga gtaaaggaga   1140
gcaggagcaa ttggctgcct gcaaagccag ctggaggtga agtgcaggaa aggaaaggtc   1200
accccattct actccatggc ctctctgctc ccagctgtgg taggctcaca tagccagtgt   1260
gatcggtttt taagaggcag tgcttttcag cttttctccc tgatatatcc attttgcttc   1320
ccagcacttt ttaggagtag tgagagcact tcctgccctt gttggaagcc ccagggtgga   1380
cactcagcac gaaggtctct cccttaactg ctgcccttcc aagacttgct cccgagatgg   1440
agtgggcgtg gtcttccagg ctggcccttc cttctcctca ccgccacctt ccctgcccca   1500
gccccagcag ccatgggtac atgggtcccc agctcaccta tggattcccg ccagtctgcc   1560
cagctgcagt actcacgccc catgggggat cttggtctgt ttttcttgtg ggagcctagt   1620
ggagagcaga cgtggctttt tatgtgtctt gttggggagg tgacttgcat ggtggggaca   1680
aggctgtcgt ggcaaccttg ggatcgagtt tgagactaaa ggatgtcatg agatccctgg   1740
cttctcccca tgttgttccc ggacaagggc agaagggagg catggcaagg gacctctgct   1800
gtccttactc aacagtggtc ctcatccctc cccacctccc actgcttcct gcaagggcac   1860
cagttgtatg agaaagttgg cctttggact taggatttct tattgtagct aagagccatc   1920
tgaagcagca ggttgcagga caaatgcttc agtccgccga gagcagtacc gtgtggccaa   1980
gaggtggact cagagccttc cttgagctaa actcggccaa ccaaggcacg cagcatgtcc   2040
cctcaggtct ccagtcagtc caggttgacc ctcagttctg gacgtgtgta tatagctgta   2100
tttaatacct caaggtcatt gtggctctgg ggatgccggg gcaggaggac gagggtgcgc   2160
tgtggacaca gcagtccgcg gaattccgtt ctgggaagcc aatggtcgcc ggcacccctt   2220
gcttcctccc tctgttgtct gcctgtgtga cacacatcaa tggcaataac ttcttccaac   2280
tcctcgcaga agtgggagag gccggcagcc tgcaccgaga ggggctttcc tctctcttgc   2340
tccccgcttc gttctgtttt ggctgcagag agtggttcat ccatactctc attccctcgc   2400
ctccccttgt ggacgggggt cttgcctttt caattcctgt gttttggtgt cttcccttat   2460
ctgctaccct gaatcacctg tcctggtctt gctgtgtgat gggaacatgc ttgtaaactg   2520
cgtaacaaat ctactttgtg tatgtgtctg tttatggggg tggtttatta tttttgctgg   2580
tccctagacc actttgtatg accgtttgca gtctgagcag gccaggggct gacagctaat   2640
gtcaggaccc tcagcggtgg agcctgctgg ggggacccag ctgctcttgg acaagtggct   2700
gagctcctat ctggcctcct cttttttttt ttttcaagta atttgtgtgt atttctaact   2760
gattgtattg aaaaaattcc tagtatttca gtaaaaatgc ctgttgtgag atgaacctcc   2820
tgtaacttct atctgttctt ttttgaggct cagggagaaa ctagcatttt tttttttcca   2880
aactactttt tgtcactgtg acagttgtaa ataaagtttg aaaatgcttt ccactctgaa   2940
aaaaaaaaaa aaaaaa                                                   2956
```

<210> SEQ ID NO 29
<211> LENGTH: 2262
<212> TYPE: DNA
<213> ORGANISM: Homo sapiens

<400> SEQUENCE: 29

-continued

```
ctggggagta atagcatggg caaccattat cctgtctcgc cgccacccag gacatggctt     60
ctgttccaat gccaagtgag tacacctatg tgaaactgag aagtgattgc tcgaggcctt    120
ccctgcaatg gtacacccga gctcaaagca agatgagaag gcccagcttg ttattaaaag    180
acatcctcaa atgtacattg cttgtgtttg gagtgtggat cctttatatc ctcaagttaa    240
attatactac tgaagaatgt gacatgaaaa aaatgcatta tgtggaccct gaccatgtaa    300
agagagctca gaaatatgct cagcaagtct tgcagaagga atgtcgtccc aagtttgcca    360
agacatcaat ggcgctgtta tttgagcaca ggtatagcgt ggacttactc ccttttgtgc    420
agaaggcccc caaagacagt gaagctgagt ccaagtacga tcctcctttt gggttccgga    480
agttctccag taaagtccag accctcttgg aactcttgcc agagcacgac ctccctgaac    540
acttgaaagc caagacctgt cggcgctgtg tggttattgg aagcggagga atactgcacg    600
gattagaact gggccacacc ctgaaccagt tcgatgttgt gataaggtta aacagtgcac    660
cagttgaggg atattcagaa catgttggaa ataaaactac tataaggatg acttatccag    720
agggcgcacc actgtctgac cttgaatatt attccaatga cttatttgtt gctgttttat    780
ttaagagtgt tgatttcaac tggcttcaag caatggtaaa aaaggaaacc ctgccattct    840
gggtacgact cttcttttgg aagcaggtgg cagaaaaaat cccactgcag ccaaaacatt    900
tcaggatttt gaatccagtt atcatcaaag agactgcctt tgacatcctt cagtactcag    960
agcctcagtc aaggttctgg ggccgagata agaacgtccc cacaatcggt gtcattgccg   1020
ttgtcttagc cacacatctg tgcgatgaag tcagtttggc gggttttgga tatgacctca   1080
atcaacccag aacacctttg cactacttcg acagtcaatg catggctgct atgaactttc   1140
agaccatgca taatgtgaca acggaaacca agttcctctt aaagctggtc aaagagggag   1200
tggtgaaaga tctcagtgga ggcattgatc gtgaattttg aacacagaaa acctcagttg   1260
aaaatgcaac tctaactctg agagctgttt ttgacagcct tcttgatgta tttctccatc   1320
ctgcagatac tttgaagtgc agctcatgtt tttaactttt aatttaaaaa cacaaaaaaa   1380
attttagctc ttcccacttt ttttttccta tttatttgag gtcagtgttt gtttttgcac   1440
accattttgt aaatgaaact taagaattga attggaaaga cttctcaaag agaattgtat   1500
gtaacgatgt tgtattgatt tttaagaaag taatttaatt tgtaaaactt ctgctcgttt   1560
acactgcaca ttgaatacag gtaactaatt ggaaggagag gggaggtcac tcttttgatg   1620
gtggccctga acctcattct ggttccctgc tgcgctgctt ggtgtgaccc acggaggatc   1680
cactcccagg atgacgtgct ccgtagctct gctgctgata ctgggtctgc gatgcagcgg   1740
cgtgaggcct gggctggttg gagaaggtca caaccccttct ctgttggtct gccttctgct   1800
gaaagactcg agaaccaacc agggaagctg tcctggaggt ccctggtcgg agagggacat   1860
agaatctgtg acctctgaca actgtgaagc caccctgggc tacagaaacc acagtcttcc   1920
cagcaattat tacaattctt gaattccttg gggatttttt actgcccttt caaagcactt   1980
aagtgttaga tctaacgtgt tccagtgtct gtctgaggtg acttaaaaaa tcagaacaaa   2040
acttctatta tccagagtca tgggagagta caccctttcc aggaataatg ttttgggaaa   2100
cactgaaatg aaatcttccc agtattataa attgtgtatt taaaaaaaag aaacttttct   2160
gaatgcctac ctggcggtgt ataccaggca gtgtgccagt ttaaaaagat gaaaaagaat   2220
aaaaactttt gaggaaaaaa aaaaaaaaaa aaaaaaaaaa aa                      2262
```

<210> SEQ ID NO 30
<211> LENGTH: 4909

```
<212> TYPE: DNA
<213> ORGANISM: Homo sapiens

<400> SEQUENCE: 30

tagacgcacc ctctgaagat ggtgactccc tcctgagaag ctggacccct tggtaaaaga     60

caaggccttc tccaagaaga atatgaaagt gttactcaga cttatttgtt tcatagctct    120

actgatttct tctctggagg ctgataaatg caaggaacgt gaagaaaaaa taattttagt    180

gtcatctgca aatgaaattg atgttcgtcc ctgtcctctt aacccaaatg aacacaaagg    240

cactataact tggtataaag atgacagcaa gacacctgta tctacagaac aagcctccag    300

gattcatcaa cacaaagaga aactttggtt tgttcctgct aaggtggagg attcaggaca    360

ttactattgc gtggtaagaa attcatctta ctgcctcaga attaaaataa gtgcaaaatt    420

tgtggagaat gagcctaact tatgttataa tgcacaagcc atatttaagc agaaactacc    480

cgttgcagga gacggaggac ttgtgtgccc ttatatggag tttttaaaaa atgaaaataa    540

tgagttacct aaattacagt ggtataagga ttgcaaacct ctacttcttg acaatataca    600

ctttagtgga gtcaaagata ggctcatcgt gatgaatgtg gctgaaaagc atagagggaa    660

ctatacttgt catgcatcct acacatactt gggcaagcaa tatcctatta cccgggtaat    720

agaatttatt actctagagg aaaacaaacc cacaaggcct gtgattgtga gcccagctaa    780

tgagacaatg gaagtagact tgggatccca gatacaattg atctgtaatg tcaccggcca    840

gttgagtgac attgcttact ggaagtggaa tgggtcagta attgatgaag atgacccagt    900

gctaggggaa gactattaca gtgtggaaaa tcctgcaaac aaaagaagga gtaccctcat    960

cacagtgctt aatatatcgg aaattgaaag tagattttat aaacatccat ttacctgttt   1020

tgccaagaat acacatggta tagatgcagc atatatccag ttaatatatc cagtcactaa   1080

tttccagaag cacatgattg gtatatgtgt cacgttgaca gtcataattg tgtgttctgt   1140

tttcatctat aaaatcttca agattgacat tgtgctttgg tacagggatt cctgctatga   1200

ttttctccca ataaaagctt cagatggaaa gacctatgac gcatatatac tgtatccaaa   1260

gactgttggg gaagggtcta cctctgactg tgatattttt gtgtttaaag tcttgcctga   1320

ggtcttggaa aaacagtgtg gatataagct gttcatttat ggaagggatg actacgttgg   1380

ggaagacatt gttgaggtca ttaatgaaaa cgtaaagaaa agcagaagac tgattatcat   1440

tttagtcaga gaaacatcag gcttcagctg gctgggtggt tcatctgaag agcaaatagc   1500

catgtataat gctcttgttc aggatggaat taaagttgtc ctgcttgagc tggagaaaat   1560

ccaagactat gagaaaatgc cagaatcgat taaattcatt aagcagaaac atggggctat   1620

ccgctggtca ggggacttta cacagggacc acagtctgca aagacaaggt tctggaagaa   1680

tgtcaggtac cacatgccag tccagcgacg gtcaccttca tctaaacacc agttactgtc   1740

accagccact aaggagaaac tgcaaagaga ggctcacgtg cctctcgggt agcatggaga   1800

agttgccaag agttctttag gtgcctcctg tcttatggcg ttgcaggcca ggttatgcct   1860

catgctgact tgcagagttc atggaatgta actatatcat cctttatccc tgaggtcacc   1920

tggaatcaga ttattaaggg aataagccat gacgtcaata gcagcccagg gcacttcaga   1980

gtagagggct tgggaagatc ttttaaaaag gcagtaggcc cggtgtggtg gctcacgcct   2040

ataatcccag cactttggga ggctgaagtg ggtggatcac cagaggtcag gagttcgaga   2100

ccagcccagc caacatggca aaccccatc tctactaaaa atacaaaaat gagctaggca    2160

tggtggcaca cgcctgtaat cccagctaca cctgaggctg aggcaggaga attgcttgaa   2220
```

-continued

```
ccggggagac ggaggttgca gtgagccgag tttgggccac tgcactctag cctggcaaca   2280
gagcaagact ccgtctcaaa aaaagggcaa taaatgccct ctctgaatgt ttgaactgcc   2340
aagaaaaggc atggagacag cgaactagaa gaaagggcaa gaaggaaata gccaccgtct   2400
acagatggct tagttaagtc atccacagcc caagggcggg gctatgcctt gtctggggac   2460
cctgtagagt cactgaccct ggagcggctc tcctgagagg tgctgcaggc aaagtgagac   2520
tgacacctca ctgaggaagg gagacatatt cttggagaac tttccatctg cttgtatttt   2580
ccatacacat ccccagccag aagttagtgt ccgaagaccg aattttattt tacagagctt   2640
gaaaactcac ttcaatgaac aaagggattc tccaggattc caaagttttg aagtcatctt   2700
agctttccac aggagggaga gaacttaaaa aagcaacagt agcagggaat tgatccactt   2760
cttaatgctt tcctccctgg catgaccatc ctgtcctttg ttattatcct gcattttacg   2820
tctttggagg aacagctccc tagtggcttc ctccgtctgc aatgtccctt gcacagccca   2880
cacatgaacc atccttccca tgatgccgct cttctgtcat cccgctcctg ctgaaacacc   2940
tcccaggggc tccacctgtt caggagctga agcccatgct ttcccaccag catgtcactc   3000
ccagaccacc tccctgccct gtcctccagc ttcccctcgc tgtcctgctg tgtgaattcc   3060
caggttggcc tggtggccat gtcgcctgcc cccagcactc ctctgtctct gctcttgcct   3120
cgacccttcc tcctcctttg cctaggaggc cttctcgcat tttctctagc tgatcagaat   3180
tttaccaaaa ttcagaacat cctccaattc cacagtctct gggagacttt ccctaagagg   3240
cgacttcctc tccagccttc tctctctggt caggcccact gcagagatgg tggtgagcac   3300
atctgggagg ctggtctccc tccagctgga attgctgctc tctgagggag aggctgtggt   3360
ggctgtctct gtccctcact gccttccagg agcaatttgc acatgtaaca tagatttatg   3420
taatgcttta tgtttaaaaa cattccccaa ttatcttatt taatttttgc aattattcta   3480
attttatata tagagaaagt gacctatttt ttaaaaaaat cacactctaa gttctattga   3540
acctaggact tgagcctcca tttctggctt ctagtctggt gttctgagta cttgatttca   3600
ggtcaataac ggtcccccct cactccacac tggcacgttt gtgagaagaa atgacatttt   3660
gctaggaagt gaccgagtct aggaatgctt ttattcaaga caccaaattc caaacttcta   3720
aatgttggaa ttttcaaaaa ttgtgtttag attttatgaa aaactcttct actttcatct   3780
attctttccc tagaggcaaa catttcttaa aatgtttcat tttcattaaa aatgaaagcc   3840
aaatttatat gccaccgatt gcaggacaca agcacagttt taagagttgt atgaacatgg   3900
agaggacttt tggtttttat atttctcgta tttaatatgg gtgaacacca acttttattt   3960
ggaataataa ttttcctcct aaacaaaaac acattgagtt taagtctctg actcttgcct   4020
ttccacctgc tttctcctgg gcccgctttg cctgcttgaa ggaacagtgc tgttctggag   4080
ctgctgttcc aacagacagg gcctagcttt catttgacac acagactaca gccagaagcc   4140
catggagcag ggatgtcacg tcttgaaaag cctattagat gttttacaaa tttaattttg   4200
cagattattt tagtctgtca tccagaaaat gtgtcagcat gcatagtgct aagaaagcaa   4260
gccaatttgg aaacttaggt tagtgacaaa attggccaga gagtgggggt gatgatgacc   4320
aagaattaca agtagaatgg cagctggaat ttaaggaggg acaagaatca atggataagc   4380
gtgggtggag gaagatccaa acagaaaagt gcaaagttat tccccatctt ccaagggttg   4440
aattctggag gaagaagaca cattcctagt tccccgtgaa cttcctttga cttattgtcc   4500
ccactaaaac aaaacaaaaa acttttaatg ccttccacat taattagatt ttcttgcagt   4560
ttttttatgg cattttttta aagatgccct aagtgttgaa gaagagtttg caaatgcaac   4620
```

```
aaaatattta attaccggtt gttaaaactg gtttagcaca atttatattt tccctctctt   4680

gcctttctta tttgcaataa aaggtattga gccatttttt aaatgacatt tttgataaat   4740

tatgtttgta ctagttgatg aaggagtttt ttttaacctg tttatataat tttgcagcag   4800

aagccaaatt ttttgtatat taaagcacca aattcatgta cagcatgcat cacggatcaa   4860

tagactgtac ttattttcca ataaaatttt caaactttgt actgttaaa              4909


<210> SEQ ID NO 31
<211> LENGTH: 2210
<212> TYPE: DNA
<213> ORGANISM: Homo sapiens

<400> SEQUENCE: 31

cgcgcccctc cctcctcgcg gacctggcgg tgccggcgcc cggagtggcc ctttaaaagg     60

cagcttattg tccggagggg gcgggcgggg ggcgccgacc gcggcctgag gcccggcccc    120

tcccctctcc ctccctctgt ccccgcgtcg ctcgctggct agctcgctgg ctcgctcgcc    180

cgtccggcgc acgctccgcc tccgtcagtt ggctccgctg tcgggtgcgc ggcgtggagc    240

ggcagccggt ctggacgcgc ggccggggct gggggctggg agcgcggcgc gcaagatctc    300

cccgcgcgag agcggcccct gccaccgggc gaggcctgcg ccgcgatggc agagatgggc    360

agtaaagggg tgacggcggg aaagatcgcc agcaacgtgc agaagaagct cacccgcgcg    420

caggagaagg ttctccagaa gctggggaag gcagatgaga ccaaggatga gcagtttgag    480

cagtgcgtcc agaatttcaa caagcagctg acggagggca cccggctgca gaaggatctc    540

cggacctacc tggcctccgt caaagccatg cacgaggctt ccaagaagct gaatgagtgt    600

ctgcaggagg tgtatgagcc cgattggccc ggcagggatg aggcaaacaa gatcgcagag    660

aacaacgacc tgctgtggat ggattaccac cagaagctgg tggaccaggc gctgctgacc    720

atggacacgt acctgggcca gttccccgac atcaagtcac gcattgccaa gcgggggcgc    780

aagctggtgg actacgacag tgcccggcac cactacgagt cccttcaaac tgccaaaaag    840

aaggatgaag ccaaaattgc caaggccgag gaggagctca tcaaagccca gaaggtgttt    900

gaggagatga atgtggatct gcaggaggag ctgccgtccc tgtggaacag ccgcgtaggt    960

ttctacgtca acacgttcca gagcatcgcg ggcctggagg aaaacttcca caaggagatg   1020

agcaagctca accagaacct caatgatgtg ctggtcggcc tggagaagca acacgggagc   1080

aacaccttca cggtcaaggc ccagcccaga aagaaaagta aactgttttc gcggctgcgc   1140

agaaagaaga acagtgacaa cgcgcctgca aaagggaaca agagcccttc gcctccagat   1200

ggctcccctg ccgccacccc cgagatcaga gtcaaccacg agccagagcc ggccggcggg   1260

gccacgcccg gggccaccct ccccaagtcc ccatctcagc cagcagaggc ctcggaggtg   1320

gcgggtggga cccaacctgc ggctggagcc caggagccag gggagacggc ggcaagtgaa   1380

gcagcctcca gctctcttcc tgctgtcgtg gtggagacct tcccagcaac tgtgaatggc   1440

accgtggagg gcggcagtgg ggccgggcgc ttggacctgc ccccaggttt catgttcaag   1500

gtacaggccc agcacgacta cacggccact gacacagacg agctgcagct caaggctggt   1560

gatgtggtgc tggtgatccc cttccagaac cctgaagagc aggatgaagg ctggctcatg   1620

ggcgtgaagg agagcgactg gaaccagcac aaggagctgg agaagtgccg tggcgtcttc   1680

cccgagaact tcactgagag ggtcccatga cggcggggcc caggcagcct ccgggcgtgt   1740

gaagaacacc tcctcccgaa aaatgtgtgg ttcttttttt tgttttgttt tcgtttttca   1800
```

-continued

```
tcttttgaag agcaaaggga aatcaagagg agacccccag gcagaggggc gttctcccaa   1860

agattaggtc gttttccaaa gagccgcgtc ccggcaagtc cggcggaatt caccagtgtt   1920

cctgaagctg ctgtgtcctc tagttgagtt tctggcgccc ctgcctgtgc ccgcatgtgt   1980

gcctggccgc agggcggggc tgggggctgc cgagccacca tgcttgcctg aagcttcggc   2040

cgcgccaccc gggcaagggt cctcttttcc tggcagctgc tgtgggtggg gcccagacac   2100

cagcctagcc tggctctgcc ccgcagacgg tctgtgtgct gtttgaaaat aaatcttagt   2160

gttcaaaaca aaatgaaaca aaaaaaaaat gataaaaact ctcaaaaaaa              2210
```

<210> SEQ ID NO 32
<211> LENGTH: 4664
<212> TYPE: DNA
<213> ORGANISM: Homo sapiens

<400> SEQUENCE: 32

```
gcagcctccc ggcgctgagc gcttttcctg cccgcccggc tcagccctgc ggaccccggg     60

agaagtttcc cagaaaaaat gcccagcgcg gcgcggggct gcggagtcgt ccggagccgc    120

tgcgcgattt atcagcaaga ctgttgaacg cataactgcc caagatgcct gtccctcccc    180

ctccagcacc cccgccgccc ccgacgtttg cactggccaa tacagagaag cctaccttga    240

ataagacaga gcaggctggg agaaatgctc tcctttctga tatcagcaaa gggaagaaac    300

taaagaagac ggtcaccaat gacagaagtg caccaatact ggacaaacct aaaggagctg    360

gtgctggagg cggtggtggt ggctttggtg gaggcggcgg atttggcgga ggaggtggtg    420

gcggaggcgg tggaagtttt ggagggggcg gacctccagg tctgggagga ttgttccagg    480

ctggaatgcc gaagctgaga tccacggcca acagggataa tgattctgga ggaagccgac    540

caccattgtt gccaccggga ggaagatcca catctgcgaa acccttttca cccccaagtg    600

gcccagggag gtttcctgtg ccttctccag gccacagaag tggtccccca gagcctcaga    660

ggaaccgaat gccgccccca aggcccgacg tgggctcaaa gcctgatagc attcctcctc    720

cagtacctag tactccaaga cccattcaat caagtccgca caaccggggg tccccaccag    780

tgcccggagg ccccaggcag cccagccccg ggcccactcc tcccccttc cctggaaacc    840

gcggcactgc tttgggagga ggctcaatac gtcagtcccc cttgagctcc tcctcgccct    900

tctccaaccg gcctcccctg ccgcctaccc ccagcagggc cttggatgac aaaccccctc    960

caccacctcc tccagtgggc aacaggccct ccatccacag ggaagcggtt cccctcctc    1020

ctcctcagaa caacaagcct ccagtgcctt ccactccgcg gccttcggcc tcctcacagg   1080

ccccacctcc gccgccacct cccagcaggc ccgggccgcc tcctctgcct ccaagttcca   1140

gcggcaatga cgaaacccca agactcccac agcggaatct gtccctcagt tcgtccacgc   1200

ccccgttacc ttcgccagga cgttcaggtc ctcttcctcc cccgcccagt gagagacccc   1260

cacctccagt gagggacccg ccaggccgat caggccccct cccaccacct cctccagtaa   1320

gcagaaacgg cagcacatct cgggccctgc ctgctacccc tcagttgcca tccaggagtg   1380

gagtagacag tcccaggagt ggacccaggc ctccccttcc tcctgatagg cccagtgctg   1440

gggcacctcc cccacctcca ccatcaacat ctattagaaa tggcttccaa gactctccat   1500

gtgaagatga gtgggaaagc agattctact tccatccgat ttccgatttg ccacctccag   1560

agccatatgt acaaacgacc aaaagttatc ccagcaaact ggcaagaaac gaaagccgga   1620

gtggatccaa ccgaagagaa aggggtgctc caccactccc tcccatcccg aggtgatctt   1680

tgcctgctct tctctaccca agctcaagag ctgcttctgt tgctatctaa gaactgcata   1740
```

-continued

```
ccctcctccc tgcttcttcc cttgtgcctc atgtatgggc aggaggaaag gtgggagggg   1800
gagtgggaat atgcgtgtgt gggtgggaat cggtaagaaa tgcacctagc ttttcatatt   1860
gtgtttattc tccaggctat tgcttgcttc agctgcagcc tgcctgtgct ggctgctggg   1920
gtcgataggc ttttgtcgta ataggcagag atgacttgca tcccagcttt ccaccaacca   1980
aattcaaaca ttcactgctt atttgttaca gactgtaatt attaaagtcc ctgagagctg   2040
ttttctcccg ttcctttttc gcatgcttgg cctcctctct gtttctatga accacagacc   2100
acctaagcaa gctgctgagt aagggctcac tggaaacttg cagtcacagg atgtccaatc   2160
tttggcagtc cgagcttggc tctaggacag agctgtccaa tagaaatata atgtgagccc   2220
catatacaat ttttacattt ctaatatatt ttaaacaagt gaagttaata tgcatccaaa   2280
atatttcaac ctgtaatcaa cataaaattt taatgagata ttttatatta tttttttggta   2340
ctgaatcttc aaaatccaga gtgtatttta cacttaccgc acatctccat tcagactagt   2400
cacattttta agtgctcagt agccacatgt ggctggtggc tactggatta gacagcacga   2460
gtctggaaga tggaagctag tgcagaaacc tcttgtttaa aaaacaaaaa aggcaagatg   2520
ggcttgagcg attcaagagg caactaaaaa taaaattagg acccagcacc ttgtttgaca   2580
cacagtttga ccttcgattt tcctccctta acttccctct tcccttaata tctgtataca   2640
agtgttgctt caaagtacca aggtcagaaa ttgattcagt acggtttact aaagtcatgt   2700
ggaataaagc cattggaaac aaatggaaag cctgtcggga cttctgggct cagaaccagc   2760
tggctcacgc actccacttg tcagctggac ttctgccttg tgaaatggaa gcagcctttg   2820
ttcctttctg gctgagcaag ctcctgaggc tgggagagac taggaaggct tggtaggagg   2880
ggaaaaaagt caggaaaaga tatcaaatca gaaacatgga agaagaaggg aaccgatttg   2940
agttggtggg caaaactcta aaaatctaaa tctgatgctt atgtaagggt tgagcgaatt   3000
agggagattg ctagtggaaa ttggagggaa tttgttttgc atcatttgtc taggatctat   3060
gcaaatatag ctccactaaa ggaccatagg gaagagccag ccttgccttt tcttatatga   3120
ttttgtttac aaaattttac tgggactttt aaatctagct atagagttgg gaaaaaatat   3180
ttccacttag atattttaca tggttttgtt taaaattacc attacttgtt ttttaaaaac   3240
acatgaccac atatgtatat gtatatctac ctaaacattg tatcatggtt tcagtatgtt   3300
attcatgtat tactgggaga tgctaccaag aaaccaaccc aaagaaaatt ctgaaaaata   3360
catttctatt tatagaataa atgtttcatt tatataaaag caaaagaact tagagttcta   3420
ataaatggga tgtctaataa attatgaagt tactgatttg aatatattat atttttataa   3480
cttccttgcc aaagtcctga tttagtacat tagagaacct gtgtttcctc tctcctctac   3540
cattcatctc tcttccatac agtcatttgg gctttttact caaagagaat caagaaataa   3600
taaggtataa caagcttggc aaagtgttgg ctttttaaaa aaaaattttt ttaatctcta   3660
gcagtttggt aatttagcag catcatttat ttgggattct tttatctgat ttcaacagtg   3720
aaaaacatcc ctatgataaa gcctaatgac ccatttcaca aaagatggaa tttgcccttc   3780
ctagaaaata tgacggagaa aagtctgact cagagaaagt gagtctgaat tttataaggg   3840
gtagtaagaa ttggacaatt cctttgcata tctgaacttg gcaggtaccg ttctaaatct   3900
gaaacagggt gatagctcaa agttgccatt catccagaat agattgtttt agaatgtagt   3960
gtttaagtga ctgtttcatt aatacaccta caccctttct ttgaaagttt gcaacctaat   4020
tgcatctaaa actatgaata agttctgtgg taaaatctta aactatggaa aattacaaaa   4080
```

-continued atgaattttt cttccctgaa atcagagctt acatgtgtgt ttttttataa cattttcaga 4140
taaatgtatt caacatgtaa tacagtattt taacattcac ctcttatttt atattgaaat 4200
gtattacagt attaaaactc agtgttcagt atttatttca ctatgcattt tatttagtaa 4260
aagccaggag aaatgtttaa tccaatggtg ccttactttg tgatttaaaa gaaatcaact 4320 ttttttttatg tctaagtagt agattatttg catatttgta aaaactgtta ggtctttata 4380
ttttaaagtg taataccagt tttgttattt tagtagcaga aatgggatga ttgttaaagt 4440
tccccaaaaa tgttggcatg aaattaattt ttccctcctt atagtcaagg accgtagagg 4500
aagaaaaact tttttttcat accatgcact atgtaaacag acacattttg ctatctgtgt 4560
catcaggata gtgtaagtgg tagggtagag actaccctag acatctgcat ctttgtaagt 4620
tagccagaca ataaagaaaa gcagaatgaa aaaaaaaaaa aaaa 4664

<210> SEQ ID NO 33
<211> LENGTH: 1166
<212> TYPE: DNA
<213> ORGANISM: Homo sapiens

<400> SEQUENCE: 33
attcccaact gccagtgatc tctgaagccg actctgaggc tccctctttg ctctaacaga 60
cagcagcgac tttaggctgg ataatagtca aattcttacc tcgctctttc actgctagta 120
agatcagatt gcgtttcttt cagttactct tcaatcgcca gtttcttgat ctgcttctaa 180
aagaagaagt agagaagata aatcctgtct tcaatacctg gaaggaaaaa caaaataacc 240
tcaactccgt tttgaaaaaa acattccaag aactttcatc agagatttta cttagatgat 300
ttacacaatg aagaaagtac atgcactttg ggcttctgta tgcctgctgc ttaatcttgc 360
ccctgcccct cttaatgctg attctgagga agatgaagaa cacacaatta tcacagatac 420
ggagttgcca ccactgaaac ttatgcattc attttgtgca ttcaaggcgg atgatggccc 480
atgtaaagca atcatgaaaa gatttttctt caatattttc actcgacagt gcgaagaatt 540
tatatatggg ggatgtgaag gaaatcagaa tcgatttgaa agtctggaag agtgcaaaaa 600
aatgtgtaca agagataatg caaacaggat tataaagaca acattgcaac aagaaaagcc 660
agatttctgc tttttggaag aagatcctgg aatatgtcga ggttatatta ccaggtattt 720
ttataacaat cagacaaaac agtgtgaacg tttcaagtat ggtggatgcc tgggcaatat 780
gaacaatttt gagacactgg aagaatgcaa gaacatttgt gaagatggtc cgaatggttt 840
ccaggtggat aattatggaa cccagctcaa tgctgtgaat aactccctga ctccgcaatc 900
aaccaaggtt cccagccttt ttgttacaaa agaaggaaca aatgatggtt ggaagaatgc 960
ggctcatatt taccaagtct ttctgaacgc cttctgcatt catgcatcca tgttctttct 1020
aggattggat agcatttcat gcctatgtta atatttgtgc ttttggcatt tccttaatat 1080
ttatatgtat acgtgatgcc tttgatagca tactgctaat aaagttttaa tatttacatg 1140
catagtaaaa aaaaaaaaaa aaaaaa 1166

<210> SEQ ID NO 34
<211> LENGTH: 8449
<212> TYPE: DNA
<213> ORGANISM: Homo sapiens

<400> SEQUENCE: 34
gcccgcgccg gctgtgctgc acagggggag gagagggaac cccaggcgcg agcgggaaga 60
ggggacctgc agccacaact tctctggtcc tctgcatccc ttctgtccct ccacccgtcc 120

-continued

```
ccttccccac cctctggccc ccaccttctt ggaggcgaca acccccggga ggcattagaa    180
gggatttttc ccgcaggttg cgaagggaag caaacttggt ggcaacttgc ctcccggtgc    240
gggcgtctct cccccaccgt ctcaacatgc ttaggggtcc ggggcccggg ctgctgctgc    300
tggccgtcca gtgcctgggg acagcggtgc cctccacggg agcctcgaag agcaagaggc    360
aggctcagca aatggttcag ccccagtccc cggtggctgt cagtcaaagc aagcccggtt    420
gttatgacaa tggaaaacac tatcagataa atcaacagtg ggagcggacc tacctaggca    480
atgcgttggt ttgtacttgt tatggaggaa gccgaggttt taactgcgag agtaaacctg    540
aagctgaaga gacttgcttt gacaagtaca ctgggaacac ttaccgagtg ggtgacactt    600
atgagcgtcc taaagactcc atgatctggg actgtacctg catcggggct gggcgaggga    660
gaataagctg taccatcgca aaccgctgcc atgaaggggg tcagtcctac aagattggtg    720
acacctggag gagaccacat gagactggtg gttacatgtt agagtgtgtg tgtcttggta    780
atggaaaagg agaatggacc tgcaagccca tagctgagaa gtgttttgat catgctgctg    840
ggacttccta tgtggtcgga gaaacgtggg agaagcccta ccaaggctgg atgatggtag    900
attgtacttg cctgggagaa ggcagcggac gcatcacttg cacttctaga aatagatgca    960
acgatcagga cacaaggaca tcctatagaa ttggagacac ctggagcaag aaggataatc   1020
gaggaaacct gctccagtgc atctgcacag gcaacggccg aggagagtgg aagtgtgaga   1080
ggcacacctc tgtgcagacc acatcgagcg gatctggccc cttcaccgat gttcgtgcag   1140
ctgtttacca accgcagcct cacccccagc ctcctcccta tggccactgt gtcacagaca   1200
gtggtgtggt ctactctgtg gggatgcagt ggctgaagac acaaggaaat aagcaaatgc   1260
tttgcacgtg cctgggcaac ggagtcagct gccaagagac agctgtaacc cagacttacg   1320
gtggcaactc aaatggagag ccatgtgtct taccattcac ctacaatggc aggacgttct   1380
actcctgcac cacagaaggg cgacaggacg gacatctttg gtgcagcaca acttcgaatt   1440
atgagcagga ccagaaatac tctttctgca cagaccacac tgttttggtt cagactcgag   1500
gaggaaattc caatggtgcc ttgtgccact tccccttcct atacaacaac cacaattaca   1560
ctgattgcac ttctgagggc agaagagaca acatgaagtg gtgtgggacc acacagaact   1620
atgatgccga ccagaagttt gggttctgcc ccatggctgc ccacgaggaa atctgcacaa   1680
ccaatgaagg ggtcatgtac cgcattggag atcagtggga taagcagcat gacatgggtc   1740
acatgatgag gtgcacgtgt gttgggaatg gtcgtgggga atggacatgc attgcctact   1800
cgcagcttcg agatcagtgc attgttgatg acatcactta caatgtgaac gacacattcc   1860
acaagcgtca tgaagagggg cacatgctga actgtacatg cttcggtcag ggtcggggca   1920
ggtggaagtg tgatcccgtc gaccaatgcc aggattcaga gactgggacg ttttatcaaa   1980
ttggagattc atgggagaag tatgtgcatg gtgtcagata ccagtgctac tgctatggcc   2040
gtggcattgg ggagtggcat tgccaacctt tacagaccta tccaagctca agtggtcctg   2100
tcgaagtatt tatcactgag actccgagtc agcccaactc ccaccccatc cagtggaatg   2160
caccacagcc atctcacatt tccaagtaca ttctcaggtg gagacctaaa aattctgtag   2220
gccgttggaa ggaagctacc ataccaggcc acttaaactc ctacaccatc aaaggcctga   2280
agcctggtgt ggtatacgag ggccagctca tcagcatcca gcagtacggc caccaagaag   2340
tgactcgctt tgacttcacc accaccagca ccagcacacc tgtgaccagc aacaccgtga   2400
caggagagac gactcccttt tctcctcttg tggccacttc tgaatctgtg accgaaatca   2460
```

-continued

```
cagccagtag ctttgtggtc tcctgggtct cagcttccga caccgtgtcg ggattccggg   2520
tggaatatga gctgagtgag gagggagatg agccacagta cctggatctt ccaagcacag   2580
ccacttctgt gaacatccct gacctgcttc ctggccgaaa atacattgta aatgtctatc   2640
agatatctga ggatggggag cagagtttga tcctgtctac ttcacaaaca acagcgcctg   2700
atgcccctcc tgacccgact gtggaccaag ttgatgacac ctcaattgtt gttcgctgga   2760
gcagacccca ggctcccatc acagggtaca gaatagtcta ttcgccatca gtagaaggta   2820
gcagcacaga actcaacctt cctgaaactg caaactccgt caccctcagt gacttgcaac   2880
ctggtgttca gtataacatc actatctatg ctgtggaaga aaatcaagaa agtacacctg   2940
ttgtcattca acaagaaacc actggcaccc cacgctcaga tacagtgccc tctcccaggg   3000
acctgcagtt tgtggaagtg acagacgtga aggtcaccat catgtggaca ccgcctgaga   3060
gtgcagtgac cggctaccgt gtggatgtga tccccgtcaa cctgcctggc gagcacgggc   3120
agaggctgcc catcagcagg aacacctttg cagaagtcac cgggctgtcc cctggggtca   3180
cctattactt caaagtcttt gcagtgagcc atgggaggga gagcaagcct ctgactgctc   3240
aacagacaac caaactggat gctcccacta acctccagtt tgtcaatgaa actgattcta   3300
ctgtcctggt gagatggact ccacctcggg cccagataac aggataccga ctgaccgtgg   3360
gccttacccg aagaggacag cccaggcagt acaatgtggg tccctctgtc tccaagtacc   3420
cactgaggaa tctgcagcct gcatctgagt acaccgtatc cctcgtggcc ataaagggca   3480
accaagagag ccccaaagcc actggagtct ttaccacact gcagcctggg agctctattc   3540
caccttacaa caccgaggtg actgagacca ccattgtgat cacatggacg cctgctccaa   3600
gaattggttt taagctgggt gtacgaccaa gccagggagg agaggcacca cgagaagtga   3660
cttcagactc aggaagcatc gttgtgtccg gcttgactcc aggagtagaa tacgtctaca   3720
ccatccaagt cctgagagat ggacaggaaa gagatgcgcc aattgtaaac aaagtggtga   3780
caccattgtc tccaccaaca aacttgcatc tggaggcaaa ccctgacact ggagtgctca   3840
cagtctcctg ggagaggagc accaccccag acattactgg ttatagaatt accacaaccc   3900
ctacaaacgg ccagcaggga aattctttgg aagaagtggt ccatgctgat cagagctcct   3960
gcacttttga taacctgagt cccggcctgg agtacaatgt cagtgtttac actgtcaagg   4020
atgacaagga aagtgtccct atctctgata ccatcatccc agctgttcct cctcccactg   4080
acctgcgatt caccaacatt ggtccagaca ccatgcgtgt cacctgggct ccacccccat   4140
ccattgattt aaccaacttc ctggtgcgtt actcacctgt gaaaaatgag gaagatgttg   4200
cagagttgtc aatttctcct tcagacaatg cagtggtctt aacaaatctc ctgcctggta   4260
cagaatatgt agtgagtgtc tccagtgtct acgaacaaca tgagagcaca cctcttagag   4320
gaagacagaa aacaggtctt gattccccaa ctggcattga cttttctgat attactgcca   4380
actcttttac tgtgcactgg attgctcctc gagccaccat cactggctac aggatccgcc   4440
atcatcccga gcacttcagt gggagacctc gagaagatcg ggtgccccac tctcggaatt   4500
ccatcaccct caccaacctc actccaggca cagagtatgt ggtcagcatc gttgctctta   4560
atggcagaga ggaaagtccc ttattgattg gccaacaatc aacagtttct gatgttccga   4620
gggacctgga agttgttgct gcgacccccca ccagcctact gatcagctgg gatgctcctg   4680
ctgtcacagt gagatattac aggatcactt acggagagac aggaggaaat agccctgtcc   4740
aggagttcac tgtgcctggg agcaagtcta cagctaccat cagcggcctt aaacctggag   4800
ttgattatac catcactgtg tatgctgtca ctggccgtgg agacagcccc gcaagcagca   4860
```

-continued

```
agccaatttc cattaattac cgaacagaaa ttgacaaacc atcccagatg caagtgaccg   4920
atgttcagga caacagcatt agtgtcaagt ggctgccttc aagttcccct gttactggtt   4980
acagagtaac caccactccc aaaaatggac caggaccaac aaaaactaaa actgcaggtc   5040
cagatcaaac agaaatgact attgaaggct tgcagcccac agtggagtat gtggttagtg   5100
tctatgctca gaatccaagc ggagagagtc agcctctggt tcagactgca gtaaccaaca   5160
ttgatcgccc taaaggactg gcattcactg atgtggatgt cgattccatc aaaattgctt   5220
gggaaagccc acaggggcaa gtttccaggt acagggtgac ctactcgagc cctgaggatg   5280
gaatccatga gctattccct gcacctgatg gtgaagaaga cactgcagag ctgcaaggcc   5340
tcagaccggg ttctgagtac acagtcagtg tggttgcctt gcacgatgat atggagagcc   5400
agcccctgat tggaacccag tccacagcta ttcctgcacc aactgacctg aagttcactc   5460
aggtcacacc cacaagcctg agcgcccagt ggacaccacc caatgttcag ctcactggat   5520
atcgagtgcg ggtgaccccc aaggagaaga ccggaccaat gaaagaaatc aaccttgctc   5580
ctgacagctc atccgtggtt gtatcaggac ttatggtggc caccaaatat gaagtgagtg   5640
tctatgctct taaggacact ttgacaagca gaccagctca gggagttgtc accactctgg   5700
agaatgtcag cccaccaaga agggctcgtg tgacagatgc tactgagacc accatcacca   5760
ttagctggag aaccaagact gagacgatca ctggcttcca agttgatgcc gttccagcca   5820
atggccagac tccaatccag agaaccatca agccagatgt cagaagctac accatcacag   5880
gtttacaacc aggcactgac tacaagatct acctgtacac cttgaatgac aatgctcgga   5940
gctcccctgt ggtcatcgac gcctccactg ccattgatgc accatccaac ctgcgtttcc   6000
tggccaccac acccaattcc ttgctggtat catggcagcc gccacgtgcc aggattaccg   6060
gctacatcat caagtatgag aagcctgggt ctcctcccag agaagtggtc cctcggcccc   6120
gccctggtgt cacagaggct actattactg gcctggaacc gggaaccgaa tatacaattt   6180
atgtcattgc cctgaagaat aatcagaaga gcgagcccct gattggaagg aaaaagacag   6240
acgagcttcc ccaactggta acccttccac accccaatct tcatggacca gagatcttgg   6300
atgttccttc cacagttcaa aagacccctt tcgtcaccca ccctgggtat gacactggaa   6360
atggtattca gcttcctggc acttctggtc agcaacccag tgttgggcaa caaatgatct   6420
ttgaggaaca tggttttagg cggaccacac cgcccacaac ggccaccccc ataaggcata   6480
ggccaagacc atacccgccg aatgtaggac aagaagctct ctctcagaca accatctcat   6540
gggccccatt ccaggacact tctgagtaca tcatttcatg tcatcctgtt ggcactgatg   6600
aagaaccctt acagttcagg gttcctggaa cttctaccag tgccactctg acaggcctca   6660
ccagaggtgc cacctacaac atcatagtgg aggcactgaa agaccagcag aggcataagg   6720
ttcgggaaga ggttgttacc gtgggcaact ctgtcaacga aggcttgaac caacctacgg   6780
atgactcgtg ctttgacccc tacacagttt cccattatgc cgttggagat gagtgggaac   6840
gaatgtctga atcaggcttt aaactgttgt gccagtgctt aggctttgga agtggtcatt   6900
tcagatgtga ttcatctaga tggtgccatg acaatggtgt gaactacaag attggagaga   6960
agtgggaccg tcagggagaa aatggccaga tgatgagctg cacatgtctt gggaacggaa   7020
aaggagaatt caagtgtgac cctcatgagg caacgtgtta tgatgatggg aagacatacc   7080
acgtaggaga acagtggcag aaggaatatc tcggtgccat ttgctcctgc acatgctttg   7140
gaggccagcg gggctggcgc tgtgacaact gccgcagacc tgggggtgaa cccagtcccg   7200
```

aaggcactac tggccagtcc tacaaccagt attctcagag ataccatcag agaacaaaca 7260
ctaatgttaa ttgcccaatt gagtgcttca tgcctttaga tgtacaggct gacagagaag 7320
attcccgaga gtaaatcatc tttccaatcc agaggaacaa gcatgtctct ctgccaagat 7380
ccatctaaac tggagtgatg ttagcagacc cagcttagag ttcttctttc tttcttaagc 7440
cctttgctct ggaggaagtt ctccagcttc agctcaactc acagcttctc caagcatcac 7500
cctgggagtt tcctgagggt tttctcataa atgagggctg cacattgcct gttctgcttc 7560
gaagtattca ataccgctca gtattttaaa tgaagtgatt ctaagatttg gtttgggatc 7620
aataggaaag catatgcagc caaccaagat gcaaatgttt tgaaatgata tgaccaaaat 7680
tttaagtagg aaagtcaccc aaacacttct gctttcactt aagtgtctgg cccgcaatac 7740
tgtaggaaca agcatgatct tgttactgtg atattttaaa tatccacagt actcactttt 7800
tccaaatgat cctagtaatt gcctagaaat atctttctct tacctgttat ttatcaattt 7860
ttcccagtat ttttatacgg aaaaaattgt attgaaaaca cttagtatgc agttgataag 7920
aggaatttgg tataattatg gtgggtgatt atttttata ctgtatgtgc caaagcttta 7980
ctactgtgga aagacaactg ttttaataaa agatttacat tccacaactt gaagttcatc 8040
tatttgatat aagacacctt cggggaaat aattcctgtg aatattcttt ttcaattcag 8100
caaacatttg aaaatctatg atgtgcaagt ctaattgttg atttcagtac aagattttct 8160
aaatcagttg ctacaaaaac tgattggttt ttgtcacttc atctcttcac taatggagat 8220
agctttacac tttctgcttt aatagattta agtggacccc aatatttatt aaaattgcta 8280
gtttaccgtt cagaagtata atagaaataa tctttagttg ctcttttcta accattgtaa 8340
ttcttccctt cttccctcca cctttccttc attgaataaa cctctgttca aagagattgc 8400
ctgcaaggga aataaaaatg actaagatat taaaaaaaaa aaaaaaaaa 8449

<210> SEQ ID NO 35
<211> LENGTH: 4625
<212> TYPE: DNA
<213> ORGANISM: Homo sapiens

<400> SEQUENCE: 35
agcgctccgc agtcacgtga cgctcgtccg caacctctgc tgtcctccgc ggcgccccct 60
tccgcctgac gcgcccccgg cggcggccgc gcagccctgg ctcctcgcgg gctcgggcgg 120
cggctgcggc ggggctatgg cgagcggcgg tggcgggggt aacactggcg cgggtggggg 180
gccggggatg ggcctgagcc tggcctggg tctgggtctg agcctaggca tgagtgaggc 240
caccagtgag gcagaggagg aggcggccac ggccgaggcg gtgggacgcc tggccacgac 300
gctgtggctg cggctccgcg gctgggaggc ggtgctggcg gcggcgcagc ggttgctggt 360
gtgggagaag ccgctgcaca gcctggtcac ggcggccgcg ctcaacggcc tcttctggtt 420
gctgtcttcc tcgtccctcc ggcccttctt cctactcagc gtctcacttt tggcctattt 480
tctgctggat ctctggcagc ctcgctttct ccctgacgtt tcagcatcat ccccagagga 540
gccacactct gacagtgagg gtgcggggtc aggcgcccgg ccgcacctgc tgagtgtgcc 600
cgagttgtgc agatacctgg ctgagagctg gctcaccttc cagattcacc tgcaggagct 660
gctgcagtac aagaggcaga atccagctca gttctgcgtt cgagtctgct ctggctgtgc 720
tgtgttggct gtgttgggac actatgttcc agggattatg atttcctaca ttgtcttgtt 780
gagtatcctg ctgtggcccc tggtggttta tcatgagctg atccagagga tgtacactcg 840
cctggagccc ctgctcatgc agctggacta cagcatgaag gcagaagcca atgccctgca 900

-continued

```
tcacaaacac gacaagagga agcgtcaggg gaagaatgca cccccaggag gtgatgagcc    960
actggcagag acagagagtg aaagcgaggc agagctggct ggcttctccc cagtggtgga   1020
tgtgaagaaa acagcattgg ccttggccat tacagactca gagctgtcag atgaggaggc   1080
ttctatcttg gagagtggtg gcttctccgt atcccgggcc acaactccgc agctgactga   1140
tgtctccgag gatttggacc agcagagcct gccaagtgaa ccagaggaga ccctaagccg   1200
ggacctaggg gagggagagg agggagagct ggcccctccc gaagacctac taggccgtcc   1260
tcaagctctg tcaaggcaag ccctggactc ggaggaagag gaagaggatg tggcagctaa   1320
ggaaaccttg ttgcggctct catcccccct ccactttgtg aacacgcact tcaatggggc   1380
agggtccccc ccagatggag tgaaatgctc ccctggagga ccagtggaga cactgagccc   1440
cgagacagtg agtggtggcc tcactgctct gcccggcacc ctgtcacctc cactttgcct   1500
tgttggaagt gacccagccc cctccccttc cattctccca cctgttcccc aggactcacc   1560
ccagcccctg cctgcccctg aggaagaaga ggcactcacc actgaggact ttgagttgct   1620
ggatcagggg gagctggagc agctgaatgc agagctgggc ttggagccag agacaccgcc   1680
aaaacccccct gatgctccac ccctggggcc cgacatccat tctctggtac agtcagacca   1740
agaagctcag gccgtggcag agccatgagc cagccgttga ggaaggagct gcaggcacag   1800
tagggcttcc tggctaggag tgttgctgtt tcctcctttg cctaccactc tggggtgggg   1860
cagtgtgtgg ggaagctggc tgtcggatgg tagctattcc accctctgcc tgcctgcctg   1920
cctgctgtcc tgggcatggt gcagtacctg tgcctaggat tggttttaaa tttgtaaata   1980
attttccatt tgggttagtg gatgtgaaca gggctaggga agtccttccc acagcctgcg   2040
cttgcctccc tgcctcatct ctattctcat tccactatgc cccaagccct ggtggtctgg   2100
ccctttcttt ttcctcctat cctcagggac ctgtgctgct ctgccctcat gtcccacttg   2160
gttgtttagt tgaggcactt tataattttt ctcttgtctt gtgttccttt ctgctttatt   2220
tccctgctgt gtcctgtcct tagcagctca accccatcct ttgccagctc ctcctatccc   2280
gtgggcactg gccaagcttt agggaggctc ctggtctggg aagtaaagag taaacctggg   2340
gcagtgggtc aggccagtag ttacactctt aggtcactgt agtctgtgta accttcactg   2400
catccttgcc ccattcagcc cggcctttca tgatgcagga gagcagggat cccgcagtac   2460
atggcgccag cactggagtt ggtgagcatg tgctctctct tgagattagg agcttcctta   2520
ctgctcctct gggtgatcca agtgtagtgg gacccccctac tagggtcagg aagtggacac   2580
taacatctgt gcaggtgttg acttgaaaaa taaagtgttg attggctaga actgctgcct   2640
ccctgactgt gagctgcctt ccacaccctg cactgcactg tgttctctcc tcacccttaa   2700
cctgcttcac tccagtctgt tctggctgtt tattaccttg ttgcaaaaca gggccgaagc   2760
aaggattacc ttgacaaccc tagcttctcc ttagccatct tccttgacag tgtgatctgt   2820
ttagtgagat ttagcatgtg tgaataaagt atatgcagga ggaaattgct ttgtcttccc   2880
aatcggtaga aattcgggac cataaaaatt gtgttttacc atgtggccta caaccttaac   2940
actgctttct taagaagtct tcacccatct acatgctaac aactcactca gcctggattt   3000
atctttactg gggaagccaa acaagcaata gaggaccttt acctgtgtta gaaatgagtt   3060
ggagccaagg aacactgaag aaatagtatc ttaacagtta ctgagtccat tgtatgtgct   3120
tggctctgct ctgagtgatt tatatgtatt aagatttttc ctcacaggtc agatatatac   3180
tgttactaac ttcattttat agacaggtta agcttcctga aggccacagg tcccagtaaa   3240
```

ttgtggagcc agaacccaaa cccaagaagt tttggcttca gcaaatgcat cagacagccc 3300
ctgtccatta atagggcaca ggtaggaaga tgcacaagga tgtgggaact atagagaacc 3360
aatctgatgc cttggcttaa caaagagtgg acatggcaag ccttcctctt tggggaagaa 3420
aagcccagaa ctgagcagat ggcctccttt atgagttcat gtcctccgcc ttcagctgga 3480
ggtaccatat ggcgatgcta cctgtctttc tgctggaggt accatatggt aatgctgcct 3540
ggctgtctgc tggaggtacc atatggtaat gctgcctgtc tttctgaggt tgacttttat 3600
gccatgtctt tcctaagtgt gtaagaattt ttctgtttgc ttcacatttg actgagaatc 3660
attctagggt ttgattgagc ccctgtcctg tgccactaaa ggaactcgaa cttttcatca 3720
cttagagatt tcagagggga atggaaaaac agttctaatc aataagcaag caattcaaga 3780
aaaatagaat taatcaggca atgactgcaa catgtcctat ctttaatcta ttttcttatt 3840
aagcttggac attgacaata gaaccagaag cttgtagctg gatcaaaata ttctccatag 3900
gcctggagtt tcatgagggt ctattctttt gttgttgttg ttttggtttt ttgtttttttg 3960 tgggtttttt ttttttttt tttgagacgg agtcttgttc tgttgcccag gctggagtgc 4020
aatggtgcag tcttggttca ctgcaacctc tgcctcccag gttcaaacaa ttctcctgcc 4080
tcagccgtcc aagtagctgg gattacaggt gcatgccacg atgcctggct attttttgta 4140
tttttagtag aggtggggtt tcaccatgtt ggccaggctg gtctcgaact cctgacctca 4200
ggtgattcac ccacctcggc ctcccaaagt gctgggatta caggtgtgag ccacggcgcc 4260
cagcctcatg agggtctatt ctttacattc accatggtct gatggttgct acatgtttgt 4320
ctatgatttt tttttctat tatcaggtgt cttggccggt tcatgcccca cgatgaaagg 4380
gccagaggtt ttcatatgag taaaagaaaa aagcagaaat gtgaaaccta caattaggct 4440
aaacaaaaat caactggaaa agtacaggct gaggggagaa gagttggcta catgtttatg 4500
ttaggggagg agggagtaca ttttagctat gtattcaaac agctaatagt ttaatgttgc 4560
tgcttataaa cttaatttta ggctgcatta ataaaagtgt agtctccaaa acaaaaaaaa 4620
aaaaa 4625

<210> SEQ ID NO 36
<211> LENGTH: 7556
<212> TYPE: DNA
<213> ORGANISM: Homo sapiens

<400> SEQUENCE: 36
gcaggcgcct tcgcggaccg agcctgacgg agccggaggc tgggagccgc ggcggcctgg 60
ggaagtgttt ggattgtgag ctatttcaga actgttctca ggactcatta ttttaacatt 120
tgggagaaac acagccagaa gatgcacact tgactgaagg aggacaggga atctgaagac 180
tccggatgac atcagagcta cttttcaaca gccttctcaa ttttctttct cagaaagcag 240
aggctcagag cttggagaca gacgaacact gatatttgca tttaatgggg aacaaaagat 300
gaagaaggaa aaggaatata ttcactaagg attctatctg cttactgcta cagacctatg 360
tgttaaggaa ttcttctcct cctccttgcg tagaagttga tcagcactgt ggtcagactg 420
catttatctt gtcattgcca gaagaaatct tggacagaat gtaacagtac gtctctctct 480
gattgcgatg gaaggtgata aactgatact cctttattaa agttacatcg cactcaccac 540
agaaaaccat tctttaaagt gaatagaaac caagcccttg tgaacacttc tattgaacat 600
gactcatgga gaagagcttg gctctgatgt gcaccaggat tctattgttt taacttacct 660
agaaggatta ctaatgcatc aggcagcagg gggatcaggt actgccgttg acaaaaagtc 720

```
tgctgggcat aatgaagagg atcagaactt taacatttct ggcagtgcat ttcccacctg    780
tcaaagtaat ggtccagttc tcaatacaca tacatatcag gggtctggca tgctgcacct    840
caaaaaagcc agactgttgc agtcttctga ggactggaat gcagcaaagc ggaagaggct    900
gtctgattct atcatgaatt taaacgtaaa gaaggaagct ttgctagctg gcatggttga    960
cagtgtgcct aaaggcaaac aggatagcac attactggcc tctttgcttc agtcattcag   1020
ctctaggctg cagactgttg ctctgtcaca acaaatcagg cagagcctca aggagcaagg   1080
atatgccctc agtcatgatt ctttaaaagt ggagaaggat ttaaggtgct atggtgttgc   1140
atcaagtcac ttaaaaactt tgttgaagaa aagtaaagtt aaagatcaaa agcctgatac   1200
gaatcttcct gatgtgacta aaaacctcat cagagatagg tttgcagagt ctcctcatca   1260
tgttggacaa agtggaacaa aggtcatgag tgaaccgttg tcatgtgctg caagattaca   1320
ggctgttgca agcatggtgg aaaaaagggc tagtcctgcc acctcaccta aacctagtgt   1380
tgcttgtagc cagttagcat tacttctgtc aagcgaagcc catttgcagc agtattctcg   1440
agaacacgct ttaaaaacgc aaaatgcaaa tcaagcagca agtgaaagac ttgctgctat   1500
ggccagattg caagaaaatg gccagaagga tgttggcagt taccagctcc caaaaggaat   1560
gtcaagccat cttaatggtc aggcaagaac atcatcaagc aaactgatgg ctagcaaaag   1620
tagtgctaca gtgtttcaaa atccaatggg tatcattcct tcttccccta aaaatgcagg   1680
ttataagaac tcactggaaa gaaacaatat aaaacaagct gctaacaata gtttgctttt   1740
acatcttctt aaaagccaga ctatacctaa gccaatgaat ggacacagtc acagtgagag   1800
aggaagcatt tttgaggaaa gtagtacacc tacaactatt gatgaatatt cagataacaa   1860
tcctagtttt acagatgaca gcagtggtga tgaaagttct tattccaact gtgttcccat   1920
agacttgtct tgcaaacacc gaactgaaaa atcagaatct gaccaacctg tttccctgga   1980
taacttcact caatccttgc taaacacttg ggatccaaaa gtcccagatg tagatatcaa   2040
agaagatcaa gatacctcaa agaattctaa gctaaactca caccagaaag taacacttct   2100
tcaattgcta cttggccata agaatgaaga aaatgtagaa aaaaacacca gccctcaggg   2160
agtacacaat gatgtgagca agttcaatac acaaaattat gcaaggactt ctgtgataga   2220
aagccccagt acaaatcgga ctactccagt gagcactcca cctttactta catcaagcaa   2280
agcagggtct cccatcaatc tctctcaaca ctctctggtc atcaaatgga attccccacc   2340
atatgtctgc agtactcagt ctgaaaagct aacaaatact gcatctaacc actcaatgga   2400
ccttacaaaa agcaaagacc caccaggaga gaaaccagcc caaaatgaag gtgcacagaa   2460
ctctgcaacg tttagtgcca gtaagctgtt acaaaattta gcacaatgtg gaatgcagtc   2520
atccatgtca gtggaagagc agagacccag caaacagctg ttaactggaa acacagataa   2580
accgataggt atgattgata gattaaatag ccctttgctc tcaaataaaa caaatgcagt   2640
tgaagaaaat aaagcattta gtagtcaacc aacaggtcct gaaccagggc tttctggttc   2700
tgaaatagaa aatctgcttg aaagacgtac tgtcctccag ttgctcctgg ggaaccccaa   2760
caaagggaag agtgaaaaaa aagagaaaac tcccttaaga gatgaaagta ctcaggaaca   2820
ctcagagaga gctttaagtg aacaaatact gatggtgaaa ataaaatctg agccttgtga   2880
tgacttacaa attcctaaca caaatgtgca cttgagccat gatgctaaga gtgccccatt   2940
cttgggtatg gctcctgctg tgcagagaag cgcacctgcc ttaccagtgt ccgaagactt   3000
taaatcggag cctgtttcac ctcaggattt ttctttctcc aagaatggtc tgctaagtcg   3060
```

-continued

```
attgctaaga caaaatcaag atagttacct ggcagatgat tcagacagga gtcacagaaa   3120
taatgaaatg gcacttctag aatcaaagaa tctttgcatg gtccctaaga aaaggaagct   3180
ttatactgag ccattagaaa atccatttaa aaagatgaaa aacaacattg ttgatgctgc   3240
aaacaatcac agtgccccag aagtactgta tgggtccttg cttaaccagg aagagctgaa   3300
atttagcaga aatgatcttg aatttaaata tcctgctggt catggctcag ccagcgaaag   3360
tgaacacagg agttgggcca gagagagcaa aagctttaat gttctgaaac agctgcttct   3420
ctcagaaaac tgtgtgcgag atttgtcccc gcacagaagt aactctgtgg ctgacagtaa   3480
aaagaaagga cacaaaaata atgtgaccaa cagcaaacct gaatttagca tttcttcttt   3540
aaatggactg atgtacagtt ccactcagcc cagcagttgc atggataaca ggacattttc   3600
atacccaggt gtagtaaaaa ctcctgtgag tcctactttc cctgagcact tgggctgtgc   3660
agggtctaga ccagaatctg ggcttttgaa tgggtgttcc atgcccagtg agaaaggacc   3720
cattaagtgg gttatcactg atgcggagaa gaatgagtat gaaaaagact ctccaagatt   3780
gaccaaaacc aacccaatac tatattacat gcttcaaaaa ggaggcaatt ctgttaccag   3840
tcgagaaaca caagacaagg acatttggag ggaggcttca tctgctgaaa gtgtctcaca   3900
ggtcacagcc aaagaagagt tacttcctac tgcagaaacg aaagcttctt tctttaattt   3960
aagaagccct tacaatagcc atatgggaaa taatgcttct cgcccacaca gcgcaaatgg   4020
agaagtttat ggacttctgg gaagcgtgct aacgataaag aaagaatcag aataaaatgt   4080
acctgccatc cagttttgga tctttttaaa actaatgagt atgaacttga gatctgtata   4140
aataagagca tgatttgaaa aaaagcatgg tataattgaa actttttttca ttttgaaaag   4200
tattggttac tggtgatgtt gaaatatgca tactaatttt tgcttaacat tagatgtcat   4260
gaggaaacta ctgaactagc aattggttgt ttaacacttc tgtatgcatc agataacaac   4320
tgtgagtagc ctatgaatga aattctttta taaatattag gcataaatta aaatgtaaaa   4380
ctccattcat agtggattaa tgcattttgc tgcctttatt agggtacttt attttgcttt   4440
tcagaagtca gcctacataa cacattttta aagtctaaac tgttaaacaa ctctttaaag   4500
gataattatc caataaaaaa aaacctagtg ctgattcaca gcttattatc caattcaaaa   4560
ataaattaga aaaatatatg cttacatttt tcacttttgc taaaaagaaa aaaaaaaggt   4620
gtttattttt aactcttgga agaggttttg tggttcccaa tgtgtctgtc ccaccctgat   4680
ccttttcaat atatatttct ttaaaccttg tgctacttag taaaaattga ttacaattga   4740
gggaagtttg atagatcctt taaaaaaaag gcagatttcc atttttttgta ttttaactac   4800
tttactaaat taatactcct ccttttacag aattagaaaa gttaacattt atctttaggt   4860
ggtttcctga aaagttgaat atttaagaaa ttgtttttaa cagaagcaaa atggcttttc   4920
tttggacagt tttcaccatc tcttgtaaaa gttaattctc accattcctg tggtacctgc   4980
gagtgttatg accaggattc cttaaacctg aactcagacc acttgcatta gaaccatctg   5040
gagcacttgt tttaaaatgc agattcatag gcagcatctc agatctacag aacaagaatc   5100
tctgctaagt ggacctggaa tcttccatct gcatcttaac atgctctcta ggtgtttctt   5160
gtgtttgaga accatgactt atgactttcc tcagaacatg agactgtaaa acaaaaacaa   5220
aaaactatgt gatgcctcta ttttccccaa tacagtcaca catcagctca aaatttgcaa   5280
tattgtagtt catatattac cgttatgtct ttggaaatcg ggttcagaac actttttatg   5340
acaaaaattg ggtggagggg ataactttca tatctggctc aacatctcag gaaaatctgt   5400
gattatttgt gtgttctaat gagtaacatc tacttagtta gccttaggga tggaaaaaca   5460
```

```
gggccactta ccaaactcag gtgattccag gatggtttgg aaacttctcc tgaatgcatc   5520

cttaaccttt attaaaacca ttgtcctaag aacaatgcca acaaagctta caacatttag   5580

tttaaaccca agaagggcac taaactcaga ttgactaaat aaaaagtaca aagggcacat   5640

atacgtgaca gaattgtaca caatcactcc attggatctt ttactttaaa gtagtgatga   5700

aaagtacatg ttgatactgt cttagaagaa attaatatat tagtgaagcc acatggggtt   5760

tcagttgcga aacaggtctg tttttatgtt cagtttgtac aatccacaat tcattcacca   5820

gatattttgt tcttaattgt gaaccaggtt agcaaatgac ctatcaaaaa ttattctata   5880

atcactacta gttaggatat tgatttaaaa ttgttctact tgaagtggtt tctaagattt   5940

ttatattaaa aataggtgtg atttcctaat atgatctaaa accctaaatg gttatttttc   6000

ctcagaatga tttgtaaata gctactggaa atattataca gtaataggag tgggtattat   6060

gcaacatcat ggagaagtga aggcataggc ttattctgac ataaaattcc actggccagt   6120

tgaatatatt ctattccatg tccatactat gacaatctta ttgtcaacac tatataaata   6180

agcttttaaa caagtcattt ttcttgatcg ttgtggaagg tttggagcct tagaggtatg   6240

tcagaaaaaa tatgttggta ttctcccttg ggtaggggga aatgaccttt ttacaagaga   6300

gtgaaattta ggtcagggaa aagaccaagg gccagcattg ctacttttgt gtgtgtgtgt   6360

gtgggttttg ttttgttttt ttggttggct ggttgttttc gttgttgtta acaaaggaat   6420

gagaatatgt aatacttaaa taaacatgac cacgaagaat gctgttctga tttactagag   6480

aatgttccca atttgaattt agggtgattt taaagaacag tgagaaaggg catacatcca   6540

cagattcact ttgtttatgc atatgtagat acaaggatgc acatatacac attttcaagg   6600

actattttag atatctagac aatttcttct aataaagtca tttgtgaaag ggtactacag   6660

cttattgaca tcagtaaggt agcattcatt acctgtttat tctctgctgc atcttacaga   6720

agagtaaact ggtgagagta tatattttat atatatatat atatatatat atataatatg   6780

tatatatata tatattgact tgttacatga agatgttaaa atcggttttt aaaggtgatg   6840

taaatagtga tttccttaat gaaaaataca tattttgtat tgttctaatg caacagaaaa   6900

gccttttaat ctctttggtt cctgtatatt ccatgtataa gtgtaaatat aatcagacag   6960

gtttaaaagt tgtgcatgta tgtatacagt tgcaagtctg gacaaatgta tagaataaac   7020

cttttattta agttgtgatt acctgctgca tgaaaagtgc atgggggacc ctgtgcatct   7080

gtgcatttgg caaaatgtct taacaaatca gatcagatgt tcatcctaac atgacagtat   7140

tccatttctg gacatgacgt ctgtggttta agctttgtga aagaatgtgc tttgattcga   7200

agggtcttaa agaatttttt taatcgtcaa ccacttttaa acataaagaa ttcacacaac   7260

tactttcatg aattttttaa tcccattgca aacattattc caagagtatc ccagtattag   7320

caatactgga atataggcac attaccattc atagtaagaa ttctggtgtt tacacaacca   7380

aatttgatgc gatctgctca gtaatataat ttgccatttt tattagaaat ttaatttctt   7440

catgtgatgt catgaaactg tacatactgc agtgtgaatt tttttgtttt gtttttttaat   7500

cttttagtgt ttacttcctg cagtgaattt gaataaatga gaaaaaatgc attgtc       7556
```

<210> SEQ ID NO 37
<211> LENGTH: 1516
<212> TYPE: DNA
<213> ORGANISM: Homo sapiens

<400> SEQUENCE: 37

-continued

```
tgccccacca ccgctgctcc tcagcaggcg cctcaccagc ctccacaccc cttgcgcccg     60

cagaaacgcg cctggccctg agctgtcacc accgacactc tccaggctcc ggacacgatg    120

caggccatca agtgtgtggt ggtgggagat ggggccgtgg gcaagacctg ccttctcatc    180

agctacacca ccaacgcctt tcccggagag tacatcccca ccgtgtttga caactattca    240

gccaatgtga tggtggacag caagccagtg aacctggggc tgtgggacac tgctgggcag    300

gaggactacg accgtctccg gccgctctcc tatccacaga cggacgtctt cctcatctgc    360

ttctccctcg tcagcccagc ctcttatgag aacgtccgcg ccaagtggtt cccagaagtg    420

cggcaccact gccccagcac acccatcatc ctggtgggca ccaagctgga cctgcgggac    480

gacaaggaca ccatcgagaa actgaaggag aagaagctgg ctcccatcac ctacccgcag    540

ggcctggcac tggccaagga gattgactcg gtgaaatacc tggagtgctc agctctcacc    600

cagagaggcc tgaaaaccgt gttcgacgag gccatccggg ccgtgctgtg ccctcagccc    660

acgcggcagc agaagcgcgc ctgcagcctc ctctaggggt tgcaccccag cgctcccacc    720

tagatgggtc tgatcctcca ggatccccac ccaaagcctg atggcacccc ggctggccat    780

gctgtcccct ccctgtggcg tttcttagca gatggctgca gagcttcgtt gatggtcttt    840

tctgtactgg aggcctcctg aggccaggaa cgtgcaaatt tgcaggtgct gcatcccaag    900

cccctcatgc tcctgccttc ctgagggcca gaggggagcc ccaggaccca ttaagccacc    960

cccgtgttcc tgccgtcagt gccaactgcc gcatgtggaa gcatctaccc gttcactcca   1020

gtcccacccc acgcctgact cccctctgga aactgcaggc cagatggttg ctgccacaac   1080

ttgtgtacct tcagggatgg ggctcttact ccctcctgag gccagctgct ctaatatcga   1140

tggtcctgct tgccagagag ttcctctacc cagcaaaaat gagtgtctca gaagtgtgct   1200

cctctggcct cagttctcct cttttggaac aacataaaac aaatttaatt ttctacgcct   1260

ctggggatat ctgctcagcc aatggaaaat ctgggttcaa ccagcccctg ccatttctta   1320

agactttctg ctgcactcac aggatcctga gctgcactta cctgtgagag tcttcaaact   1380

tttaaacctt gccagtcagg acttttgcta ttgcaaatag aaaacccaac tcaacctgct   1440

taagcagaaa ataaatttat tgattcaaaa aaaaaaaaaa aaaaaaaaaa aaaaaaaaaa   1500

aaaaaaaaaa aaaaaa                                                   1516
```

```
<210> SEQ ID NO 38
<211> LENGTH: 1641
<212> TYPE: DNA
<213> ORGANISM: Homo sapiens

<400> SEQUENCE: 38

ctccctgtgt tggtggagga tgtctgcagc agcatttaaa ttctgggagg gcttggttgt     60

cagcagcagc aggaggaggc agagcacagc atcgtcggga ccagactcgt ctcaggccag    120

ttgcagcctt ctcagccaaa cgccgaccaa ggaaaactca ctaccatgag aattgcagtg    180

atttgctttt gcctcctagg catcacctgt gccataccag ttaaacaggc tgattctgga    240

agttctgagg aaaagcagct ttacaacaaa tacccagatg ctgtggccac atggctaaac    300

cctgacccat ctcagaagca gaatctccta gccccacaga atgctgtgtc ctctgaagaa    360

accaatgact ttaaacaaga gacccttcca agtaagtcca acgaaagcca tgaccacatg    420

gatgatatgg atgatgaaga tgatgatgac catgtggaca gccaggactc cattgactcg    480

aacgactctg atgatgtaga tgacactgat gattctcacc agtctgatga gtctcaccat    540

tctgatgaat ctgatgaact ggtcactgat tttcccacgg acctgccagc aaccgaagtt    600
```

```
ttcactccag ttgtccccac agtagacaca tatgatggcc gaggtgatag tgtggtttat    660
ggactgaggt caaaatctaa gaagtttcgc agacctgaca tccagtaccc tgatgctaca    720
gacgaggaca tcacctcaca catggaaagc gaggagttga atggtgcata caaggccatc    780
cccgttgccc aggacctgaa cgcgccttct gattgggaca gccgtgggaa ggacagttat    840
gaaacgagtc agctggatga ccagagtgct gaaacccaca gccacaagca gtccagatta    900
tataagcgga aagccaatga tgagagcaat gagcattccg atgtgattga tagtcaggaa    960
ctttccaaag tcagccgtga attccacagc catgaatttc acagccatga agatatgctg   1020
gttgtagacc ccaaaagtaa ggaagaagat aaacacctga aatttcgtat ttctcatgaa   1080
ttagatagtg catcttctga ggtcaattaa aaggagaaaa aatacaattt ctcactttgc   1140
atttagtcaa aagaaaaaat gctttatagc aaaatgaaag agaacatgaa atgcttcttt   1200
ctcagtttat tggttgaatg tgtatctatt tgagtctgga aataactaat gtgtttgata   1260
attagtttag tttgtggctt catggaaact ccctgtaaac taaaagcttc agggttatgt   1320
ctatgttcat tctatagaag aaatgcaaac tatcactgta ttttaatatt tgttattctc   1380
tcatgaatag aaatttatgt agaagcaaac aaaatacttt tacccactta aaaagagaat   1440
ataacatttt atgtcactat aatcttttgt tttttaagtt agtgtatatt ttgttgtgat   1500
tatcttttttg tggtgtgaat aaatctttta tcttgaatgt aataagaatt tggtggtgtc   1560
aattgcttat ttgttttccc acggttgtcc agcaattaat aaaacataac ctttttttact   1620
gcctaaaaaa aaaaaaaaaa a                                             1641
```

<210> SEQ ID NO 39
<211> LENGTH: 6463
<212> TYPE: DNA
<213> ORGANISM: Homo sapiens

<400> SEQUENCE: 39

```
ctctcttgct cgctcgctcc ctctctctcc tgctggctgc ctgttctagg aagccagcgc     60
ggagaggggg gggatgcaca gcacagggga gagagattgc gcatgttggt cagtcgtgtt    120
ttaaagagta cagtgcgggg aggctgagag gggcgcatgc aacaacaact tttggaagga    180
tggaagagaa gaggcgaaaa tactccatca gcagtgacaa ctctgacacc actgacagtc    240
atgcgacatc tacatccgca tcaagatgct ccaaactgcc cagcagcacc aagtcgggct    300
ggccccgaca gaacgaaaag aagccctccg aggttttccg gacagacttg atcacagcca    360
tgaagatccc ggactcatac cagctcagcc cggatgacta ctacatcctg gcagacccat    420
ggcgacagga atgggagaaa ggtgtgcagg tgcctgccgg ggcagaggcc atcccagagc    480
ccgtggtgag gatcctccca ccactggaag gcccccctgc ccaggcatcc ccgagcagca    540
ccatgcttgg tgagggctcc cagcctgatt ggccaggggg cagccgctat gacttggacg    600
agattgatgc ctactggctg gagctcatca actcggagct taaggagatg gagaggccgg    660
agctggacga gctgacatta gagcgtgtgc tggaggagct ggagaccctg tgccaccaga    720
atatggccag ggccattgag acgcaggagg ggctgggcat cgagtacgac gaggatgttg    780
tctgcgacgt gtgtcgctct cctgagggcg aggatggcaa cgagatggtc ttctgtgaca    840
agtgcaacgt ctgtgtgcat caggcatgct acgggatcct caaggtgccc acgggcagct    900
ggctgtgccg gacgtgtgcc ctgggtgtcc agccaaagtg cctgctctgc cccaagcgag    960
gaggagcctt gaagcccact agaagtggga ccaagtgggt gcatgtcagc tgtgccctat   1020
```

ggattcctga ggtcagcatc ggctgcccag agaagatgga gcccatcacc aagatctcgc 1080
atatcccagc cagccgctgg gctctgtcct gcagcctctg caaggaatgc acaggcacct 1140
gcatccagtg ttccatgcct tcctgcgtca cagcgttcca tgtcacatgc gcctttgacc 1200
acggcctgga aatgcggact atattagcag acaacgatga ggtcaagttc aagtcattct 1260
gccaggagca cagtgacggg ggcccacgta atgagcccac atctgagccc acggaaccca 1320
gccaggctgg cgaggacctg gaaaaggtga ccctgcgcaa gcagcggctg cagcagctag 1380
aggaggactt ctacgagctg gtggagccgg ctgaggtggc tgagcggctg gacctggctg 1440
aggcactggt cgacttcatc taccagtact ggaagctgaa gaggaaagcc aatgccaacc 1500
agccgctgct gacccccaag accgacgagg tggacaacct ggcccagcag gagcaggacg 1560
tcctctaccg ccgcctgaag ctcttcaccc atctgcggca ggacctagag agggttagaa 1620
atctgtgcta catggtgaca aggcgcgaga gaacgaaaca cgccatctgc aaactccagg 1680
agcagatatt ccacctgcag atgaaactta ttgaacagga tctgtgtcga ggcctgtcca 1740
cctcattccc catcgatggc accttcttca acagctggct ggcacagtcg gtgcagatca 1800
cagcagagaa catggccatg agcgagtggc cactgaacaa tgggcaccgc gaggaccctg 1860
ctccagggct gctgtcagag gaactgctgc aggacgagga gacactgctc agcttcatgc 1920
gggacccctc gctgcgacct ggtgaccctg ctaggaaggc ccgaggccgc acccgcctgc 1980
ctgccaagaa gaaaccacca ccaccaccac cgcaggacgg gcctggttca cggacgactc 2040
cagacaaagc cccaagaag acctggggcc aggatgcagg cagtggcaag gggggtcaag 2100
ggccacctac caggaagcca ccacgtcgga catcttctca cttgccgtcc agccctgcag 2160
ccggggactg tcccatccta gccacccctg aaagcccccc gccactggcc cctgagaccc 2220
cggacgaggc agcctcagta gctgctgact cagatgtcca agtgcctggc cctgcagcaa 2280
gccctaagcc tttgggccgg ctccggccac cccgcgagag caaggtaacc cggagattgc 2340
cgggtgccag gcctgatgct gggatgggac caccttcagc tgtggctgag aggcccaagg 2400
tcagcctgca ttttgacact gagactgatg gctacttctc tgatggggag atgagcgact 2460
cagatgtaga ggccgaggac ggtggggtgc agcggggtcc ccgggaggca ggggcagagg 2520
aggtggtccg catgggcgta ctggcctcct aactcacccc cttccctgtc ccaggccctg 2580
ccctggtccc cccacaaggc ctcagcccag tcacaactgc catttccagt ctctgctgag 2640
tgtcccagac cctcgaggct gccactccgt cgtggtttta tttttaatat agagagagtt 2700
ttgaattcta cactgttgtc tttcctctgt gctggcctag gacattagga ttccttccac 2760
ggctccggcc gctaggaccc tgccaggtcc cgcgcaccat ccctgccctg cccacgtggt 2820
attgctgggc tcctggctag atgcaagcaa ggtggacaag agctcaggac tccagcccac 2880
tgccactggg tgacacagac tgtcgtttgg gcattatttc atggcagatg ggccagtcca 2940
gggcctaccc cgccttgccc ccagatccca ctggggtcca tttgggggt cctgctacac 3000 tccaccgatc cccaaggaag tataataaac gatacccagc cagagtctac tcactgtcac 3060
aagcacaacg agtttatatg agaaagcact gagggggtgc agagggcccg ctagttccag 3120
gggaactgaa agctgttcct gatcagcccg tatcatctga ggcctgcctg cccaccctgc 3180
caccctcccc tcccttgctg ctctgcccct gccagtgccc agcccagcgg ctctgggaag 3240
gggttcccag aatccctcct gagctgtgcc atttactcag gggactccca aacagccagc 3300
tgccagtgca ggtggagggc tgtaggggag ggccagtgcc cagacagggt catggggctc 3360
agaccagccc actgtagaga atcactctga ggctccaact tccttccttc cttcggggcc 3420

```
agtctcggcc gaagtctggt cacgctcaga cagagctgac cagaccagac cgtttgcctt   3480
ttcaagtttc ctagtcctgc tacaagatga gcttcttccg tggtttcctt ttggaaactc   3540
ctccttccaa caagcagtgg gatcccgggg cccagggcgg gccggtgttg gccgctgggg   3600
ctgttgtaag tcttgctgga tgttcccctg ttcctgagcc ttaacccctc gcacagccat   3660
cccccccccc gtcctgccat cccccccgc cgtcctgcct tccccacccc acccttaggt   3720
cccaggtagt tgctctgaag agtttcagta gagtggcccc agggtgatag ctcagggaac   3780
aacaaaaaag gaattccgtg aaaacatttt tttttctttg atgaattact cctgggtcac   3840
ttccaccact ggtaaagcca gaacttctcc aaaaagaacc ttgcaaaaag tccagtgaat   3900
cagtcgaatc attctgtgga tgccaaagaa tattttgacc ataatacagc acagcctgga   3960
cctgacaact tgtcatttgg actttttttt aaatggagtt ctttagcaac aaagtataga   4020
aacatgttca ttgcacacac ccaaggagaa gagctcaagc gcttggaaga ggatgctttg   4080
ctgctgctga agtgtacctg ggtgttagat ttcagatcct gggctgagcc cactgtgagc   4140
tttcctaaac tgtgagactc acagagggga aagatactga cggtgaaacc agcatggaaa   4200
acgtctttac catgtggttc cctcctcccc aaatacataa agcaaataag caggatgggg   4260
aacagcttga ccttcatcca cccctaactc caaaactatc aaggtacgac agtggcattg   4320
tcatcgacac tcaatttcat gtgaatttta gcaaaacagg aaacaaagat aatgactcag   4380
ttcagaggat cggacaaatg tgtctagtcc gggtggactc ggagggagtg gggtgggctt   4440
caaggattct gggcgttggg atggcatgag ctaccctgta gagtttagtc tgcctgcccg   4500
ccttggtagt agtgaccagt cagtgtcagc atcagtgtcc caaccccagt ctctgtttac   4560
tgcctttgaa cagaacttct tccttcccca tgctttgggt cacctcgggc tgcaaccctg   4620
tctgtgccag attgcccggt ctgaccctgc aggaagcaaa gaggtgagct taaagaacaa   4680
ccaaactctg ccaggggtcc cagaaagccc agggtccagc agtctcagca cttggcccct   4740
tgccccttca caccatcctg gggcaggggc tgggcctccc tggtggcagg ggtgggtgga   4800
gaattaggga gagggtgcaa cgagtctggc cccttgcctc gggctggctg gtgttcttcc   4860
aagagcctct gctcacattg ttggcctctg gattctggcc cttcttcatt ggctgttgct   4920
ttggactgga ctgttgctga gcctgtgtcc tgcagaaccc agatgtctgt taggctggct   4980
ggctgctgcg aggggagggg ggtggccttt catttggggt gccctttcac tcccaggcca   5040
agccctggag caatcttctt caggcagctg tctccacctc caggatgtcc agcaggctgc   5100
aaggagaagg atgccagcca cccatcctcc cccagttccc agcctttccc ctgttggtca   5160
cagccgcttc tgtctttttc cggtctactg tccccagtgt agagggcttt gctgtccctg   5220
agactgaggc aggttccttt tccaggtcag aggtggaggt agatctttct ctcaaccaca   5280
tctgcctcca cacacagctc ctccgcaggg aaggagaagc tgctctgtaa ctcattctgg   5340
ctatcgtccc ccttctcact gacctgaccg cccaccacct ccttcccccct catcacatga   5400
caaaggataa tgtgcaagaa aagtattttt atgtatcata aatgtatttt gaaacaaatg   5460
agaagaagaa aggtagaagg gtttatttta ttaaatgagc ctgacttagt gacagtgtgt   5520
gagcatttgc aatgtaaggg cctcagcttc cttggagaag ccaccccagg tttccagaca   5580
tagatgttga attgtttgtg gggggtgtgc caggccacgt ctcgtgtgtc cgtatgcagg   5640
catgcctgtg tatactgtgt atgggcacac tgggactagc tgggacaatt cctagagatt   5700
caactgccca attctaacca acattggcag cggctgaact tggcatttcc ttgctaactg   5760
```

-continued

```
ccagatgtgg ccaacctttg tccatatgca aaccactgaa aaatgatctg gatttctata   5820

gcaaggccct tggggagggc actctcccat gcccttggcc tcgctggcca cattggccaa   5880

tgagccaggg ctggagtctg agacctttgg ttgttcttta aggcacctcc tgccactttc   5940

tccctcagag gcacaaacac tttgtgttcc acgtcagttt gaggggacgg tggggggatg   6000

atatgaatgt cacaggagga gacaccttct gtctttgttt caaagaaagt gatgtgccat   6060

ttgttaatat acaagagaaa tattgaaaat atattgaaaa gagcaatttt aaattatttt   6120

tggcttatgt tgcaatattt attttcttgt attagaaaag attcctttgt agagaaaaaa   6180

tgtatttttc attaacgcaa agacctattt ctccttttg tacattgtcc atgtgcgcaa    6240

cccttaacga gcaatagaat gtatggtcac ctgggtgtgg ccagtgcccg ctgtgccctg   6300

catgattctg tgttgccgct gctgcatagt tcccagcccc atcctgtcct gctcactcat   6360

gggggcttcc agaccccggc cccaccaggg cttgtgtcat agggagccct ttgcactcct   6420

cgtgtgttgg caaacgcagt taataaagca gtgttttctg tgc                     6463
```

<210> SEQ ID NO 40
<211> LENGTH: 2828
<212> TYPE: DNA
<213> ORGANISM: Homo sapiens

<400> SEQUENCE: 40

```
catagatgaa aatggcaagt tccctggctt tccttctgct caactttcat gtctccctcc     60

tcttggtcca gctgctcact ccttgctcag ctcagttttc tgtgcttgga ccctctgggc    120

ccatcctggc catggtgggt gaagacgctg atctgccctg tcacctgttc ccgaccatga    180

gtgcagagac catggagctg aagtgggtaa gttccagcct aaggcaggtg gtgaacgtgt    240

atgcagatgg aaaggaagtg gaagacaggc agagtgcacc gtatcgaggg agaacttcga    300

ttctgcggga tggcatcact gcagggaagg ctgctctccg aatacacaac gtcacagcct    360

ctgacagtgg aaagtacttg tgttatttcc aagatggtga cttctatgaa aaagccctgg    420

tggagctgaa ggttgcagca ctgggttcta atcttcacgt cgaagtgaag ggttatgagg    480

atggagggat ccatctggag tgcaggtcca ccggctggta cccccaaccc caaatacagt    540

ggagcaacgc caagggagag aacatcccag ctgtggaagc acctgtggtt gcagatggag    600

tgggcctata tgaagtagca gcatctgtga tcatgagagg cggctccggg gagggtgtat    660

cctgcatcat cagaaattcc ctcctcggcc tggaaaagac agccagcatt tccatcgcag    720

accccttctt caggagcgcc cagccctgga tcgcagccct ggcagggacc ctgcctatct    780

tgctgctgct tctcgccgga gccagttact tcttgtggag acaacagaag gaaataactg    840

ctctgtccag tgagatagaa agtgagcaag agatgaaaga aatgggatat gctgcaacag    900

agcgggaaat aagcctaaga gagagcctcc aggaggaact caagaggaaa aaaatccagt    960

acttgactcg tggagaggag tcttcgtccg ataccaataa gtcagcctga tgctctaatg   1020

gaaaaatggc cctcttcaag cctggaaaaa tggctgaccc catggacacc tcctcaaact   1080

ctctgcagca gatgtaattc tgtatccaga catggcaaat gccatcctcc ttgtttctga   1140

ggaccagagg agtgtacagc gtgctgagga gccccatgac ctaccagaca accctgagag   1200

atttgaatgg cgttactgtg tgcttggctg tgaaagcttc atgtcagaga gacactactg   1260

ggaggtggaa gtgggggaca gaaaagagtg gcatattggg gtatgtagta agaacgtgga   1320

gaggaaaaaa gtttgggtca aaatgacacc ggagaacgga tactggacta tgggcctgac   1380

tgatgggaat aagtatcggg ctctcactga gcccagaacc aacctgaaac ttcctgagcc   1440
```

```
tcctaggaaa gtgggggtca tcctggacta tgagactgga catatctcgt tctacaatgc   1500

cacggatgga tctcatatct acacatttct gcacgcctct tcctctgagc ctctgtatcc   1560

tgtattcaga attttgacct tggagcccac tgccctgacc gtttgcccaa taccaaaagt   1620

agagagttcc cccgatcccg acctagtgcc tgatcattcc ctggagatac cactgacccc   1680

aggcttagct aatgaaagtg gggagcctca ggctgaagta acatctctgc ttctccctgc   1740

ccagcctgga gctaagggtc tcaccctcca caacagccag tcagaaccat aaagctacag   1800

gcacacactg aagcacttta ctgatattca ttcaattatt ccataggaca gttgtttgag   1860

tttggtgcca ccttattggc ccctttatac agataaggaa actggggtgt agaaaagtgt   1920

attgacttta caaagcagac aggaatagtg aacaacagag ctgggatctg aacaacaatg   1980

actaacatta atggagaatt taaaacgttc tgagtgctgt gttatgagct ttggtgggtg   2040

tcactccttt aatcctcaca acaccctgtc aggtagtctc atttggcaag tatggaagca   2100

gaggcagggc aacattaagt agcttacata actcacacgg taatttgtgc agttgggaga   2160

tgttcagctt cagtccctgg ccaattgccc gttcttttcc agcctgattt ttcctgcatg   2220

ggaagagccc acatgtagcc ctgaggttcc cttcccagga cagctccagg atcgagatca   2280

ctgtgagtgg ttgtggagtt aagacccta tggactcctt cccagctgat tatcagagcc   2340

ttagacccag cactccttgg attggctctg cagagtgtct tggttgagag aataacgttg   2400

cagttcccac agggcatgtg actttgaaag agactagagg ccacactcag ttaataatgg   2460

ggcacagatg tgttcccacc caacaaatgt gataagtgat cgtgcagcca gagccagcct   2520

tccttcagtc aaggtttcca ggcagagcaa ataccctaga gattctctgt aatattggta   2580

atttggatga aggaagctag aagaattaca gggatgtttt taatcccact atggactcag   2640

tctcctggaa aaggatctgt ccactcctgg tcattggtgg atgttaaacc catattcctt   2700

tcaactgctg cctgctaggg aaaactgctc ctcattatca tcactattat tgctcaccac   2760

tgtatcccct ctactgggca agtgcttgtc aagttctagt tgttcaataa atttgttaat   2820

aatgctga                                                            2828
```

<210> SEQ ID NO 41
<211> LENGTH: 2698
<212> TYPE: DNA
<213> ORGANISM: Homo sapiens

<400> SEQUENCE: 41

```
gccgtccgtg ctgactgagg cgctgcagcc aggagccgcg gccggctgcc cagcgctcgc     60

cgcctccgcg cgtccgcagc cgtccccgcg ccgacatgcg cttggccgcc gccgcgaacg    120

aggcgtacac ggccccttg gcggtctcgg ggctgctggg ctgcaagcag tgcggcgggg     180

gccgcgacca ggacgaggaa cttggcatta gaattcctcg accactagga cagggaccaa    240

gcagattcat cccagaaaag gagatcctcc aagtggggag tgaagacgca cagatgcatg    300

ctttatttgc agattctttt gctgctttgg gccgtttgga taacattacg ttagtgatgg    360

ttttccaccc acaatattta gaaagtttct taaaaactca gcactatcta ctgcaaatgg    420

atgggccgtt acccctacat tatcgtcact acattggaat aatggctgcg gcaagacatc    480

agtgctccta cttagtgaac ctgcatgtaa atgatttcct tcatgttggt ggggaccccca    540

agtggctcaa tggtttagag aatgctcctc aaaaactaca gaatttagga gaacttaaca    600

aagtgttagc ccatagacct tggcttatta ccaaagaaca cattgaggga cttttaaaag    660
```

ctgaagagca cagctggtcc cttgcggaat tggtacatgc agtagtttta ctcacacact 720
atcattctct tgcctcattc acattcggct gtggaatcag tccagaaatt cattgtgatg 780
gtggccacac attcagacct ccttctgtta gcaactactg catctgtgac attacaaatg 840
gcaatcacag tgtggatgag atgccggtca actcagcaga aaatgtttct gtaagtgatt 900
ctttctttga ggttgaagcc ctcatggaaa agatgaggca gttacaggaa tgtcgagatg 960
aagaagaggc aagtcaggaa gagatggctt cacgttttga aatagaaaaa agagagagta 1020
tgtttgtctt ctcttcagat gatgaagaag ttacaccagc aagagctgta tctcgtcatt 1080
ttgaggatac tagttatggc tataaagatt tctctagaca tgggatgcat gttccaacat 1140
ttcgtgtcca ggactattgc tgggaagatc atggttattc tttggtaaat cgcctttatc 1200
cagatgtggg acagttgatt gatgaaaaat ttcacattgc ttacaatctt acttataata 1260
caatggcaat gcacaaagat gttgatacct caatgcttag acgggcaatt tggaactata 1320
ttcactgcat gtttggaata agatatgatg attatgacta tggtgaaatt aaccagctat 1380
tggatcgtag ctttaaagtt tatatcaaaa ctgttgtttg cactcctgaa aaggttacca 1440
aaagaatgta tgatagcttc tggaggcagt tcaagcactc tgagaaggtt catgttaatc 1500
tgcttcttat agaagctagg atgcaagcag aactccttta tgctctgaga gccattaccc 1560
gctatatgac ctgatgcctt tccttcatta aagatgattc tggaatgatc agcagatata 1620
gtctacaagg gggaaggtac taagccccag gaccaatggt agacaaaata attcagaaat 1680
ccattgtgcc atgattcctt tagtttctgc tatttttctg tggaaaacca ctgctggcac 1740
aagcagtgac tgtttggcag cttcaagttt agagctgtga agacaggctg ccattcacag 1800
tattttgctt tttgacagta caagatgctg tgtaactgtt ttaatacagc aaatagtaac 1860
tctccaaatc ctgttgcttt tatgttaaat aagataacaa gaattggagc atgcaaagaa 1920
tgggacttgg ataatgactt aagctttata tgtaaagaat tttagaagat cttggtgctg 1980
ctattcctgc tggaggaatg aatagatggc tgtttcagtt aagctattag taataaaagt 2040
gaacattgct actatctgag cctacataca taacttgtgt gatttcaaat taaacttgca 2100
ttatgtgtta attttcttgc atctaaaaaa gcatagaatt cctactcaca cagctcagca 2160
acaaccattt tgatggtaac agttaatttc tttcattagt tttttaaatt cagggttctg 2220
gatattaaat taaaatggca ttcttaaaga ttttcttcaa aaagcaatcc taaatgaaag 2280
tgtgtaaatt ataagaagct ggcgatcttt tgatatgctg tttcacagga tcctgacact 2340
ggagggcagc tgtcttgtgc attacttgtg tttccagcac caaagttgtg ggacatgttg 2400
ctgtagactg ctgcgcagtc ctgggtgcat tcagtctctc tgcctctgcc tgcctcctgg 2460
tccccacttt aaaggctgtg cagctcctta aataataaag ctggaaaata tttttagtcg 2520
ggttatcaaa tttgatttac aaaaacgcta actttgtttg aaatgcaaac aggtttgaaa 2580
atatgtatta agtactttgt attctggaag cgtgaattgc ttttgaagtc tgtcagtatt 2640
actggtattt ttaaataaag aagaattttt ctccaatttt aaaaaaaaaa aaaaaaaa 2698

<210> SEQ ID NO 42
<211> LENGTH: 5215
<212> TYPE: DNA
<213> ORGANISM: Homo sapiens

<400> SEQUENCE: 42
cgagcgcggc gcccttgagc tgcaccgcgg cgcaggtttg cgagccgact tgtcagccgg 60
ccaagaaaag gaagctccgt cccttcccgc tcacccggct tccccacccc ttgtactcta 120

-continued

```
aactctgcag agggcgagcg gcgcggccac ggaggcgccg aggaggagcg agccgccgcc    180
gggcagcggc gtgccctcgg gggagagggc gccggagagg aggcggcggc gcggcggcga    240
gggcgcggcg cgcgatggca gctgcttagc ccggcgggcg cggagcagcc ccgagctgtg    300
gctggccagg cggtgcggct gggcggggga cgccgccgcc gttgctgccc ggcccggaga    360
gatgagcacg gaggcggacg agggcatcac tttctctgtg ccacccttcg ccccctcggg    420
cttctgcacc atccccgagg gcggcatctg caggaggggga ggagcggcgg cggtgggcga    480
gggcgaggag caccagctgc caccgccgcc gccgggcagc ttctggaacg tggagagcgc    540
cgctgcccct ggcatcggtt gtccggcggc cacctcctcg agcagtgcca cccgaggccg    600
gggcagctct gttggcgggg gcagccgacg gaccacggtg gcatatgtga tcaacgaagc    660
gagccaaggg caactggtgg tggccgagag cgaggccctg cagagcttgc gggaggcgtg    720
cgagacagtg ggcgccaccc tggaaaccct gcattttggg aaactcgact ttggagaaac    780
caccgtgctg gaccgctttt acaatgcaga tattgcggtg gtggagatga gcgatgcctt    840
ccggcagccg tccttgtttt accaccttgg ggtgagagaa agtttcagca tggccaacaa    900
catcatcctc tactgtgata ctaactcgga ctctctgcag tcactgaagg aaataatttg    960
ccagaagaat actatgtgca ctgggaacta cacctttgtt ccttacatga taactccaca   1020
taacaaagtc tactgctgtg acagcagctt catgaagggg ttgacagagc tcatgcaacc   1080
gaacttcgag ctgcttcttg gacccatctg cttacctctt gtggatcgtt ttattcaact   1140
tttgaaggtg gcacaagcaa gttctagcca gtacttccgg gaatctatac tcaatgacat   1200
caggaaagct cgtaatttat acactggtaa agaattggca gctgagttgg caagaattcg   1260
gcagcgagta gataatatcg aagtcttgac agcagatatt gtcataaatc tgttactttc   1320
ctacagagat atccaggact atgattctat tgtgaagctg gtagagactt tagaaaaact   1380
gccaaccttt gatttggcct cccatcacca tgtgaagttt cattatgcat ttgcactgaa   1440
taggagaaat ctccctggtg acagagcaaa agctcttgat attatgattc ccatggtgca   1500
aagcgaagga caagttgctt cagatatgta ttgcctagtt ggtcgaatct acaaagatat   1560
gtttttggac tctaatttca cggacactga aagcagagac catggagctt cttggttcaa   1620
aaaggcattt gaatctgagc caacactaca gtcaggaatt aattatgcgg tcctcctcct   1680
ggcagctgga caccagtttg aatcttcctt tgagctccgg aaagttgggg tgaagctaag   1740
tagtcttctt ggtaaaaagg gaaacttgga aaaactccag agctactggg aagttggatt   1800
ttttctgggg gccagcgtcc tagccaatga ccacatgaga gtcattcaag catctgaaaa   1860
gctttttaaa ctgaagacac cagcatggta cctcaagtct attgtagaga caattttaat   1920
atataagcat tttgtgaaac tgaccacaga acagcctgtg gccaagcaag aacttgtgga   1980
cttttggatg gatttcctgg tcgaggccac aaagacagat gttactgtgg ttaggtttcc   2040
agtattaata ttagaaccaa ccaaaatcta tcaaccttct tatttgtcta tcaacaatga   2100
agttgaggaa aagacaatct ctatttggca cgtgcttcct gatgacaaga aaggtataca   2160
tgagtggaat tttagtgcct cttctgtcag gggagtgagt atttctaaat ttgaagaaag   2220
atgctgcttt ctttatgtgc ttcacaattc tgatgatttc caaatctatt tctgtacaga   2280
acttcattgt aaaaagtttt ttgagatggt gaacaccatt accgaagaga aggggagaag   2340
cacagaggaa ggagactgtg aaagtgactt gctggagtat gactatgaat atgatgaaaa   2400
tggtgacaga gtcgttttag gaaaaggcac ttatgggata gtctacgcag gtcgggactt   2460
```

-continued

```
gagcaaccaa gtcagaattg ctattaagga aatcccagag agagacagca gatactctca   2520
gcccctgcat gaagaaatag cattgcataa acacctgaag cacaaaaata ttgtccagta   2580
tctgggctct ttcagtgaga atggtttcat taaaatcttc atggagcagg tccctggagg   2640
aagtctttct gctctccttc gttccaaatg gggtccatta aaagacaatg agcaaacaat   2700
tggcttttat acaaagcaaa tactggaagg attaaaatat ctccatgaca atcagatagt   2760
tcaccgggac ataaagggtg acaatgtgtt gattaatacc tacagtggtg ttctcaagat   2820
ctctgacttc ggaacatcaa agaggcttgc tggcataaac ccctgtactg aaacttttac   2880
tggtaccctc cagtatatgg caccagaaat aatagataaa ggaccaagag gctacggaaa   2940
agcagcagac atctggtctc tgggctgtac aatcattgaa atggccacag gaaaaccccc   3000
attttatgaa ctgggagaac cacaagcagc tatgttcaag gtgggaatgt ttaaagtcca   3060
ccctgagatc ccagagtcca tgtctgcaga ggccaaggca ttcatactga aatgttttga   3120
accagatcct gacaagagag cctgtgctaa cgacttgctt gttgatgagt ttttaaaagt   3180
ttcaagcaaa aagaaaaaga cacaacctaa gctttcagct ctttcagctg gatcaaatga   3240
atatctcagg agtatatcct tgccggtacc tgtgctggtg gaggacacca gcagcagcag   3300
tgagtacggc tcagtttcac ccgacacgga gttgaaagtg gacccccttct ctttcaaaac   3360
aagagccaag tcctgcggag aaagagatgt caagggaatt cggacactct ttttgggcat   3420
tccagatgag aattttgaag atcacagtgc tcctccttcc cctgaagaaa aagattctgg   3480
attcttcatg ctgaggaagg acagtgagag gcgagctacc cttcacagga tcctgacgga   3540
agaccaagac aaaattgtga gaaacctaat ggaatcttta gctcaggggg ctgaagaacc   3600
gaaactaaaa tgggaacaca tcacaaccct cattgcaagc ctcagagaat ttgtgagatc   3660
cactgaccga aaaatcatag ccaccacact gtcaaagctg aaactggagc tggacttcga   3720
cagccatggc attagccaag tccaggtggt actctttggt tttcaagatg ctgtcaataa   3780
agttcttcgg aatcataaca tcaagccgca ctggatgttt gccttagaca gtatcattcg   3840
gaaggcggta cagacagcca ttaccatcct ggttccagaa ctaaggccac atttcagcct   3900
tgcatctgag agtgatactg ctgatcaaga agacttggat gtagaagatg accatgagga   3960
acagccttca aatcaaactg tccgaagacc tcaggctgtc attgaagatg ctgtggctac   4020
ctcaggcgtg agcacgctca gttctactgt gtctcatgat tcccagagtg ctcaccggtc   4080
actgaatgta cagcttggaa ggatgaaaat agaaaccaat agattactgg aagaattggt   4140
tcggaaagag aaagaattac aagcactcct tcatcgagct attgaagaaa aagaccaaga   4200
aattaaacac ctgaagctta agtcccaacc catagaaatt cctgaattgc ctgtatttca   4260
tctaaattct tctggcacaa atactgaaga ttctgaactt accgactggc tgagagtgaa   4320
tggagctgat gaagacacta taagccggtt tttggctgaa gattatacac tattggatgt   4380
tctctactat gttacacgtg atgacttaaa atgcttgaga ctaaggggag ggatgctgtg   4440
cacactgtgg aaggctatca ttgactttcg aaacaaacag acttgactgt tgctcaatct   4500
aatcttcgat ggaaattcta aaaattaata cagagctgat cttcttgggg gtgggaaaat   4560
cgaagggaga ggagaaaggc gctgcacttt aaatccagta tttgtttact catgttaaaa   4620
aaaaaaaaaa cagacaaaac acactgaaat ttcctaacta catctatttc tataattttt   4680
aaggactctt cataaggact cttaaaataa tcctgaacat tagaacccta atgttcagga   4740
agattttaat ctaagcattt ttatggaaat atttttaatg cagcagctat tgcacttcag   4800
ccaaatgttt atttcacaca aaacggatgt aacatttcat gtgatcgtgc accactggaa   4860
```

caaaaccaaa atgtgaccat aactgtttag gcttctgtgt gtttgtaata tgctctaata 4920
atctgagtag aaatgcgtaa tttcaattac tgtataaagt ttatgttttt ttaagtgtgc 4980
agaatctgag agcaatggtt tttacttctc tgtgttaatt gtaatattga ctctattttg 5040
taacttaagt ttctgacctg tcgtacattt gtttgagtcg tttatgtact actgaactgt 5100
accagttgca catgcttgaa ctgtagtaat gttagcttgt tctaaagcta tccattgtgt 5160
catatttact ctaaaaatta aagagactct caacaaaaaa aaaaaaaaaa aaaaa 5215

<210> SEQ ID NO 43
<211> LENGTH: 4655
<212> TYPE: DNA
<213> ORGANISM: Homo sapiens

<400> SEQUENCE: 43
tctgtgcacc ttgcggtggg cggcgaacgg cagccgcggc agcagctagg gggcttgtgc 60
acacagcgag ggagacttag ggactggcag acggacggac ggacggcgag gaccctaccc 120
gagcccccga gccatggccg agagaaagca atccgggaag gcggcagagg acgaagaggt 180
ccctgctttt tttaaaaacc tgggctccgg cagccccaag ccccggcaga aattctgtgg 240
catgttctgc ccggtggaag ggtcctcgga gaacaagacc atcgacttcg actcgctgtc 300
ggtgggccgg ggctcggggc aggtggtggc tcagcagcgg gacgtcgccc acttgggccc 360
ggacccgcag ccgccgtact cgcggcaggg ccggcgcgcc ggcggagagc catctgttga 420
atcgggccgg aaggtggaga tccggagggc ctcgggcaaa gaagccctgc agaacatcaa 480
cgaccagagc gatcgtcttc tgatcaaagg aggtaaaatt gttaatgatg accagtcgtt 540
ctatgcagac atatacatgg aagatgggtt gatcaagcaa ataggagaaa atctgattgt 600
gccaggagga gtgaagacca tcgaggccca ctcccggatg gtgatccccg gaggaattga 660
cgtccacact cgtttccaga tgcctgatca gggaatgacg tctgctgatg atttcttcca 720
aggaaccaag gcggccctgg ctgggggaac cactatgatc attgaccacg ttgttcctga 780
gcctgggaca agcctgctcg ctgcctttga ccagtggagg gaatgggccg acagcaagtc 840
ctgctgtgac tactctctgc atgtggacat cagcgagtgg cataagggca tccaggagga 900
gatggaagcg cttgtgaagg atcacggggt aaattccttc ctcgtgtaca tggctttcaa 960
agatcgcttc cagctaacgg attgccagat ttatgaagta ctgagtgtga tccgggatat 1020
tggcgccata gcccaagtcc acgcagaaaa tggcgacatc attgcagagg agcagcagag 1080
gatcctggat ctgggcatca cgggccccga gggacatgtg ctgagccgac ctgaggaggt 1140
cgaggccgaa gccgtgaatc gtgccatcac catcgccaac cagaccaact gcccgctgta 1200
tatcaccaag gtgatgagca aaagctctgc tgaggtcatc gcccaggcac ggaagaaggg 1260
aactgtggtg tatggcgagc ccatcactgc cagcttggga acggacggct cccattactg 1320
gagcaagaac tgggccaagg ctgctgcctt tgtcacctcc ccacccttga gccctgatcc 1380
aaccactcca gactttctca actccttgct gtcctgtgga gacctccagg tcacgggcag 1440
tgcccattgc acgtttaaca ctgcccagaa ggctgtagga aaggacaact tcaccctgat 1500
tccggagggc accaatggca ctgaggagcg gatgtccgtc atctgggaca aggctgtggt 1560
cactgggaag atggatgaga accagtttgt ggctgtgacc agcaccaatg cagccaaagt 1620
cttcaacctt tacccccgga aaggccgcat tgctgtggga tccgatgccg acctggtcat 1680
ctgggacccc gacagcgtta aaaccatctc tgccaagaca cacaacagct ctctcgagta 1740

-continued caacatcttt gaaggcatgg agtgccgcgg ctccccactg gtggtcatca gccaggggaa 1800
gattgtcctg gaggacggca ccctgcatgt caccgaaggc tctggacgct acattccccg 1860
gaagcccttc cctgatttg tttacaagcg tatcaaggca aggagcaggc tggctgagct 1920
gagaggggtt cctcgtggcc tgtatgacgg acctgtgtgt gaagtgtctg tgacgcccaa 1980
gacagtcact ccagcctcct cggccaagac gtctcctgcc aagcagcagg ccccacctgt 2040
ccggaacctg caccagtctg gattcagttt gtctggtgct cagattgatg acaacattcc 2100
ccgccgcacc acccagcgta tcgtggcgcc ccccggtggc cgtgccaaca tcaccagcct 2160
gggctagagc tcctgggctg tgccgtccac tggggactgg ggatgggaca cctgaggaca 2220
ttctgagact tctttcttcc ttcctttttt tttttttgtt ttttttttta agagcctgtg 2280
atagttactg tggagcagcc agttcatggg gtccccccttg gggccccaca ccccgtctct 2340
caccaagagt tactgatttt gctcatccac ttccctacac atctatgggt atcacaccca 2400
agactaccca ccaagctcat acagggaacc acacccaaca cttagacatg cgaacaagca 2460
gcccccagcg agggtctcct tcgccttcaa cctcctagtg tctgttagca tcttcctttt 2520
catgggggga gggaagataa agtgaattgc ccagagctgc ctttttcttt tctttttaaa 2580
aattttaaga agtttcttt gtggggctgg ggaggggccg gggtcaggga gagtcttttt 2640
tttttttttt tttaaatact aaattggaac atttaattcc atattaatac aaggggtttg 2700
aactggacat cctaatgatg caattacgtc atcacccagc tgattccggg tggttggcaa 2760
actcatcgtg tctgtcctga gaggctccac aatgcccacc cgcatcgcca ttctgtagtc 2820
ttcagggtca gctgttgata aaggggcagg cttgcgttat tggcctagat tttgctgcag 2880
attaaatcct ttgaggattc tcttctcttt taccattttt ctgcgtgctc tcactctctc 2940
tttctctctc tagcttttta attcatgaat attttcgtgt ctgtctctct ctctctctgt 3000
gtttcctcca gcccttgtct cggagacggt gttttcctcc cttgccccat tatcttttca 3060
cctcccaggt ctaccatttc atggtggtcg ttgggtccgc ctaaaggatt tgagcgtttg 3120
ccattgcaag catagtgctg tgtcatcctg gtccatgtag gactggtgct aaccacctgc 3180
catcatgagg atgtgtgcta gagtgtggga ccctggccaa gtgcaggaat gggccatgcc 3240
gtctcaccca cagtatcaca cgtggaaccg cagacagggc ccagaagctt tagaggtatg 3300
aggctgcaga accggagaga ttttcctctg tgcagtgctc tctggctaaa gtcacggtca 3360
aacctaaaca ccgagcctca ttaacccaag tgaaccaacc aaagtcacca gttcagaagt 3420
gctaagctaa taggagtctg acccgagggc ctgctgcttc ctggttaagt atcttttgag 3480
attctagaac acatgggagc tttttatttt cggggaaaaa ccgtattttt ttcttgtcca 3540
attatttcta aagacacact acatagaaag aggccctata aactcaaaaa gtcattggga 3600
aacttaaagt ctattctact ttgcaagagg agaaatgtgt tttatgaacg atagatcaca 3660
tcagaactcc tgtggggagg aaaccttata aattaaacac atggcccccct tagagaccac 3720
aggtgatgtc tgtctccatc cttccctctc cttttctgtc acctttcccc ctagctggct 3780
cctttggacc taccccctgtc cttgctgact tgtgttgcat tgtattccaa acgtgtttac 3840
aggttctctt aagcaatgtt gtatttgcag gcttttctga ataccaaatc tgctttttgt 3900
aaagcgtaaa aacatcacaa agtaggtcat tccatcacca cccttgtctc tctacacatt 3960
ttgcctttgg ggatctggtt ggggttttgg gttttttgtt gttgttgttt atttgttatt 4020
ttaaaggtaa attgcacttt taaaaaaata attggttgac ttaatatatt tgcttttttt 4080
ctcacctgca cttagaggaa atttgaacaa gttggaaaaa aacaattttt gtttcaattc 4140
taagaaacac ttgcagctct agtattcact tgagtcttcc tgtttttcct gtaccgggtc 4200
atggtaattt ttggttgttt tggttgtttt cttaaaaaac aagttaaaac ctgacgattt 4260
ctgcaggctg tgtaagcatg tttacctgtt ggcttgcttt gtgtgtctgt taaatgaatg 4320
tcatatgtaa atgctaaaat aaatcgacag tgtctcagaa ctgaataact gcagtgactt 4380
gatgctctaa aacagtgtag gatttaagaa tagatggttt ttaatcctgg aaattgtgat 4440
tgtgacccat gagtggagga actttcagtt ctaaagctga taaagtgtgt agccagaaga 4500
gtactttttt ttttgtaacc actgtcttga tggcaaaata attatggtaa aaaacaagtc 4560
tcgtgtttat tattccttaa gaactctgtg ttatattacc atggaacgcc taataaagca 4620
aaatgtggtt gtttcaggaa aaaaaaaaaa aaaaa 4655

<210> SEQ ID NO 44
<211> LENGTH: 4417
<212> TYPE: DNA
<213> ORGANISM: Homo sapiens

<400> SEQUENCE: 44
gctgtaacac tcaccgtgaa ggtctgcagc ttcactcccg agccagcgag accacgaacc 60
caccagaagg aagaaactct gaacacatct gaacatcaga agggacagac tccagacgcg 120
ccaccactct gctaacacca gatagtggaa agaaaccatg tgctgaaatg tttgacgaca 180
ctgatggttt gactctgcta actggaatgg cttattgtgc aagaaagtac acctggtcgg 240
gtcctggggc tcatctctag caccagcaaa gatttctgaa gacgtctttc tagaaatgac 300
tggaaagttt caagaggcat aagatacagc atttcttctg aggccctgaa gaagtatcaa 360
gtgggctttg acattgcggt ggtgagagcg acccctcctc acctggagaa ctgggaaatg 420
tggattctca gggaccgcgc tgttcacgag ctccaggctg tgctgctggc cctggtcctg 480
gggcgctgag ccgcatctgc aatagcacac ttgcccggcc acctgctgcc gtgagccttt 540
gctgctgaag cccctggggt cgcctctacc tgatgaggat gtgcaccccc attagggggc 600
tgctcatggc ccttgcagtg atgtttggga cagcgatggc atttgcaccc ataccccgga 660
tcacctggga gcacagagag gtgcacctgg tgcagtttca tgagccagac atctacaact 720
actcagcctt gctgctgagc gaggacaagg acaccttgta cataggtgcc cgggaggcgg 780
tcttcgctgt gaacgcactc aacatctccg agaagcagca tgaggtgtat tggaaggtct 840
cagaagacaa aaaagcaaaa tgtgcagaaa aggggaaatc aaaacagaca gagtgcctca 900
actacatccg ggtgctgcag ccactcagcg ccacttccct ttacgtgtgt gggaccaacg 960
cattccagcc ggcctgtgac cacctgaact taacatcctt taagtttctg ggaaaaaatg 1020
aagatggcaa aggaagatgt ccctttgacc cagcacacag ctacacatcc gtcatggttg 1080
atggagaact ttattcgggg acgtcgtata attttttggg aagtgaaccc atcatctccc 1140
gaaattcttc ccacagtcct ctgaggacag aatatgcaat cccttggctg aacgagccta 1200
gtttcgtgtt tgctgacgtg atccgaaaaa gcccagacag ccccgacggc gaggatgaca 1260
gggtctactt cttcttcacg gaggtgtctg tggagtatga gtttgtgttc agggtgctga 1320
tcccacggat agcaagagtg tgcaaggggg accagggcgg cctgaggacc ttgcagaaga 1380
aatggacctc cttcctgaaa gcccgactca tctgctcccg gccagacagc ggcttggtct 1440
tcaatgtgct gcgggatgtc ttcgtgctca ggtccccggg cctgaaggtg cctgtgttct 1500
atgcactctt caccccacag ctgaacaacg tggggctgtc ggcagtgtgc gcctacaacc 1560

-continued

```
tgtccacagc cgaggaggtc ttctcccacg ggaagtacat gcagagcacc acagtggagc   1620
agtcccacac caagtgggtg cgctataatg gcccggtacc caagccgcgg cctggagcgt   1680
gcatcgacag cgaggcacgg gccgccaact acaccagctc cttgaatttg ccagacaaga   1740
cgctgcagtt cgttaaagac caccctttga tggatgactc ggtaacccca atagacaaca   1800
ggcccaggtt aatcaagaaa gatgtgaact acacccagat cgtggtggac cggacccagg   1860
ccctggatgg gactgtctat gatgtcatgt ttgtcagcac agaccgggga gctctgcaca   1920
aagccatcag cctcgagcac gctgttcaca tcatcgagga gacccagctc ttccaggact   1980
ttgagccagt ccagaccctg ctgctgtctt caaagaaggg caacaggttt gtctatgctg   2040
gctctaactc gggcgtggtc caggccccgc tggccttctg tgggaagcac ggcacctgcg   2100
aggactgtgt gctggcgcgg gacccctact gcgcctggag cccgcccaca gcgacctgcg   2160
tggctctgca ccagaccgag agccccagca ggggtttgat tcaggagatg agcggcgatg   2220
cttctgtgtg cccggcctcg tctcctaagc cctccctcc tcctggctcc tcttccctgt   2280
cctgtctggg ccatgtgggg gacaggaggc tttcctctcc ctggaccccc tggccagcct   2340
cgggtgcggg gcccgacagc agctcgaggg tctccttgct gccgcccttc ctgagtgacc   2400
aggcacagca cgtgcacgcc ctggggaact tctacctctt ctgccaggcc acaggtcctg   2460
cagacattcg ctttgtctgg gagaagaatg ggcgagctct ggagacctgt gtccctgtgc   2520
agacccatgc actgcccgat ggcagggccc atgcactcag ctggctgcag gacgccatca   2580
gggaaagcgc tgagtatcgc tgctctgtcc tctcctcagc agggaacaag acttcgaagg   2640
tgcaggttgc tgtgatgaga cctgaagtga cccaccagga gaggtggacc agagagctct   2700
ctgcctggag ggctgtggct ggggagcacg accggatgat gcagagctgg aggaaggcgt   2760
gggaaagctg tagcaaggac accctgtagc caccaggaag gagtccctga caccgacctc   2820
aaccccaaca agaccctgct gccactgacc acagccaccc ccggagaagg cctggtcccc   2880
cacaactgtg aactgtcttg cccaagcctg ctctgaacac agccattggg ccaccacctg   2940
atgggcagag gcgggacagt ggagaagcct ggaacccaag tgggcctgtg acaggaacta   3000
agacttaaaa aattaggtgc ttacctggga cagtaagttc tgtctggcac aagcaggtaa   3060
ccaggatggc taacaggctt tgatagctgc tcgtgaacta aaacagcagg gtgtgtgcag   3120
gttcctcctc tacggtcagg cagcaggctc tgaaggctga tcctacaccg tcccagtgac   3180
tcccttgac agagtgcccc cacccctaa tagccaacag ggttagcatg gccagcacag   3240
atcgctgctt ttattgatgc aaatcaagcc tgctgcttct cctccctgca gacttagcca   3300
aggaactcca agatgcatga ctgggacaag aaaaggtgag actccacatg gaaatgcctt   3360
gccctaaacc ttgaatgact gtgagatgcg atctgggagt gcatctgtca agtctttgtg   3420
ttttcttcac taacctcaga atactgggct ctattttatc aagcgctgca gtttatgcct   3480
ctgtcccgtc aatgctcagc ttctgcaaca ggacaccaaa cttgatgcag aaagccaaat   3540
aggtcaatta tgcaaatctc ctggtgccat attaaatttc ttgacgatgg aatgagtctc   3600
atgagtgttt tgttctacct gctttcaagt ctctaattat taaagctgta tctctgaaga   3660
ctgtgtcact gtgtgtgtga acttgtccta aagctactca gcctttaatc ttacacacac   3720
gtctcttctt gtctgttgaa tgacagtttt catgtctatc ataaaaccaa agcctctgtt   3780
aaaagtcaag ccgcacccct ctggtgatcc tagcaaatac tgagtgtctt cccagcagtg   3840
tgacaatgac ctgttttgca tcccctcttt ctggagctgg acaaattctc taccagcctt   3900
tgtgtgggat cagcatacat cgcctgctaa ttccttcagg atccatcaca acaggtgtcc   3960
```

```
tgaagatgct ggagacaccc tggttgtctc cacacgttcc ccctccgcac cccaagtcga   4020

gaggcccagc tgcctgtgag gtgtgtgctt gcccatccag ccaaggatgc cagtcttgct   4080

cacggaacca tcacatactc ataacctgaa gttttcctgt aaaatatcca tcagctcact   4140

gtggttcttg ctttgggtgt ggcttcaacc actacaaact gatgagtgaa atgctatggg   4200

ctttaggctt atattcttgg tgctgttttc tgtctcttct cctgaagtct ggatttcaag   4260

cactttcaca cttaacaaaa taattacata cttgaagttt tcgtaatgtg gagtgttcta   4320

ctgggaaatg gagttatgag gatgaatttc tgagtctttc tttgctctgc tggaaaaaat   4380

aaaaatagag ttgtacattg aaaaaaaaaa aaaaaaa                            4417
```

<210> SEQ ID NO 45
<211> LENGTH: 3108
<212> TYPE: DNA
<213> ORGANISM: Homo sapiens

<400> SEQUENCE: 45

```
gcctctggct cctcagggca ttcccggcgg ctccgggttt ggcaacgagg acgggggagt     60

gcgactgcgt ctcgggcagc atggccgaga agcggcacac acgggactcc gaagcccagc    120

ggctccccga ctccttcaag gacagcccca gtaagggcct tggaccttgc ggatggattt    180

tggtggcgtt ctcattctta ttcaccgtta taactttccc aatctcaata tggatgtgca    240

taaagattat aaaagagtat gaaagagcca tcatctttag attgggtcgc attttacaag    300

gaggagccaa aggacctggt ttgtttttta ttctgccatg cactgacagc ttcatcaaag    360

tggacatgag aactatttca tttgatattc ctcctcagga gatcctcaca aaggattcag    420

tgacaattag cgtggatggt gtggtctatt accgcgttca gaatgcaacc ctggctgtgg    480

caaatatcac caacgctgac tcagcaaccc gtcttttggc acaaactact ctgaggaatg    540

ttctgggcac caagaatctt tctcagatcc tctctgacag agaagaaatt gcacacaaca    600

tgcagtctac tctggatgat gccactgatg cctggggaat aaaggtggag cgtgtggaaa    660

ttaaggatgt gaaactacct gtgcagctcc agagagctat ggctgcagaa gcagaagcgt    720

cccgcgaggc ccgcgccaag gttattgcag ccgaaggaga aatgaatgca tccagggctc    780

tgaaagaagc ctccatggtc atcactgaat ctcctgcagc ccttcagctc cgatacctgc    840

agacactgac caccattgct gctgagaaaa actcaacaat tgtcttccct ctgcccatag    900

atatgctgca aggaatcata ggggcaaaac acagccatct aggctagtgt agagatgagc    960

gctagccttc caagcatgaa gtcggggacc aaattagcct ttaactcata aagagagggt   1020

agggcttttc tttttccata tgtcaattgt ggtgttccca gaatgtatag cagttataaa   1080

aataggtgaa agaattgtta gcttgtaaat actgagagat tggtgattta tataaggtaa   1140

tctgttagtc ttaaaatagt taaaagtttg tatttttaga ttattatgta gtaggttaga   1200

tccctcttgt tttgacttcc actgactcat tctgaacccc ctaagcaccc aggccagagg   1260

caagaacctg ggctgtaact gccacctgac accgctgact ggctaaatgc tttgcagaaa   1320

gtgatgacct tacaccacaa ccagcttctc caggtcatat gtgccttacc tccagagagt   1380

cttttttttt ttttttctga gatggagttt cactcttgtt gcccaggctg gagtgcaata   1440

gcatgatctc ggctcactgc aacctccgcc tcctgggttc aagagattct cctgcctcag   1500

cctccccagt agctgggatt acaggctcat gccaccatgc ccagctaatt tttgtattat   1560

tattattgtt ttttagtaga gacggggttt caccatgttg gccaggctag tcacgaactc   1620
```

```
ctaacctcag gtgatccacc cacctctgcc tcccaaagtg ctgggattac aggcatgagc   1680
taccacacct ggtttggaga gtcttaatta aggaaatttc cctaatgttc atttattttc   1740
taaatccaga ccgtgtttca gaataatcct tacttgagag tagccatttt cttgcctgta   1800
cttgtcagaa ctagaggaaa tagccaagac taatgaaaaa gattactcta acccttaaaa   1860
gacttttaaa ttcactacta gagtggtcat tttaaaaata catccatgtt ttaacttatt   1920
tgagccttct ttatgagtaa atgattcctc cttgttctgt ctttcaaacc agctaaatat   1980
ttgtcacaaa agtgcttttt tctcactgtt gcctattttc atatatcagg ttttaaatag   2040
ttttaatttt ttaataaaat tttctctacg ttctatatgc aattgttata tatctatttg   2100
aatagctgaa ggactaaaat acttttttaa gagataactt caggaaacca ttatatttta   2160
ctatctgcat gctgttaact gtggtacact gtgaaatatg ttgattacaa acccattcat   2220
tacatagtat aaggaattca cagtatattg actatatagt gtctaatgat cttgggcaga   2280
tactgtcaaa cttacaatat ctatatagat gtaggtcttt ttaaatttac ctagtcattc   2340
ttctatcatg tatattgatg ctgaaagagg aactggtcag ctcctctgga caacaaattc   2400
ttagtctata atattaggag acatcttctg ttttgcaaat gtctgtgaat ctgagcaacc   2460
tggcattctg cttactggcc agaaagctgg cgggtgacat ttgtaacatt tcctctttga   2520
gactctgagt tcacctagag aagtctaagc ataacagctt tctttcccag cacgagcctt   2580
tatagctctc tttagctcaa ccactctgtc catccagcca atggatgtcc cttcccctgt   2640
accccaattt caagcttatt ttaggaagcc ttgaactacc atgtatcctg gctcctagct   2700
gagtttatta gaggtatgga gcagtgcaac ttaaactcaa gttgcactta cattttgaat   2760
tttaaaatga tggttttatc tgttgtgtga agtggttcac ccttgaggac caggagcctc   2820
catatcctga ctgaaaacct tttctgagac ttagagtaac agtgcttttg gttccttgag   2880
ttctcctgtc tccagatacc aaatgacctt gacttttctg ccttgtgaat tcgtagtcca   2940
atcagctgaa attaaatcac ttgggaggga cgcatagaag gagctctagg aacacagtgc   3000
cagtgcagaa gtttctccag gtggcctccc tttccaacaa tgtacataat aaagtgtatg   3060
cactttcact aataaaaaaa aaaaaaaaaa aaaaaaaaaa aaaaaaaa                3108
```

<210> SEQ ID NO 46
<211> LENGTH: 4090
<212> TYPE: DNA
<213> ORGANISM: Homo sapiens

<400> SEQUENCE: 46

```
gggcgctccc ggagtatcag caaaagggtt cgccccgccc acagtgcccg gctccccccg     60
ggtatcaaaa gaaggatcgg ctccgccccc gggctccccg ggggagttga tagaagggtc    120
cttcccaccc tttgccgtcc ccactcctgt gcctacgacc caggagcgtg tcagccaaag    180
catggagaat caagagaagg cgagtatcgc gggccacatg ttcgacgtag tcgtgatcgg    240
aggtggcatt tcaggactat ctgctgccaa actcttgact gaatatggcg ttagtgtttt    300
ggttttagaa gctcgggaca gggttggagg aagaacatat actataagga atgagcatgt    360
tgattacgta gatgttggtg gagcttatgt gggaccaacc caaaacagaa tcttacgctt    420
gtctaaggag ctgggcatag agacttacaa agtgaatgtc agtgagcgtc tcgttcaata    480
tgtcaagggg aaaacatatc catttcgggg cgcctttcca ccagtatgga atcccattgc    540
atatttggat tacaataatc tgtggaggac aatagataac atggggaagg agattccaac    600
tgatgcaccc tgggaggctc aacatgctga caaatgggac aaaatgacca tgaaagagct    660
```

-continued

```
cattgacaaa atctgctgga caaagactgc taggcggttt gcttatcttt ttgtgaatat    720
caatgtgacc tctgagcctc acgaagtgtc tgccctgtgg ttcttgtggt atgtgaagca    780
gtgcgggggc accactcgga tattctctgt caccaatggt ggccaggaac ggaagtttgt    840
aggtggatct ggtcaagtga gcgaacggat aatggacctc ctcggagacc aagtgaagct    900
gaaccatcct gtcactcacg ttgaccagtc aagtgacaac atcatcatag agacgctgaa    960
ccatgaacat tatgagtgca aatacgtaat taatgcgatc cctccgacct tgactgccaa   1020
gattcacttc agaccagagc ttccagcaga gagaaaccag ttaattcagc ggcttccaat   1080
gggagctgtc attaagtgca tgatgtatta caaggaggcc ttctggaaga agaaggatta   1140
ctgtggctgc atgatcattg aagatgaaga tgctccaatt tcaataacct tggatgacac   1200
caagccagat gggtcactgc ctgccatcat gggcttcatt cttgcccgga aagctgatcg   1260
acttgctaag ctacataagg aaataaggaa gaagaaaatc tgtgagctct atgccaaagt   1320
gctgggatcc caagaagctt tacatccagt gcattatgaa gagaagaact ggtgtgagga   1380
gcagtactct gggggctgct acacggccta cttccctcct gggatcatga ctcaatatgg   1440
aagggtgatt cgtcaacccg tgggcaggat tttctttgcg ggcacagaga ctgccacaaa   1500
gtggagcggc tacatggaag gggcagttga ggctggagaa cgagcagcta gggaggtctt   1560
aaatggtctc gggaaggtga ccgagaaaga tatctgggta caagaacctg aatcaaagga   1620
cgttccagcg gtagaaatca cccacacctt ctgggaaagg aacctgccct ctgtttctgg   1680
cctgctgaag atcattggat tttccacatc agtaactgcc ctggggtttg tgctgtacaa   1740
atacaagctc ctgccacggt cttgaagttc tgttcttatg ctctctgctc actggttttc   1800
aataccacca agaggaaaat attgacaagt ttaaaggctg tgtcattggg ccatgtttaa   1860
gtgtactgga tttaactacc tttggcttaa ttccaatcat tgttaaagta aaaacaattc   1920
aaagaatcac ctaattaatt tcagtaagat caagctccat cttatttgtc agtgtagatc   1980
aactcatgtt aattgataga ataaagcctt gtgatcactt tctgaaattc acaaagttaa   2040
acgtgatgtg ctcatcagaa acaatttctg tgtcctgttt ttattccctt caatgcaaaa   2100
tacatgatga tttcagaaac aaagcatttg actttctgtc tgtggaggtg gagtaggtga   2160
aggcccagcc tgtaactgtc ctttttcttc ccttaggcaa tggtgaactg tcattacaga   2220
gcctagaggc tcacagcctc ctggaggaag cagcctccac tttggatcag gaaatagtaa   2280
aggaaagcag tgttgggggt agcggcatgc agaccctcag accagaatgg ggacatcttg   2340
tggtctgctg cctcaggaat ctcctgacca cttgtagtcc ctccgacttc tctagacatc   2400
tagtctcagt gctagcttat ttgtattttt cctctttcac ttcttatgga ggagagtgtt   2460
taactgagtt agaatgttga aactgacttg ctgtgactta tgtgcagctt tccagttgag   2520
cagaggaaaa tagtggcagg actgtccccc aggaggactc cctgcttagc tctgtgggag   2580
accaactacg actggcatct tctcttcccc ctggaaggca gctagacacc aatggatcct   2640
tgtcagttgt aacattctat ttcaacttca ggaaagcagc agttttcttt taatttttcc   2700
tatgaccata aaattagaca tacctctcaa cttacatatg tcttcaacat ggttacctct   2760
gcataaatat tagcaaagca tgccaatttc tcttaagtac tgaaatacat atgataaatt   2820
tgactgttat ttgttgagac tatcaaacag aaaagaaatt agggctctaa tttccttaaa   2880
gcaagctcac ttgctttagt tgttaagttt tataaaagac atgaaattga gtcattttat   2940
atatgaaaac taagttctct atcttaggag taatgtcggc ccacaagggt gcccacctct   3000
```

-continued

```
tgttttcccc ttttaaaaac tcagattttt aaaagccctt tccaaaggtt tcaactgtaa   3060
aatacttctt tttacaatgt atcaacatat ttttatttaa ggggaattaa caattgccag   3120
ggaaaccagc caacccaagt ttattatatc attaacctta tcataaattc aaacctaagt   3180
tgctggaccc tggtgtgagg acataaatct tccaaagttt tgcctatcct aagagctgca   3240
tttttctact gctctttacc ttgcatttta gctaatttag gagttttgag aatgtattgg   3300
atacgctcca gtacataagg agttgccgca tattatatca gactgctttg agaaatctca   3360
tccctagtct attgcagttg tttctattag cttactgatt aactcagtcc tgacacacct   3420
tttgggaaat gctgatttaa acttcttaac tggcaacagt tggaacagta atcagtttgc   3480
taacatattt aaagtcttga atgttgaaga actcatgtga tttacccttt tcaacttttt   3540
ggaaaacgat ttaatttatt ctaattagat taaccctatt aatctatgga ttgggtatca   3600
aaatgaatgc cagtccagat gtgcctagac acgaaattgg agctgaggac tctcacgata   3660
tgcaagttca tccaacgtga agataccata agctttttct ctgaaccaga gaaatgaaag   3720
tcagtttaag aggctgatag atcttggccc tgttaaggca tccacttcac agttctgaag   3780
gctgagtcag ccccactcca cagttaggcc aagaattaga ttttaaaact tcatctgtct   3840
gtcccagtta actgttaaat aaggcctcat cctccactga agagtatgga ttgaaggatt   3900
gtgaactatg tttagtgtga ttgtgaactt ggtgcctaat gttccatgtc tgaagtttgc   3960
cccagtgcta cacgttggag tatacctatg tgtgtgcttt gccactgaag taagattttg   4020
cctgtatggt actgttttgt ttgttaataa agtgcactgc cacccccaat gcaaaaaaaa   4080
aaaaaaaaaa                                                          4090
```